US009125896B2

(12) United States Patent
Setiady et al.

(10) Patent No.: US 9,125,896 B2
(45) Date of Patent: Sep. 8, 2015

(54) EGFR-BINDING MOLECULES AND IMMUNOCONJUGATES THEREOF

(71) Applicant: ImmunoGen, Inc., Waltham, MA (US)

(72) Inventors: Julianto Setiady, Waltham, MA (US); Peter U. Park, Somerville, MA (US); Lingyun Rui, Weston, MA (US); Thomas Chittenden, Sudbury, MA (US); Gillian Payne, Waban, MA (US)

(73) Assignee: ImmunoGen, Inc., Waltham, MA (US)

( * ) Notice: Subject to any disclaimer, the term of this patent is extended or adjusted under 35 U.S.C. 154(b) by 100 days.

(21) Appl. No.: 13/800,624

(22) Filed: Mar. 13, 2013

(65) Prior Publication Data

US 2014/0099308 A1 Apr. 10, 2014

Related U.S. Application Data

(62) Division of application No. 13/284,398, filed on Oct. 28, 2011, now Pat. No. 8,790,649.

(60) Provisional application No. 61/408,497, filed on Oct. 29, 2010, provisional application No. 61/477,086, filed on Apr. 19, 2011.

(51) Int. Cl.

| | |
|---|---|
| ***A61K 39/395*** | (2006.01) |
| ***A61K 47/48*** | (2006.01) |
| ***C07K 16/28*** | (2006.01) |
| ***A61K 45/06*** | (2006.01) |

(Continued)

(52) U.S. Cl.

CPC ........... *A61K 39/39558* (2013.01); *A61K 45/06* (2013.01); *A61K 47/48384* (2013.01); *A61K 47/48561* (2013.01); *C07K 16/2863* (2013.01); *A61K 2039/505* (2013.01); *C07K 2317/24* (2013.01); *C07K 2317/33* (2013.01); *C07K 2317/34* (2013.01); *C07K 2317/73* (2013.01); *C07K 2317/732* (2013.01); *C07K 2317/76* (2013.01); *C07K 2317/92* (2013.01)

(58) Field of Classification Search

None

See application file for complete search history.

(56) References Cited

U.S. PATENT DOCUMENTS

| | | | |
|---|---|---|---|
| 4,256,746 | A | 3/1981 | Miyashita et al. |
| 4,294,757 | A | 10/1981 | Asai |

(Continued)

FOREIGN PATENT DOCUMENTS

| | | | |
|---|---|---|---|
| EP | 1 033 406 | A1 | 9/2000 |
| EP | 2 457 586 | A1 | 5/2012 |

(Continued)

OTHER PUBLICATIONS

Akashi, Y., et al., "Enhancement of the antitumor activity of ionising radiation by nimotuzumab, a humanised monoclonal antibody to the epidermal growth factor receptor, in non-small cell lung cancer cell lines of differing epidermal growth factor receptor status," *British Journal of Cancer 98*:749-755, Cancer Research UK, United Kingdom (2008).

(Continued)

*Primary Examiner* — Claire Kaufman

(74) *Attorney, Agent, or Firm* — Sterne, Kessler, Goldstein & Fox PLLC

(57) ABSTRACT

Novel anti-cancer agents, including, but not limited to, antibodies and immunoconjugates, that bind to EGFR are provided. Methods of using the agents, antibodies, or immunoconjugates, such as methods of inhibiting tumor growth are further provided.

39 Claims, 36 Drawing Sheets

HSC2 xenograft

(51) Int. Cl.
*C07K 14/71* (2006.01)
*A61K 39/00* (2006.01)

(56) References Cited

U.S. PATENT DOCUMENTS

| | | | |
|---|---|---|---|
| 4,307,016 | A | 12/1981 | Asai et al. |
| 4,313,946 | A | 2/1982 | Powell et al. |
| 4,315,929 | A | 2/1982 | Freedman et al. |
| 4,322,348 | A | 3/1982 | Asai et al. |
| 4,331,598 | A | 5/1982 | Hasegawa et al. |
| 4,361,650 | A | 11/1982 | Asai et al. |
| 4,362,663 | A | 12/1982 | Kida et al. |
| 4,364,866 | A | 12/1982 | Asai et al. |
| 4,371,533 | A | 2/1983 | Akimoto et al. |
| 4,424,219 | A | 1/1984 | Hashimoto et al. |
| 4,450,254 | A | 5/1984 | Isley et al. |
| 4,563,304 | A | 1/1986 | Carlsson et al. |
| 4,943,533 | A | 7/1990 | Mendelsohn et al. |
| 5,208,020 | A | 5/1993 | Chari et al. |
| 5,416,064 | A | 5/1995 | Chari et al. |
| 5,459,061 | A | 10/1995 | Sato et al. |
| 5,470,571 | A | 11/1995 | Herlyn et al. |
| 5,475,092 | A | 12/1995 | Chari et al. |
| 5,558,864 | A | 9/1996 | Bendig et al. |
| 5,585,499 | A | 12/1996 | Chari et al. |
| 5,731,168 | A | 3/1998 | Carter et al. |
| 5,750,373 | A | 5/1998 | Garrard et al. |
| 5,756,291 | A | 5/1998 | Griffin et al. |
| 5,844,093 | A | 12/1998 | Kettleborough et al. |
| 5,846,545 | A | 12/1998 | Chari et al. |
| 5,891,996 | A | 4/1999 | Mateo de Acosta del Rio et al. |
| 5,942,602 | A | 8/1999 | Wels et al. |
| 6,129,915 | A | 10/2000 | Wels et al. |
| 6,217,866 | B1 | 4/2001 | Schlessinger et al. |
| 6,235,883 | B1 | 5/2001 | Jakobovits et al. |
| 6,333,410 | B1 | 12/2001 | Chari et al. |
| 6,441,163 | B1 | 8/2002 | Chari et al. |
| 6,506,883 | B2 | 1/2003 | Meteo de Acosta del Rio et al. |
| 6,716,821 | B2 | 4/2004 | Zhao et al. |
| 6,979,726 | B1 | 12/2005 | von Hoegen et al. |
| 7,097,840 | B2 | 8/2006 | Erickson et al. |
| 7,129,332 | B2 | 10/2006 | Pastan et al. |
| 7,132,511 | B2 | 11/2006 | Carr et al. |
| 7,247,301 | B2 | 7/2007 | van de Winkel et al. |
| 7,276,497 | B2 | 10/2007 | Chari et al. |
| 7,303,749 | B1 | 12/2007 | Chari |
| 7,368,565 | B2 | 5/2008 | Chari et al. |
| 7,473,796 | B2 | 1/2009 | Chari et al. |
| 7,479,543 | B2 | 1/2009 | Tsuchiya et al. |
| 7,575,748 | B1 | 8/2009 | Erickson et al. |
| 7,585,857 | B2 | 9/2009 | Chari et al. |
| 7,589,180 | B2 | 9/2009 | Old et al. |
| 7,595,378 | B2 | 9/2009 | van de Winkel et al. |
| 7,598,350 | B2 | 10/2009 | Liu et al. |
| 7,601,354 | B2 | 10/2009 | Chari |
| 7,628,986 | B2 | 12/2009 | Weber et al. |
| 7,736,644 | B2 | 6/2010 | Weber et al. |
| 7,749,697 | B2 | 7/2010 | Oleksiewicz et al. |
| 7,780,964 | B2 | 8/2010 | Ellis et al. |
| 7,846,443 | B2 | 12/2010 | Presta et al. |
| 7,887,805 | B2 | 2/2011 | Pedersen et al. |
| 7,892,777 | B2 | 2/2011 | Fisher et al. |
| 7,935,793 | B2 | 5/2011 | Balasa et al. |
| 7,989,598 | B2 | 8/2011 | Steeves et al. |
| 8,088,387 | B2 | 1/2012 | Steeves et al. |
| 8,101,183 | B2 | 1/2012 | Siadak et al. |
| 8,137,669 | B2 | 3/2012 | Goldmakher et al. |
| 8,163,888 | B2 | 4/2012 | Steeves et al. |
| 8,198,417 | B2 | 6/2012 | Steeves et al. |
| 8,236,319 | B2 | 8/2012 | Chari et al. |
| 8,337,856 | B2 | 12/2012 | Blättler et al. |
| RE43,899 | E | 1/2013 | Blättler et al. |
| 8,388,960 | B2 | 3/2013 | Goldmakher et al. |
| 8,563,509 | B2 | 10/2013 | Chari et al. |
| 8,613,930 | B2 | 12/2013 | Chari et al. |
| RE44,704 | E | 1/2014 | Chari et al. |
| 8,685,920 | B2 | 4/2014 | Chari et al. |
| 8,790,649 | B2 | 7/2014 | Setiady et al. |
| 2002/0001587 | A1 | 1/2002 | Erickson et al. |
| 2004/0031072 | A1 | 2/2004 | La Rosa et al. |
| 2004/0259942 | A1 | 12/2004 | Shaw et al. |
| 2005/0107325 | A1 | 5/2005 | Manoharan et al. |
| 2005/0169933 | A1 | 8/2005 | Steeves et al. |
| 2006/0147959 | A1 | 7/2006 | Bell et al. |
| 2006/0233814 | A1 | 10/2006 | Goldmakher et al. |
| 2007/0009972 | A1 | 1/2007 | Chao et al. |
| 2007/0213292 | A1 | 9/2007 | Stoffel et al. |
| 2008/0027130 | A1 | 1/2008 | Chari et al. |
| 2008/0171040 | A1 | 7/2008 | Ebens et al. |
| 2009/0155282 | A1 | 6/2009 | Weber et al. |
| 2009/0156790 | A1 | 6/2009 | Weber et al. |
| 2009/0175887 | A1 | 7/2009 | Weber et al. |
| 2009/0240038 | A1 | 9/2009 | Weber et al. |
| 2009/0252681 | A1 | 10/2009 | Laeremans et al. |
| 2009/0258442 | A1 | 10/2009 | Polakiewicz et al. |
| 2009/0269343 | A1 | 10/2009 | Bigner et al. |
| 2010/0008929 | A1 | 1/2010 | van de Winkel et al. |
| 2010/0111979 | A1 | 5/2010 | Weber et al. |
| 2010/0129314 | A1 | 5/2010 | Singh et al. |
| 2010/0166744 | A1 | 7/2010 | Wong |
| 2010/0190247 | A1 | 7/2010 | Lazar et al. |
| 2011/0287036 | A1 | 11/2011 | Matsumura et al. |
| 2012/0156217 | A1 | 6/2012 | Setiady et al. |
| 2013/0108620 | A1 | 5/2013 | Blättler et al. |
| 2013/0131322 | A1 | 5/2013 | Kaneda et al. |
| 2013/0156796 | A1 | 6/2013 | Setiady et al. |
| 2014/0023662 | A1 | 1/2014 | Setiady et al. |

FOREIGN PATENT DOCUMENTS

| | | | |
|---|---|---|---|
| JP | 6-319396 | A | 11/1994 |
| WO | WO 2008/098145 | A1 | 8/2008 |
| WO | WO 2009/030239 | A1 | 3/2009 |
| WO | WO 2009/134976 | A1 | 11/2009 |
| WO | WO 2010/009124 | A2 | 1/2010 |
| WO | WO 2010/022736 | A2 | 3/2010 |
| WO | WO 2010/042904 | A2 | 4/2010 |
| WO | WO 2010/055950 | A1 | 5/2010 |
| WO | WO 2011/145629 | A2 | 11/2011 |
| WO | WO 2012/058588 | A2 | 5/2012 |
| WO | WO 2012/058592 | A2 | 5/2012 |
| WO | WO 2013/078271 | A1 | 5/2013 |

OTHER PUBLICATIONS

Clarke, J., et al., "Duration of chronic toxicity studies for biotechnology-derived pharmaceuticals: Is 6 months still appropriate?" *Regulatory Toxicology and Pharmacology 50*:2-22, Elsevier Inc., United States (2008).

Talavera, A., et al., "Nimotuzumab, an Antitumor Antibody that Targets the Epidermal Growth Factor Receptor, Blocks Ligand Binding while Permitting the Active Receptor Conformation," *Cancer Res 69*(14):5851-5859, American Association for Cancer Research, United States (2009).

Eurasian Search Report, completed Nov. 25, 2013, in Eurasian Application No. 201390472, Moscow, Russia.

Notice of Allowance, mailed on Nov. 21, 2013, in U.S. Appl. No. 13/284,398, inventors Setiady et al., filed Oct. 28, 2011.

Corrected Notice of Allowance, mailed on Feb. 18, 2014, in U.S. Appl. No. 13/284,398, inventors Setiady et al., filed Oct. 28, 2011.

Guo, L., et al., "Studies of Ligand-Induced Site-Specific Phosphorylation of Epidermal Growth Factor Receptor," *J Am Soc Mass Spectrom 14*:1022-1031, American Society for Mass Spectrometry, United States (2003).

Kovtun, Y.V., et al., "Antibody-Maytansinoid Conjugates Designed to Bypass Multidrug Resistance," *Cancer Research 70*(6):2528-2537, American Association for Cancer Research, United States (2010).

Maloney, E.M., et al., "Designing Potent Antibody-Maytansinoid Conjugated (AMCs): The Impact of Lysosomal Processing Efficient and Conjugate Linker Selection on Anticancer Activity," 2009

(56) References Cited

OTHER PUBLICATIONS

AACR-NCI-EORTC International Conference on Molecular Targets and Cancer Therapeutics, Boston, MA (Nov. 15-19, 2009) Abstract #B120 Poster, American Association for Cancer Research, United States (Nov. 15, 2009).
Ojima, I., et al., "Tumor-Specific Novel Taxoid—Monoclonal Anitbody Conjugates," *Journal of Medicinal Chemistry 45*(26):5620-5623, American Chemical Society, United States (2002).
Ojima, I., "Guided Molecular Missiles for Tumor-Targeting Chemotherapy—Case Studies Using the Second Generation Taxoids as Warheads," *Accounts of chemical research 41*(1):108-119, American Chemical Society, United States (2008).
Schmiedel, J., et al., "Matuzumab binding to EGFR prevents the conformational rearrangement required for dimerization," *Cancer Cell 13*(4):365-373, Cell Press, United States (2008).
Singh, R., and Maloney, E.K., "Labeling of Antibodies by in Situ Modification of Thiol Groups Generated from Selenol-Catalyzed Reduction of Native Disulfide Bonds," *Analytical Biochemistry 304*(2):147-156, Academic Press, United States (2002).
Singh, R. and Erickson, H.K., "Antibody-Cytotoxic Agent Conjugates: Preparation and Characterization," in *Therapeutic Antibodies: Methods and Protocols*, Dimitrov, A.S., Ed., Chapter 23, pp. 455-467, Humana Press, United States (2009).
Wu, X., and Ojima, I., "Tumor Specific Novel Taxoid-Monoclonal Antibody Conjugates," *Current Medicinal Chemistry 11*(4):429-438, Bentham Science Publishers Ltd., Netherlands (2004).
Eurasian Search Report, completed Feb. 7, 2014, in Eurasian Application No. 201390575, Moscow, Russia.
Maloney, E., et al., "Designing Potent Antibody-Drug Conjugates (ADCs): The Impact of Lysosomal Processing Efficiency and Conjugate Linker Selection on Anticancer Activity," 2009 AACR-NCI-EORTC International Conference on Molecular Targets and Cancer Therapeutics, Boston, MA (Nov. 15-19, 2009) Abstract #B120, American Association for Cancer Research, United States (submitted electronically on Sep. 9, 2009).
Unpublished U.S. Appl. No. 14/032,046, filed Sep. 19, 2013, now US 2014/0212411.
Ramakrishnan, M.S., "Nimotuzumab, a promising therapeutic monoclonal for treatment of turmors of epithelial origin," *mAbs 1*(1):41-48, Landes Bioscience, United States (2009).
Skartved, N.J.O., et al., "Preclinical pharmacokinetics and safety of Sym0004: A synergistic antibody mixture directed against epidermal growth factor receptor," Clin. Cancer Res. 17:5962-5972, American Association for Cancer Research, United States (2011).
Takeda, M., et al., "Nimotuzumab, a novel monoclonal antibody to the epidermal growth factor receptor, in the treatment of non-small cell lung cancer," *Lung Cancer: Targets and Therapy 2*:59-67, Dove Medical Press Ltd., United Kingdom (2011).
Willmarth, N.E., et al., "Autocrine and Juxtacrine Effects of Amphiregulin on the Proliferative, Invasive, and Migratory Properties of Normal and Neoplastic Human Mammary Epithelial Cells," *J. Biol. Chem. 281*:37728-37737, The American Society for Biochemistry and Molecular Biology, Inc., United States (2006).
International Preliminary Report on Patentability for International Application No. PCT/US2011/058385, U.S. Patent Office, United States, mailed May 10, 2013.
International Preliminary Report on Patentability for International Application No. PCT/US2011/058378, U.S. Patent Office, United States, mailed May 10, 2013.
Office Action mailed on Aug. 12, 2013 in U.S. Appl. No. 13/284,398, inventors Setiady et al., filed Oct. 28, 2011.
Bardelli, A., and Siena, S., "Molecular Mechanisms of Resistance to Cetuximab and Pantiumumab in Colorectal Cancer," *J. Clin. Oncol. 28*(7):1254-1261, American Society of Clinical Oncology, United States (Mar. 2010).
Baselga, J., and Arteaga, C.L., "Critical Update and Emerging Trends in Epidermal Growth Factor Receptor Targeting in Cancer," *J. Clin. Oncol. 23*(11):2445-2459, American Society of Clinical Oncology, United States (Apr. 2005).
DeRook, W., et al., "Effects of *KRAS, BRAF, NRAS*, and *PIK3CA* mutations on the efficacy of cetuximab plus chemotherapy in chemotherapy-refractory metastatic colorectal cancer: a retrospective consortium analysis," *Lancet Oncol. 11*:753-762, Lancet Pub. Group, England (Aug. 2010).
Gill, G.N., et al., "Monclonal Anti-epidermal Growth Factor Receptor Antibodies Which Are Inhibitors of Epidermal Growth Factor Binding and Antagonists of Epidermal Growth Factor-stimulated Tyrosine Protein Kinase Activity," *J. Biol. Chem. 259*(12):7755-7760, American Society for Biochemistry and Molecular Biology, England (Jun. 1984).
Goldstein, N.I., et al., "Biological Efficacy of a Chimeric Antibody to the Epidermal Growth Factor Receptor in a Human Tumor Xenograft Model," *Clin. Cancer Res. 1*:1311-1318, American Association for Cancer Research, United States (Nov. 1995).
Li, T., and Perez-Soler, R., "Skin toxicities associated with epidermal growth factor receptor inhibitors," *Targ. Oncol. 4*:107-119, Springer-Verlag, France (2009).
Linardou, H., et al., "Somatic *EGFR* mutations and efficacy of tyrosine kinase inhibitors in NSCLC," *Nat. Rev. Clin. Oncol. 6*:352-366, Macmillian Limited, England (Jun. 2009).
Paz-Ares, L., et al., "Clinical outcomes in non-small-cell lung cancer patients with *EGFR* mutations: pooled analysis," *J Cell. Mol. Med. 14*(1-2):51-69, F. Hoffmann-La Roche Ltd., Switzerland (2010).
Prewett, M., et al., "Mouse-Human Chimeric Anti-Epidermal Growth Factor Receptor Antibody C225 Inhibits the Growth of Human Renal Cell Carcinoma Xenografts in Nude Mice," *Clin. Cancer Res. 4*:2957-2966, American Association for Cancer Research, United States (Dec. 1998).
Stoll, S.W., et al., "EGF receptor signaling inhibits keratinocyte apoptosis: evidence for mediation by Bcl-$X_L$," *Oncogene 16*:1493-1499, Stockton Press, United Kingdom (Mar. 1998).
Widdison, W.C., et al., "Semisynthetic Maytansine Analogues for the Targeted Treatment of Cancer," *J. Med. Chem. 49*:4392-4408, American Chemical Society, United States (2006).
Baselga, J., "Why the Epidermal Growth Factor Receptor? The Rationale for Cancer Therapy," *The Oncologist 7*(suppl 4):2-8, AlphaMed Press, United States (2002).
Carlsson, J., et al., "Protein Thiolation and Reversible Protein-Protein Conjugation," *Biochem. J. 173*:723-737, Portland Press, England (1978).
Friess, T., et al., "Combination Treatment with Erlotinib and Pertuzumab against Human Tumor Xenografts Is Superior to Monotherapy," *Clin Cancer Res 11*(14):5300-5309, American Association for Cancer Research, United States (2005).
Hashida, S., et al., "More Useful Maleimide Compounds for the Conjugation of Fab' to Horseradish Peroxidase through Thiol Groups in the Hinge," *Journal of Applied Biochemistry 6*:56-63, Academic Press Inc., United States (1984).
Jost, M., et al., "Matrix-independent Survival of Human Keratinocytes through an EGF Receptor/MAPK-Kinase-dependent Pathway," *Molecular Biology of the Cell 12*:1519-1527, The American Society for Cell Biology, United States (2001).
Kamat, V., et al., "Enhanced EGFR inhibition and distinct epitope recognition by EGFR antagonistic mAbs C225 and 425," *Cancer Biology & Therapy 7*(5):726-733, Landes Bioscience, United States (2008).
Kim, S., et al., "E-cadherin promotes EGFR-mediated cell differentiation and MUC5AC mucin expression in cultured human airway epithelial cells," Am *J Physiol Lung Cell Mol Physiol 289*:L1049-L1060, the American Physiological Society, United States (2005).
Kimura, H., et al., "Antibody-dependent cellular cytotoxicity of cetuximab against tumor cells with wild-type or mutant epidermal growth factor receptor," *Cancer sci 98*(8):1275-1280, Japanese Cancer Association, Japan (2007).
Lammerts van Bueren, J.L., et al., "The antibody zalutumumab inhibits epidermal growth factor receptor signaling by limiting intra- and intermolecular flexibility," *PNAS 105*(16):6109-6114, The National Academy of Sciences of the USA, United States (2008).
Laux, I., et al., "Epidermal growth factor receptor dimerization status determines skin toxicity to HER-kinase targeted therapies," *British Journal of Cancer 94*:85-92, Cancer Research UK, England (2006).

(56) References Cited

OTHER PUBLICATIONS

Liu, F-T, et al., "New Procedures for Preparation and isolation of Conjugates of Proteins and a Synthetic Copolymer of D-Amino Acids and Immunochemical Characterization of Such Conjugates," *Biochemistry 18*:690-697, American Chemical Society, United States (1979).
Modjtahedi, H., et al., "Anti-EGFR Monoclonal Antibodies which Act as EGF, TGFα HB-EGF and BTC Antagonists Block the Binding of Epiregulin to EGFR-Expressing Tumours," *Int. J. Cancer 75*:310-316, Wiley-Liss, Inc., United States (1998).
Mok, T., et al., "A Small Step Towards Personalized Medicine for Non-small Cell Lung Cancer," *Discovery Medicine 8*(43): 227-231, Discovery Medicine, United States (2009).
Mutsaers, A.J., et al., "Dose-Dependent Increases in Circulating TGF-α and Other EGFR Ligands Act as Pharmacodynamic Markers for Optimal Biological Dosing of Cetuximab and Are Tumor Independent," *Clin Cancer Res 15*(7):2397-2405, American Association for Cancer Research, United States (2009).
Nygren, P-A., "Alternative binding proteins: Affibody binding proteins developed from a small three-helix bundle scaffold," *FEBS Journal 275*:2668-2676, The Author Journal compilation, FEBS, England (2008).
Ocvirk, J, "Management of cetuximab-induced skin toxicity with the prophylactic use of topical vitamin K1 cream," *Radiol Oncol 44*(4):256-266, Versita, Slovenia (2010).
Raben, D., et al., "The Effects of Cetuximab Alone and in Combination With Radiation and/or Chemotherapy in Lung Cancer," *Clinical Cancer Research 11*:795-805, American Association for Cancer Research, United States (2005).
Shalaby, M.R., et al., "Development of Humanized Bispecific Antibodies Reactive with Cytotoxic Lymphocytes and Tumor Cells Overexpressing the HER2 Protooncogene," *J. Exp. Med. 175*:217-225, The Rockefeller University Press, United States (1992).
Sheets, M.D., et al., "Efficient construction of a large nonimmune phage antibody library: The production of high-affinity human single-chain antibodies to protein antigens," *Proc. Natl. Acad. Sci. USA 95*:6157-6162, The National Academy of Sciences, United States (1998).
Steiner, P., et al., "Tumor Growth Inhibition with Cetuximab and Chemotherapy in Non-Small Cell Lung Cancer Xenografts Expressing Wild-type and Mutated Epidermal Growth Factor Receptor," *Clin Cancer Res 13*(5):1540-1551, American Association for Cancer Research, United States (2007).
Ullrich, A., et al., "Human epidermal growth factor receptor cDNA sequences and aberrant expression of the amplified gene in A431 epidermoid carcinoma cells," *Nature 309*:418-425, Nature Publishing Group, England (1984).
Yang, X-D, et al., "Eradication of Established Tumors by a fully Human Monoclonal Antibody to the Epidermal Growth Factor Receptor without Concomitant Chemotherapy," *Cancer Research 59*:1236-1243, American Association for Cancer Research, United States (1999).
Yarden, Y., and Sliwkowski, M.X., "Untangling the ErbB Signalling Network," *Nature Reviews Molecular Cell Biology 2*:127-137, Macmillan Magazines Ltd, England (2001).
Yoshitakes, S., et al., "Conjugation of Glucose Oxidase from *Aspergillus niger* and Rabbit Antibodies Using N-Hydroxysuccinimide Ester of *N*-(4-Carboxycyclohexylmehtyl)-Maleimide," *Eur. J. Biochem.101*:395-399, Blackwell Science Ltd., England (1979).
NCBI Entrex, GenBank Report, Accession No. AY208307.1, Zhang, J.Q., and Davidson, W.F., Entry Date Mar. 2004.
NCBI Entrex, GenBank Report, Accession No. M15225.1, Chua, M.M., et al., Entry Date Apr. 1993.
"UniProt_B4NGM2, GK21222," UniProt.com, accessed at http://www.uniprot.org/uniprot/B4NGM2, accessed on Dec. 5, 2012, 3 pages.
International Search Report for International Application No. PCT/US11/58378, European Patent Office, Netherlands, mailed on Jun. 8, 2012.
International Search Report for International Application No. PCT/US11/58385, European Patent Office, Netherlands, mailed on Jun. 21, 2012.
Sasaki, T., et al., "A Novel ALK Secondary Mutation and EGFR Signaling Cause Resistance to ALK Kinase Inhibitors," *Cancer Res 71*(18):6051-6060, American Association for Cancer Research, United States (2011).
International Search Report for International Application No. PCT/US12/66205, U.S. Patent Office, United States, mailed on Feb. 26, 2013.
Lamminmaki, U., et al., "Crystal Structure of a recombinant anti-estradiol Fab fragment in complex with 17beta-estradiol," *J. Biol. Chem. 276*(39): 36687-36694, American Society for Biochemistry and Molecular Biology, United States (2001).
Li, S., et al., "Structural basis for inhibition of the epidermal growth factor receptor by cetuximab," *Cancer Cell 7*:301-311, Cambridge, United States (2005).
MacCallum, R.M., et al., "Antibody-antigen Interactions: Contact Analysis and Binding Site Topography," *J. Mol. Biol. 262*:732-745, Elsevier, England (1996).
Rudikoff, S., et al., "Single amino acid substitution altering antigen-binding specificity," *Proc. Natl. Acad. Sci. USA 7*: 1979-1983, National Academy of the Sciences, United States (1982).
Office Action mailed on Mar. 18, 2013 in U.S. Appl. No. 13/284,398, inventors Setiady et al., filed Oct. 28, 2011.
Brown, M., et al., "Tolerance to a Single, but Not Multiple, Amino Acid Replacements in Antibody $V_h$ CDR2: A Means of Minimizing B Cell Wastage from Somatic Hypermutation?" *The Journal of Immunology 156*(9):3285-3291, The American Association of Immunologists, Inc., United States (1996).
Fakih, M. and Vincent, M., "Adverse events associated with anti-EGFR therapies for the treatment of metastatic colorectal cancer," *Current Oncology 17*(Suppl. 1):S18-S30, Multimed, Canada (2010).
Milenic, D.E., et al., "Cetuximab: Preclinical Evaluation of a Monoclonal Antibody Targeting EGFR for Radioimmunodiagnostics and Radioimmunotherapeutic Applications," *Cancer Biotherapy & Radiopharmaceuticals 23*(5):619-632, Mary Ann Liebert, Inc., United States (2008).
Winkler, K., et al., "Changing the Antigen Binding Specificity by Single Point Mutations of an Anti-p24 (HIV-1) Antibody," *The Journal of Immunology 165*(8):4505-4514, The American Association of Immunologists, Inc., United States (2000).
Supplementary European Search Report and European Search Opinion for European Application No. EP 11837192, European Patent Office, Germany, mailed on Sep. 19, 2014.
Kalinowski, F.C., et al., "Regulation of Epidermal Growth Factor Receptor Signaling and Erlotinib Sensitivity in Head and Neck Cancer Cells by miR-7," *PLoS One 7*(10):e47067, Public Library of Science, United States (Oct. 2012).
Inukai, M., et al., "Presence of *Epidermal Growth Factor Receptor Gene* T790M Mutation as a Minor Clone in Non-Small Cell Lung Cancer," *Cancer Research 66*(16):7854-7858, American Association for Cancer Research, United States (2006).
Non-Final Office Action mailed Oct. 17, 2014, in U.S. Appl. No. 13/682,948, inventors Setiady, J., et al., filed Nov. 21, 2012.
Bianco, R., et al., "Intrinsic and acquired resistance to EGFR inhibitors in human cancer therapy," *Endocrine-Related Cancer 12*:S159-S171, Society for Endocrinology, Great Britain (2005).
Office Action, mailed on Jun. 6, 2014, in U.S. Appl. No. 13/682,948, inventors Setiady et al., filed Nov. 21, 2012.
Extended European Search Report for EP Application No. EP 11 83 7196, European Patent Office, The Hague, mailed on Feb. 13, 2015.

| Ab clone# | huEGFR Kd | moEGFR Kd |
|---|---|---|
| 2 | 4.68E-10 | 6.40E-11 |
| 5 | 4.31E-10 | 1.80E-10 |
| 6 | 4.56E-10 | 1.30E-10 |
| 7 | 4.03E-10 | 1.30E-10 |
| 9 | 4.90E-10 | 1.50E-10 |
| 10 | 5.73E-10 | 2.20E-10 |
| 12 | 6.90E-10 | 1.45E-10 |
| 13 | 4.80E-10 | 9.90E-11 |
| 15 | 6.42E-10 | 1.40E-10 |
| 17 | 4.86E-10 | 2.00E-10 |
| cetuximab | 5.66E-10 | 5.50E-11 |
| panitumumab | 5.72E-10 | 1.20E-10 |

FIGURE 1

Agonistic activity

EGF induced MCF10A proliferation

EGFR-7 variant alignments

Light Chain

```
                                                     CDR1                      CDR2
muEGFR7LC  (SEQ ID NO:24)  DIQMTQSPSSLSASLGGKVTITCKASQDINNYLAWYQHKPGKGPRLLIHYTSTLHPGIPS
muEGFR2LC  (SEQ ID NO:86)  ----------------------------I-------------------------------
muEGFR5LC  (SEQ ID NO:86)  ----------------------------I-------------------------------
muEGFR6LC  (SEQ ID NO:86)  ----------------------------I-------------------------------
muEGFR9LC  (SEQ ID NO:86)  ----------------------------I-------------------------------
muEGFR10LC (SEQ ID NO:86)  ----------------------------I-------------------------------
muEGFR13LC (SEQ ID NO:24)  ------------------------------------------------------------
muEGFR15LC (SEQ ID NO:86)  ----------------------------I-------------------------------
muEGFR17LC (SEQ ID NO:87)  ----------------------------I-----------E-------------------

                                                       CDR3
muEGFR7LC  (SEQ ID NO:24)  RFSGSGSGRDYSFSISNLEPEDIATYYCLQYDNLLYTFGGGTKLEIKR
muEGFR2LC  (SEQ ID NO:86)  ------------------------------------------------
muEGFR5LC  (SEQ ID NO:86)  ------------------------------------------------
muEGFR6LC  (SEQ ID NO:86)  ------------------------------------------------
muEGFR9LC  (SEQ ID NO:86)  ------------------------------------------------
muEGFR10LC (SEQ ID NO:86)  ------------------------------------------------
muEGFR13LC (SEQ ID NO:24)  ------------------------------------------------
muEGFR15LC (SEQ ID NO:86)  ------------------------------------------------
muEGFR17LC (SEQ ID NO:87)  ------------------------------------------------
```

Heavy Chain

```
                                                         CDR1                 CDR2
muEGFR7HC  (SEQ ID NO:19)  QVQLQQSGAELARPGASVKLSCKASGYTFTSYWMQWVKQRPGQGLECIGTIYPGDGDTTY
muEGFR2HC  (SEQ ID NO:88)  -------------------------------------------------A--------S-
muEGFR5HC  (SEQ ID NO:89)  ----------------------------------------------------------R-
muEGFR6HC  (SEQ ID NO:90)  -------------------------------------------------AL------AR-
muEGFR9HC  (SEQ ID NO:91)  ----------------------------------------------------------R-
muEGFR10HC (SEQ ID NO:90)  -------------------------------------------------AL------AR-
muEGFR13HC (SEQ ID NO:92)  ------------------------------------------------------------
muEGFR15HC (SEQ ID NO:93)  --------T-------------------------------------------------R-
muEGFR17HC (SEQ ID NO:91)  ----------------------------------------------------------R-
                           KabExt                                   CDR3
muEGFR7HC  (SEQ ID NO:19)  TQKFKGKATLTADKSSSTAYMQLSSLASEDSAVYYCARYDAPGYAMDYWGQGTSVTVSS
muEGFR2HC  (SEQ ID NO:88)  -----------------------------------------------------------
muEGFR5HC  (SEQ ID NO:89)  --------------------------------------------T--------------
muEGFR6HC  (SEQ ID NO:90)  -------------R-------------------------------------------A-
muEGFR9HC  (SEQ ID NO:91)  -----------------------------------------------------------
muEGFR10HC (SEQ ID NO:90)  -------------R-------------------------------------------A-
muEGFR13HC (SEQ ID NO:92)  -----------------------N-----------------------------------
muEGFR15HC (SEQ ID NO:93)  I----------------------------------------------------------
muEGFR17HC (SEQ ID NO:91)  -----------------------------------------------------------
```

Alignment of the murine EGFR-7 variant light and heavy chain variable region sequences. Dashes "-" denote sequence identity with EGFR-7. The resurfacing CDR's are underlined and the extended Kabat heavy chain CDR2 is shown in double underline.

FIGURE 9

Resurfacing of EGFR-7

A

| EGFR7- $V_L$ | | | |
|---|---|---|---|
| Kabat position | Murine residue | Human v1.0 residue | Human v1.01 residue |
| 1 | D | D | D |
| 3 | Q | Q | Q |
| 5 | **T** | T | T |
| 9 | S | S | S |
| 10 | S | S | S |
| **15** | **L** | ***V*** | ***V*** |
| **17** | **G** | ***D*** | ***D*** |
| **18** | **K** | ***R*** | ***R*** |
| 40 | P | P | P |
| 41 | G | G | G |
| 42 | K | K | K |
| **45** | **R** | ***K*** | ***K*** |
| 57 | G | G | G |
| 60 | S | S | S |
| 67 | S | S | S |
| **77** | **N** | ***S*** | ***S*** |
| 80 | P | P | P |
| 81 | E | E | E |
| **100** | **G** | ***Q*** | ***Q*** |
| 107 | K | K | K |
| 108 | R | R | R |
| **24** | **K** | ***R*** | K |

B

| EGFR7- $V_H$ | | |
|---|---|---|
| Kabat position | Murine residue | Human residue |
| 1 | Q | Q |
| 3 | Q | Q |
| **5** | **Q** | ***V*** |
| 9 | A | A |
| **11** | **L** | ***V*** |
| **13** | **R** | ***K*** |
| 14 | P | P |
| 19 | K | K |
| 23 | K | K |
| 28 | T | T |
| 41 | P | P |
| 42 | G | G |
| 43 | Q | Q |
| 61 | Q | Q |
| 62 | K | K |
| **64** | **K** | ***Q*** |
| 65 | G | G |
| 73 | K | K |
| 74 | S | S |
| 82b | S | S |
| **83** | **A** | ***R*** |
| 84 | S | S |
| 85 | E | E |
| 105 | Q | Q |
| 108 | S | ***L*** |
| 112 | S | S |

FIGURE 10

Resurfacing of EGFR-12

A

| EGFR12-$V_L$ | | | |
|---|---|---|---|
| Kabat position | Murine residue | Human v1.0 residue | Human v1.01 residue |
| 1 | D | D | D |
| 3 | Q | Q | Q |
| 9 | S | S | S |
| **10** | **Y** | ***S*** | ***S*** |
| **15** | **P** | ***V*** | ***V*** |
| **18** | **T** | ***R*** | ***R*** |
| 40 | P | P | P |
| 41 | G | G | G |
| 42 | K | K | K |
| 57 | G | G | G |
| 60 | S | S | S |
| 67 | S | S | S |
| 80 | P | P | P |
| 81 | E | E | E |
| **100** | **G** | ***Q*** | ***Q*** |
| 103 | K | K | K |
| 105 | E | E | E |
| 107 | K | K | K |
| 108 | R | R | R |
| **27** | **K** | ***Q*** | K |
| **31** | K | ***R*** | **K** |

B

| EGFR12-$V_H$ | | |
|---|---|---|
| Kabat position | Murine residue | Human residue |
| 1 | Q | Q |
| 3 | Q | Q |
| **5** | **Q** | ***V*** |
| **9** | T | ***A*** |
| **11** | L | ***V*** |
| **13** | R | ***K*** |
| 14 | P | P |
| 19 | K | K |
| 23 | K | K |
| 28 | T | T |
| 41 | P | P |
| 42 | G | G |
| 43 | Q | Q |
| 61 | Q | Q |
| 62 | K | K |
| **64** | **K** | ***Q*** |
| 65 | G | G |
| 73 | K | K |
| 74 | S | S |
| 82B | S | S |
| **83** | **A** | ***R*** |
| 84 | S | S |
| 85 | E | E |
| 105 | S | S |
| **108** | **S** | ***L*** |
| 112 | S | S |

FIGURE 11

Resurfacing alignments

A

```
                                      1                                                          60
muEGFR-7 VL       (SEQ ID NO:24)  DIQMTQSPSSLSASLGGKVTITCKASQDINNYLAWYQHKPGKGPRLLIHYTSTLHPGIPS
huEGFR-7 VLv1.0   (SEQ ID NO:26)  --------------V-DR-----R--------------------K---------------
huEGFR-7 VLv1.01  (SEQ ID NO:27)  --------------V-DR--------------------------K---------------

                                  61                                            108
muEGFR-7 VL       (SEQ ID NO:24)  RFSGSGSGRDYSFSISNLEPEDIATYYCLQYDNLLYTFGGGTKLEIKR
huEGFR-7 VLv1.0   (SEQ ID NO:26)  ----------------S----------------------Q--------
huEGFR-7 VLv.101  (SEQ ID NO:27)  ----------------S----------------------Q--------
```

B

```
                                  1                                                          60
muEGFR-7 VH  (SEQ ID NO:19)  QVQLQQSGAELARPGASVKLSCKASGYTFTSYWMQWVKQRPGQGLECIGTIYPGDGDTTY
huEGFR-7 VH  (SEQ ID NO:21)  ----V-----V-K-----------------------------------------------

                             61                                                        119
muEGFR-7 VH  (SEQ ID NO:19)  TQKFKGKATLTADKSSSTAYMQLSSLASEDSAVYYCARYDAPGYAMDYWGQGTSVTVSS
huEGFR-7 VH  (SEQ ID NO:21)  ----Q---------------------R--------------------------L-----
```

C

```
                                  1                                                          60
muEGFR-12 VL       (SEQ ID NO:25)  DVQITQSPSYLAASPGETITINCRASKSISKYLAWYQEKPGKTNKLLIYSGSTLQSGIPS
huEGFR-12 VLv1.0   (SEQ ID NO:29)  ---------S----V--R--------Q---R-----------------------------
huEGFR-12 VLv.101  (SEQ ID NO:30)  ---------S----V--R------------------------------------------

                                   61                                            108
muEGFR-12 VL       (SEQ ID NO:25)  RFSGSGSGTDFTLTISSLEPEDFAMYYCQQHNEYPWTFGGGTKLEIKR
huEGFR-12 VLv1.0   (SEQ ID NO:29)  ---------------------------------------Q--------
huEGFR-12 VLv1.01  (SEQ ID NO:30)  ---------------------------------------Q--------
```

D

```
                              1                                                          60
muEGFR-12 VH  (SEQ ID NO:20)  QVQLQQSGTELARPGASVKLSCKASGYTFTSYWMQWVKQRPGQGLECIGTIYPGDGDTRY
huEGFR-12 VH  (SEQ ID NO:23)  ----V---A-V-K-----------------------------------------------

                              61                                                        119
muEGFR-12 VH  (SEQ ID NO:20)  IQKFKGKATLTADKSSSTAYMQLSSLASEDSAVYYCARYDAPGYAMDYWGQGTSVTVSS
huEGFR-12 VH  (SEQ ID NO:23)  ----Q---------------------R--------------------------L-----
```

FIGURE 12

CDR-grafting of EGFR-7

A

| EGFR7- $V_L$ | | |
|---|---|---|
| Kabat position | Murine residue | Human (CDR-graft) residue |
| 15 | L | V |
| 17 | G | D |
| 18 | K | R |
| 38 | H | Q |
| 43 | G | A |
| 45 | R | K |
| 49 | H | Y |
| 58 | I | V |
| 69 | R | T |
| 71 | Y | F |
| 72 | S | T |
| 74 | S | T |
| 77 | N | S |
| 79 | E | Q |
| 100 | G | Q |
| 104 | L | V |
| 24 | K | R |

B

| EGFR7- $V_H$ | | |
|---|---|---|
| Kabat position | Murine residue | Human (CDR-graft) residue |
| 5 | Q | V |
| 11 | L | V |
| 12 | A | K |
| 13 | R | K |
| 20 | L | V |
| 38 | K | R |
| 40 | R | A |
| 47 | C | W |
| 48 | I | M |
| 66 | K | R |
| 67 | A | V |
| 69 | L | M |
| 71 | A | R |
| 73 | K | T |
| 75 | S | T |
| 78 | A | V |
| 81 | Q | E |
| 83 | A | R |
| 87 | S | T |
| 109 | S | L |

FIGURE 13

CDR grafting alignments

A

```
                                  1                                                          60
muEGFR7_VL  (SEQ ID NO:24)  DIQMTQSPSSLSASLGGKVTITCKASQDINNYLAWYQHKPGKGPRLLIHYTSTLHPGIPS
hEGFR7_VLG  (SEQ ID NO:28)  --------------V-DR-----R-------------Q----A-K---Y--------V--

                                  61                                              108
muEGFR7_VL  (SEQ ID NO:24)  RFSGSGSGRDYSFSISNLEPEDIATYYCLQYDNLLYTFGGGTKLEIKR
hEGFR7_VLG  (SEQ ID NO:28)  --------T-FT-T--S-Q--------------------Q---V----
```

B

```
                                  1                                                          60
muEGFR7_VH  (SEQ ID NO:19)  QVQLQQSGAELARPGASVKLSCKASGYTFTSYWMQWVKQRPGQGLECIGTIYPGDGDTTY
hEGFR7_VHG  (SEQ ID NO:22)  ----V-----VKK------V-----------------R-A------WM------------

                                  61                                                        119
muEGFR7_VH  (SEQ ID NO:19)  TQKFKGKATLTADKSSSTAYMQLSSLASEDSAVYYCARYDAPGYAMDYWGQGTSVTVSS
hEGFR7_VHG  (SEQ ID NO:22)  ------RV-M-R-T-T--V--E----R---T---------------------L-----
```

FIGURE 14

HuAb and muAb binding competition
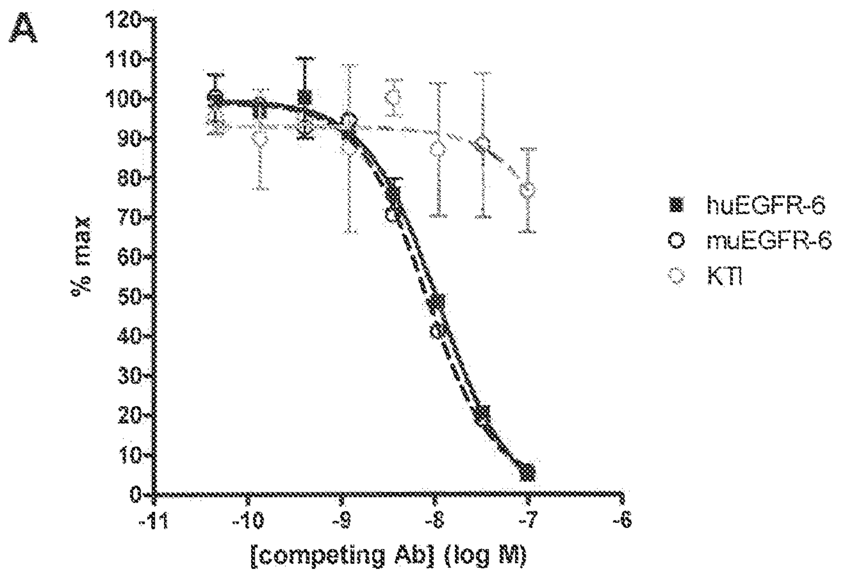
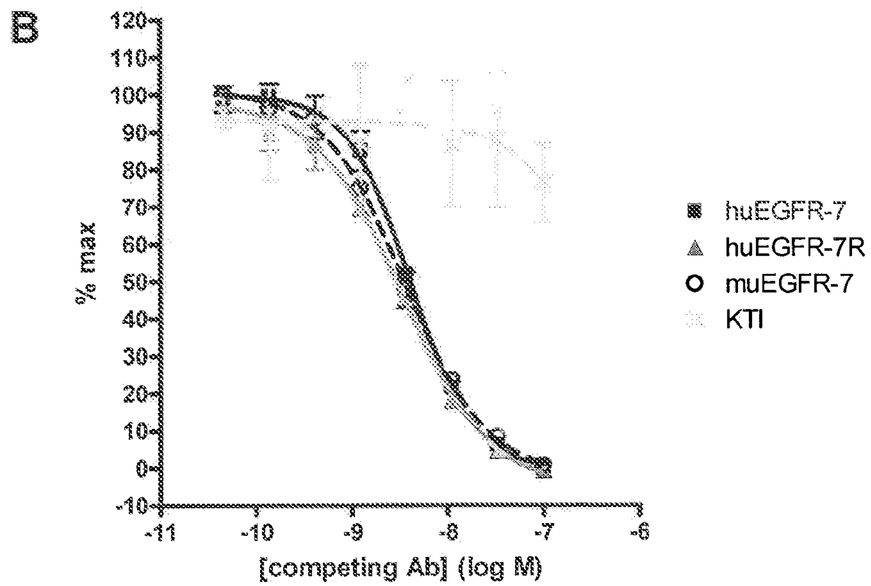
FIGURE 15

Naked huAb vs muAb activity

Binding curves

Cytotox assay in cell lines dependent on EGFR pathway
A
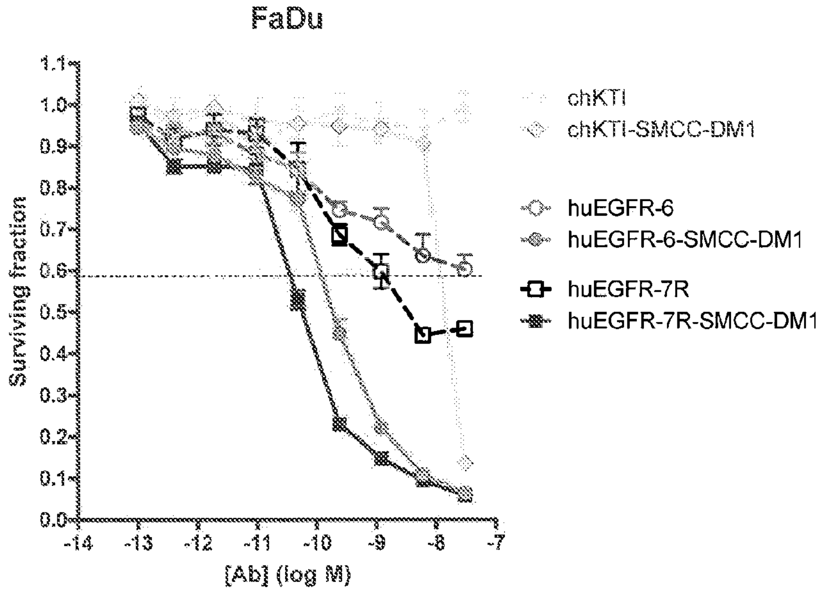
B
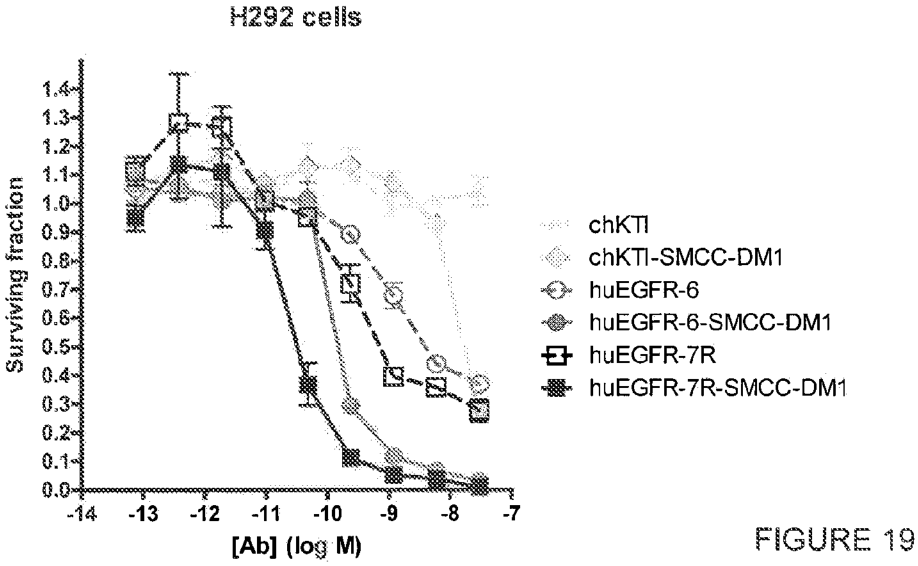
FIGURE 19

Cytotox assay in cell lines independent of EGFR pathway
A
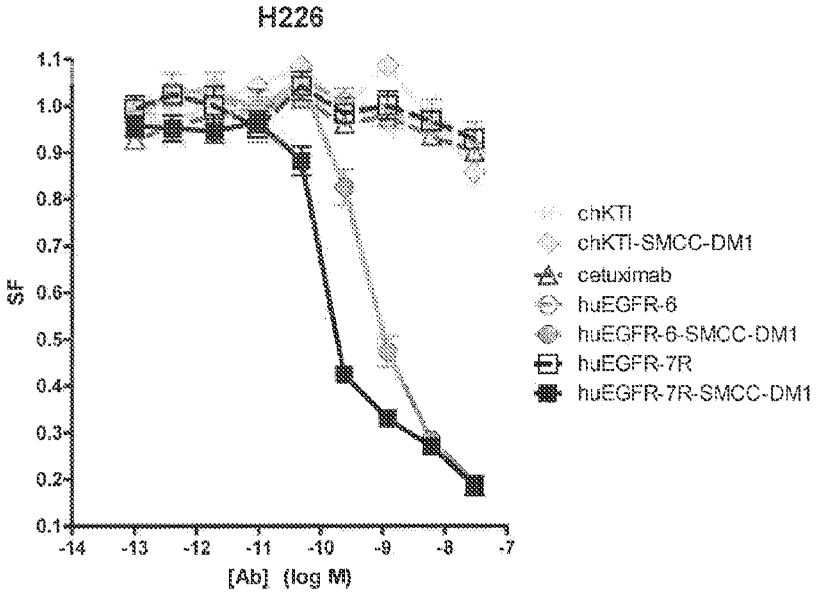
B
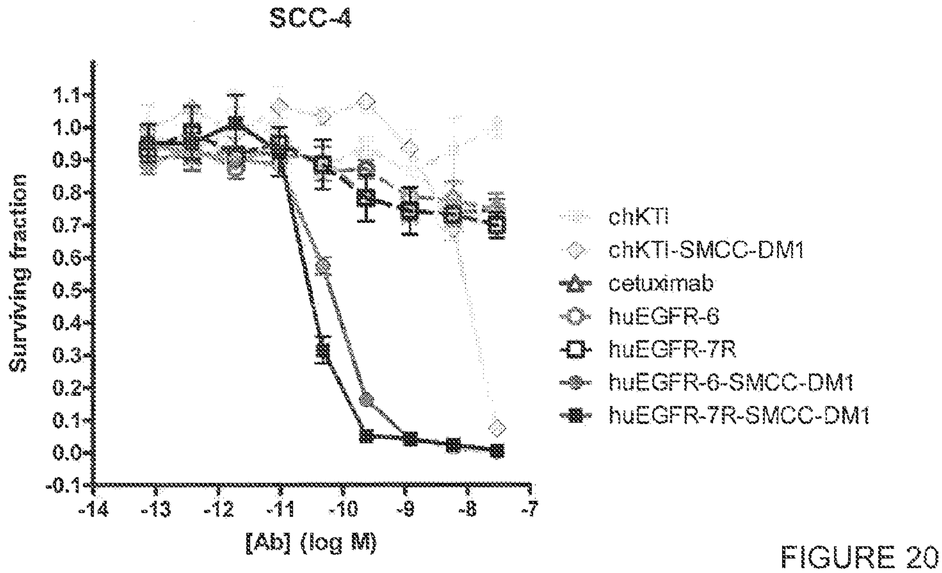
FIGURE 20

A
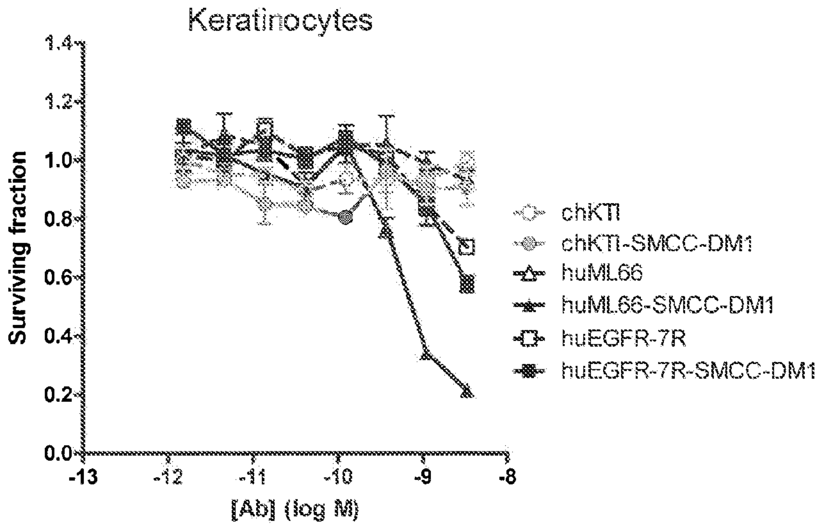
B
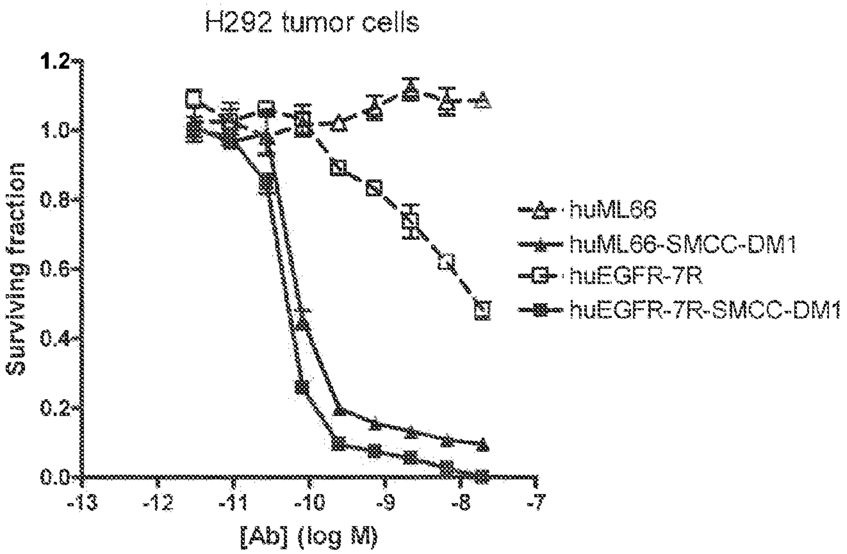
FIGURE 23

H292 xenograft

Figure 28. Alignment of human and murine EGFR ECD sequences. Domains I-IV are indicated by arrows.

| | | |
|---|---|---|
| | | 1 Domain I 52 |
| human EGFR ECD | (SEQ ID NO:94) | LEEKKVCQGTSNKLTQLGTFEDHFLSLQRMFNNCEVVLGNLEITYVQRNYDL |
| murine EGFR ECD | (SEQ ID NO:95) | ------------R-----------------Y--------------------- |
| | | 53 104 |
| human EGFR ECD | (SEQ ID NO:94) | SFLKTIQEVAGYVLIALNTVERIPLENLQIIRGNMYYENSYALAVLSNYDAN |
| murine EGFR ECD | (SEQ ID NO:95) | ----------------------------------AL----T----I---GT- |
| | | 105 156 |
| human EGFR ECD | (SEQ ID NO:94) | KTGLKELPMRNLQEILHGAVRFSNNPALCNVESIQWRDIVSSDFLSNMSMDF |
| murine EGFR ECD | (SEQ ID NO:95) | R---R-----------I---------I---MDT-------QNV-M------L |
| | | 157 ↓ Domain II 208 |
| human EGFR ECD | (SEQ ID NO:94) | QNHLGSCQKCDPSCPNGSCWGAGEENCQKLTKIICAQQCSGRCRGKSPSDCC |
| murine EGFR ECD | (SEQ ID NO:95) | -S-PS--P-------------G------------------H----R------ |
| | | 209 260 |
| human EGFR ECD | (SEQ ID NO:94) | HNQCAAGCTGPRESDCLVCRKFRDEATCKDTCPPLMLYNPTTYQMDVNPEGK |
| murine EGFR ECD | (SEQ ID NO:95) | -------------------Q--Q----------------------------- |
| | | 261 ↓312 |
| human EGFR ECD | (SEQ ID NO:94) | YSFGATCVKKCPRNYVVTDHGSCVRACGADSYEMEEDGVRKCKKCEGPCRKV |
| murine EGFR ECD | (SEQ ID NO:95) | ----------------------------P-Y--V----I------D------ |
| | | 313 Domain III 364 |
| human EGFR ECD | (SEQ ID NO:94) | CNGIGIGEFKDSLSINATNIKHFKNCTSISGDLHILPVAFRGDSFTHTPPLD |
| murine EGFR ECD | (SEQ ID NO:95) | -----------T------------Y--A------------K-----R----- |
| | | 365 416 |
| human EGFR ECD | (SEQ ID NO:94) | PQELDILKTVKEITGFLLIQAWPENRTDLHAFENLEIIRGRTKQHGQFSLAV |
| murine EGFR ECD | (SEQ ID NO:95) | -R--E------------------D-W-------------------------- |
| | | 417 468 |
| human EGFR ECD | (SEQ ID NO:94) | VSLNITSLGLRSLKEISDGDVIISGNKNLCYANTINWKKLFGTSGQKTKIIS |
| murine EGFR ECD | (SEQ ID NO:95) | -G------------------------R----------------PN-----MN |
| | | 469 ↓ Domain IV 520 |
| human EGFR ECD | (SEQ ID NO:94) | NRGENSCKATGQVCHALCSPEGCWGPEPRDCVSCRNVSRGRECVDKCNLLEG |
| murine EGFR ECD | (SEQ ID NO:95) | --A-KD---VNH--NP---S--------------Q---------E---I--- |
| | | 521 572 |
| human EGFR ECD | (SEQ ID NO:94) | EPREFVENSECIQCHPECLPQAMNITCTGRGPDNCIQCAHYIDGPHCVKTCP |
| murine EGFR ECD | (SEQ ID NO:95) | ---------------------------------------------------- |
| | | 573 618 |
| human EGFR ECD | (SEQ ID NO:94) | AGVMGENNTLVWKYADAGHVCHLCHPNCTYGCTGPGLEGCPTNGPK |
| murine EGFR ECD | (SEQ ID NO:95) | --I--------------NN------A------A----Q--EVWPSG |

Figure 29. Alignment of the sequences of huEGFRdIII, muEGFRdIII and chEGFRdIII. The region that was mutated to the human EGFR sequence in chEGFRdIII is marked in box and the arrow indicates the end of domain III.

```
                                 310                                              359
huEGFR-dIII   (SEQ ID NO:96)     RKVCNGIGIGEFKDSLSINATNIKHFKNCTSISGDLHILPVAFRGDSFTH
muEGFR-dIII   (SEQ ID NO:97)     --------------T------------Y--A------------K-----R
chEGFR-dIII   (SEQ ID NO:98)     --------------T------------Y--A------------K-----R

                                 360                                              409
huEGFR-dIII   (SEQ ID NO:96)     TPPLDPQELDILKTVKEITGFLLIQAWPENRTDLHAFENLEIIRGRTKQH
muEGFR-dIII   (SEQ ID NO:97)     ------R--E------------------D-W-------------------
chEGFR-dIII   (SEQ ID NO:98)     ------R--E------------------D-W-------------------

                                 410                                              459
huEGFR-dIII   (SEQ ID NO:96)     GQFSLAVVSLNITSLGLRSLKEISDGDVIISGNKNLCYANTINWKKLFGT
muEGFR-dIII   (SEQ ID NO:97)     ---------G-----------------------R----------------
chEGFR-dIII   (SEQ ID NO:98)     ---------G-----------------------R----------------

                                 460                  ↓                   501
huEGFR-dIII   (SEQ ID NO:96)     [SGQKTKIISNRGENSCKATGQ]VCHALCSPEGCWGPEPRDCVS
muEGFR-dIII   (SEQ ID NO:97)     PH-----MN--A-KD---VRH--NP---S-------------
chEGFR-dIII   (SEQ ID NO:98)     -----------------------NP---S-------------
```

Figure 30. Binding of huEGFR-7R antibody to huEGFR, huEGFRdIII, muEGFRdIII and chEGFRdIII.
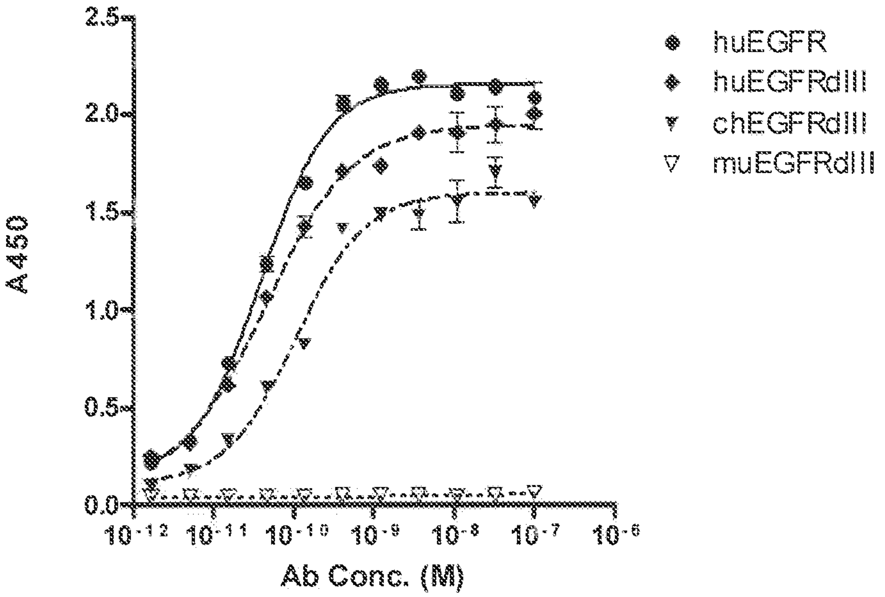
| Antigen | EC50 (M) |
|---|---|
| huEGFR | $3.88 \times 10^{-11}$ |
| huEGFRdIII | $4.45 \times 10^{-11}$ |
| chEGFRdIII | $1.07 \times 10^{-10}$ |

Figure 31. Binding of humanized EGFR-6 antibody to huEGFR, huEGFRdIII, muEGFRdIII and chEGFRdIII.
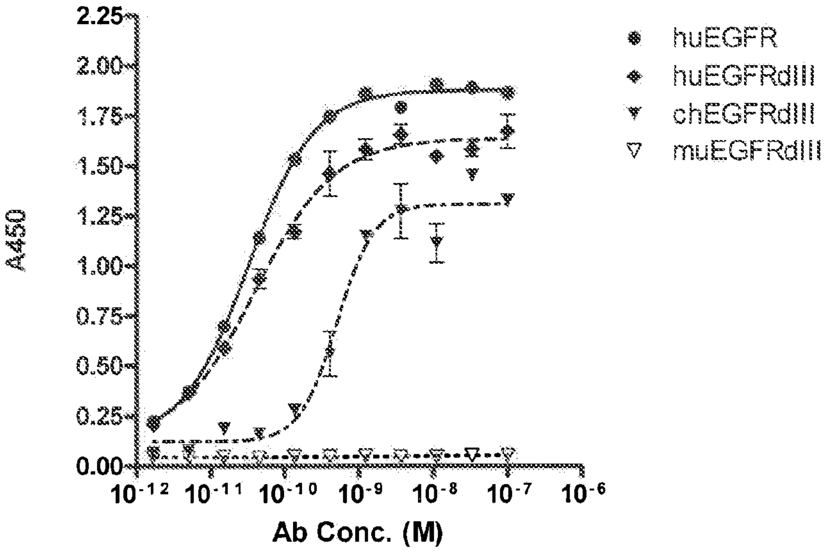
| Antigen | EC50 (M) |
|---|---|
| huEGFR | $3.28 \times 10^{-11}$ |
| huEGFRdIII | $4.01 \times 10^{-11}$ |
| chEGFRdIII | $5.09 \times 10^{-10}$ |

Figure 32. Binding of murine EGFR-7 antibody to huEGFR, huEGFRdIII, muEGFRdIII and chEGFRdIII.
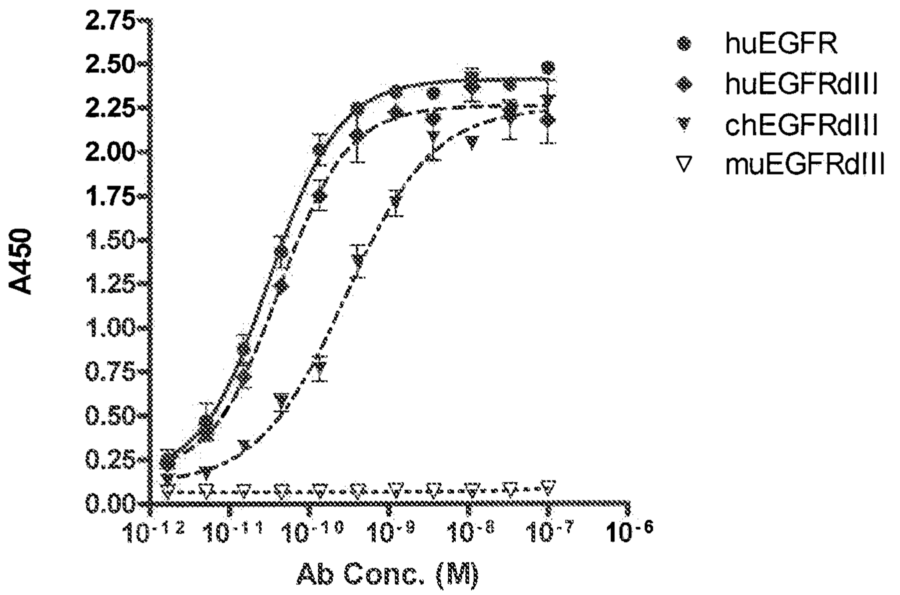
| Antigen | EC50 (M) |
|---|---|
| huEGFR | $3.28 \times 10^{-11}$ |
| huEGFRdIII | $4.30 \times 10^{-11}$ |
| chEGFRdIII | $2.94 \times 10^{-10}$ |

Figure 33. Binding of murine EGFR-6 antibody to huEGFR, huEGFRdIII, muEGFRdIII and chEGFRdIII.
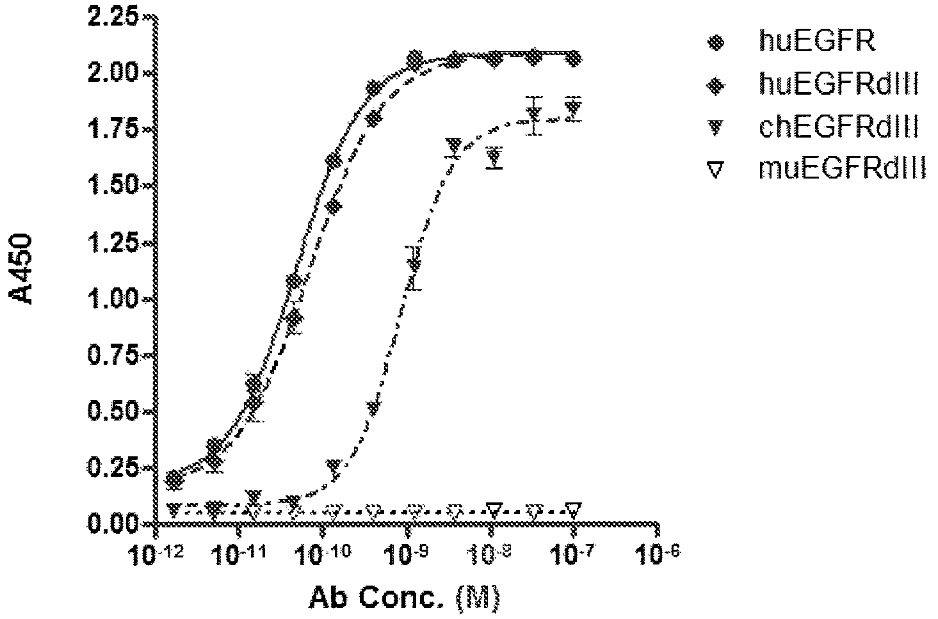
| Antigen | EC50 (M) |
|---|---|
| huEGFR | $4.84 \times 10^{-11}$ |
| huEGFRdIII | $6.94 \times 10^{-11}$ |
| chEGFRdIII | $8.67 \times 10^{-10}$ |

Figure 34. Binding of murine EGFR-12 antibody to huEGFR, huEGFRdIII, muEGFRdIII and chEGFRdIII.
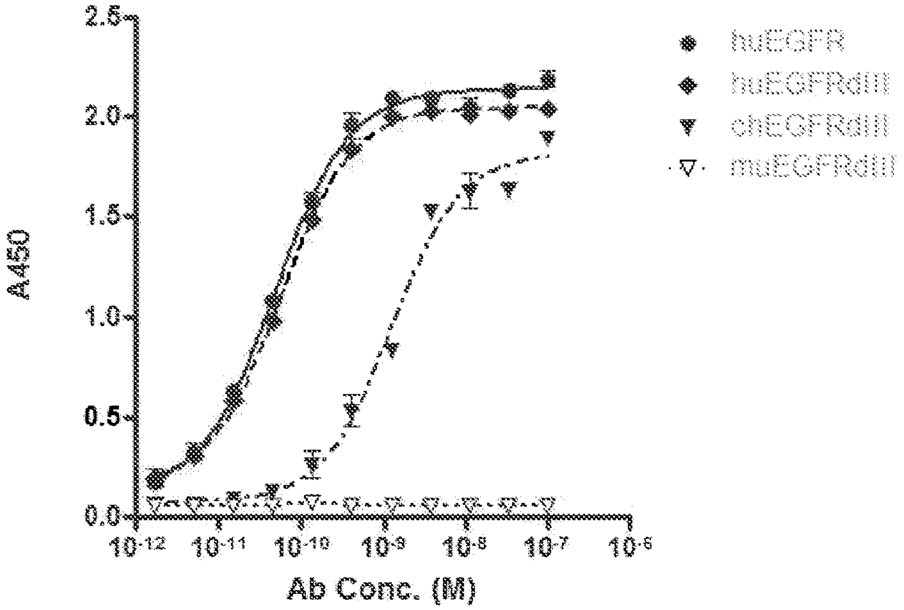
| Antigen | EC50 (M) |
|---|---|
| huEGFR | $4.85 \times 10^{-11}$ |
| huEGFRdIII | $5.72 \times 10^{-11}$ |
| chEGFRdIII | $1.24 \times 10^{-9}$ |

Figure 35. Binding of murine EGFR-13 antibody to huEGFR, huEGFRdIII, muEGFRdIII and chEGFRdIII.
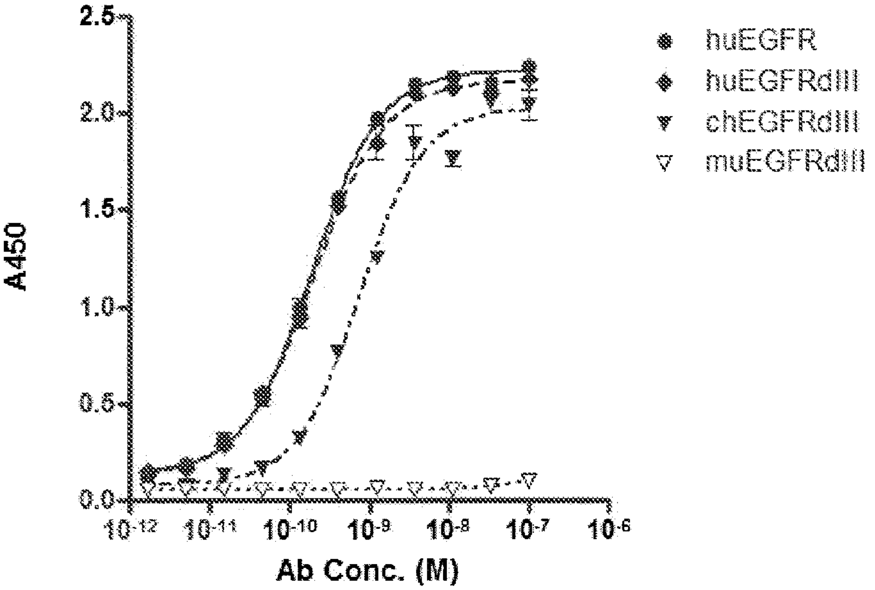
| Antigen | EC50 (M) |
|---|---|
| huEGFR | $1.90 \times 10^{-10}$ |
| huEGFRdIII | $1.95 \times 10^{-10}$ |
| chEGFRdIII | $7.58 \times 10^{-10}$ |

Figure 36. Binding of cetuximab to huEGFR, huEGFRdIII, muEGFRdIII and chEGFRdIII.
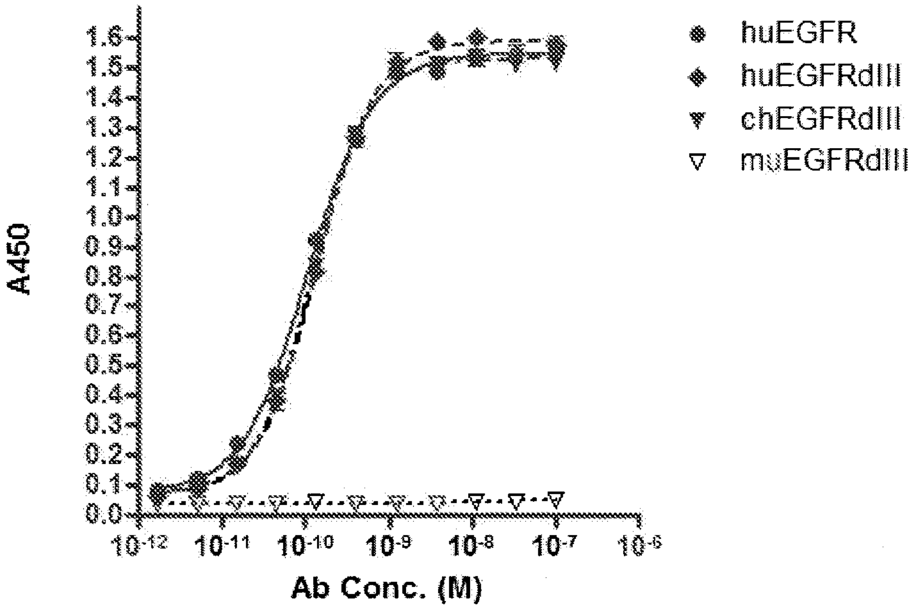
| Antigen | EC50 (M) |
|---|---|
| huEGFR | $1.07 \times 10^{-10}$ |
| huEGFRdIII | $1.38 \times 10^{-10}$ |
| chEGFRdIII | $1.23 \times 10^{-10}$ |

SEQUENCE LISTING

<160> NUMBER OF SEQ ID NOS: 98

<210> SEQ ID NO 1
<211> LENGTH: 6
<212> TYPE: PRT
<213> ORGANISM: Artificial Sequence
<220> FEATURE:
<223> OTHER INFORMATION: EGFR-7 VH-CDR1

<400> SEQUENCE: 1

Thr Ser Tyr Trp Met Gln
1               5

<210> SEQ ID NO 2
<211> LENGTH: 10
<212> TYPE: PRT
<213> ORGANISM: Artificial Sequence
<220> FEATURE:
<223> OTHER INFORMATION: EGFR-7 VH-CDR2

<400> SEQUENCE: 2

Thr Ile Tyr Pro Gly Asp Gly Asp Thr Thr
1               5                   10

<210> SEQ ID NO 3
<211> LENGTH: 10
<212> TYPE: PRT
<213> ORGANISM: Artificial Sequence
<220> FEATURE:
<223> OTHER INFORMATION: EGFR-7  VH-CDR3

<400> SEQUENCE: 3

Tyr Asp Ala Pro Gly Tyr Ala Met Asp Tyr
1               5                   10

<210> SEQ ID NO 4
<211> LENGTH: 10
<212> TYPE: PRT
<213> ORGANISM: Artificial Sequence
<220> FEATURE:
<223> OTHER INFORMATION: EGFR-7  VH-CDR2
<220> FEATURE:
<221> NAME/KEY: MISC_FEATURE
<222> LOCATION: (1)..(1)
<223> OTHER INFORMATION: X is T or A
<220> FEATURE:
<221> NAME/KEY: MISC_FEATURE
<222> LOCATION: (2)..(2)
<223> OTHER INFORMATION: X is I or L
<220> FEATURE:
<221> NAME/KEY: MISC_FEATURE
<222> LOCATION: (9)..(9)
<223> OTHER INFORMATION: X is T or A
<220> FEATURE:
<221> NAME/KEY: MISC_FEATURE
<222> LOCATION: (10)..(10)
<223> OTHER INFORMATION: X is T, R, or S

<400> SEQUENCE: 4

Xaa Xaa Tyr Pro Gly Asp Gly Asp Xaa Xaa
1               5                   10

<210> SEQ ID NO 5
<211> LENGTH: 10
<212> TYPE: PRT
<213> ORGANISM: Artificial Sequence
<220> FEATURE:
<223> OTHER INFORMATION: EGFR-7 VH-CDR3
<220> FEATURE:
<221> NAME/KEY: MISC_FEATURE -continued
<222> LOCATION: (7)..(7)
<223> OTHER INFORMATION: X is A or T

<400> SEQUENCE: 5

Tyr Asp Ala Pro Gly Tyr Xaa Met Asp Tyr
1 5 10

<210> SEQ ID NO 6
<211> LENGTH: 16
<212> TYPE: PRT
<213> ORGANISM: Artificial Sequence
<220> FEATURE:
<223> OTHER INFORMATION: EGFR-7 Kabat HC CDR2
<220> FEATURE:
<221> NAME/KEY: MISC_FEATURE
<222> LOCATION: (1)..(1)
<223> OTHER INFORMATION: X is T or A
<220> FEATURE:
<221> NAME/KEY: MISC_FEATURE
<222> LOCATION: (2)..(2)
<223> OTHER INFORMATION: X is I or L
<220> FEATURE:
<221> NAME/KEY: MISC_FEATURE
<222> LOCATION: (9)..(9)
<223> OTHER INFORMATION: X is T or A
<220> FEATURE:
<221> NAME/KEY: MISC_FEATURE
<222> LOCATION: (10)..(10)
<223> OTHER INFORMATION: X is T, R or S
<220> FEATURE:
<221> NAME/KEY: MISC_FEATURE
<222> LOCATION: (11)..(11)
<223> OTHER INFORMATION: X is Y, T, or I
<220> FEATURE:
<221> NAME/KEY: MISC_FEATURE
<222> LOCATION: (15)..(15)
<223> OTHER INFORMATION: X is Q or K

<400> SEQUENCE: 6

Xaa Xaa Tyr Pro Gly Asp Gly Asp Xaa Xaa Xaa Gln Lys Phe Xaa Gly
1 5 10 15

<210> SEQ ID NO 7
<211> LENGTH: 10
<212> TYPE: PRT
<213> ORGANISM: Artificial Sequence
<220> FEATURE:
<223> OTHER INFORMATION: EGFR-12 VH-CDR1

<400> SEQUENCE: 7

Thr Ile Tyr Pro Gly Asp Gly Asp Thr Arg
1 5 10

<210> SEQ ID NO 8
<211> LENGTH: 17
<212> TYPE: PRT
<213> ORGANISM: Artificial Sequence
<220> FEATURE:
<223> OTHER INFORMATION: Kabat HC VH-CDR2

<400> SEQUENCE: 8

Thr Ile Tyr Pro Gly Asp Gly Asp Thr Arg Tyr Ile Gln Lys Phe Lys
1 5 10 15

Gly

<210> SEQ ID NO 9
<211> LENGTH: 17
<212> TYPE: PRT
<213> ORGANISM: Artificial Sequence
<220> FEATURE:

<223> OTHER INFORMATION: Kabat HC VH-CDR2

<400> SEQUENCE: 9

Thr Ile Tyr Pro Gly Asp Gly Asp Thr Arg Tyr Ile Gln Lys Phe Gln
1 5 10 15

Gly

<210> SEQ ID NO 10
<211> LENGTH: 11
<212> TYPE: PRT
<213> ORGANISM: Artificial Sequence
<220> FEATURE:
<223> OTHER INFORMATION: EGFR-7 VL-CDR1

<400> SEQUENCE: 10

Lys Ala Ser Gln Asp Ile Asn Asn Tyr Leu Ala
1 5 10

<210> SEQ ID NO 11
<211> LENGTH: 7
<212> TYPE: PRT
<213> ORGANISM: Artificial Sequence
<220> FEATURE:
<223> OTHER INFORMATION: EGFR-7 VL-CDR2

<400> SEQUENCE: 11

Tyr Thr Ser Thr Leu His Pro
1 5

<210> SEQ ID NO 12
<211> LENGTH: 9
<212> TYPE: PRT
<213> ORGANISM: Artificial Sequence
<220> FEATURE:
<223> OTHER INFORMATION: EGFR-7 VL-CDR3

<400> SEQUENCE: 12

Leu Gln Tyr Asp Asn Leu Leu Tyr Thr
1 5

<210> SEQ ID NO 13
<211> LENGTH: 11
<212> TYPE: PRT
<213> ORGANISM: Artificial Sequence
<220> FEATURE:
<223> OTHER INFORMATION: VL-CDR1

<400> SEQUENCE: 13

Arg Ala Ser Gln Asp Ile Asn Asn Tyr Leu Ala
1 5 10

<210> SEQ ID NO 14
<211> LENGTH: 11
<212> TYPE: PRT
<213> ORGANISM: Artificial Sequence
<220> FEATURE:
<223> OTHER INFORMATION: EGFR-7 VL-CDR1
<220> FEATURE:
<221> NAME/KEY: MISC_FEATURE
<222> LOCATION: (1)..(1)
<223> OTHER INFORMATION: X is K or R
<220> FEATURE:
<221> NAME/KEY: MISC_FEATURE
<222> LOCATION: (10)..(10)
<223> OTHER INFORMATION: X is L or I

<400> SEQUENCE: 14

-continued

Xaa Ala Ser Gln Asp Ile Asn Asn Tyr Xaa Ala
1 5 10

<210> SEQ ID NO 15
<211> LENGTH: 11
<212> TYPE: PRT
<213> ORGANISM: Artificial Sequence
<220> FEATURE:
<223> OTHER INFORMATION: EGFR-12 VL-CDR1

<400> SEQUENCE: 15

Arg Ala Ser Lys Ser Ile Ser Lys Tyr Leu Ala
1 5 10

<210> SEQ ID NO 16
<211> LENGTH: 11
<212> TYPE: PRT
<213> ORGANISM: Artificial Sequence
<220> FEATURE:
<223> OTHER INFORMATION: VL-CDR1

<400> SEQUENCE: 16

Arg Ala Ser Gln Ser Ile Ser Arg Tyr Leu Ala
1 5 10

<210> SEQ ID NO 17
<211> LENGTH: 7
<212> TYPE: PRT
<213> ORGANISM: Artificial Sequence
<220> FEATURE:
<223> OTHER INFORMATION: VL-CDR2

<400> SEQUENCE: 17

Ser Gly Ser Thr Leu Gln Ser
1 5

<210> SEQ ID NO 18
<211> LENGTH: 9
<212> TYPE: PRT
<213> ORGANISM: Artificial Sequence
<220> FEATURE:
<223> OTHER INFORMATION: VL-CDR3

<400> SEQUENCE: 18

Gln Gln His Asn Glu Tyr Pro Trp Thr
1 5

<210> SEQ ID NO 19
<211> LENGTH: 119
<212> TYPE: PRT
<213> ORGANISM: Artificial Sequence
<220> FEATURE:
<223> OTHER INFORMATION: muEGFR-7 VH

<400> SEQUENCE: 19

Gln Val Gln Leu Gln Gln Ser Gly Ala Glu Leu Ala Arg Pro Gly Ala
1 5 10 15

Ser Val Lys Leu Ser Cys Lys Ala Ser Gly Tyr Thr Phe Thr Ser Tyr
20 25 30

Trp Met Gln Trp Val Lys Gln Arg Pro Gly Gln Gly Leu Glu Cys Ile
35 40 45

Gly Thr Ile Tyr Pro Gly Asp Gly Asp Thr Thr Tyr Thr Gln Lys Phe
50 55 60

Lys Gly Lys Ala Thr Leu Thr Ala Asp Lys Ser Ser Ser Thr Ala Tyr
65 70 75 80

```
Met Gln Leu Ser Ser Leu Ala Ser Glu Asp Ser Ala Val Tyr Tyr Cys
                85                  90                  95

Ala Arg Tyr Asp Ala Pro Gly Tyr Ala Met Asp Tyr Trp Gly Gln Gly
            100                 105                 110

Thr Ser Val Thr Val Ser Ser
        115


<210> SEQ ID NO 20
<211> LENGTH: 119
<212> TYPE: PRT
<213> ORGANISM: Artificial Sequence
<220> FEATURE:
<223> OTHER INFORMATION: muEGFR-12 VH

<400> SEQUENCE: 20

Gln Val Gln Leu Gln Gln Ser Gly Thr Glu Leu Ala Arg Pro Gly Ala
1               5                   10                  15

Ser Val Lys Leu Ser Cys Lys Ala Ser Gly Tyr Thr Phe Thr Ser Tyr
            20                  25                  30

Trp Met Gln Trp Val Lys Gln Arg Pro Gly Gln Gly Leu Glu Cys Ile
        35                  40                  45

Gly Thr Ile Tyr Pro Gly Asp Gly Asp Thr Arg Tyr Ile Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Ala Ser Glu Asp Ser Ala Val Tyr Tyr Cys
                85                  90                  95

Ala Arg Tyr Asp Ala Pro Gly Tyr Ala Met Asp Tyr Trp Gly Gln Gly
            100                 105                 110

Thr Ser Val Thr Val Ser Ser
        115


<210> SEQ ID NO 21
<211> LENGTH: 119
<212> TYPE: PRT
<213> ORGANISM: Artificial Sequence
<220> FEATURE:
<223> OTHER INFORMATION: huEGFR-7 VH

<400> SEQUENCE: 21

Gln Val Gln Leu Val Gln Ser Gly Ala Glu Val Ala Lys Pro Gly Ala
1               5                   10                  15

Ser Val Lys Leu Ser Cys Lys Ala Ser Gly Tyr Thr Phe Thr Ser Tyr
            20                  25                  30

Trp Met Gln Trp Val Lys Gln Arg Pro Gly Gln Gly Leu Glu Cys Ile
        35                  40                  45

Gly Thr Ile Tyr Pro Gly Asp Gly Asp Thr Thr Tyr Thr Gln Lys Phe
    50                  55                  60

Gln Gly Lys Ala Thr Leu Thr Ala Asp Lys Ser Ser Ser Thr Ala Tyr
65                  70                  75                  80

Met Gln Leu Ser Ser Leu Arg Ser Glu Asp Ser Ala Val Tyr Tyr Cys
                85                  90                  95

Ala Arg Tyr Asp Ala Pro Gly Tyr Ala Met Asp Tyr Trp Gly Gln Gly
            100                 105                 110

Thr Leu Val Thr Val Ser Ser
        115
```

<210> SEQ ID NO 22
<211> LENGTH: 119
<212> TYPE: PRT
<213> ORGANISM: Artificial Sequence
<220> FEATURE:
<223> OTHER INFORMATION: huEGFR-7 VH CDR

<400> SEQUENCE: 22

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met Gln Trp Val Arg Gln Ala Pro Gly Gln Gly Leu Glu Trp Met
        35                  40                  45

Gly Thr Ile Tyr Pro Gly Asp Gly Asp Thr Thr Tyr Thr Gln Lys Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Tyr Asp Ala Pro Gly Tyr Ala Met Asp Tyr Trp Gly Gln Gly
            100                 105                 110

Thr Leu Val Thr Val Ser Ser
        115
```

<210> SEQ ID NO 23
<211> LENGTH: 119
<212> TYPE: PRT
<213> ORGANISM: Artificial Sequence
<220> FEATURE:
<223> OTHER INFORMATION: huEGFR-12 VH

<400> SEQUENCE: 23

```
Gln Val Gln Leu Val Gln Ser Gly Ala Glu Val Ala Lys Pro Gly Ala
1               5                   10                  15

Ser Val Lys Leu Ser Cys Lys Ala Ser Gly Tyr Thr Phe Thr Ser Tyr
            20                  25                  30

Trp Met Gln Trp Val Lys Gln Arg Pro Gly Gln Gly Leu Glu Cys Ile
        35                  40                  45

Gly Thr Ile Tyr Pro Gly Asp Gly Asp Thr Arg Tyr Ile Gln Lys Phe
    50                  55                  60

Gln Gly Lys Ala Thr Leu Thr Ala Asp Lys Ser Ser Ser Thr Ala Tyr
65                  70                  75                  80

Met Gln Leu Ser Ser Leu Arg Ser Glu Asp Ser Ala Val Tyr Tyr Cys
                85                  90                  95

Ala Arg Tyr Asp Ala Pro Gly Tyr Ala Met Asp Tyr Trp Gly Gln Gly
            100                 105                 110

Thr Leu Val Thr Val Ser Ser
        115
```

<210> SEQ ID NO 24
<211> LENGTH: 108
<212> TYPE: PRT
<213> ORGANISM: Artificial Sequence
<220> FEATURE:
<223> OTHER INFORMATION: muEGFR-7 VL and muEGFR13LC

<400> SEQUENCE: 24

```
Asp Ile Gln Met Thr Gln Ser Pro Ser Ser Leu Ser Ala Ser Leu Gly
1               5                   10                  15
```

```
Gly Lys Val Thr Ile Thr Cys Lys Ala Ser Gln Asp Ile Asn Asn Tyr
            20                  25                  30

Leu Ala Trp Tyr Gln His Lys Pro Gly Lys Gly Pro Arg Leu Leu Ile
        35                  40                  45

His Tyr Thr Ser Thr Leu His Pro Gly Ile Pro Ser Arg Phe Ser Gly
    50                  55                  60

Ser Gly Ser Gly Arg Asp Tyr Ser Phe Ser Ile Ser Asn Leu Glu Pro
65                  70                  75                  80

Glu Asp Ile Ala Thr Tyr Tyr Cys Leu Gln Tyr Asp Asn Leu Leu Tyr
                85                  90                  95

Thr Phe Gly Gly Gly Thr Lys Leu Glu Ile Lys Arg
            100                 105


<210> SEQ ID NO 25
<211> LENGTH: 108
<212> TYPE: PRT
<213> ORGANISM: Artificial Sequence
<220> FEATURE:
<223> OTHER INFORMATION: muEGFR-12 VL

<400> SEQUENCE: 25

Asp Val Gln Ile Thr Gln Ser Pro Ser Tyr Leu Ala Ala Ser Pro Gly
1               5                   10                  15

Glu Thr Ile Thr Ile Asn Cys Arg Ala Ser Lys Ser Ile Ser Lys Tyr
            20                  25                  30

Leu Ala Trp Tyr Gln Glu Lys Pro Gly Lys Thr Asn Lys Leu Leu Ile
        35                  40                  45

Tyr Ser Gly Ser Thr Leu Gln Ser Gly Ile Pro Ser Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Met Tyr Tyr Cys Gln Gln His Asn Glu Tyr Pro Trp
                85                  90                  95

Thr Phe Gly Gly Gly Thr Lys Leu Glu Ile Lys Arg
            100                 105


<210> SEQ ID NO 26
<211> LENGTH: 108
<212> TYPE: PRT
<213> ORGANISM: Artificial Sequence
<220> FEATURE:
<223> OTHER INFORMATION: huEGFR-7 VL v1.0

<400> SEQUENCE: 26

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Asn Tyr
            20                  25                  30

Leu Ala Trp Tyr Gln His Lys Pro Gly Lys Gly Pro Lys Leu Leu Ile
        35                  40                  45

His Tyr Thr Ser Thr Leu His Pro Gly Ile Pro Ser Arg Phe Ser Gly
    50                  55                  60

Ser Gly Ser Gly Arg Asp Tyr Ser Phe Ser Ile Ser Ser Leu Glu Pro
65                  70                  75                  80

Glu Asp Ile Ala Thr Tyr Tyr Cys Leu Gln Tyr Asp Asn Leu Leu Tyr
                85                  90                  95

Thr Phe Gly Gln Gly Thr Lys Leu Glu Ile Lys Arg
```

100 105

<210> SEQ ID NO 27
<211> LENGTH: 108
<212> TYPE: PRT
<213> ORGANISM: Artificial Sequence
<220> FEATURE:
<223> OTHER INFORMATION: huEGFR-7 VL v1.01

<400> SEQUENCE: 27

Asp Ile Gln Met Thr Gln Ser Pro Ser Ser Leu Ser Ala Ser Val Gly
1 5 10 15

Asp Arg Val Thr Ile Thr Cys Lys Ala Ser Gln Asp Ile Asn Asn Tyr
20 25 30

Leu Ala Trp Tyr Gln His Lys Pro Gly Lys Gly Pro Lys Leu Leu Ile
35 40 45

His Tyr Thr Ser Thr Leu His Pro Gly Ile Pro Ser Arg Phe Ser Gly
50 55 60

Ser Gly Ser Gly Arg Asp Tyr Ser Phe Ser Ile Ser Ser Leu Glu Pro
65 70 75 80

Glu Asp Ile Ala Thr Tyr Tyr Cys Leu Gln Tyr Asp Asn Leu Leu Tyr
85 90 95

Thr Phe Gly Gln Gly Thr Lys Leu Glu Ile Lys Arg
100 105

<210> SEQ ID NO 28
<211> LENGTH: 108
<212> TYPE: PRT
<213> ORGANISM: Artificial Sequence
<220> FEATURE:
<223> OTHER INFORMATION: huEGFR-7 VL_CDR grafted

<400> SEQUENCE: 28

Asp Ile Gln Met Thr Gln Ser Pro Ser Ser Leu Ser Ala Ser Val Gly
1 5 10 15

Asp Arg Val Thr Ile Thr Cys Arg Ala Ser Gln Asp Ile Asn Asn Tyr
20 25 30

Leu Ala Trp Tyr Gln Gln Lys Pro Gly Lys Ala Pro Lys Leu Leu Ile
35 40 45

Tyr Tyr Thr Ser Thr Leu His Pro Gly Val Pro Ser Arg Phe Ser Gly
50 55 60

Ser Gly Ser Gly Thr Asp Phe Thr Phe Thr Ile Ser Ser Leu Gln Pro
65 70 75 80

Glu Asp Ile Ala Thr Tyr Tyr Cys Leu Gln Tyr Asp Asn Leu Leu Tyr
85 90 95

Thr Phe Gly Gln Gly Thr Lys Val Glu Ile Lys Arg
100 105

<210> SEQ ID NO 29
<211> LENGTH: 108
<212> TYPE: PRT
<213> ORGANISM: Artificial Sequence
<220> FEATURE:
<223> OTHER INFORMATION: huEGFR-12 VL v1.0

<400> SEQUENCE: 29

Asp Val Gln Ile Thr Gln Ser Pro Ser Ser Leu Ala Ala Ser Val Gly
1 5 10 15

Glu Arg Ile Thr Ile Asn Cys Arg Ala Ser Gln Ser Ile Ser Arg Tyr
20 25 30

```
Leu Ala Trp Tyr Gln Glu Lys Pro Gly Lys Thr Asn Lys Leu Leu Ile
        35                  40                  45

Tyr Ser Gly Ser Thr Leu Gln Ser Gly Ile Pro Ser Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Met Tyr Tyr Cys Gln Gln His Asn Glu Tyr Pro Trp
                85                  90                  95

Thr Phe Gly Gln Gly Thr Lys Leu Glu Ile Lys Arg
            100                 105


<210> SEQ ID NO 30
<211> LENGTH: 108
<212> TYPE: PRT
<213> ORGANISM: Artificial Sequence
<220> FEATURE:
<223> OTHER INFORMATION: huEGFR-12 VL v1.01

<400> SEQUENCE: 30

Asp Val Gln Ile Thr Gln Ser Pro Ser Ser Leu Ala Ala Ser Val Gly
1               5                   10                  15

Glu Arg Ile Thr Ile Asn Cys Arg Ala Ser Lys Ser Ile Ser Lys Tyr
            20                  25                  30

Leu Ala Trp Tyr Gln Glu Lys Pro Gly Lys Thr Asn Lys Leu Leu Ile
        35                  40                  45

Tyr Ser Gly Ser Thr Leu Gln Ser Gly Ile Pro Ser Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Met Tyr Tyr Cys Gln Gln His Asn Glu Tyr Pro Trp
                85                  90                  95

Thr Phe Gly Gln Gly Thr Lys Leu Glu Ile Lys Arg
            100                 105


<210> SEQ ID NO 31
<211> LENGTH: 448
<212> TYPE: PRT
<213> ORGANISM: Artificial Sequence
<220> FEATURE:
<223> OTHER INFORMATION: huEGFR-7 HC

<400> SEQUENCE: 31

Gln Val Gln Leu Val Gln Ser Gly Ala Glu Val Ala Lys Pro Gly Ala
1               5                   10                  15

Ser Val Lys Leu Ser Cys Lys Ala Ser Gly Tyr Thr Phe Thr Ser Tyr
            20                  25                  30

Trp Met Gln Trp Val Lys Gln Arg Pro Gly Gln Gly Leu Glu Cys Ile
        35                  40                  45

Gly Thr Ile Tyr Pro Gly Asp Gly Asp Thr Thr Tyr Thr Gln Lys Phe
    50                  55                  60

Gln Gly Lys Ala Thr Leu Thr Ala Asp Lys Ser Ser Ser Thr Ala Tyr
65                  70                  75                  80

Met Gln Leu Ser Ser Leu Arg Ser Glu Asp Ser Ala Val Tyr Tyr Cys
                85                  90                  95

Ala Arg Tyr Asp Ala Pro Gly Tyr Ala Met Asp Tyr Trp Gly Gln Gly
            100                 105                 110

Thr Leu Val Thr Val Ser Ser Ala Ser Thr Lys Gly Pro Ser Val Phe
```

-continued

```
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445
```

<210> SEQ ID NO 32
<211> LENGTH: 448
<212> TYPE: PRT
<213> ORGANISM: Artificial Sequence
<220> FEATURE:
<223> OTHER INFORMATION: huEGFR-7 HC CDR grafted

<400> SEQUENCE: 32

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met Gln Trp Val Arg Gln Ala Pro Gly Gln Gly Leu Glu Trp Met
```

-continued

```
        35                  40                  45

Gly Thr Ile Tyr Pro Gly Asp Gly Asp Thr Thr Tyr Thr Gln Lys Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Tyr Asp Ala Pro Gly Tyr Ala Met Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445
```

<210> SEQ ID NO 33

```
<211> LENGTH: 214
<212> TYPE: PRT
<213> ORGANISM: Artificial Sequence
<220> FEATURE:
<223> OTHER INFORMATION: huEGFR-7 LCv1.0

<400> SEQUENCE: 33

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Asn Tyr
            20                  25                  30

Leu Ala Trp Tyr Gln His Lys Pro Gly Lys Gly Pro Lys Leu Leu Ile
        35                  40                  45

His Tyr Thr Ser Thr Leu His Pro Gly Ile Pro Ser Arg Phe Ser Gly
    50                  55                  60

Ser Gly Ser Gly Arg Asp Tyr Ser Phe Ser Ile Ser Ser Leu Glu Pro
65                  70                  75                  80

Glu Asp Ile Ala Thr Tyr Tyr Cys Leu Gln Tyr Asp Asn Leu Leu Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 34
<211> LENGTH: 214
<212> TYPE: PRT
<213> ORGANISM: Artificial Sequence
<220> FEATURE:
<223> OTHER INFORMATION: huEGFR-7 LCv1.01

<400> SEQUENCE: 34

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Asn Tyr
            20                  25                  30

Leu Ala Trp Tyr Gln His Lys Pro Gly Lys Gly Pro Lys Leu Leu Ile
        35                  40                  45

His Tyr Thr Ser Thr Leu His Pro Gly Ile Pro Ser Arg Phe Ser Gly
    50                  55                  60

Ser Gly Ser Gly Arg Asp Tyr Ser Phe Ser Ile Ser Ser Leu Glu Pro
65                  70                  75                  80

Glu Asp Ile Ala Thr Tyr Tyr Cys Leu Gln Tyr Asp Asn Leu Leu Tyr
                85                  90                  95

Thr Phe Gly Gln Gly Thr Lys Leu Glu Ile Lys Arg Thr Val Ala Ala
```

```
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 35
<211> LENGTH: 214
<212> TYPE: PRT
<213> ORGANISM: Artificial Sequence
<220> FEATURE:
<223> OTHER INFORMATION: huEGFR-7 LC_CDR grafted

<400> SEQUENCE: 35

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Asn Tyr
            20                  25                  30

Leu Ala Trp Tyr Gln Gln Lys Pro Gly Lys Ala Pro Lys Leu Leu Ile
        35                  40                  45

Tyr Tyr Thr Ser Thr Leu His Pro Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Leu Gln Tyr Asp Asn Leu Leu Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 36
<211> LENGTH: 445
<212> TYPE: PRT
```

<213> ORGANISM: Artificial Sequence
<220> FEATURE:
<223> OTHER INFORMATION: huEGFR-12 HC

<400> SEQUENCE: 36

Gln Val Gln Leu Val Gln Ser Gly Ala Glu Val Ala Lys Pro Gly Ala
1 5 10 15

Ser Val Lys Leu Ser Cys Lys Ala Ser Gly Tyr Thr Phe Thr Ser Tyr
20 25 30

Trp Met Gln Trp Val Lys Gln Arg Pro Gly Gln Gly Leu Glu Cys Ile
35 40 45

Gly Thr Ile Tyr Pro Gly Asp Gly Asp Thr Arg Tyr Ile Gln Lys Phe
50 55 60

Gln Gly Lys Ala Thr Leu Thr Ala Asp Lys Ser Ser Ser Thr Ala Tyr
65 70 75 80

Met Gln Leu Ser Ser Leu Arg Ser Glu Asp Ser Ala Val Tyr Tyr Cys
85 90 95

Ala Arg Tyr Asp Ala Pro Gly Tyr Ala Met Asp Tyr Trp Gly Gln Gly
100 105 110

Thr Leu Val Thr Val Ser Ser Ala Ser Thr Lys Gly Pro Ser Val Phe
115 120 125

Pro Leu Ala Pro Ser Ser Lys Ser Thr Ser Gly Gly Thr Ala Ala Leu
130 135 140

Gly Cys Leu Val Lys Asp Tyr Phe Pro Glu Pro Val Thr Val Ser Trp
145 150 155 160

Asn Ser Gly Ala Leu Thr Ser Gly Val His Thr Phe Pro Ala Val Leu
165 170 175

Gln Ser Ser Gly Leu Tyr Ser Leu Ser Ser Val Val Thr Val Pro Ser
180 185 190

Ser Ser Leu Gly Thr Gln Thr Tyr Ile Cys Asn Val Asn His Lys Pro
195 200 205

Ser Asn Thr Lys Val Asp Lys Lys Val Glu Pro Lys Ser Cys Asp Lys
210 215 220

Thr His Thr Cys Pro Pro Cys Pro Ala Pro Glu Leu Leu Gly Gly Pro
225 230 235 240

Ser Val Phe Leu Phe Pro Pro Lys Pro Lys Asp Thr Leu Met Ile Ser
245 250 255

Arg Thr Pro Glu Val Thr Cys Val Val Val Asp Val Ser His Glu Asp
260 265 270

Pro Glu Val Lys Phe Asn Trp Tyr Val Asp Gly Val Glu Val His Asn
275 280 285

Ala Lys Thr Lys Pro Arg Glu Glu Gln Tyr Asn Ser Thr Tyr Arg Val
290 295 300

Val Ser Val Leu Thr Val Leu His Gln Asp Trp Leu Asn Gly Lys Glu
305 310 315 320

Tyr Lys Cys Lys Val Ser Asn Lys Ala Leu Pro Ala Pro Ile Glu Lys
325 330 335

Thr Ile Ser Lys Ala Lys Gly Gln Pro Arg Glu Pro Gln Val Tyr Thr
340 345 350

Leu Pro Pro Ser Arg Asp Glu Leu Thr Lys Asn Gln Val Ser Leu Thr
355 360 365

Cys Leu Val Lys Gly Phe Tyr Pro Ser Asp Ile Ala Val Glu Trp Glu
370 375 380

Ser Asn Gly Gln Pro Glu Asn Asn Tyr Lys Thr Thr Pro Pro Val Leu

-continued

```
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu
        435                 440                 445


<210> SEQ ID NO 37
<211> LENGTH: 214
<212> TYPE: PRT
<213> ORGANISM: Artificial Sequence
<220> FEATURE:
<223> OTHER INFORMATION: huEGFR-12 HC

<400> SEQUENCE: 37

Asp Val Gln Ile Thr Gln Ser Pro Ser Ser Leu Ala Ala Ser Val Gly
1               5                   10                  15

Glu Arg Ile Thr Ile Asn Cys Arg Ala Ser Gln Ser Ile Ser Arg Tyr
            20                  25                  30

Leu Ala Trp Tyr Gln Glu Lys Pro Gly Lys Thr Asn Lys Leu Leu Ile
        35                  40                  45

Tyr Ser Gly Ser Thr Leu Gln Ser Gly Ile Pro Ser Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Met Tyr Tyr Cys Gln Gln His Asn Glu Tyr Pro Trp
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 38
<211> LENGTH: 214
<212> TYPE: PRT
<213> ORGANISM: Artificial Sequence
<220> FEATURE:
<223> OTHER INFORMATION: huEGFR-12 LCv.1.01

<400> SEQUENCE: 38

Asp Val Gln Ile Thr Gln Ser Pro Ser Ser Leu Ala Ala Ser Val Gly
1               5                   10                  15

Glu Arg Ile Thr Ile Asn Cys Arg Ala Ser Lys Ser Ile Ser Lys Tyr
            20                  25                  30
```

```
Leu Ala Trp Tyr Gln Glu Lys Pro Gly Lys Thr Asn Lys Leu Leu Ile
        35                  40                  45

Tyr Ser Gly Ser Thr Leu Gln Ser Gly Ile Pro Ser Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Met Tyr Tyr Cys Gln Gln His Asn Glu Tyr Pro Trp
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 39
<211> LENGTH: 357
<212> TYPE: DNA
<213> ORGANISM: Artificial Sequence
<220> FEATURE:
<223> OTHER INFORMATION: muEGFR-7 VH

<400> SEQUENCE: 39

caggttcagc tccagcagtc tggggctgag ctggcaagac ctggggcttc agtgaagttg      60

tcctgcaagg cttctggcta cacctttact agctactgga tgcagtgggt aaaacagagg     120

cctggacagg gtctggaatg tattgggact atttatcctg gagatggtga tactacgtac     180

actcagaagt tcaagggcaa ggccacattg actgcagata aatcctccag cacagcctac     240

atgcaactca gcagcttggc atctgaggac tctgcggtct attactgtgc aagatatgat     300

gcccccggct atgctatgga ctactggggt caaggaacct cagtcaccgt ctcctca        357


<210> SEQ ID NO 40
<211> LENGTH: 357
<212> TYPE: DNA
<213> ORGANISM: Artificial Sequence
<220> FEATURE:
<223> OTHER INFORMATION: muEGFR-12 VH

<400> SEQUENCE: 40

caggttcagc tccagcagtc tgggactgag ctggcaagac ctggggcttc agtgaagttg      60

tcctgcaagg cttctggcta cacctttact agctactgga tgcagtgggt aaaacagagg     120

cctggacagg gtctggaatg tattgggact atctatcctg gagatggtga tactaggtac     180

attcagaagt tcaagggcaa ggccacattg actgcagata aatcctccag cacagcctac     240

atgcaactca gcagcttggc atctgaggac tctgcggtct attactgtgc aagatatgat     300

gcccccggct atgctatgga ctactggggt caaggaacct cagtcaccgt ctcctca        357
```

<210> SEQ ID NO 41
<211> LENGTH: 443
<212> TYPE: DNA
<213> ORGANISM: Artificial Sequence
<220> FEATURE:
<223> OTHER INFORMATION: huEGFR-7 VH

<400> SEQUENCE: 41
aagcttgcca ccatgggctg gtcatgtatc attctgttcc tggtggccac cgcaaccggt 60
gtccattccc aggtgcagct cgtgcagagc ggggctgaag tggccaagcc aggtgcttct 120
gtcaaattgt cttgtaaggc cagtgggtac accttcacaa gctactggat gcagtgggtt 180
aagcaacgcc caggccaggg actggagtgc atcggcacca tttatccagg ggatggagat 240
accacttata cacaaaagtt tcaaggcaaa gccaccctga ccgccgacaa atccagcagc 300
acagcataca tgcagctttc tagcctcagg tctgaagact ccgccgtgta ctattgtgcc 360
cgctacgacg cccccggcta tgcaatggat tactggggcc agggtactct ggtcacagtg 420
tcctccgcct ctacaaaggg ccc 443

<210> SEQ ID NO 42
<211> LENGTH: 443
<212> TYPE: DNA
<213> ORGANISM: Artificial Sequence
<220> FEATURE:
<223> OTHER INFORMATION: huEGFR-7 VH CDR grafted

<400> SEQUENCE: 42
aagcttgcca ccatggggtg gtcctgtata atactgtttc tggtggccac tgccacagga 60
gtccacagcc aagtgcagct ggtgcagagt ggcgctgagg tcaagaagcc tggggcatcc 120
gtcaaggttt cttgtaaggc atctggatat accttcactt cctattggat gcagtgggtg 180
agacaggcac caggacaggg actggagtgg atgggcacta tttatccagg tgacggtgac 240
actacttata ctcagaaatt caaggggcga gtgaccatga ctcgtgatac tagcactagt 300
accgtgtata tggagcttag ttctctccgg tccgaggaca cagcagtcta ctactgtgct 360
agatatgacg cacccggata tgccatggac tattgggggc agggcaccct ggtcaccgtg 420
agttccgcca gcactaaggg ccc 443

<210> SEQ ID NO 43
<211> LENGTH: 443
<212> TYPE: DNA
<213> ORGANISM: Artificial Sequence
<220> FEATURE:
<223> OTHER INFORMATION: huEGFR-12 VH

<400> SEQUENCE: 43
aagcttgcca ccatgggctg gtcctgtatt atcctctttt tggtggccac tgctaccggc 60
gtacacagtc aggtgcagct ggtgcagtcc ggggctgaag tggcaaagcc cggggcctcc 120
gtaaagctct cttgcaaggc atccggctac acttttactt cctactggat gcagtgggtc 180
aaacagcgcc caggacaggg gttggaatgt ataggtacaa tctatcccgg cgatggtgac 240
acacgatata tccagaagtt ccagggcaag gctaccctga ctgccgacaa atcttctagc 300
accgcttata tgcagctgtc atctcttcga agtgaagact ctgcagtgta ttactgcgcc 360
cgatatgacg cacccggtta cgccatggat tactggggtc aggggacctt ggtaaccgta 420
tcaagcgcca gtaccaaggg ccc 443

<210> SEQ ID NO 44
<211> LENGTH: 324
<212> TYPE: DNA
<213> ORGANISM: Artificial Sequence
<220> FEATURE:
<223> OTHER INFORMATION: muEGFR-7 VL

<400> SEQUENCE: 44
gacatccaga tgacacagtc tccatcctca ctgtctgcat ctctgggagg caaagtcacc 60
atcacttgca aggcaagcca agacattaac aactatttgg cttggtacca acacaagcct 120
ggaaaaggtc ctaggctgct catacattac acatctacat tacatccagg catcccatca 180
aggttcagtg gaagtgggtc tgggagagat tattccttca gcatcagcaa cctggagcct 240
gaagatattg caacttatta ttgtctacag tatgataatc ttctgtacac gttcggaggg 300
gggaccaagc tggaaataaa acgg 324

<210> SEQ ID NO 45
<211> LENGTH: 324
<212> TYPE: DNA
<213> ORGANISM: Artificial Sequence
<220> FEATURE:
<223> OTHER INFORMATION: muEGFR-12 VL

<400> SEQUENCE: 45
gatgtccaga taacccagtc tccatcttat cttgctgcat ctcctggaga aaccattact 60
attaattgca gggcaagtaa gagcattagc aaatatttag cctggtatca agagaaacct 120
gggaaaacta ataagcttct tatctactct ggatccactt tgcaatctgg aattccatca 180
aggttcagtg gcagtggatc tggtacagat ttcactctca ccatcagtag cctggagcct 240
gaagattttg caatgtatta ctgtcaacag cataatgaat acccgtggac gttcggtgga 300
ggcaccaagc tggaaatcaa acgg 324

<210> SEQ ID NO 46
<211> LENGTH: 396
<212> TYPE: DNA
<213> ORGANISM: Artificial Sequence
<220> FEATURE:
<223> OTHER INFORMATION: huEGFR-7 VL v1.0

<400> SEQUENCE: 46
gaattcgcca ccatgggctg gagctgcatc atcttgttct tggtcgccac tgccacagga 60
gtgcatagcg atattcagat gacccagtct cccagctctc tgagcgctag cgtgggcgat 120
cgggtgacta ttacttgccg tgcatcccag gatatcaaca actacttggc ctggtaccag 180
cacaagcccg gcaaaggccc aaagctgctg atccactata ccagtacact gcaccctggt 240
atcccttcta gattcagcgg ctccggtagt ggtcgggatt actcattctc tatctcttcc 300
ctggagcccg aggatatagc tacatattat tgtctccagt acgataatct cttgtacaca 360
tttggacagg ggacaaagct ggagatcaag cgtacg 396

<210> SEQ ID NO 47
<211> LENGTH: 396
<212> TYPE: DNA
<213> ORGANISM: Artificial Sequence
<220> FEATURE:
<223> OTHER INFORMATION: huEGFR-7 VL v1.01

<400> SEQUENCE: 47
gaattcgcca ccatgggatg gtcctgcatt atccttttcc tggtcgccac cgccacaggc 60

```
gtccactctg acatacaaat gacccagtcc ccttcttcac tgagcgcctc cgttggggat    120

agagttacaa tcacttgtaa agctagccag gacatcaaca actatctggc ttggtatcag    180

cataaacctg ggaagggacc caagctcttg attcattaca cctctacctt gcacccaggc    240

ataccaagcc gctttagcgg tagtggcagt ggccgcgatt actcattctc catcagttcc    300

ttggaaccag aagatatagc cacctattat tgtctccagt atgataattt gctctacact    360

tttggccagg gcaccaaact tgagatcaag cgtacg                              396


<210> SEQ ID NO 48
<211> LENGTH: 396
<212> TYPE: DNA
<213> ORGANISM: Artificial Sequence
<220> FEATURE:
<223> OTHER INFORMATION: huEGFR-7 VL CDR grafted

<400> SEQUENCE: 48

gaattcgcca ccatgggatg gagttgcatt attttgtttc tggtagctac cgctacaggc     60

gttcatagcg acattcagat gacacagagc cctcctcttt tgtccgcctc cgtgggcgat    120

agagtcacaa tcacctgccg cgcaagccag gatatcaaca actaccttgc atggtaccag    180

cagaagcctg gaaaagcccc aaagctgctc atatactaca cctccaccct tcacccagga    240

gttccatcca ggttctctgg gtctggaagt ggaacagatt ttaccttcac aatcagctca    300

ttgcaacccg aggacatagc tacatattac tgcctgcagt atgacaatct gctgtacaca    360

tttggacagg gaaccaaagt tgaaatcaag cgtacg                              396


<210> SEQ ID NO 49
<211> LENGTH: 396
<212> TYPE: DNA
<213> ORGANISM: Artificial Sequence
<220> FEATURE:
<223> OTHER INFORMATION: huEGFR-12 VL v1.0

<400> SEQUENCE: 49

gaattcgcca ccatgggctg gagttgcatc atcctgttct tggttgctac cgcaaccgga     60

gtacactccg acgtgcagat cacccaatct ccatcatccc tcgccgccag tgtgggagaa    120

cgaattacta tcaactgccg agcaagccag agtatcagcc gttatctggc atggtaccag    180

gagaaacccg gtaagactaa caaactgttg atttactcag gcagtacact gcaatctggt    240

atccctagcc gctttagcgg ctccggcagt ggcaccgatt tcaccctgac aatttcctcc    300

ctggagccag aggatttcgc aatgtattat tgtcagcaac acaacgagta cccatggaca    360

tttggccagg gcacaaagct ggagattaag cgtacg                              396


<210> SEQ ID NO 50
<211> LENGTH: 396
<212> TYPE: DNA
<213> ORGANISM: Artificial Sequence
<220> FEATURE:
<223> OTHER INFORMATION: huEGFR-12 VL v1.01

<400> SEQUENCE: 50

gaattcgcca ccatgggatg gtcctgcatt atcctgttcc tcgtggcaac agctacaggg     60

gtgcatagcg atgtgcagat cacccagtcc ccaagctccc ttgcagcttc cgttggtgag    120

cgcattacca tcaactgtcg agctagtaag tctatttcca agtacctggc ttggtatcaa    180

gagaagccag gaaagacaaa caagctgctc atttacagtg gctctaccct tcagtccggt    240
```

-continued

```
attccctcta gatttagtgg cagtggtagt ggaaccgatt ttacccttac aattagctct    300

ctggaaccag aagacttcgc aatgtactac tgccagcaac acaatgagta cccatggact    360

tttggccagg gaacaaagct ggaaattaaa cgtacg                              396


<210> SEQ ID NO 51
<211> LENGTH: 1422
<212> TYPE: DNA
<213> ORGANISM: Artificial Sequence
<220> FEATURE:
<223> OTHER INFORMATION: huEGFR-7 HC

<400> SEQUENCE: 51

aagcttgcca ccatgggctg gtcatgtatc attctgttcc tggtggccac cgcaaccggt     60

gtccattccc aggtgcagct cgtgcagagc ggggctgaag tggccaagcc aggtgcttct    120

gtcaaattgt cttgtaaggc cagtgggtac accttcacaa gctactggat gcagtgggtt    180

aagcaacgcc caggccaggg actggagtgc atcggcacca tttatccagg ggatggagat    240

accacttata cacaaaagtt tcaaggcaaa gccaccctga ccgccgacaa atccagcagc    300

acagcataca tgcagctttc tagcctcagg tctgaagact ccgccgtgta ctattgtgcc    360

cgctacgacg cccccggcta tgcaatggat tactggggcc agggtactct ggtcacagtg    420

tcctccgcct ctacaaaggg cccatcagtt ttccccttgg ctccaagttc taaatccaca    480

agcggtggaa cagctgcact gggatgcctc gttaaagatt atttccctga gcctgtgaca    540

gtgagctgga atagcggagc attgacttca ggtgtgcaca cttttcccgc tgtgttgcag    600

tcctccggtc tgtactcact gtccagtgtc gtaaccgtcc cttctagcag cttgggaacc    660

cagacctaca tctgtaacgt caaccataaa ccatccaaca caaaggtgga taagaaggtt    720

gaaccaaaga gctgtgataa gacacataca tgccctcctt gtcctgcacc agagctcctc    780

ggaggtccat ctgtgttcct gtttcccccc aaacccaagg acactcttat gatctctcgt    840

actccagagg tcacctgtgt tgttgtcgac gtgagccatg aagatcccga ggttaaattc    900

aactggtacg tggatggagt cgaggttcac aatgccaaga ccaagcccag ggaggagcaa    960

tataattcta catatcgggt agtgagcgtt ctgaccgtgc tccaccaaga ttggctcaat   1020

ggaaaagagt acaagtgcaa ggtgtccaac aaggctcttc ccgctcccat tgagaaaact   1080

atctccaaag ccaaggggca gccacgggaa ccccaggtgt atacattgcc cccatctaga   1140

gacgagctga ccaagaacca ggtgagtctc acttgtctgg tcaaggggtt ttacccttct   1200

gacattgctg tagagtggga gtctaacgga cagccagaaa acaactacaa gacaactccc   1260

ccagtgctgg acagcgacgg gagcttcttc ctctactcca agttgactgt agacaagtct   1320

agatggcagc aaggaaacgt tttctcctgc tcagtaatgc atgaggctct gcacaatcac   1380

tatacccaga aatcactgtc ccttagccca gggtgactcg ag                      1422


<210> SEQ ID NO 52
<211> LENGTH: 714
<212> TYPE: DNA
<213> ORGANISM: Artificial Sequence
<220> FEATURE:
<223> OTHER INFORMATION: huEGFR-7 LC v1.0

<400> SEQUENCE: 52

gaattcgcca ccatgggctg gagctgcatc atcttgttct tggtcgccac tgccacagga     60

gtgcatagcg atattcagat gacccagtct cccagctctc tgagcgctag cgtgggcgat    120

cgggtgacta ttacttgccg tgcatcccag gatatcaaca actacttggc ctggtaccag    180
```

cacaagcccg gcaaaggccc aaagctgctg atccactata ccagtacact gcaccctggt 240
atcccttcta gattcagcgg ctccggtagt ggtcgggatt actcattctc tatctcttcc 300
ctggagcccg aggatatagc tacatattat tgtctccagt acgataatct cttgtacaca 360
tttggacagg ggacaaagct ggagatcaag cgtacggtgg ctgcaccatc tgtcttcatc 420
ttcccgccat ctgatgagca gttgaaatct ggaactgcct ctgttgtgtg cctgctgaat 480
aacttctatc ccagagaggc caaagtacag tggaaggtgg ataacgccct ccaatcgggt 540
aactcccagg agagtgtcac agagcaggac agcaaggaca gcacctacag cctcagcagc 600
accctgacgc tgagcaaagc agactacgag aaacacaaag tctacgcctg cgaagtcacc 660
catcagggcc tgagctcgcc cgtcacaaag agcttcaaca ggggagagtg ttag 714

<210> SEQ ID NO 53
<211> LENGTH: 714
<212> TYPE: DNA
<213> ORGANISM: Artificial Sequence
<220> FEATURE:
<223> OTHER INFORMATION: huEGFR-7 LC v1.01

<400> SEQUENCE: 53
gaattcgcca ccatgggatg gtcctgcatt atccttttcc tggtcgccac cgccacaggc 60
gtccactctg acatacaaat gacccagtcc ccttcttcac tgagcgcctc cgttggggat 120
agagttacaa tcacttgtaa agctagccag gacatcaaca actatctggc ttggtatcag 180
cataaacctg ggaagggacc caagctcttg attcattaca cctctacctt gcacccaggc 240
ataccaagcc gctttagcgg tagtggcagt ggccgcgatt actcattctc catcagttcc 300
ttggaaccag aagatatagc cacctattat tgtctccagt atgataattt gctctacact 360
tttggccagg gcaccaaact tgagatcaag cgtacggtgg ctgcaccatc tgtcttcatc 420
ttcccgccat ctgatgagca gttgaaatct ggaactgcct ctgttgtgtg cctgctgaat 480
aacttctatc ccagagaggc caaagtacag tggaaggtgg ataacgccct ccaatcgggt 540
aactcccagg agagtgtcac agagcaggac agcaaggaca gcacctacag cctcagcagc 600
accctgacgc tgagcaaagc agactacgag aaacacaaag tctacgcctg cgaagtcacc 660
catcagggcc tgagctcgcc cgtcacaaag agcttcaaca ggggagagtg ttag 714

<210> SEQ ID NO 54
<211> LENGTH: 1422
<212> TYPE: DNA
<213> ORGANISM: Artificial Sequence
<220> FEATURE:
<223> OTHER INFORMATION: huEGFR-7 HC_CDR grafted

<400> SEQUENCE: 54
aagcttgcca ccatggggtg gtcctgtata atactgtttc tggtggccac tgccacagga 60
gtccacagcc aagtgcagct ggtgcagagt ggcgctgagg tcaagaagcc tggggcatcc 120
gtcaaggttt cttgtaaggc atctggatat accttcactt cctattggat gcagtgggtg 180
agacaggcac caggacaggg actggagtgg atgggcacta tttatccagg tgacggtgac 240
actacttata ctcagaaatt caaggggcga gtgaccatga ctcgtgatac tagcactagt 300
accgtgtata tggagcttag ttctctccgg tccgaggaca cagcagtcta ctactgtgct 360
agatatgacg cacccggata tgccatggac tattgggggc agggcaccct ggtcaccgtg 420
agttccgcca gcactaaggg cccatcagtt ttccccttgg ctccaagttc taaatccaca 480

-continued

```
agcggtggaa cagctgcact gggatgcctc gttaaagatt atttccctga gcctgtgaca    540

gtgagctgga atagcggagc attgacttca ggtgtgcaca cttttcccgc tgtgttgcag    600

tcctccggtc tgtactcact gtccagtgtc gtaaccgtcc cttctagcag cttgggaacc    660

cagacctaca tctgtaacgt caaccataaa ccatccaaca caaaggtgga taagaaggtt    720

gaaccaaaga gctgtgataa gacacataca tgccctcctt gtcctgcacc agagctcctc    780

ggaggtccat ctgtgttcct gtttcccccc aaacccaagg acactcttat gatctctcgt    840

actccagagg tcacctgtgt tgttgtcgac gtgagccatg aagatcccga ggttaaattc    900

aactggtacg tggatggagt cgaggttcac aatgccaaga ccaagcccag ggaggagcaa    960

tataattcta catatcgggt agtgagcgtt ctgaccgtgc tccaccaaga ttggctcaat   1020

ggaaaagagt acaagtgcaa ggtgtccaac aaggctcttc ccgctcccat tgagaaaact   1080

atctccaaag ccaaggggca gccacgggaa ccccaggtgt atacattgcc cccatctaga   1140

gacgagctga ccaagaacca ggtgagtctc acttgtctgg tcaaggggtt ttacccttct   1200

gacattgctg tagagtggga gtctaacgga cagccagaaa acaactacaa gacaactccc   1260

ccagtgctgg acagcgacgg gagcttcttc ctctactcca agttgactgt agacaagtct   1320

agatggcagc aaggaaacgt tttctcctgc tcagtaatgc atgaggctct gcacaatcac   1380

tatacccaga aatcactgtc ccttagccca gggtgactcg ag                      1422
```

<210> SEQ ID NO 55
<211> LENGTH: 714
<212> TYPE: DNA
<213> ORGANISM: Artificial Sequence
<220> FEATURE:
<223> OTHER INFORMATION: huEGFR-7 LC_CDR grafted

<400> SEQUENCE: 55

```
gaattcgcca ccatgggatg gagttgcatt attttgtttc tggtagctac cgctacaggc     60

gttcatagcg acattcagat gacacagagc ccctcctctt tgtccgcctc cgtgggcgat    120

agagtcacaa tcacctgccg cgcaagccag gatatcaaca actaccttgc atggtaccag    180

cagaagcctg gaaaagcccc aaagctgctc atatactaca cctccaccct tcacccagga    240

gttccatcca ggttctctgg gtctggaagt ggaacagatt ttaccttcac aatcagctca    300

ttgcaacccg aggacatagc tacatattac tgcctgcagt atgacaatct gctgtacaca    360

tttggacagg gaaccaaagt tgaaatcaag cgtacggtgg ctgcaccatc tgtcttcatc    420

ttcccgccat ctgatgagca gttgaaatct ggaactgcct ctgttgtgtg cctgctgaat    480

aacttctatc ccagagaggc caaagtacag tggaaggtgg ataacgccct ccaatcgggt    540

aactcccagg agagtgtcac agagcaggac agcaaggaca gcacctacag cctcagcagc    600

accctgacgc tgagcaaagc agactacgag aaacacaaag tctacgcctg cgaagtcacc    660

catcagggcc tgagctcgcc cgtcacaaag agcttcaaca ggggagagtg ttag          714
```

<210> SEQ ID NO 56
<211> LENGTH: 1422
<212> TYPE: DNA
<213> ORGANISM: Artificial Sequence
<220> FEATURE:
<223> OTHER INFORMATION: huEGFR-12 HC

<400> SEQUENCE: 56

```
aagcttgcca ccatgggctg gtcctgtatt atcctctttt tggtggccac tgctaccggc     60

gtacacagtc aggtgcagct ggtgcagtcc ggggctgaag tggcaaagcc cggggcctcc    120
```

gtaaagctct cttgcaaggc atccggctac acttttactt cctactggat gcagtgggtc 180
aaacagcgcc caggacaggg gttggaatgt ataggtacaa tctatcccgg cgatggtgac 240
acacgatata tccagaagtt ccagggcaag gctaccctga ctgccgacaa atcttctagc 300
accgcttata tgcagctgtc atctcttcga agtgaagact ctgcagtgta ttactgcgcc 360
cgatatgacg cacccggtta cgccatggat tactggggtc aggggacctt ggtaaccgta 420
tcaagcgcca gtaccaaggg cccatcagtt ttccccttgg ctccaagttc taaatccaca 480
agcggtggaa cagctgcact gggatgcctc gttaaagatt atttccctga gcctgtgaca 540
gtgagctgga atagcggagc attgacttca ggtgtgcaca cttttcccgc tgtgttgcag 600
tcctccggtc tgtactcact gtccagtgtc gtaaccgtcc cttctagcag cttgggaacc 660
cagacctaca tctgtaacgt caaccataaa ccatccaaca caaaggtgga taagaaggtt 720
gaaccaaaga gctgtgataa gacacataca tgccctcctt gtcctgcacc agagctcctc 780
ggaggtccat ctgtgttcct gtttcccccc aaacccaagg acactcttat gatctctcgt 840
actccagagg tcacctgtgt tgttgtcgac gtgagccatg aagatcccga ggttaaattc 900
aactggtacg tggatggagt cgaggttcac aatgccaaga ccaagcccag ggaggagcaa 960
tataattcta catatcgggt agtgagcgtt ctgaccgtgc tccaccaaga ttggctcaat 1020
ggaaaagagt acaagtgcaa ggtgtccaac aaggctcttc ccgctcccat tgagaaaact 1080
atctccaaag ccaaggggca gccacgggaa ccccaggtgt atacattgcc cccatctaga 1140
gacgagctga ccaagaacca ggtgagtctc acttgtctgg tcaaggggtt ttacccttct 1200
gacattgctg tagagtggga gtctaacgga cagccagaaa acaactacaa gacaactccc 1260
ccagtgctgg acagcgacgg gagcttcttc ctctactcca agttgactgt agacaagtct 1320
agatggcagc aaggaaacgt tttctcctgc tcagtaatgc atgaggctct gcacaatcac 1380
tatacccaga aatcactgtc ccttagccca gggtgactcg ag 1422

<210> SEQ ID NO 57
<211> LENGTH: 714
<212> TYPE: DNA
<213> ORGANISM: Artificial Sequence
<220> FEATURE:
<223> OTHER INFORMATION: huEGFR-12 LC v1.0

<400> SEQUENCE: 57
gaattcgcca ccatgggctg gagttgcatc atcctgttct tggttgctac cgcaaccgga 60
gtacactccg acgtgcagat cacccaatct ccatcatccc tcgccgccag tgtgggagaa 120
cgaattacta tcaactgccg agcaagccag agtatcagcc gttatctggc atggtaccag 180
gagaaacccg gtaagactaa caaactgttg atttactcag gcagtacact gcaatctggt 240
atccctagcc gctttagcgg ctccggcagt ggcaccgatt tcaccctgac aatttcctcc 300
ctggagccag aggatttcgc aatgtattat tgtcagcaac acaacgagta cccatggaca 360
tttggccagg gcacaaagct ggagattaag cgtacggtgg ctgcaccatc tgtcttcatc 420
ttcccgccat ctgatgagca gttgaaatct ggaactgcct ctgttgtgtg cctgctgaat 480
aacttctatc ccagagaggc caaagtacag tggaaggtgg ataacgccct ccaatcgggt 540
aactcccagg agagtgtcac agagcaggac agcaaggaca gcacctacag cctcagcagc 600
accctgacgc tgagcaaagc agactacgag aaacacaaag tctacgcctg cgaagtcacc 660
catcagggcc tgagctcgcc cgtcacaaag agcttcaaca ggggagagtg ttag 714

<210> SEQ ID NO 58
<211> LENGTH: 714
<212> TYPE: DNA
<213> ORGANISM: Artificial Sequence
<220> FEATURE:
<223> OTHER INFORMATION: huEGFR-12 LC v1.01

<400> SEQUENCE: 58
gaattcgcca ccatgggatg gtcctgcatt atcctgttcc tcgtggcaac agctacaggg 60
gtgcatagcg atgtgcagat cacccagtcc ccaagctccc ttgcagcttc cgttggtgag 120
cgcattacca tcaactgtcg agctagtaag tctatttcca agtacctggc ttggtatcaa 180
gagaagccag gaaagacaaa caagctgctc atttacagtg gctctaccct tcagtccggt 240
attccctcta gatttagtgg cagtggtagt ggaaccgatt ttacccttac aattagctct 300
ctggaaccag aagacttcgc aatgtactac tgccagcaac acaatgagta cccatggact 360
tttggccagg gaacaaagct ggaaattaaa cgtacggtgg ctgcaccatc tgtcttcatc 420
ttcccgccat ctgatgagca gttgaaatct ggaactgcct ctgttgtgtg cctgctgaat 480
aacttctatc ccagagaggc caaagtacag tggaaggtgg ataacgccct ccaatcgggt 540
aactcccagg agagtgtcac agagcaggac agcaaggaca gcacctacag cctcagcagc 600
accctgacgc tgagcaaagc agactacgag aaacacaaag tctacgcctg cgaagtcacc 660
catcagggcc tgagctcgcc cgtcacaaag agcttcaaca ggggagagtg ttag 714

<210> SEQ ID NO 59
<211> LENGTH: 32
<212> TYPE: PRT
<213> ORGANISM: Artificial Sequence
<220> FEATURE:
<223> OTHER INFORMATION: EcoMH1

<400> SEQUENCE: 59

Cys Thr Thr Cys Cys Gly Gly Ala Ala Thr Thr Cys Ser Ala Arg Gly
1               5                   10                  15

Thr Asn Met Ala Gly Cys Thr Gly Ser Ala Gly Ser Ala Gly Thr Cys
            20                  25                  30

<210> SEQ ID NO 60
<211> LENGTH: 35
<212> TYPE: PRT
<213> ORGANISM: Artificial Sequence
<220> FEATURE:
<223> OTHER INFORMATION: EcoMH2

<400> SEQUENCE: 60

Cys Thr Thr Cys Cys Gly Gly Ala Ala Thr Thr Cys Ser Ala Arg Gly
1               5                   10                  15

Thr Asn Met Ala Gly Cys Thr Gly Ser Ala Gly Ser Ala Gly Thr Cys
            20                  25                  30

Trp Gly Gly
        35

<210> SEQ ID NO 61
<211> LENGTH: 36
<212> TYPE: PRT
<213> ORGANISM: Artificial Sequence
<220> FEATURE:
<223> OTHER INFORMATION: BamIgG1

<400> SEQUENCE: 61

-continued

Gly Gly Ala Gly Gly Ala Thr Cys Cys Ala Thr Ala Gly Ala Cys Ala
1 5 10 15

Gly Ala Thr Gly Gly Gly Gly Gly Thr Gly Thr Cys Gly Thr Thr Thr
20 25 30

Thr Gly Gly Cys
35

<210> SEQ ID NO 62
<211> LENGTH: 31
<212> TYPE: PRT
<213> ORGANISM: Artificial Sequence
<220> FEATURE:
<223> OTHER INFORMATION: SacIMK

<400> SEQUENCE: 62

Gly Gly Ala Gly Cys Thr Cys Gly Ala Tyr Ala Thr Thr Gly Thr Gly
1 5 10 15

Met Thr Ser Ala Cys Met Cys Ala Arg Trp Cys Thr Met Cys Ala
20 25 30

<210> SEQ ID NO 63
<211> LENGTH: 17
<212> TYPE: PRT
<213> ORGANISM: Artificial Sequence
<220> FEATURE:
<223> OTHER INFORMATION: Murine HC CDR2

<400> SEQUENCE: 63

Thr Ile Tyr Pro Gly Asp Gly Asp Thr Thr Tyr Thr Gln Lys Phe Lys
1 5 10 15

Gly

<210> SEQ ID NO 64
<211> LENGTH: 17
<212> TYPE: PRT
<213> ORGANISM: Artificial Sequence
<220> FEATURE:
<223> OTHER INFORMATION: Humanized HC CDR2

<400> SEQUENCE: 64

Thr Ile Tyr Pro Gly Asp Gly Asp Thr Thr Tyr Thr Gln Lys Phe Gln
1 5 10 15

Gly

<210> SEQ ID NO 65
<211> LENGTH: 10
<212> TYPE: PRT
<213> ORGANISM: Artificial Sequence
<220> FEATURE:
<223> OTHER INFORMATION: EGFR-6 VH-CDR2

<400> SEQUENCE: 65

Ala Leu Tyr Pro Gly Asp Gly Asp Ala Arg
1 5 10

<210> SEQ ID NO 66
<211> LENGTH: 17
<212> TYPE: PRT
<213> ORGANISM: Artificial Sequence
<220> FEATURE:
<223> OTHER INFORMATION: Kabat HC (murine) VH-CDR2

<400> SEQUENCE: 66

Ala Leu Tyr Pro Gly Asp Gly Asp Ala Arg Tyr Thr Gln Lys Phe Lys

-continued 1 5 10 15

Gly

<210> SEQ ID NO 67
<211> LENGTH: 17
<212> TYPE: PRT
<213> ORGANISM: Artificial Sequence
<220> FEATURE:
<223> OTHER INFORMATION: Kabat HC (resurfaced) VH-CDR2

<400> SEQUENCE: 67

Ala Leu Tyr Pro Gly Asp Gly Asp Ala Arg Tyr Thr Gln Lys Phe Gln
1 5 10 15

Gly

<210> SEQ ID NO 68
<211> LENGTH: 11
<212> TYPE: PRT
<213> ORGANISM: Artificial Sequence
<220> FEATURE:
<223> OTHER INFORMATION: EGFR-6 (murine) VL-CDR1

<400> SEQUENCE: 68

Lys Ala Ser Gln Asp Ile Asn Asn Tyr Ile Ala
1 5 10

<210> SEQ ID NO 69
<211> LENGTH: 119
<212> TYPE: PRT
<213> ORGANISM: Artificial Sequence
<220> FEATURE:
<223> OTHER INFORMATION: muEGFR-6 VH

<400> SEQUENCE: 69

Gln Val Gln Leu Gln Gln Ser Gly Ala Glu Leu Ala Arg Pro Gly Ala
1 5 10 15

Ser Val Lys Leu Ser Cys Lys Ala Ser Gly Tyr Thr Phe Thr Ser Tyr
20 25 30

Trp Met Gln Trp Val Lys Gln Arg Pro Gly Gln Gly Leu Glu Cys Ile
35 40 45

Gly Ala Leu Tyr Pro Gly Asp Gly Asp Ala Arg Tyr Thr Gln Lys Phe
50 55 60

Lys Gly Lys Ala Thr Leu Thr Ala Asp Arg Ser Ser Ser Thr Ala Tyr
65 70 75 80

Met Gln Leu Ser Ser Leu Ala Ser Glu Asp Ser Ala Val Tyr Tyr Cys
85 90 95

Ala Arg Tyr Asp Ala Pro Gly Tyr Ala Met Asp Tyr Trp Gly Gln Gly
100 105 110

Thr Ser Val Thr Val Ala Ser
115

<210> SEQ ID NO 70
<211> LENGTH: 108
<212> TYPE: PRT
<213> ORGANISM: Artificial Sequence
<220> FEATURE:
<223> OTHER INFORMATION: muEGFR6 VL

<400> SEQUENCE: 70

Asp Ile Gln Met Thr Gln Ser Pro Ser Ser Leu Ser Ala Ser Leu Gly
1 5 10 15

```
Gly Lys Val Thr Ile Thr Cys Lys Ala Ser Gln Asp Ile Asn Asn Tyr
            20                  25                  30

Ile Ala Trp Tyr Gln His Lys Pro Gly Lys Gly Pro Arg Leu Leu Ile
        35                  40                  45

His Tyr Thr Ser Thr Leu His Pro Gly Ile Pro Ser Arg Phe Ser Gly
    50                  55                  60

Ser Gly Ser Gly Arg Asp Tyr Ser Phe Ser Ile Ser Asn Leu Glu Pro
65                  70                  75                  80

Glu Asp Ile Ala Thr Tyr Tyr Cys Leu Gln Tyr Asp Asn Leu Leu Tyr
                85                  90                  95

Thr Phe Gly Gly Gly Thr Lys Leu Glu Ile Lys Arg
            100                 105


<210> SEQ ID NO 71
<211> LENGTH: 119
<212> TYPE: PRT
<213> ORGANISM: Artificial Sequence
<220> FEATURE:
<223> OTHER INFORMATION: huEGFR-6 VH v1.0

<400> SEQUENCE: 71

Gln Val Gln Leu Val Gln Ser Gly Ala Glu Val Ala Lys Pro Gly Ala
1               5                   10                  15

Ser Val Lys Leu Ser Cys Lys Ala Ser Gly Tyr Thr Phe Thr Ser Tyr
            20                  25                  30

Trp Met Gln Trp Val Lys Gln Arg Pro Gly Gln Gly Leu Glu Cys Ile
        35                  40                  45

Gly Ala Leu Tyr Pro Gly Asp Gly Asp Ala Arg Tyr Thr Gln Lys Phe
    50                  55                  60

Gln Gly Lys Ala Thr Leu Thr Ala Asp Thr Ser Ser Ser Thr Ala Tyr
65                  70                  75                  80

Met Gln Leu Ser Ser Leu Arg Ser Glu Asp Ser Ala Val Tyr Tyr Cys
                85                  90                  95

Ala Arg Tyr Asp Ala Pro Gly Tyr Ala Met Asp Tyr Trp Gly Gln Gly
            100                 105                 110

Thr Leu Val Thr Val Ser Ser
        115


<210> SEQ ID NO 72
<211> LENGTH: 119
<212> TYPE: PRT
<213> ORGANISM: Artificial Sequence
<220> FEATURE:
<223> OTHER INFORMATION: huEGFR-6 VH v1.11

<400> SEQUENCE: 72

Gln Val Gln Leu Val Gln Ser Gly Ala Glu Val Ala Lys Pro Gly Ala
1               5                   10                  15

Ser Val Lys Leu Ser Cys Lys Ala Ser Gly Tyr Thr Phe Thr Ser Tyr
            20                  25                  30

Trp Met Gln Trp Val Lys Gln Arg Pro Gly Gln Gly Leu Glu Trp Ile
        35                  40                  45

Gly Ala Leu Tyr Pro Gly Asp Gly Asp Ala Arg Tyr Thr Gln Lys Phe
    50                  55                  60

Gln Gly Lys Ala Thr Leu Thr Ala Asp Thr Ser Ser Ser Thr Ala Tyr
65                  70                  75                  80

Met Gln Leu Ser Ser Leu Arg Ser Glu Asp Ser Ala Val Tyr Tyr Cys
                85                  90                  95
```

-continued

```
Ala Arg Tyr Asp Ala Pro Gly Tyr Ala Met Asp Tyr Trp Gly Gln Gly
            100                 105                 110

Thr Leu Val Thr Val Ser Ser
        115


<210> SEQ ID NO 73
<211> LENGTH: 119
<212> TYPE: PRT
<213> ORGANISM: Artificial Sequence
<220> FEATURE:
<223> OTHER INFORMATION: huEGFR-7 VH v1.11

<400> SEQUENCE: 73

Gln Val Gln Leu Val Gln Ser Gly Ala Glu Val Ala Lys Pro Gly Ala
1               5                   10                  15

Ser Val Lys Leu Ser Cys Lys Ala Ser Gly Tyr Thr Phe Thr Ser Tyr
            20                  25                  30

Trp Met Gln Trp Val Lys Gln Arg Pro Gly Gln Gly Leu Glu Trp Ile
        35                  40                  45

Gly Thr Ile Tyr Pro Gly Asp Gly Asp Thr Thr Tyr Thr Gln Lys Phe
    50                  55                  60

Gln Gly Lys Ala Thr Leu Thr Ala Asp Lys Ser Ser Ser Thr Ala Tyr
65                  70                  75                  80

Met Gln Leu Ser Ser Leu Arg Ser Glu Asp Ser Ala Val Tyr Tyr Cys
                85                  90                  95

Ala Arg Tyr Asp Ala Pro Gly Tyr Ala Met Asp Tyr Trp Gly Gln Gly
            100                 105                 110

Thr Leu Val Thr Val Ser Ser
        115


<210> SEQ ID NO 74
<211> LENGTH: 448
<212> TYPE: PRT
<213> ORGANISM: Artificial Sequence
<220> FEATURE:
<223> OTHER INFORMATION: huEGFR-6 HCv1.0

<400> SEQUENCE: 74

Gln Val Gln Leu Val Gln Ser Gly Ala Glu Val Ala Lys Pro Gly Ala
1               5                   10                  15

Ser Val Lys Leu Ser Cys Lys Ala Ser Gly Tyr Thr Phe Thr Ser Tyr
            20                  25                  30

Trp Met Gln Trp Val Lys Gln Arg Pro Gly Gln Gly Leu Glu Cys Ile
        35                  40                  45

Gly Ala Leu Tyr Pro Gly Asp Gly Asp Ala Arg Tyr Thr Gln Lys Phe
    50                  55                  60

Gln Gly Lys Ala Thr Leu Thr Ala Asp Thr Ser Ser Ser Thr Ala Tyr
65                  70                  75                  80

Met Gln Leu Ser Ser Leu Arg Ser Glu Asp Ser Ala Val Tyr Tyr Cys
                85                  90                  95

Ala Arg Tyr Asp Ala Pro Gly Tyr Ala Met Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
```

145 150 155 160

Asn Ser Gly Ala Leu Thr Ser Gly Val His Thr Phe Pro Ala Val Leu
165 170 175

Gln Ser Ser Gly Leu Tyr Ser Leu Ser Ser Val Val Thr Val Pro Ser
180 185 190

Ser Ser Leu Gly Thr Gln Thr Tyr Ile Cys Asn Val Asn His Lys Pro
195 200 205

Ser Asn Thr Lys Val Asp Lys Lys Val Glu Pro Lys Ser Cys Asp Lys
210 215 220

Thr His Thr Cys Pro Pro Cys Pro Ala Pro Glu Leu Leu Gly Gly Pro
225 230 235 240

Ser Val Phe Leu Phe Pro Pro Lys Pro Lys Asp Thr Leu Met Ile Ser
245 250 255

Arg Thr Pro Glu Val Thr Cys Val Val Val Asp Val Ser His Glu Asp
260 265 270

Pro Glu Val Lys Phe Asn Trp Tyr Val Asp Gly Val Glu Val His Asn
275 280 285

Ala Lys Thr Lys Pro Arg Glu Glu Gln Tyr Asn Ser Thr Tyr Arg Val
290 295 300

Val Ser Val Leu Thr Val Leu His Gln Asp Trp Leu Asn Gly Lys Glu
305 310 315 320

Tyr Lys Cys Lys Val Ser Asn Lys Ala Leu Pro Ala Pro Ile Glu Lys
325 330 335

Thr Ile Ser Lys Ala Lys Gly Gln Pro Arg Glu Pro Gln Val Tyr Thr
340 345 350

Leu Pro Pro Ser Arg Asp Glu Leu Thr Lys Asn Gln Val Ser Leu Thr
355 360 365

Cys Leu Val Lys Gly Phe Tyr Pro Ser Asp Ile Ala Val Glu Trp Glu
370 375 380

Ser Asn Gly Gln Pro Glu Asn Asn Tyr Lys Thr Thr Pro Pro Val Leu
385 390 395 400

Asp Ser Asp Gly Ser Phe Phe Leu Tyr Ser Lys Leu Thr Val Asp Lys
405 410 415

Ser Arg Trp Gln Gln Gly Asn Val Phe Ser Cys Ser Val Met His Glu
420 425 430

Ala Leu His Asn His Tyr Thr Gln Lys Ser Leu Ser Leu Ser Pro Gly
435 440 445

<210> SEQ ID NO 75
<211> LENGTH: 448
<212> TYPE: PRT
<213> ORGANISM: Artificial Sequence
<220> FEATURE:
<223> OTHER INFORMATION: huEGFR-6 HCv1.11

<400> SEQUENCE: 75

Gln Val Gln Leu Val Gln Ser Gly Ala Glu Val Ala Lys Pro Gly Ala
1 5 10 15

Ser Val Lys Leu Ser Cys Lys Ala Ser Gly Tyr Thr Phe Thr Ser Tyr
20 25 30

Trp Met Gln Trp Val Lys Gln Arg Pro Gly Gln Gly Leu Glu Trp Ile
35 40 45

Gly Ala Leu Tyr Pro Gly Asp Gly Asp Ala Arg Tyr Thr Gln Lys Phe
50 55 60

Gln Gly Lys Ala Thr Leu Thr Ala Asp Thr Ser Ser Ser Thr Ala Tyr

-continued

```
65                  70                  75                  80

Met Gln Leu Ser Ser Leu Arg Ser Glu Asp Ser Ala Val Tyr Tyr Cys
                85                  90                  95

Ala Arg Tyr Asp Ala Pro Gly Tyr Ala Met Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445
```

<210> SEQ ID NO 76
<211> LENGTH: 448
<212> TYPE: PRT
<213> ORGANISM: Artificial Sequence
<220> FEATURE:
<223> OTHER INFORMATION: huEGFR-7 HCv1.11

<400> SEQUENCE: 76

```
Gln Val Gln Leu Val Gln Ser Gly Ala Glu Val Ala Lys Pro Gly Ala
1               5                   10                  15

Ser Val Lys Leu Ser Cys Lys Ala Ser Gly Tyr Thr Phe Thr Ser Tyr
            20                  25                  30

Trp Met Gln Trp Val Lys Gln Arg Pro Gly Gln Gly Leu Glu Trp Ile
        35                  40                  45

Gly Thr Ile Tyr Pro Gly Asp Gly Asp Thr Thr Tyr Thr Gln Lys Phe
    50                  55                  60

Gln Gly Lys Ala Thr Leu Thr Ala Asp Lys Ser Ser Ser Thr Ala Tyr
65                  70                  75                  80

Met Gln Leu Ser Ser Leu Arg Ser Glu Asp Ser Ala Val Tyr Tyr Cys
                85                  90                  95

Ala Arg Tyr Asp Ala Pro Gly Tyr Ala Met Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415
```

```
Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445
```

<210> SEQ ID NO 77
<211> LENGTH: 357
<212> TYPE: DNA
<213> ORGANISM: Artificial Sequence
<220> FEATURE:
<223> OTHER INFORMATION: muEGFR-6 VH

<400> SEQUENCE: 77

```
caggttcagc tccagcagtc tggggctgag ctggcaagac ctggggcttc agtgaagttg     60

tcctgcaagg cttctggcta cacctttact agctactgga tgcagtgggt aaaacagagg    120

cctggacagg gtctggaatg tattggggct ctttatcctg gagatggtga tgctaggtac    180

actcagaaat tcaagggcaa ggccacattg actgcagata gatcctccag cacagcctac    240

atgcaactca gcagcttggc atctgaggac tctgcggtct attactgtgc aagatatgat    300

gcccccggct atgctatgga ctactggggt caaggaacct cagtcaccgt cgcctca       357
```

<210> SEQ ID NO 78
<211> LENGTH: 443
<212> TYPE: DNA
<213> ORGANISM: Artificial Sequence
<220> FEATURE:
<223> OTHER INFORMATION: huEGFR-6 VH v1.0

<400> SEQUENCE: 78

```
aagcttgcca ccatggggtg gagttgtatc atcctcttcc ttgtcgctac cgccactgga     60

gtgcattccc aggtgcagtt ggtgcaatct ggcgccgagg tggccaagcc cggtgcctcc    120

gtaaaattga gttgtaaagc ctctggctat acatttacat cttattggat gcagtgggtc    180

aagcagcgcc ctggtcaagg cctggagtgc atcggagctc tgtatcctgg cgacggggac    240

gcccgttaca ctcagaaatt tcagggcaaa gctaccctca ccgcagatac atccagcagc    300

actgcttata tgcaacttag tagcctccgc agcgaggata gtgccgtgta ctactgtgcc    360

agatatgacg ccccaggtta tgctatggac tactggggtc aaggaaccct ggtgacagtg    420

tcaagcgcta gcacaaaggg ccc                                            443
```

<210> SEQ ID NO 79
<211> LENGTH: 443
<212> TYPE: PRT
<213> ORGANISM: Artificial Sequence
<220> FEATURE:
<223> OTHER INFORMATION: huEGFR-6 VH v1.11

<400> SEQUENCE: 79

```
Ala Ala Gly Cys Thr Thr Gly Cys Cys Ala Cys Cys Ala Thr Gly Gly
1               5                   10                  15

Gly Gly Thr Gly Gly Ala Gly Thr Thr Gly Thr Ala Thr Cys Ala Thr
            20                  25                  30

Cys Cys Thr Cys Thr Thr Cys Cys Thr Thr Gly Thr Cys Gly Cys Thr
        35                  40                  45

Ala Cys Cys Gly Cys Cys Ala Cys Thr Gly Gly Ala Gly Thr Gly Cys
    50                  55                  60

Ala Thr Thr Cys Cys Cys Ala Gly Gly Thr Gly Cys Ala Gly Thr Thr
65                  70                  75                  80
```

-continued

```
Gly Gly Thr Gly Cys Ala Ala Thr Cys Thr Gly Gly Cys Gly Cys Cys
                85                  90                  95

Gly Ala Gly Gly Thr Gly Gly Cys Cys Ala Ala Gly Cys Cys Cys Gly
            100                 105                 110

Gly Thr Gly Cys Cys Thr Cys Cys Gly Thr Ala Ala Ala Ala Thr Thr
        115                 120                 125

Gly Ala Gly Thr Thr Gly Thr Ala Ala Ala Gly Cys Cys Thr Cys Thr
    130                 135                 140

Gly Gly Cys Thr Ala Thr Ala Cys Ala Thr Thr Thr Ala Cys Ala Thr
145                 150                 155                 160

Cys Thr Thr Ala Thr Thr Gly Gly Ala Thr Gly Cys Ala Gly Thr Gly
                165                 170                 175

Gly Gly Thr Cys Ala Ala Gly Cys Ala Gly Cys Gly Cys Cys Cys Thr
            180                 185                 190

Gly Gly Thr Cys Ala Ala Gly Gly Cys Cys Thr Gly Gly Ala Gly Thr
        195                 200                 205

Gly Gly Ala Thr Cys Gly Gly Ala Gly Cys Thr Cys Thr Gly Thr Ala
    210                 215                 220

Thr Cys Cys Thr Gly Gly Cys Gly Ala Cys Gly Gly Gly Gly Ala Cys
225                 230                 235                 240

Gly Cys Cys Cys Gly Thr Thr Ala Cys Ala Cys Thr Cys Ala Gly Ala
                245                 250                 255

Ala Ala Thr Thr Thr Cys Ala Gly Gly Gly Cys Ala Ala Ala Gly Cys
            260                 265                 270

Thr Ala Cys Cys Cys Thr Cys Ala Cys Cys Gly Cys Ala Gly Ala Thr
        275                 280                 285

Ala Cys Ala Thr Cys Cys Ala Gly Cys Ala Gly Cys Ala Cys Thr Gly
    290                 295                 300

Cys Thr Thr Ala Thr Ala Thr Gly Cys Ala Ala Cys Thr Thr Ala Gly
305                 310                 315                 320

Thr Ala Gly Cys Cys Thr Cys Cys Gly Cys Ala Gly Cys Gly Ala Gly
                325                 330                 335

Gly Ala Thr Ala Gly Thr Gly Cys Cys Gly Thr Gly Thr Ala Cys Thr
            340                 345                 350

Ala Cys Thr Gly Thr Gly Cys Cys Ala Gly Ala Thr Ala Thr Gly Ala
        355                 360                 365

Cys Gly Cys Cys Cys Cys Ala Gly Gly Thr Thr Ala Thr Gly Cys Thr
    370                 375                 380

Ala Thr Gly Gly Ala Cys Thr Ala Cys Thr Gly Gly Gly Gly Thr Cys
385                 390                 395                 400

Ala Ala Gly Gly Ala Ala Cys Cys Cys Thr Gly Gly Thr Gly Ala Cys
                405                 410                 415

Ala Gly Thr Gly Thr Cys Ala Ala Gly Cys Gly Cys Thr Ala Gly Cys
            420                 425                 430

Ala Cys Ala Ala Ala Gly Gly Gly Cys Cys Cys
        435                 440
```

<210> SEQ ID NO 80
<211> LENGTH: 443
<212> TYPE: PRT
<213> ORGANISM: Artificial Sequence
<220> FEATURE:
<223> OTHER INFORMATION: huEGFR-7 VH v1.11

<400> SEQUENCE: 80

```
Ala Ala Gly Cys Thr Thr Gly Cys Cys Ala Cys Cys Ala Thr Gly Gly
1               5                   10                  15

Gly Cys Thr Gly Gly Thr Cys Ala Thr Gly Thr Ala Thr Cys Ala Thr
            20                  25                  30

Thr Cys Thr Gly Thr Thr Cys Cys Thr Gly Gly Thr Gly Gly Cys Cys
        35                  40                  45

Ala Cys Cys Gly Cys Ala Ala Cys Cys Gly Gly Thr Gly Thr Cys Cys
    50                  55                  60

Ala Thr Thr Cys Cys Cys Ala Gly Gly Thr Gly Cys Ala Gly Cys Thr
65                  70                  75                  80

Cys Gly Thr Gly Cys Ala Gly Ala Gly Cys Gly Gly Gly Gly Cys Thr
                85                  90                  95

Gly Ala Ala Gly Thr Gly Gly Cys Cys Ala Ala Gly Cys Cys Ala Gly
            100                 105                 110

Gly Thr Gly Cys Thr Thr Cys Thr Gly Thr Cys Ala Ala Ala Thr Thr
        115                 120                 125

Gly Thr Cys Thr Thr Gly Thr Ala Ala Gly Gly Cys Cys Ala Gly Thr
    130                 135                 140

Gly Gly Gly Thr Ala Cys Ala Cys Cys Thr Thr Cys Ala Cys Ala Ala
145                 150                 155                 160

Gly Cys Thr Ala Cys Thr Gly Gly Ala Thr Gly Cys Ala Gly Thr Gly
                165                 170                 175

Gly Gly Thr Thr Ala Ala Gly Cys Ala Ala Cys Gly Cys Cys Cys Ala
            180                 185                 190

Gly Gly Cys Cys Ala Gly Gly Gly Ala Cys Thr Gly Gly Ala Gly Thr
        195                 200                 205

Gly Gly Ala Thr Cys Gly Gly Cys Ala Cys Cys Ala Thr Thr Thr Ala
    210                 215                 220

Thr Cys Cys Ala Gly Gly Gly Gly Ala Thr Gly Gly Ala Gly Ala Thr
225                 230                 235                 240

Ala Cys Cys Ala Cys Thr Thr Ala Thr Ala Cys Ala Cys Ala Ala Ala
                245                 250                 255

Ala Gly Thr Thr Thr Cys Ala Ala Gly Gly Cys Ala Ala Ala Gly Cys
            260                 265                 270

Cys Ala Cys Cys Cys Thr Gly Ala Cys Cys Gly Cys Cys Gly Ala Cys
        275                 280                 285

Ala Ala Ala Thr Cys Cys Ala Gly Cys Ala Gly Cys Ala Cys Ala Gly
    290                 295                 300

Cys Ala Thr Ala Cys Ala Thr Gly Cys Ala Gly Cys Thr Thr Thr Cys
305                 310                 315                 320

Thr Ala Gly Cys Cys Thr Cys Ala Gly Gly Thr Cys Thr Gly Ala Ala
                325                 330                 335

Gly Ala Cys Thr Cys Cys Gly Cys Cys Gly Thr Gly Thr Ala Cys Thr
            340                 345                 350

Ala Thr Thr Gly Thr Gly Cys Cys Cys Gly Cys Thr Ala Cys Gly Ala
        355                 360                 365

Cys Gly Cys Cys Cys Cys Cys Gly Gly Cys Thr Ala Thr Gly Cys Ala
    370                 375                 380

Ala Thr Gly Gly Ala Thr Thr Ala Cys Thr Gly Gly Gly Gly Cys Cys
385                 390                 395                 400

Ala Gly Gly Gly Thr Ala Cys Thr Cys Thr Gly Gly Thr Cys Ala Cys
                405                 410                 415
```

Ala Gly Thr Gly Thr Cys Cys Thr Cys Cys Gly Cys Cys Thr Cys Thr
420 425 430

Ala Cys Ala Ala Ala Gly Gly Gly Cys Cys Cys
435 440

<210> SEQ ID NO 81
<211> LENGTH: 324
<212> TYPE: DNA
<213> ORGANISM: Artificial Sequence
<220> FEATURE:
<223> OTHER INFORMATION: muEGFR-6 VL

<400> SEQUENCE: 81
gacatccaga tgacacagtc tccatcctca ctgtctgcat ctctgggagg caaagtcacc 60
atcacttgca aggcaagcca agacattaac aactatatag cttggtacca acacaagcct 120
ggaaaaggtc ctaggctgct cattcattac acatctacat tacatccagg catcccatca 180
aggttcagtg gaagtgggtc tgggagagat tattccttca gcatcagcaa cctggagcct 240
gaagatattg caacttatta ttgtctacag tatgataatc ttctgtacac gttcggaggg 300
gggaccaagc tggaaataaa acgg 324

<210> SEQ ID NO 82
<211> LENGTH: 1422
<212> TYPE: DNA
<213> ORGANISM: Artificial Sequence
<220> FEATURE:
<223> OTHER INFORMATION: huEGFR-6 HC v1.0

<400> SEQUENCE: 82
aagcttgcca ccatggggtg gagttgtatc atcctcttcc ttgtcgctac cgccactgga 60
gtgcattccc aggtgcagtt ggtgcaatct ggcgccgagg tggccaagcc cggtgcctcc 120
gtaaaattga gttgtaaagc ctctggctat acatttacat cttattggat gcagtgggtc 180
aagcagcgcc ctggtcaagg cctggagtgc atcggagctc tgtatcctgg cgacggggac 240
gcccgttaca ctcagaaatt tcagggcaaa gctaccctca ccgcagatac atccagcagc 300
actgcttata tgcaacttag tagcctccgc agcgaggata gtgccgtgta ctactgtgcc 360
agatatgacg ccccaggtta tgctatggac tactggggtc aaggaaccct ggtgacagtg 420
tcaagcgcta gcacaaaggg cccatcagtt ttccccttgg ctccaagttc taaatccaca 480
agcggtggaa cagctgcact gggatgcctc gttaaagatt atttccctga gcctgtgaca 540
gtgagctgga atagcggagc attgacttca ggtgtgcaca cttttcccgc tgtgttgcag 600
tcctccggtc tgtactcact gtccagtgtc gtaaccgtcc cttctagcag cttgggaacc 660
cagacctaca tctgtaacgt caaccataaa ccatccaaca caaaggtgga taagaaggtt 720
gaaccaaaga gctgtgataa gacacataca tgccctcctt gtcctgcacc agagctcctc 780
ggaggtccat ctgtgttcct gtttcccccc aaacccaagg acactcttat gatctctcgt 840
actccagagg tcacctgtgt tgttgtcgac gtgagccatg aagatcccga ggttaaattc 900
aactggtacg tggatggagt cgaggttcac aatgccaaga ccaagcccag ggaggagcaa 960
tataattcta catatcgggt agtgagcgtt ctgaccgtgc tccaccaaga ttggctcaat 1020
ggaaaagagt acaagtgcaa ggtgtccaac aaggctcttc ccgctcccat tgagaaaact 1080
atctccaaag ccaaggggca gccacgggaa ccccaggtgt atacattgcc cccatctaga 1140
gacgagctga ccaagaacca ggtgagtctc acttgtctgg tcaaggggtt ttacccttct 1200
gacattgctg tagagtggga gtctaacgga cagccagaaa acaactacaa gacaactccc 1260
ccagtgctgg acagcgacgg gagcttcttc ctctactcca agttgactgt agacaagtct 1320
agatggcagc aaggaaacgt tttctcctgc tcagtaatgc atgaggctct gcacaatcac 1380
tatacccaga aatcactgtc ccttagccca gggtgactcg ag 1422

<210> SEQ ID NO 83
<211> LENGTH: 1422
<212> TYPE: DNA
<213> ORGANISM: Artificial Sequence
<220> FEATURE:
<223> OTHER INFORMATION: huEGFR-6 HC v1.11

<400> SEQUENCE: 83
aagcttgcca ccatggggtg gagttgtatc atcctcttcc ttgtcgctac cgccactgga 60
gtgcattccc aggtgcagtt ggtgcaatct ggcgccgagg tggccaagcc cggtgcctcc 120
gtaaaattga gttgtaaagc ctctggctat acatttacat cttattggat gcagtgggtc 180
aagcagcgcc ctggtcaagg cctggagtgg atcggagctc tgtatcctgg cgacggggac 240
gcccgttaca ctcagaaatt tcagggcaaa gctaccctca ccgcagatac atccagcagc 300
actgcttata tgcaacttag tagcctccgc agcgaggata gtgccgtgta ctactgtgcc 360
agatatgacg ccccaggtta tgctatggac tactggggtc aaggaaccct ggtgacagtg 420
tcaagcgcta gcacaaaggg cccatcagtt ttccccttgg ctccaagttc taaatccaca 480
agcggtggaa cagctgcact gggatgcctc gttaaagatt atttccctga gcctgtgaca 540
gtgagctgga atagcggagc attgacttca ggtgtgcaca cttttcccgc tgtgttgcag 600
tcctccggtc tgtactcact gtccagtgtc gtaaccgtcc cttctagcag cttgggaacc 660
cagacctaca tctgtaacgt caaccataaa ccatccaaca caaaggtgga taagaaggtt 720
gaaccaaaga gctgtgataa gacacataca tgccctcctt gtcctgcacc agagctcctc 780
ggaggtccat ctgtgttcct gtttcccccc aaacccaagg acactcttat gatctctcgt 840
actccagagg tcacctgtgt tgttgtcgac gtgagccatg aagatcccga ggttaaattc 900
aactggtacg tggatggagt cgaggttcac aatgccaaga ccaagcccag ggaggagcaa 960
tataattcta catatcgggt agtgagcgtt ctgaccgtgc tccaccaaga ttggctcaat 1020
ggaaaagagt acaagtgcaa ggtgtccaac aaggctcttc ccgctcccat tgagaaaact 1080
atctccaaag ccaaggggca gccacgggaa ccccaggtgt atacattgcc cccatctaga 1140
gacgagctga ccaagaacca ggtgagtctc acttgtctgg tcaaggggtt ttacccttct 1200
gacattgctg tagagtggga gtctaacgga cagccagaaa acaactacaa gacaactccc 1260
ccagtgctgg acagcgacgg gagcttcttc ctctactcca agttgactgt agacaagtct 1320
agatggcagc aaggaaacgt tttctcctgc tcagtaatgc atgaggctct gcacaatcac 1380
tatacccaga aatcactgtc ccttagccca gggtgactcg ag 1422

<210> SEQ ID NO 84
<211> LENGTH: 1422
<212> TYPE: DNA
<213> ORGANISM: Artificial Sequence
<220> FEATURE:
<223> OTHER INFORMATION: huEGFR-7 HC v1.11

<400> SEQUENCE: 84
aagcttgcca ccatgggctg gtcatgtatc attctgttcc tggtggccac cgcaaccggt 60
gtccattccc aggtgcagct cgtgcagagc ggggctgaag tggccaagcc aggtgcttct 120

-continued

```
gtcaaattgt cttgtaaggc cagtgggtac accttcacaa gctactggat gcagtgggtt    180

aagcaacgcc caggccaggg actggagtgg atcggcacca tttatccagg ggatggagat    240

accacttata cacaaaagtt tcaaggcaaa gccaccctga ccgccgacaa atccagcagc    300

acagcataca tgcagctttc tagcctcagg tctgaagact ccgccgtgta ctattgtgcc    360

cgctacgacg cccccggcta tgcaatggat tactggggcc agggtactct ggtcacagtg    420

tcctccgcct ctacaaaggg cccatcagtt ttccccttgg ctccaagttc taaatccaca    480

agcggtggaa cagctgcact gggatgcctc gttaaagatt atttccctga gcctgtgaca    540

gtgagctgga atagcggagc attgacttca ggtgtgcaca cttttcccgc tgtgttgcag    600

tcctccggtc tgtactcact gtccagtgtc gtaaccgtcc cttctagcag cttgggaacc    660

cagacctaca tctgtaacgt caaccataaa ccatccaaca caaaggtgga taagaaggtt    720

gaaccaaaga gctgtgataa gacacataca tgccctcctt gtcctgcacc agagctcctc    780

ggaggtccat ctgtgttcct gtttcccccc aaacccaagg acactcttat gatctctcgt    840

actccagagg tcacctgtgt tgttgtcgac gtgagccatg aagatcccga ggttaaattc    900

aactggtacg tggatggagt cgaggttcac aatgccaaga ccaagcccag ggaggagcaa    960

tataattcta catatcgggt agtgagcgtt ctgaccgtgc tccaccaaga ttggctcaat   1020

ggaaaagagt acaagtgcaa ggtgtccaac aaggctcttc ccgctcccat tgagaaaact   1080

atctccaaag ccaaggggca gccacgggaa ccccaggtgt atacattgcc cccatctaga   1140

gacgagctga ccaagaacca ggtgagtctc acttgtctgg tcaaggggtt ttacccttct   1200

gacattgctg tagagtggga gtctaacgga cagccagaaa acaactacaa gacaactccc   1260

ccagtgctgg acagcgacgg gagcttcttc ctctactcca agttgactgt agacaagtct   1320

agatggcagc aaggaaacgt tttctcctgc tcagtaatgc atgaggctct gcacaatcac   1380

tatacccaga aatcactgtc ccttagccca gggtgactcg ag                      1422
```

<210> SEQ ID NO 85
<211> LENGTH: 46
<212> TYPE: PRT
<213> ORGANISM: Artificial Sequence
<220> FEATURE:
<223> OTHER INFORMATION: HindKL

<400> SEQUENCE: 85

```
Thr Ala Thr Ala Gly Ala Gly Cys Thr Cys Ala Ala Gly Cys Thr Thr
1               5                   10                  15

Gly Gly Ala Thr Gly Gly Thr Gly Gly Gly Ala Ala Gly Ala Thr Gly
            20                  25                  30

Gly Ala Thr Ala Cys Ala Gly Thr Thr Gly Gly Thr Gly Cys
        35                  40                  45
```

<210> SEQ ID NO 86
<211> LENGTH: 108
<212> TYPE: PRT
<213> ORGANISM: Artificial Sequence
<220> FEATURE:
<223> OTHER INFORMATION: muEGFR2LC, muEGFR5LC, muEGFR6LC, muEGFR9LC,
      muEGFR10LC, and muEGFR15LC

<400> SEQUENCE: 86

```
Asp Ile Gln Met Thr Gln Ser Pro Ser Ser Leu Ser Ala Ser Leu Gly
1               5                   10                  15

Gly Lys Val Thr Ile Thr Cys Lys Ala Ser Gln Asp Ile Asn Asn Tyr
            20                  25                  30
```

```
Ile Ala Trp Tyr Gln His Lys Pro Gly Lys Gly Pro Arg Leu Leu Ile
        35                  40                  45

His Tyr Thr Ser Thr Leu His Pro Gly Ile Pro Ser Arg Phe Ser Gly
    50                  55                  60

Ser Gly Ser Gly Arg Asp Tyr Ser Phe Ser Ile Ser Asn Leu Glu Pro
65                  70                  75                  80

Glu Asp Ile Ala Thr Tyr Tyr Cys Leu Gln Tyr Asp Asn Leu Leu Tyr
                85                  90                  95

Thr Phe Gly Gly Gly Thr Lys Leu Glu Ile Lys Arg
            100                 105


<210> SEQ ID NO 87
<211> LENGTH: 108
<212> TYPE: PRT
<213> ORGANISM: Artificial Sequence
<220> FEATURE:
<223> OTHER INFORMATION: muEGFR17LC

<400> SEQUENCE: 87

Asp Ile Gln Met Thr Gln Ser Pro Ser Ser Leu Ser Ala Ser Leu Gly
1               5                   10                  15

Gly Lys Val Thr Ile Thr Cys Lys Ala Ser Gln Asp Ile Asn Asn Tyr
            20                  25                  30

Ile Ala Trp Tyr Gln His Lys Pro Glu Lys Gly Pro Arg Leu Leu Ile
        35                  40                  45

His Tyr Thr Ser Thr Leu His Pro Gly Ile Pro Ser Arg Phe Ser Gly
    50                  55                  60

Ser Gly Ser Gly Arg Asp Tyr Ser Phe Ser Ile Ser Asn Leu Glu Pro
65                  70                  75                  80

Glu Asp Ile Ala Thr Tyr Tyr Cys Leu Gln Tyr Asp Asn Leu Leu Tyr
                85                  90                  95

Thr Phe Gly Gly Gly Thr Lys Leu Glu Ile Lys Arg
            100                 105


<210> SEQ ID NO 88
<211> LENGTH: 119
<212> TYPE: PRT
<213> ORGANISM: Artificial Sequence
<220> FEATURE:
<223> OTHER INFORMATION: muEGFR2HC

<400> SEQUENCE: 88

Gln Val Gln Leu Gln Gln Ser Gly Ala Glu Leu Ala Arg Pro Gly Ala
1               5                   10                  15

Ser Val Lys Leu Ser Cys Lys Ala Ser Gly Tyr Thr Phe Thr Ser Tyr
            20                  25                  30

Trp Met Gln Trp Val Lys Gln Arg Pro Gly Gln Gly Leu Glu Cys Ile
        35                  40                  45

Gly Ala Ile Tyr Pro Gly Asp Gly Asp Thr Ser Tyr Thr Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Ala Ser Glu Asp Ser Ala Val Tyr Tyr Cys
                85                  90                  95

Ala Arg Tyr Asp Ala Pro Gly Tyr Ala Met Asp Tyr Trp Gly Gln Gly
            100                 105                 110

Thr Ser Val Thr Val Ser Ser
```

115

<210> SEQ ID NO 89
<211> LENGTH: 119
<212> TYPE: PRT
<213> ORGANISM: Artificial Sequence
<220> FEATURE:
<223> OTHER INFORMATION: muEGFR5HC

<400> SEQUENCE: 89

Gln Val Gln Leu Gln Gln Ser Gly Ala Glu Leu Ala Arg Pro Gly Ala
1 5 10 15

Ser Val Lys Leu Ser Cys Lys Ala Ser Gly Tyr Thr Phe Thr Ser Tyr
20 25 30

Trp Met Gln Trp Val Lys Gln Arg Pro Gly Gln Gly Leu Glu Cys Ile
35 40 45

Gly Thr Ile Tyr Pro Gly Asp Gly Asp Thr Arg Tyr Thr Gln Lys Phe
50 55 60

Lys Gly Lys Ala Thr Leu Thr Ala Asp Lys Ser Ser Ser Thr Ala Tyr
65 70 75 80

Met Gln Leu Ser Ser Leu Ala Ser Glu Asp Ser Ala Val Tyr Tyr Cys
85 90 95

Ala Arg Tyr Asp Ala Pro Gly Tyr Thr Met Asp Tyr Trp Gly Gln Gly
100 105 110

Thr Ser Val Thr Val Ser Ser
115

<210> SEQ ID NO 90
<211> LENGTH: 119
<212> TYPE: PRT
<213> ORGANISM: Artificial Sequence
<220> FEATURE:
<223> OTHER INFORMATION: muEGFR6HC and muEGFR10HC

<400> SEQUENCE: 90

Gln Val Gln Leu Gln Gln Ser Gly Ala Glu Leu Ala Arg Pro Gly Ala
1 5 10 15

Ser Val Lys Leu Ser Cys Lys Ala Ser Gly Tyr Thr Phe Thr Ser Tyr
20 25 30

Trp Met Gln Trp Val Lys Gln Arg Pro Gly Gln Gly Leu Glu Cys Ile
35 40 45

Gly Ala Leu Tyr Pro Gly Asp Gly Asp Ala Arg Tyr Thr Gln Lys Phe
50 55 60

Lys Gly Lys Ala Thr Leu Thr Ala Asp Arg Ser Ser Ser Thr Ala Tyr
65 70 75 80

Met Gln Leu Ser Ser Leu Ala Ser Glu Asp Ser Ala Val Tyr Tyr Cys
85 90 95

Ala Arg Tyr Asp Ala Pro Gly Tyr Ala Met Asp Tyr Trp Gly Gln Gly
100 105 110

Thr Ser Val Thr Val Ala Ser
115

<210> SEQ ID NO 91
<211> LENGTH: 119
<212> TYPE: PRT
<213> ORGANISM: Artificial Sequence
<220> FEATURE:
<223> OTHER INFORMATION: muEGFR9HC and muEGFR17HC

<400> SEQUENCE: 91

```
Gln Val Gln Leu Gln Gln Ser Gly Ala Glu Leu Ala Arg Pro Gly Ala
1               5                   10                  15

Ser Val Lys Leu Ser Cys Lys Ala Ser Gly Tyr Thr Phe Thr Ser Tyr
            20                  25                  30

Trp Met Gln Trp Val Lys Gln Arg Pro Gly Gln Gly Leu Glu Cys Ile
        35                  40                  45

Gly Thr Ile Tyr Pro Gly Asp Gly Asp Thr Arg Tyr Thr Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Ala Ser Glu Asp Ser Ala Val Tyr Tyr Cys
                85                  90                  95

Ala Arg Tyr Asp Ala Pro Gly Tyr Ala Met Asp Tyr Trp Gly Gln Gly
            100                 105                 110

Thr Ser Val Thr Val Ser Ser
        115


<210> SEQ ID NO 92
<211> LENGTH: 119
<212> TYPE: PRT
<213> ORGANISM: Artificial Sequence
<220> FEATURE:
<223> OTHER INFORMATION: muEGFR13HC

<400> SEQUENCE: 92

Gln Val Gln Leu Gln Gln Ser Gly Ala Glu Leu Ala Arg Pro Gly Ala
1               5                   10                  15

Ser Val Lys Leu Ser Cys Lys Ala Ser Gly Tyr Thr Phe Thr Ser Tyr
            20                  25                  30

Trp Met Gln Trp Val Lys Gln Arg Pro Gly Gln Gly Leu Glu Cys Ile
        35                  40                  45

Gly Thr Ile Tyr Pro Gly Asp Gly Asp Thr Thr Tyr Thr Gln Lys Phe
    50                  55                  60

Lys Gly Lys Ala Thr Leu Thr Ala Asp Lys Ser Ser Ser Thr Ala Tyr
65                  70                  75                  80

Met Gln Leu Asn Ser Leu Ala Ser Glu Asp Ser Ala Val Tyr Tyr Cys
                85                  90                  95

Ala Arg Tyr Asp Ala Pro Gly Tyr Ala Met Asp Tyr Trp Gly Gln Gly
            100                 105                 110

Thr Ser Val Thr Val Ser Ser
        115


<210> SEQ ID NO 93
<211> LENGTH: 119
<212> TYPE: PRT
<213> ORGANISM: Artificial Sequence
<220> FEATURE:
<223> OTHER INFORMATION: muEGFR15HC

<400> SEQUENCE: 93

Gln Val Gln Leu Gln Gln Ser Gly Thr Glu Leu Ala Arg Pro Gly Ala
1               5                   10                  15

Ser Val Lys Leu Ser Cys Lys Ala Ser Gly Tyr Thr Phe Thr Ser Tyr
            20                  25                  30

Trp Met Gln Trp Val Lys Gln Arg Pro Gly Gln Gly Leu Glu Cys Ile
        35                  40                  45

Gly Thr Ile Tyr Pro Gly Asp Gly Asp Thr Arg Tyr Ile Gln Lys Phe
```

```
    50                  55                  60

Lys Gly Lys Ala Thr Leu Thr Ala Asp Lys Ser Ser Ser Thr Ala Tyr
65                  70                  75                  80

Met Gln Leu Ser Ser Leu Ala Ser Glu Asp Ser Ala Val Tyr Tyr Cys
                85                  90                  95

Ala Arg Tyr Asp Ala Pro Gly Tyr Ala Met Asp Tyr Trp Gly Gln Gly
            100                 105                 110

Thr Ser Val Thr Val Ser Ser
        115


<210> SEQ ID NO 94
<211> LENGTH: 618
<212> TYPE: PRT
<213> ORGANISM: Artificial Sequence
<220> FEATURE:
<223> OTHER INFORMATION: huEGFR ECD

<400> SEQUENCE: 94

Leu Glu Glu Lys Lys Val Cys Gln Gly Thr Ser Asn Lys Leu Thr Gln
1               5                   10                  15

Leu Gly Thr Phe Glu Asp His Phe Leu Ser Leu Gln Arg Met Phe Asn
            20                  25                  30

Asn Cys Glu Val Val Leu Gly Asn Leu Glu Ile Thr Tyr Val Gln Arg
        35                  40                  45

Asn Tyr Asp Leu Ser Phe Leu Lys Thr Ile Gln Glu Val Ala Gly Tyr
    50                  55                  60

Val Leu Ile Ala Leu Asn Thr Val Glu Arg Ile Pro Leu Glu Asn Leu
65                  70                  75                  80

Gln Ile Ile Arg Gly Asn Met Tyr Tyr Glu Asn Ser Tyr Ala Leu Ala
                85                  90                  95

Val Leu Ser Asn Tyr Asp Ala Asn Lys Thr Gly Leu Lys Glu Leu Pro
            100                 105                 110

Met Arg Asn Leu Gln Glu Ile Leu His Gly Ala Val Arg Phe Ser Asn
        115                 120                 125

Asn Pro Ala Leu Cys Asn Val Glu Ser Ile Gln Trp Arg Asp Ile Val
    130                 135                 140

Ser Ser Asp Phe Leu Ser Asn Met Ser Met Asp Phe Gln Asn His Leu
145                 150                 155                 160

Gly Ser Cys Gln Lys Cys Asp Pro Ser Cys Pro Asn Gly Ser Cys Trp
                165                 170                 175

Gly Ala Gly Glu Glu Asn Cys Gln Lys Leu Thr Lys Ile Ile Cys Ala
            180                 185                 190

Gln Gln Cys Ser Gly Arg Cys Arg Gly Lys Ser Pro Ser Asp Cys Cys
        195                 200                 205

His Asn Gln Cys Ala Ala Gly Cys Thr Gly Pro Arg Glu Ser Asp Cys
    210                 215                 220

Leu Val Cys Arg Lys Phe Arg Asp Glu Ala Thr Cys Lys Asp Thr Cys
225                 230                 235                 240

Pro Pro Leu Met Leu Tyr Asn Pro Thr Thr Tyr Gln Met Asp Val Asn
                245                 250                 255

Pro Glu Gly Lys Tyr Ser Phe Gly Ala Thr Cys Val Lys Lys Cys Pro
            260                 265                 270

Arg Asn Tyr Val Val Thr Asp His Gly Ser Cys Val Arg Ala Cys Gly
        275                 280                 285

Ala Asp Ser Tyr Glu Met Glu Glu Asp Gly Val Arg Lys Cys Lys Lys
```

-continued 290 295 300

Cys Glu Gly Pro Cys Arg Lys Val Cys Asn Gly Ile Gly Ile Gly Glu
305 310 315 320

Phe Lys Asp Ser Leu Ser Ile Asn Ala Thr Asn Ile Lys His Phe Lys
325 330 335

Asn Cys Thr Ser Ile Ser Gly Asp Leu His Ile Leu Pro Val Ala Phe
340 345 350

Arg Gly Asp Ser Phe Thr His Thr Pro Pro Leu Asp Pro Gln Glu Leu
355 360 365

Asp Ile Leu Lys Thr Val Lys Glu Ile Thr Gly Phe Leu Leu Ile Gln
370 375 380

Ala Trp Pro Glu Asn Arg Thr Asp Leu His Ala Phe Glu Asn Leu Glu
385 390 395 400

Ile Ile Arg Gly Arg Thr Lys Gln His Gly Gln Phe Ser Leu Ala Val
405 410 415

Val Ser Leu Asn Ile Thr Ser Leu Gly Leu Arg Ser Leu Lys Glu Ile
420 425 430

Ser Asp Gly Asp Val Ile Ile Ser Gly Asn Lys Asn Leu Cys Tyr Ala
435 440 445

Asn Thr Ile Asn Trp Lys Lys Leu Phe Gly Thr Ser Gly Gln Lys Thr
450 455 460

Lys Ile Ile Ser Asn Arg Gly Glu Asn Ser Cys Lys Ala Thr Gly Gln
465 470 475 480

Val Cys His Ala Leu Cys Ser Pro Glu Gly Cys Trp Gly Pro Glu Pro
485 490 495

Arg Asp Cys Val Ser Cys Arg Asn Val Ser Arg Gly Arg Glu Cys Val
500 505 510

Asp Lys Cys Asn Leu Leu Glu Gly Glu Pro Arg Glu Phe Val Glu Asn
515 520 525

Ser Glu Cys Ile Gln Cys His Pro Glu Cys Leu Pro Gln Ala Met Asn
530 535 540

Ile Thr Cys Thr Gly Arg Gly Pro Asp Asn Cys Ile Gln Cys Ala His
545 550 555 560

Tyr Ile Asp Gly Pro His Cys Val Lys Thr Cys Pro Ala Gly Val Met
565 570 575

Gly Glu Asn Asn Thr Leu Val Trp Lys Tyr Ala Asp Ala Gly His Val
580 585 590

Cys His Leu Cys His Pro Asn Cys Thr Tyr Gly Cys Thr Gly Pro Gly
595 600 605

Leu Glu Gly Cys Pro Thr Asn Gly Pro Lys
610 615

<210> SEQ ID NO 95
<211> LENGTH: 618
<212> TYPE: PRT
<213> ORGANISM: Artificial Sequence
<220> FEATURE:
<223> OTHER INFORMATION: muEGFR ECD

<400> SEQUENCE: 95

Leu Glu Glu Lys Lys Val Cys Gln Gly Thr Ser Asn Arg Leu Thr Gln
1 5 10 15

Leu Gly Thr Phe Glu Asp His Phe Leu Ser Leu Gln Arg Met Tyr Asn
20 25 30

Asn Cys Glu Val Val Leu Gly Asn Leu Glu Ile Thr Tyr Val Gln Arg

```
        35                  40                  45

Asn Tyr Asp Leu Ser Phe Leu Lys Thr Ile Gln Glu Val Ala Gly Tyr
    50                  55                  60

Val Leu Ile Ala Leu Asn Thr Val Glu Arg Ile Pro Leu Glu Asn Leu
65                  70                  75                  80

Gln Ile Ile Arg Gly Asn Ala Leu Tyr Glu Asn Thr Tyr Ala Leu Ala
                85                  90                  95

Ile Leu Ser Asn Tyr Gly Thr Asn Arg Thr Gly Leu Arg Glu Leu Pro
            100                 105                 110

Met Arg Asn Leu Gln Glu Ile Leu Ile Gly Ala Val Arg Phe Ser Asn
        115                 120                 125

Asn Pro Ile Leu Cys Asn Met Asp Thr Ile Gln Trp Arg Asp Ile Val
    130                 135                 140

Gln Asn Val Phe Met Ser Asn Met Ser Met Asp Leu Gln Ser His Pro
145                 150                 155                 160

Ser Ser Cys Pro Lys Cys Asp Pro Ser Cys Pro Asn Gly Ser Cys Trp
                165                 170                 175

Gly Gly Gly Glu Glu Asn Cys Gln Lys Leu Thr Lys Ile Ile Cys Ala
            180                 185                 190

Gln Gln Cys Ser His Arg Cys Arg Gly Arg Ser Pro Ser Asp Cys Cys
        195                 200                 205

His Asn Gln Cys Ala Ala Gly Cys Thr Gly Pro Arg Glu Ser Asp Cys
    210                 215                 220

Leu Val Cys Gln Lys Phe Gln Asp Glu Ala Thr Cys Lys Asp Thr Cys
225                 230                 235                 240

Pro Pro Leu Met Leu Tyr Asn Pro Thr Thr Tyr Gln Met Asp Val Asn
                245                 250                 255

Pro Glu Gly Lys Tyr Ser Phe Gly Ala Thr Cys Val Lys Lys Cys Pro
            260                 265                 270

Arg Asn Tyr Val Val Thr Asp His Gly Ser Cys Val Arg Ala Cys Gly
        275                 280                 285

Pro Asp Tyr Tyr Glu Val Glu Glu Asp Gly Ile Arg Lys Cys Lys Lys
    290                 295                 300

Cys Asp Gly Pro Cys Arg Lys Val Cys Asn Gly Ile Gly Ile Gly Glu
305                 310                 315                 320

Phe Lys Asp Thr Leu Ser Ile Asn Ala Thr Asn Ile Lys His Phe Lys
                325                 330                 335

Tyr Cys Thr Ala Ile Ser Gly Asp Leu His Ile Leu Pro Val Ala Phe
            340                 345                 350

Lys Gly Asp Ser Phe Thr Arg Thr Pro Pro Leu Asp Pro Arg Glu Leu
        355                 360                 365

Glu Ile Leu Lys Thr Val Lys Glu Ile Thr Gly Phe Leu Leu Ile Gln
    370                 375                 380

Ala Trp Pro Asp Asn Trp Thr Asp Leu His Ala Phe Glu Asn Leu Glu
385                 390                 395                 400

Ile Ile Arg Gly Arg Thr Lys Gln His Gly Gln Phe Ser Leu Ala Val
                405                 410                 415

Val Gly Leu Asn Ile Thr Ser Leu Gly Leu Arg Ser Leu Lys Glu Ile
            420                 425                 430

Ser Asp Gly Asp Val Ile Ile Ser Gly Asn Arg Asn Leu Cys Tyr Ala
        435                 440                 445

Asn Thr Ile Asn Trp Lys Lys Leu Phe Gly Thr Pro Asn Gln Lys Thr
    450                 455                 460
```

```
Lys Ile Met Asn Asn Arg Ala Glu Lys Asp Cys Lys Ala Val Asn His
465                 470                 475                 480

Val Cys Asn Pro Leu Cys Ser Ser Glu Gly Cys Trp Gly Pro Glu Pro
                485                 490                 495

Arg Asp Cys Val Ser Cys Gln Asn Val Ser Arg Gly Arg Glu Cys Val
            500                 505                 510

Glu Lys Cys Asn Ile Leu Glu Gly Glu Pro Arg Glu Phe Val Glu Asn
        515                 520                 525

Ser Glu Cys Ile Gln Cys His Pro Glu Cys Leu Pro Gln Ala Met Asn
    530                 535                 540

Ile Thr Cys Thr Gly Arg Gly Pro Asp Asn Cys Ile Gln Cys Ala His
545                 550                 555                 560

Tyr Ile Asp Gly Pro His Cys Val Lys Thr Cys Pro Ala Gly Ile Met
                565                 570                 575

Gly Glu Asn Asn Thr Leu Val Trp Lys Tyr Ala Asp Ala Asn Asn Val
            580                 585                 590

Cys His Leu Cys His Ala Asn Cys Thr Tyr Gly Cys Ala Gly Pro Gly
        595                 600                 605

Leu Gln Gly Cys Glu Val Trp Pro Ser Gly
    610                 615


<210> SEQ ID NO 96
<211> LENGTH: 192
<212> TYPE: PRT
<213> ORGANISM: Artificial Sequence
<220> FEATURE:
<223> OTHER INFORMATION: huEGFR-dIII

<400> SEQUENCE: 96

Arg Lys Val Cys Asn Gly Ile Gly Ile Gly Glu Phe Lys Asp Ser Leu
1               5                   10                  15

Ser Ile Asn Ala Thr Asn Ile Lys His Phe Lys Asn Cys Thr Ser Ile
            20                  25                  30

Ser Gly Asp Leu His Ile Leu Pro Val Ala Phe Arg Gly Asp Ser Phe
        35                  40                  45

Thr His Thr Pro Pro Leu Asp Pro Gln Glu Leu Asp Ile Leu Lys Thr
    50                  55                  60

Val Lys Glu Ile Thr Gly Phe Leu Leu Ile Gln Ala Trp Pro Glu Asn
65                  70                  75                  80

Arg Thr Asp Leu His Ala Phe Glu Asn Leu Glu Ile Ile Arg Gly Arg
                85                  90                  95

Thr Lys Gln His Gly Gln Phe Ser Leu Ala Val Val Ser Leu Asn Ile
            100                 105                 110

Thr Ser Leu Gly Leu Arg Ser Leu Lys Glu Ile Ser Asp Gly Asp Val
        115                 120                 125

Ile Ile Ser Gly Asn Lys Asn Leu Cys Tyr Ala Asn Thr Ile Asn Trp
    130                 135                 140

Lys Lys Leu Phe Gly Thr Ser Gly Gln Lys Thr Lys Ile Ile Ser Asn
145                 150                 155                 160

Arg Gly Glu Asn Ser Cys Lys Ala Thr Gly Gln Val Cys His Ala Leu
                165                 170                 175

Cys Ser Pro Glu Gly Cys Trp Gly Pro Glu Pro Arg Asp Cys Val Ser
            180                 185                 190


<210> SEQ ID NO 97
```

<211> LENGTH: 192
<212> TYPE: PRT
<213> ORGANISM: Artificial Sequence
<220> FEATURE:
<223> OTHER INFORMATION: muEGFR-dIII

<400> SEQUENCE: 97

```
Arg Lys Val Cys Asn Gly Ile Gly Ile Gly Glu Phe Lys Asp Thr Leu
1               5                   10                  15

Ser Ile Asn Ala Thr Asn Ile Lys His Phe Lys Tyr Cys Thr Ala Ile
            20                  25                  30

Ser Gly Asp Leu His Ile Leu Pro Val Ala Phe Lys Gly Asp Ser Phe
        35                  40                  45

Thr Arg Thr Pro Pro Leu Asp Pro Arg Glu Leu Glu Ile Leu Lys Thr
    50                  55                  60

Val Lys Glu Ile Thr Gly Phe Leu Leu Ile Gln Ala Trp Pro Asp Asn
65                  70                  75                  80

Trp Thr Asp Leu His Ala Phe Glu Asn Leu Glu Ile Ile Arg Gly Arg
                85                  90                  95

Thr Lys Gln His Gly Gln Phe Ser Leu Ala Val Val Gly Leu Asn Ile
            100                 105                 110

Thr Ser Leu Gly Leu Arg Ser Leu Lys Glu Ile Ser Asp Gly Asp Val
        115                 120                 125

Ile Ile Ser Gly Asn Arg Asn Leu Cys Tyr Ala Asn Thr Ile Asn Trp
    130                 135                 140

Lys Lys Leu Phe Gly Thr Pro Asn Gln Lys Thr Lys Ile Met Asn Asn
145                 150                 155                 160

Arg Ala Glu Lys Asp Cys Lys Ala Val Asn His Val Cys Asn Pro Leu
                165                 170                 175

Cys Ser Ser Glu Gly Cys Trp Gly Pro Glu Pro Arg Asp Cys Val Ser
            180                 185                 190
```

<210> SEQ ID NO 98
<211> LENGTH: 192
<212> TYPE: PRT
<213> ORGANISM: Artificial Sequence
<220> FEATURE:
<223> OTHER INFORMATION: chEGFR-dIII

<400> SEQUENCE: 98

```
Arg Lys Val Cys Asn Gly Ile Gly Ile Gly Glu Phe Lys Asp Thr Leu
1               5                   10                  15

Ser Ile Asn Ala Thr Asn Ile Lys His Phe Lys Tyr Cys Thr Ala Ile
            20                  25                  30

Ser Gly Asp Leu His Ile Leu Pro Val Ala Phe Lys Gly Asp Ser Phe
        35                  40                  45

Thr Arg Thr Pro Pro Leu Asp Pro Arg Glu Leu Glu Ile Leu Lys Thr
    50                  55                  60

Val Lys Glu Ile Thr Gly Phe Leu Leu Ile Gln Ala Trp Pro Asp Asn
65                  70                  75                  80

Trp Thr Asp Leu His Ala Phe Glu Asn Leu Glu Ile Ile Arg Gly Arg
                85                  90                  95

Thr Lys Gln His Gly Gln Phe Ser Leu Ala Val Val Gly Leu Asn Ile
            100                 105                 110

Thr Ser Leu Gly Leu Arg Ser Leu Lys Glu Ile Ser Asp Gly Asp Val
        115                 120                 125

Ile Ile Ser Gly Asn Arg Asn Leu Cys Tyr Ala Asn Thr Ile Asn Trp
```

-continued

```
    130                 135                 140

Lys Lys Leu Phe Gly Thr Ser Gly Gln Lys Thr Lys Ile Ile Ser Asn
145                 150                 155                 160

Arg Gly Glu Asn Ser Cys Lys Ala Thr Gly Gln Val Cys Asn Pro Leu
                165                 170                 175

Cys Ser Ser Glu Gly Cys Trp Gly Pro Glu Pro Arg Asp Cys Val Ser
            180                 185                 190
```

EGFR-BINDING MOLECULES AND IMMUNOCONJUGATES THEREOF

CROSS-REFERENCE TO RELATED APPLICATIONS

This application is a divisional application of U.S. application Ser. No. 13/284,398, filed Oct. 28, 2011, which claims the priority benefit of U.S. Provisional Application No. 61/408,497, filed Oct. 29, 2010, and U.S. Provisional Application No. 61/477,086, filed Apr. 19, 2011, each of which is hereby incorporated by reference herein in its entirety

FIELD OF THE INVENTION

The present invention generally relates to antibodies, antigen-binding fragments thereof, polypeptides, and immunoconjugates that bind to EGFR. The present invention also relates to methods of using such EGFR-binding molecules for diagnosing and treating diseases, such as malignancies.

BACKGROUND OF THE INVENTION

The epidermal growth factor receptor (EGFR or ErbB1 or HER1) is a transmembrane glycoprotein of 170 kDa that is encoded by the c-erbB1 proto-oncogene located in the 7q22 chromosome. EGFR is a member of the human epidermal growth factor receptor (HER) family of receptor tyrosine kinases (RTK) which includes HER2 (ErbB2), HER3 (ErbB3) and HER4 (ErbB4). These RTKs share a homologous structure that consists of a ligand-binding extracellular domain (ECD), a single span transmembrane domain and an intracellular domain that contain catalytic-kinase domain and a C-terminal tail. HER kinase signaling pathways are initiated by the binding of extracellular ligand that induces receptor homodimerization or heterodimerization with other HER kinase member and transphosphorylation of the intracellular regions. These events generate the initial signal leading to activation of numerous downstream signaling pathways that are critical for cell proliferation and survival.

EGFR is over-expressed in many malignant tumor types of epithelial cell origin such as head and neck, colorectal, lung, ovarian, renal, pancreatic, skin and other solid tumors. EGFR-mediated signaling pathways play a significant role in the progression of tumor growth and metastases, making EGFR a good target for tumor therapy (Baselga, Oncologist, 7:2-8 (2002), Yarden and Sliwkowski, Nat Rev Mol Cell Biol, 2:127-137 (2001)). At present, four EGFR targeting agents including two small molecules tyrosine kinase inhibitors (TKIs) (erlotinib (Tarceva from Genentech and OSI Pharmaceuticals) and gefitinib (Iressa from AstraZeneca and Teva Pharmaceuticals)) and two naked monoclonal antibodies cetuximab (Erbitux from ImClone and BMS) and panitumumab (Vectibix from Amgen)) have been approved for treatment of colorectal cancer, pancreatic cancer, head and neck cancer, and non-small cell lung cancer (NSCLC). These anti-EGFR agents strongly inhibit EGFR activation and downstream signaling. The TKIs compete with ATP for binding to the EGFR's intracellular kinase domain (Baselga and Arteaga, J Clin Oncol, 23:2445-2459 (20005)), whereas the two monoclonal antibodies compete with the EGFR ligands for binding to the receptor (Gill et al., J Biol Chem, 259:7755-7760 (1984), Goldstein et al., Clin Cancer Res, 1:1311-1318 (1995), Prewett et al., Clin Cancer Res, 4:2957-2966 (1998)).

Anti-EGFR therapies are not perfect. Inhibition of EGFR signaling is only effective in certain tumor type. For example, the efficacy of anti-EGFR antibodies is significantly reduced in colorectal cancer patients with KRAS, BRAF, PIK3CA and PTEN mutations (De Roock et al., Lancet Oncol, 11:753-762 (2010), Bardelli and Sienna, J Clin Oncol, 28: 1254-1261 (2010)). Additionally, the activity of small molecule EGFR inhibitors is limited to NSCLC patients with activating EGFR mutations (Linardou et al., Nat Rev Clin Oncol, 6: 352-366 (2009), Paz-Ares et al., J Cell Mol Med, 14: 51-69 (2009), Mok et al., Discov Med, 8: 227-231 (2009)). EGFR therapies also result in skin toxicity. EGFR expression in normal basal epithelial cells of the skin plays a crucial role in normal development and physiology of epidermis, and inhibition of EGFR signaling causes various skin toxicities including acneiform skin rash, skin dryness, pruritus, paronychia, hair abnormality, mucositis and increased growth of the eyelashes or facial hair (reviewed in Li and Perez-Soler, Targ Oncol 4:107-119 (2009)). Although rarely life-threatening, the skin toxicities cause significant physical and psycho-social discomfort that decrease the patient's life quality. Additionally, in around 10% of patients, the skin toxicity is so severe that it requires treatment interruption or discontinuation that impairs the clinical outcomes of EGFR inhibitors.

Accordingly, the need exists for improved anti-EGFR therapy which is harmless to normal tissues but still very effective in treating EGFR overexpressing malignant tumors, in particular, tumors that are resistant to the current EGFR therapies. To address this particular need, the present invention focuses on a unique novel class of EGFR antibodies that are very potent in killing EGFR expressing tumor cells but have no or little impact on normal epithelial cell growth. Furthermore, while the conjugation of the EGFR antibodies of the invention with cytotoxic agents potentiates the anti-tumor activity of these antibodies, it does not cause additional toxicity to normal epithelial cells.

BRIEF SUMMARY OF THE INVENTION

The present invention generally relates to antibodies, antigen-binding fragments thereof, polypeptides, and immunoconjugates that bind to EGFR. The present invention also relates to methods of using such EGFR-binding molecules for diagnosing and treating diseases, such as malignancies.

Thus, in one embodiment the invention provides an antibody or antigen binding fragment thereof that specifically binds to human EGFR, wherein said antibody has at least one characteristic selected from the group consisting of: (a) inhibits at least 80% of epidermal growth factor (EGF) and transforming growth factor alpha (TGFα) binding to A431 cells at a concentration of 10 nM or higher, (b) causes at least 50% inhibition of H292 and HCC827 tumor cell proliferation at 30 nM or higher, and (c) does not inhibit more than 20% proliferation of keratinocytes and MCF-10A epithelial cells at 60 nM or lower. In another embodiment, the antibody has at least two characteristics selected from the group consisting of: (a) inhibits at least 80% of EGF and TGFα binding to A431 cells at a concentration of 10 nM or higher, (b) causes at least 50% inhibition of H292 and HCC827 tumor cell proliferation at 30 nM or higher, and (c) does not inhibit more than 20% proliferation of keratinocytes and MCF-10A epithelial cells at 60 nM or lower. In another embodiment, the antibody or antigen binding fragment thereof that specifically binds to human EGFR, wherein said antibody (a) inhibits at least 80% of EGF and TGFα binding to A431 cells at a concentration of 10 nM or higher, (b) causes at least 50% inhibition of H292 and HCC827 tumor cell proliferation at 30 nM or higher, and (c) does not inhibit more than 20% proliferation of keratinocytes and MCF-10A epithelial cells at 60 nM or lower.

In one embodiment, the invention provides an antibody which comprises (a) a VH sequence at least 90% identical to a reference VH sequence selected from the group consisting of SEQ ID NOs:19-23 and 69-73; and (b) a VL sequence at least 90% identical to a reference VL sequence selected from the group consisting of SEQ ID NOs:24-30 and 70. In another embodiment, the VH and VL sequences are at least 95% identical to the reference VH and VL sequences. In another embodiment, the VH and VL sequences are at least 99% identical to the reference VH and VL sequences.

In one embodiment, the invention provides an antibody or antigen binding fragment thereof which comprises (a) a VH sequence selected from the group consisting of SEQ ID NOs: 19-23 and 69-73; and (b) a VL sequence selected from the group consisting of SEQ ID NOs:24-30 and 70. In another embodiment, the antibody or antigen binding fragment thereof comprises SEQ ID NO:19 and SEQ ID NO:24. In another embodiment, the antibody or antigen binding fragment thereof comprises SEQ ID NO:20 and SEQ ID NO:25. In another embodiment, the antibody or antigen binding fragment thereof comprises SEQ ID NO:21 and SEQ ID NO:26. In another embodiment, the antibody or antigen binding fragment thereof comprises SEQ ID NO:21 and SEQ ID NO:27. In another embodiment, the antibody or antigen binding fragment thereof comprises SEQ ID NO:22 and SEQ ID NO:28. In another embodiment, the antibody or antigen binding fragment thereof comprises SEQ ID NO:23 and SEQ ID NO:29. In another embodiment, the antibody or antigen binding fragment thereof comprises SEQ ID NO:23 and SEQ ID NO:30. In another embodiment, the antibody or antigen binding fragment thereof comprises SEQ ID NO:69 and SEQ ID NO:70. In another embodiment, the antibody or antigen binding fragment thereof comprises SEQ ID NO:71 and SEQ ID NO:26. In another embodiment, the antibody or antigen binding fragment thereof comprises SEQ ID NO:71 and SEQ ID NO:27. In another embodiment, the antibody or antigen binding fragment thereof comprises SEQ ID NO:72 and SEQ ID NO:26. In another embodiment, the antibody or antigen binding fragment thereof comprises SEQ ID NO:72 and SEQ ID NO:27. In another embodiment, the antibody or antigen binding fragment thereof comprises SEQ ID NO:73 and SEQ ID NO:26. In another embodiment, the antibody or antigen binding fragment thereof comprises SEQ ID NO:73 and SEQ ID NO:27.

In one embodiment, the invention provides an antibody or antigen binding fragment thereof produced by hybridoma selected from the group consisting of ATCC Deposit Designation PTA-11331, deposited with the ATCC on Oct. 6, 2010, ATCC Deposit Designation PTA-11332, deposited with the ATCC on Oct. 6, 2010, and ATCC Deposit Designation PTA-11333, deposited with the ATCC on Oct. 6, 2010. In another embodiment, the invention provides an antibody or antigen binding fragment thereof that specifically binds to the same EGFR epitope as an antibody selected from the group consisting of ATCC Deposit Designation PTA-11331, deposited with the ATCC on Oct. 6, 2010, ATCC Deposit Designation PTA-11332, deposited with the ATCC on Oct. 6, 2010, and ATCC Deposit Designation PTA-11333, deposited with the ATCC on Oct. 6, 2010. In yet another embodiment, the invention provides an antibody or antigen binding fragment thereof that competitively inhibits binding of a reference antibody to human EGFR, wherein said reference antibody is selected from the group consisting of ATCC Deposit Designation PTA-11331, deposited with the ATCC on Oct. 6, 2010, ATCC Deposit Designation PTA-11332, deposited with the ATCC on Oct. 6, 2010, and ATCC Deposit Designation PTA-11333, deposited with the ATCC on Oct. 6, 2010.

In one embodiment, the invention provides an antibody or antigen binding fragment thereof that specifically binds to the same EGFR epitope as an antibody selected from the group consisting of: (a) an antibody comprising the VH polypeptide of SEQ ID NO:19 and the VL polypeptide of SEQ ID NO:24; (b) an antibody comprising the VH polypeptide of SEQ ID NO:20 and the VL polypeptide of SEQ ID NO:25; (c) an antibody comprising the VH polypeptide of SEQ ID NO:21 and the VL polypeptide of SEQ ID NO:26; (d) an antibody comprising the VH polypeptide of SEQ ID NO:21 and the VL polypeptide of SEQ ID NO:27; (e) an antibody comprising the VH polypeptide of SEQ ID NO:22 and the VL polypeptide of SEQ ID NO:28; (f) an antibody comprising the VH polypeptide of SEQ ID NO:23 and the VL polypeptide of SEQ ID NO:29; (g) an antibody comprising the VH polypeptide of SEQ ID NO:23 and the VL polypeptide of SEQ ID NO:30; (h) an antibody comprising the VH polypeptide of SEQ ID NO:69 and the VL polypeptide of SEQ ID NO:70; (i) an antibody comprising the VH polypeptide of SEQ ID NO:71 and the VL polypeptide of SEQ ID NO: 26; (j) an antibody comprising the VH polypeptide of SEQ ID NO:71 and the VL polypeptide of SEQ ID NO:27; (k) an antibody comprising the VH polypeptide of SEQ ID NO:72 and the VL polypeptide of SEQ ID NO:26; (l) an antibody comprising the VH polypeptide of SEQ ID NO:72 and the VL polypeptide of SEQ ID NO:27; (m) an antibody comprising the VH polypeptide of SEQ ID NO:73 and the VL polypeptide of SEQ ID NO:26; and (n) an antibody comprising the VH polypeptide of SEQ ID NO:73 and the VL polypeptide of SEQ ID NO:27.

In one embodiment, the invention provides an antibody or antigen binding fragment thereof that competitively inhibits binding of a reference antibody to human EGFR, wherein said reference antibody is selected from the group consisting of: (a) an antibody comprising the VH polypeptide of SEQ ID NO:19 and the VL polypeptide of SEQ ID NO:24; (b) an antibody comprising the VH polypeptide of SEQ ID NO:20 and the VL polypeptide of SEQ ID NO:25; (c) an antibody comprising the VH polypeptide of SEQ ID NO:21 and the VL polypeptide of SEQ ID NO:26; (d) an antibody comprising the VH polypeptide of SEQ ID NO:21 and the VL polypeptide of SEQ ID NO:27; (e) an antibody comprising the VH polypeptide of SEQ ID NO:22 and the VL polypeptide of SEQ ID NO:28; (f) an antibody comprising the VH polypeptide of SEQ ID NO:23 and the VL polypeptide of SEQ ID NO:29; (g) an antibody comprising the VH polypeptide of SEQ ID NO:23 and the VL polypeptide of SEQ ID NO:30; (h) an antibody comprising the VH polypeptide of SEQ ID NO:69 and the VL polypeptide of SEQ ID NO:70; (i) an antibody comprising the VH polypeptide of SEQ ID NO:71 and the VL polypeptide of SEQ ID NO:26; (j) an antibody comprising the VH polypeptide of SEQ ID NO:71 and the VL polypeptide of SEQ ID NO:27; (k) an antibody comprising the VH polypeptide of SEQ ID NO:72 and the VL polypeptide of SEQ ID NO:26; (l) an antibody comprising the VH polypeptide of SEQ ID NO:72 and the VL polypeptide of SEQ ID NO:27; (m) an antibody comprising the VH polypeptide of SEQ ID NO:73 and the VL polypeptide of SEQ ID NO:26; and (n) an antibody comprising the VH polypeptide of SEQ ID NO:73 and the VL polypeptide of SEQ ID NO:27.

In one embodiment, the invention provides an antibody or antigen binding fragment thereof that specifically binds to human EGFR, wherein the antibody or antigen binding fragment thereof comprises: (a) an immunoglobulin heavy chain variable region comprising CDR1, CDR2, and CDR3, which, with the exception of 1, 2, or 3 conservative amino acid substitutions, are respectively identical to the reference heavy chain CDR1 sequence of SEQ ID NO:1, the reference heavy chain CDR2 sequence of SEQ ID NO: 2, 4, 6, 63, or 64, and the reference heavy chain CDR3 sequence of SEQ ID NO: 3 or 5; and (b) an immunoglobulin a light chain variable region comprising CDR1, CDR2, and CDR3, which, with the exception of 1, 2, or 3 conservative amino acid substitutions, are respectively identical to the reference light chain CDR1 sequence of SEQ ID NO: 10, 13, or 14, the reference light chain sequence CDR2 of SEQ ID NO:11, and the reference light chain CDR3 sequence of SEQ ID NO: 12. In another embodiment, the antibody comprises: (a) an immunoglobulin heavy chain variable region comprising CDR1, CDR2, and CDR3, which are respectively identical to the reference heavy chain CDR1 sequence of SEQ ID NO:1, the reference heavy chain CDR2 sequence of SEQ ID NO: 2, 4, 6, 63, or 64, and the reference heavy chain CDR3 sequence of SEQ ID NO: 3 or 5; and (b) an immunoglobulin a light chain variable region comprising CDR1, CDR2, and CDR3, which are respectively identical to the reference light chain CDR1 sequence of SEQ ID NO: 10, 13, or 14, the reference light chain sequence CDR2 of SEQ ID NO:11, and the reference light chain CDR3 sequence of SEQ ID NO: 12.

In one embodiment, the invention provides an antibody or antigen binding fragment thereof that specifically binds to human EGFR, wherein the antibody or antigen binding fragment thereof comprises: (a) an immunoglobulin heavy chain variable region comprising CDR1, CDR2, and CDR3, which, with the exception of 1, 2, or 3 conservative amino acid substitutions, are respectively identical to the reference heavy chain CDR1 sequence of SEQ ID NO:1, the reference heavy chain CDR2 sequence of SEQ ID NO: 7, 8, or 9, and the reference heavy chain CDR3 sequence of SEQ ID NO: 3; and (b) an immunoglobulin a light chain variable region comprising CDR1, CDR2, and CDR3, which, with the exception of 1, 2, or 3 conservative amino acid substitutions, are respectively identical to the reference light chain CDR1 sequence of SEQ ID NO: 15 or 16, the reference light chain CDR2 sequence of SEQ ID NO:17, and the reference light chain CDR3 sequence of SEQ ID NO: 18. In another embodiment, the antibody comprises: (a) an immunoglobulin heavy chain variable region comprising CDR1, CDR2, and CDR3, which are respectively identical to the reference heavy chain CDR1 sequence of SEQ ID NO:1, the reference heavy chain CDR2 sequence of SEQ ID NO: 7, 8, or 9, and the reference heavy chain CDR3 sequence of SEQ ID NO: 3; and (b) an immunoglobulin a light chain variable region comprising CDR1, CDR2, and CDR3, which are respectively identical to the reference light chain CDR1 sequence of SEQ ID NO: 15 or 16, the reference light chain CDR2 sequence of SEQ ID NO:17, and the reference light chain CDR3 sequence of SEQ ID NO: 18.

In one embodiment, the invention provides an antibody or antigen binding fragment thereof that specifically binds to human EGFR, wherein the antibody or antigen binding fragment thereof comprises: (a) an immunoglobulin heavy chain variable region comprising CDR1, CDR2, and CDR3, which, with the exception of 1, 2, or 3 conservative amino acid substitutions, are respectively identical to the reference heavy chain CDR1 sequence of SEQ ID NO:1, the reference heavy chain CDR2 sequence of SEQ ID NO: 65, 66, or 67, and the reference heavy chain CDR3 sequence of SEQ ID NO: 3; and (b) an immunoglobulin a light chain variable region comprising CDR1, CDR2, and CDR3, which, with the exception of 1, 2, or 3 conservative amino acid substitutions, are respectively identical to the reference light chain CDR1 sequence of SEQ ID NO: 68 or 13, the reference light chain sequence CDR2 of SEQ ID NO:11, and the reference light chain CDR3 sequence of SEQ ID NO: 12. In another embodiment, the antibody comprises: (a) an immunoglobulin heavy chain variable region comprising CDR1, CDR2, and CDR3, which are respectively identical to the reference heavy chain CDR1 sequence of SEQ ID NO:1, the reference heavy chain CDR2 sequence of SEQ ID NO: 65, 66, or 67, and the reference heavy chain CDR3 sequence of SEQ ID NO: 3; and (b) an immunoglobulin a light chain variable region comprising CDR1, CDR2, and CDR3, which are respectively identical to the reference light chain CDR1 sequence of SEQ ID NO: 68 or 13, the reference light chain sequence CDR2 of SEQ ID NO:11, and the reference light chain CDR3 sequence of SEQ ID NO: 12.

In one embodiment, the antibody or antigen binding fragment of the invention is murine, non-human, humanized, chimeric, resurfaced, or human. In another embodiment, the antibody or antigen binding fragment thereof is a full length antibody. In another embodiment, the antibody or antigen binding fragment thereof is an antigen binding fragment. In another embodiment, the antibody or antigen binding fragment thereof comprises a Fab, Fab', F(ab')2, Fd, single chain Fv or scFv, disulfide linked Fv, V-NAR domain, IgNar, intrabody, IgGΔCH2, minibody, F(ab')3, tetrabody, triabody, diabody, single-domain antibody, DVD-Ig, Fcab, mAb2, (scFv) 2, or scFv-Fc.

The invention also provides a polypeptide comprising the VH and VL sequences described herein.

In one embodiment, the invention provides an antibody or polypeptide that binds both human and macaque EGFR with a substantially similar binding affinity. In one embodiment, the antibody or polypeptide binds to human and macaque EGFR with a Kd of about 1.0 to about 10 nM. In another embodiment, the antibody or polypeptide of binds to human and macaque EGFR with a Kd of about 1.0 nM or better. In another embodiment, binding affinity is measured by flow cytometry, Biacore, or radioimmunoassay.

In one embodiment, the invention provides an isolated cell producing an antibody or antigen binding fragment thereof, or polypeptide described herein.

In one embodiment, the invention provides a method of making an antibody or antigen binding fragment thereof, or polypeptide described herein comprising (a) culturing a cell that expresses the antibody, antigen-binding fragment thereof, or polypeptide, and (b) isolating said antibody, antigen-binding fragment thereof, or polypeptide from said cultured cell. In one embodiment the cell is a eukaryotic cell.

In one embodiment, the invention provides an immunoconjugate having the formula (A)-(L)-(C), wherein: (A) is an antibody or antigen binding fragment thereof, or polypeptide described herein; (L) is a linker; and (C) is a cytotoxic agent; and wherein said linker (L) links (A) to (C). In another embodiment, the linker is selected from the group consisting of a cleavable linker, a non-cleavable linker, a hydrophilic linker, and a dicarboxylic acid based linker. In another embodiment, the linker is a non-cleavable linker. In another embodiment, the linker is selected from the group consisting: N-succinimidyl 4-(2-pyridyldithio)pentanoate (SPP); N-succinimidyl 4-(2-pyridyldithio)butanoate (SPDB) or N-succinimidyl 4-(2-pyridyldithio)-2-sulfobutanoate (sulfo-SPDB); N-succinimidyl 4-(maleimidomethyl)cyclohexanecarboxylate (SMCC); N-sulfosuccinimidyl 4-(maleimidomethyl)cyclohexanecarboxylate (sulfoSMCC); N-succinimidyl-4-(iodoacetyl)-aminobenzoate (SIAB); and N-succinimidyl-[(N-maleimidopropionamido)-tetraethyleneglycol]ester (NHS-PEG4-maleimide). In a further embodiment, the linker is N-succinimidyl-[(N-maleimidopropionamido)-tetraethyleneglycol]ester (NHS-PEG4-maleimide).

In another embodiment, the immunoconjugate comprises a cytotoxic agent selected from the group consisting of a maytansinoid, maytansinoid analog, doxorubicin, a modified doxorubicin, benzodiazepine, taxoid, CC-1065, CC-1065 analog, duocarmycin, duocarmycin analog, calicheamicin, dolastatin, dolastatin analog, aristatin, tomaymycin derivative, and leptomycin derivative or a prodrug of the agent. In another embodiment, the cytotoxic agent is a maytansinoid. In a further embodiment, the cytotoxic agent is N(2')-deacetyl-N(2)-(3-mercapto-1-oxopropyl)-maytansine (DM1) or N(2)-deacetyl-N2-(4-mercapto-4-methyl-1-oxopentyl)-maytansine (DM4).

In one embodiment, the invention provides a pharmaceutical composition comprising an antibody or antigen binding fragment thereof, or polypeptide described herein, or an immunoconjugate described herein and a pharmaceutically acceptable carrier. In another embodiment, the pharmaceutical composition comprises a second anti-cancer agent.

In one embodiment, the invention provides a diagnostic reagent comprising an antibody or antigen binding fragment thereof, polypeptide, or immunoconjugate of the invention which is labeled. In one embodiment, the label is selected from the group consisting of a radiolabel, a fluorophore, a chromophore, an imaging agent and a metal ion.

In one embodiment, the invention provides a kit comprising an antibody or antigen binding fragment thereof, polypeptide, or immunoconjugate described herein.

In one embodiment, the invention provides a method for inhibiting the growth of a cell expressing EGFR comprising contacting the cell with an immunoconjugate or the pharmaceutical composition described herein. In another embodiment, the cell is a tumor cell.

In one embodiment, the invention provides a method for treating a patient having a neoplasm comprising administering to said patient a therapeutically effective amount of an immunoconjugate or pharmaceutical composition described herein. In another embodiment, the neoplasm is selected from the group consisting of: abdominal, bone, breast, digestive system, liver, pancreas, peritoneum, adrenal, parathyroid, pituitary, testicles, ovary, thymus, thyroid, eye, head and neck, central nervous system, peripheral nervous system, lymphatic system, pelvic, skin, soft tissue, spleen, thoracic region, and urogenital system. In another embodiment, the method comprises administering a second anti-cancer agent to the subject. In a farther embodiment, the second anti-cancer agent is a chemotherapeutic agent.

In one embodiment, the invention provides a method for treating a cell proliferative disorder in a patient comprising administering to said patient a therapeutically effective amount of an immunoconjugate or pharmaceutical composition described herein. In another embodiment, the cell proliferative disorder is selected from the group consisting of: adrenal cortex hyperplasia (Cushing's disease), congenital adrenal hyperplasia, endometrial hyperplasia, benign prostatic hyperplasia, breast hyperplasia, intimal hyperplasia, focal epithelial hyperplasia (Heck's disease), sebaceous hyperplasia, compensatory liver hyperplasia, and any other cell proliferation disease, besides neoplasia.

In one embodiment, the invention provides an isolated polynucleotide comprising a sequence that encodes a polypeptide at least 90% identical to a sequence selected from the group consisting of SEQ ID NOs: 39-43, 77-80, and 82-84. In another embodiment, the sequence is at least 95% identical a sequence selected from the group consisting of SEQ ID NOs: 39-43, 77-80, and 82-84. In another embodiment, the sequence is at least 99% identical to a sequence selected from the group consisting of SEQ ID NOs: 39-43, 77-80, and 82-84.

In one embodiment, the invention provides an isolated polynucleotide which comprises a sequence that is at least 90% identical to SEQ ID NOs: 44-50 and 81. In another embodiment, the polynucleotide comprises a sequence that is at least 95% identical to SEQ ID NOs: 44-50 and 81. In another embodiment, the polynucleotide comprises a sequence that is at least 99% identical to SEQ ID NOs: 44-50 and 81. In another embodiment, the invention provides an isolated polynucleotide comprising a sequence selected from the group consisting of SEQ ID NOs:39-58 and 77-84. In another embodiment, the invention provides a vector comprising the polynucleotides described herein. In another embodiment, the invention provides a host cell comprising the vectors described herein.

BRIEF DESCRIPTION OF THE DRAWINGS/FIGURES

FIG. 1 is a table describing the binding affinity of the indicated anti-EGFR antibodies to human EGFR (huEGFR) and monkey EGFR (moEGFR) antigen.

FIG. 9 is the alignment of the murine EGFR-7 variant light and heavy chain variable region sequences.

FIG. 10 is tables depicting specific framework surface residue changes in resurfacing of EGFR-7 $V_L$ (A) and $V_H$ (B).

FIG. 11 is tables depicting specific framework surface residue changes in resurfacing of EGFR-12 $V_L$ (A) and $V_H$ (B).

FIG. 12 is alignment of the resurfaced sequences and murine counterparts of EGFR-7 $V_L$ (A), EGFR-7 $V_H$ (B), EGFR-12 $V_L$ (C) and EGFR-12 $V_H$ (D).

FIG. 13 is tables depicting specific framework surface residue changes in CDR grafting of EGFR-7 $V_L$ (A) and $V_H$ (B).

FIG. 14 is alignment of the CDR grafted sequences and the murine counterparts of EGFR-7 $V_L$ (A) and EGFR-7 VH (B).

FIG. 15 shows line graphs depicting the binding competition between the murine antibody and its corresponding humanized antibody.

FIG. 19 shows line graphs depicting the cytotoxic activity of the indicated antibody and the corresponding antibody-maytansinoid conjugate in FaDu (A) and H292 (B) cell lines.

FIG. 20 shows line graphs depicting the cytotoxic activity of the indicated antibody and the corresponding antibody-maytansinoid conjugate in H226 (A) and SCC-4 (B) cell lines.

FIG. 23 shows line graphs depicting the capacity of the indicated antibodies and conjugates in inhibiting the growth of human primary keratinocytes (A) and H292 tumor cells (B).

FIG. 28 shows alignment of human and murine EGFR extracellular domain (ECD) sequences.

FIG. 29 shows alignment of sequences of huEGFRdIII, muEGFRdIII and chEGFRdIII.

FIG. 30 shows a line graph depicting the binding of huEGFR-7R antibody to the huEGFR, huEGFRdIII, muEGFRdIII and chEGFRdIII.

FIG. 31 shows a line graph depicting the binding of huEGFR-6 antibody to the huEGFR, huEGFRdIII, muEGFRdIII and chEGFRdIII.

FIG. 32 shows a line graph depicting the binding of muEGFR-7 antibody to the huEGFR, huEGFRdIII, muEGFRdIII and chEGFRdIII.

FIG. 33 shows a line graph depicting the binding of muEGFR-6 antibody to the huEGFR, huEGFRdIII, muEGFRdIII and chEGFRdIII.

FIG. 34 shows a line graph depicting the binding of muEGFR-12 antibody to the huEGFR, huEGFRdIII, muEGFRdIII and chEGFRdIII.

FIG. 35 shows a line graph depicting the binding of muEGFR-13 antibody to the huEGFR, huEGFRdIII, muEGFRdIII and chEGFRdIII.

FIG. 36 shows a line graph depicting the binding of cetuximab to the huEGFR, huEGFRdIII, muEGFRdIII and chEGFRdIII.

DETAILED DESCRIPTION OF THE INVENTION

Figure 2:
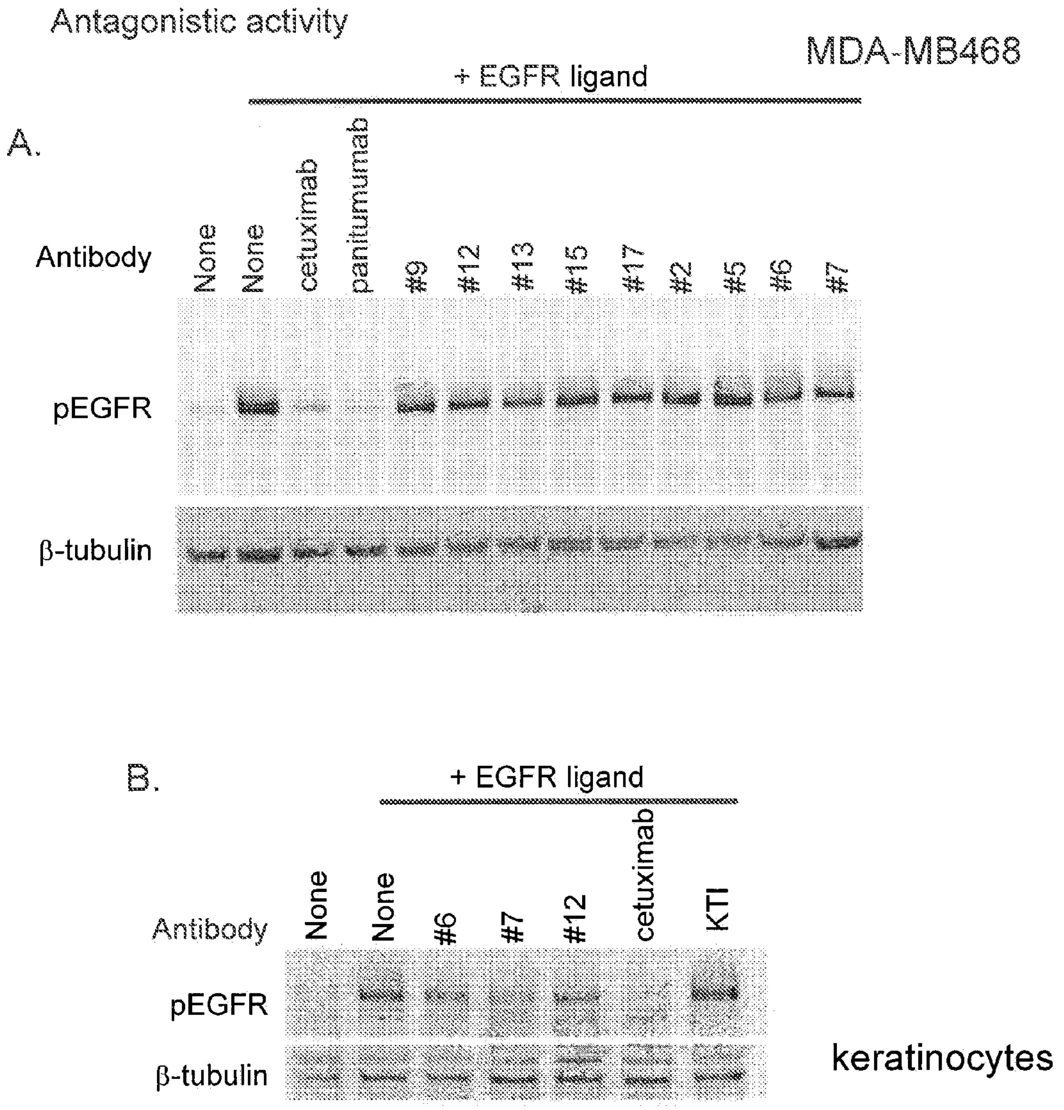
FIG. 2 is a Western blot data depicting the effect of the indicated anti-EGFR antibodies in ligand-induced EGFR phosphorylation in MDA-MB468 cells (A) and in human primary keratinocytes (B).

The present invention provides a new class of EGFR binding molecules which partially inhibit EGFR signaling, have no effect on EGFR-positive normal epithelial cells, including primary keratinocytes, but are highly cytotoxic to EGFR-overexpressing tumor cells. Further, immunoconjugates of anti-EGFR antibodies potentiate the anti-tumor activity of the antibodies.

I. Definitions

To facilitate an understanding of the present invention, a number of terms and phrases are defined below.

As used herein, "epidermal growth factor receptor" or "EGFR" refers to the mature, tyrosine kinase cell surface receptor. The term "soluble EGFR" or "sEGFR" refers to a portion of EGFR containing the extracellular, ligand-binding domain of EGFR. More specifically, sEGFR contains amino acids 1-619 of mature EGFR (Ullrich et al., Human Epidermal Growth Factor cDNA Sequence and Aberrant Expression of the Amplified Gene in A-431 Epidermoid Carcinoma Cells, Nature, Vol. 309, 418-25 (1986)).

The phrase "EGFR mediated cancer" refers to a cancer characterized by epithelial tumors in which EGFR is abnormally activated to levels greater than in normal, corresponding epithelial tissue. These greater levels of EGFR activity promote tumor growth in many types of cancer. Such cancers include, but are not limited to, non-small cell lung cancer, breast cancer, colorectal cancer, head and neck cancers, and prostate cancer. Abnormal activation of EGFR can arise from overexpression of the receptor, gene amplification, activating mutations, overexpression of receptor ligands, and/or loss of regulators of EGFR activity.

The term "antibody" means an immunoglobulin molecule that recognizes and specifically binds to a target, such as a protein, polypeptide, peptide, carbohydrate, polynucleotide, lipid, or combinations of the foregoing through at least one antigen recognition site within the variable region of the immunoglobulin molecule. As used herein, the term "antibody" encompasses intact polyclonal antibodies, intact monoclonal antibodies, antibody fragments (such as Fab, Fab', F(ab')2, and Fv fragments), single chain Fv (scFv) mutants, multispecific antibodies such as bispecific antibodies generated from at least two intact antibodies, chimeric antibodies, humanized antibodies, human antibodies, fusion proteins comprising an antigen determination portion of an antibody, and any other modified immunoglobulin molecule comprising an antigen recognition site so long as the antibodies exhibit the desired biological activity. An antibody can be of any the five major classes of immunoglobulins: IgA, IgD, IgE, IgG, and IgM, or subclasses (isotypes) thereof (e.g. IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well known subunit structures and three-dimensional configurations. Antibodies can be naked or conjugated to other molecules such as toxins, radioisotopes, etc.

A "blocking" antibody or an "antagonist" antibody is one which inhibits or reduces biological activity of the antigen it binds, such as EGFR. In some embodiments, blocking antibodies or antagonist antibodies substantially or completely inhibit the biological activity of the antigen. The biological activity can be reduced by 10%, 20%, 30%, 50%, 70%, 80%, 90%, 95%, or even 100%.

The phrase "ability to inhibit EGFR activation" with respect to an antibody as used herein, is intended to refer to an antibody whose binding to EGFR results in inhibition of human EGFR activation and the biological activity of human EGFR that occurs upon activation of the receptor. Measuring one or more indicators of EGFR biological activity as determined using either a cell proliferation assay, an apoptosis assay, a receptor binding assay, a receptor phosphorylation assay, or a mouse tumor model (see Examples) can assess an antibody's ability to inhibit EGFR activation.

The term "anti-EGFR antibody" or "an antibody that binds to EGFR" refers to an antibody that is capable of binding EGFR with sufficient affinity such that the antibody is useful as a diagnostic and/or therapeutic agent in targeting EGFR. Several anti-EGFR antibodies are known in the art. For example, cetuximab (Ab 225) and 528 Ab are described in U.S. Pat. No. 4,943,533, which is herein incorporated by reference.

The extent of binding of an anti-EGFR antibody to an unrelated, non-EGFR protein can be less than about 10% of the binding of the antibody to EGFR as measured, e.g., by a radioimmunoassay (RIA). In certain embodiments, an antibody that binds to EGFR has a dissociation constant (Kd) of ≤1 μM, ≤100 nM, ≤10 nM, ≤1 nM, or ≤0.1 nM.

As used herein, the term "epithelial toxicity" refers to an abnormality or dysfunction of the epithelium, and can be manifested in a patient being treated for cancer by administration of an EGFR inhibitor by one or more symptoms or conditions selected from skin rash, diarrhea, corneal thinning, hair atrophy or loss, hair follicle dysplasia, degeneration, necrosis or inflammation, interfollicular epidermal hyperplasia, or a failure to heal or a delayed healing after injury, among other symptoms. In one embodiment, the epithelial toxicity is manifested as a skin toxicity such as acneform or macro-papular rash.

The term "antibody fragment" refers to a portion of an intact antibody and refers to the antigenic determining variable regions of an intact antibody. Examples of antibody fragments include, but are not limited to Fab, Fab', F(ab')2, and Fv fragments, linear antibodies, single chain antibodies, and multispecific antibodies formed from antibody fragments.

A "monoclonal antibody" refers to a homogeneous antibody population involved in the highly specific recognition and binding of a single antigenic determinant, or epitope. This is in contrast to polyclonal antibodies that typically include different antibodies directed against different antigenic determinants. The term "monoclonal antibody" encompasses both intact and full-length monoclonal antibodies as well as antibody fragments (such as Fab, Fab', F(ab')2, Fv), single chain (scFv) mutants, fusion proteins comprising an antibody portion, and any other modified immunoglobulin molecule comprising an antigen recognition site. Furthermore, "monoclonal antibody" refers to such antibodies made in any number of manners including but not limited to by hybridoma, phage selection, recombinant expression, and transgenic animals.

The term "humanized antibody" refers to forms of non-human (e.g. murine) antibodies that are specific immunoglobulin chains, chimeric immunoglobulins, or fragments thereof that contain minimal non-human (e.g., murine) sequences. Typically, humanized antibodies are human immunoglobulins in which residues from the complementary determining region (CDR) are replaced by residues from the CDR of a non-human species (e.g. mouse, rat, rabbit, hamster) that have the desired specificity, affinity, and capability (Jones et al., 1986, *Nature,* 321:522-525; Riechmann et al., 1988, *Nature,* 332:323-327; Verhoeyen et al., 1988, *Science,* 239:1534-1536). In some instances, the Fv framework region (FR) residues of a human immunoglobulin are replaced with the corresponding residues in an antibody from a non-human species that has the desired specificity, affinity, and capability. The humanized antibody can be further modified by the substitution of additional residues either in the Fv framework region and/or within the replaced non-human residues to refine and optimize antibody specificity, affinity, and/or capability. In general, the humanized antibody will comprise substantially all of at least one, and typically two or three, variable domains containing all or substantially all of the CDR regions that correspond to the non-human immunoglobulin whereas all or substantially all of the FR regions are those of a human immunoglobulin consensus sequence. The humanized antibody can also comprise at least a portion of an immunoglobulin constant region or domain (Fc), typically that of a human immunoglobulin. Examples of methods used to generate humanized antibodies are described in U.S. Pat. No. 5,225,539.

A "variable region" of an antibody refers to the variable region of the antibody light chain or the variable region of the antibody heavy chain, either alone or in combination. The variable regions of the heavy and light chain each consist of four framework regions (FR) connected by three complementarity determining regions (CDRs) also known as hypervariable regions. The CDRs in each chain are held together in close proximity by the FRs and, with the CDRs from the other chain, contribute to the formation of the antigen-binding site of antibodies. There are at least two techniques for determining CDRs: (1) an approach based on cross-species sequence variability (i.e., Kabat et al. Sequences of Proteins of Immunological Interest, (5th ed., 1991, National Institutes of Health, Bethesda Md.)); and (2) an approach based on crystallographic studies of antigen-antibody complexes (Al-lazikani et al (1997) J. *Molec. Biol.* 273:927-948)). In addition, combinations of these two approaches are sometimes used in the art to determine CDRs.

The Kabat numbering system is generally used when referring to a residue in the variable domain (approximately residues 1-107 of the light chain and residues 1-113 of the heavy chain) (e.g, Kabat et al., Sequences of Immunological Interest. 5th Ed. Public Health Service, National Institutes of Health, Bethesda, Md. (1991)).

The amino acid position numbering as in Kabat, refers to the numbering system used for heavy chain variable domains or light chain variable domains of the compilation of antibodies in Kabat et al., Sequences of Proteins of Immunological Interest, 5th Ed. Public Health Service, National Institutes of Health, Bethesda, Md. (1991). Using this numbering system, the actual linear amino acid sequence can contain fewer or additional amino acids corresponding to a shortening of, or insertion into, a FR or CDR of the variable domain. For example, a heavy chain variable domain can include a single amino acid insert (residue 52a according to Kabat) after residue 52 of H2 and inserted residues (e.g. residues 82a, 82b, and 82c, etc according to Kabat) after heavy chain FR residue 82, The Kabat numbering of residues can be determined for a given antibody by alignment at regions of homology of the sequence of the antibody with a "standard" Kabat numbered sequence. Chothia refers instead to the location of the structural loops (Chothia and Lesk J. Mol. Biol. 196:901-917 (1987)). The end of the Chothia CDR-H1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). The AbM hypervariable regions represent a compromise between the Kabat CDRs and Chothia structural loops, and are used by Oxford Molecular's AbM antibody modeling software.

| Loop | Kabat | AbM | Chothia |
|---|---|---|---|
| L1 | L24-L34 | L24-L34 | L24-L34 |
| L2 | L50-L56 | L50-L56 | L50-L56 |
| L3 | L89-L97 | L89-L97 | L89-L97 |
| H1 | H31-H35B | H26-H35B | H26-H32..34 |
| | (Kabat Numbering) | | |
| H1 | H31-H35 | H26-H35 | H26-H32 |
| | (Chothia Numbering) | | |
| H2 | H50-H65 | H50-H58 | H52-H56 |
| H3 | H95-H102 | H95-H102 | H95-H102 |

The term "human antibody" means an antibody produced by a human or an antibody having an amino acid sequence corresponding to an antibody produced by a human made using any technique known in the art. This definition of a human antibody includes intact or full-length antibodies, fragments thereof, and/or antibodies comprising at least one human heavy and/or light chain polypeptide such as, for example, an antibody comprising murine light chain and human heavy chain polypeptides.

The term "chimeric antibodies" refers to antibodies wherein the amino acid sequence of the immunoglobulin molecule is derived from two or more species. Typically, the variable region of both light and heavy chains corresponds to the variable region of antibodies derived from one species of mammals (e.g. mouse, rat, rabbit, etc) with the desired specificity, affinity, and capability while the constant regions are homologous to the sequences in antibodies derived from another (usually human) to avoid eliciting an immune response in that species.

The term "epitope" or "antigenic determinant" are used interchangeably herein and refer to that portion of an antigen capable of being recognized and specifically bound by a particular antibody. When the antigen is a polypeptide, epitopes can be formed both from contiguous amino acids and noncontiguous amino acids juxtaposed by tertiary folding of a protein. Epitopes formed from contiguous amino acids are typically retained upon protein denaturing, whereas epitopes formed by tertiary folding are typically lost upon protein denaturing. An epitope typically includes at least 3, and more usually, at least 5 or 8-10 amino acids in a unique spatial conformation.

"Binding affinity" generally refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention. Specific illustrative embodiments are described in the following.

"Or better" when used herein to refer to binding affinity refers to a stronger binding between a molecule and its binding partner. "Or better" when used herein refers to a stronger binding, represented by a smaller numerical Kd value. For example, an antibody which has an affinity for an antigen of "0.6 nM or better", the antibody's affinity for the antigen is $<0.6$ nM, i.e. 0.59 nM, 0.58 nM, 0.57 nM etc. or any value less than 0.6 nM.

By "specifically binds," it is generally meant that an antibody binds to an epitope via its antigen binding domain, and that the binding entails some complementarity between the antigen binding domain and the epitope. According to this definition, an antibody is said to "specifically bind" to an epitope when it binds to that epitope, via its antigen binding domain more readily than it would bind to a random, unrelated epitope. The term "specificity" is used herein to qualify the relative affinity by which a certain antibody binds to a certain epitope. For example, antibody "A" may be deemed to have a higher specificity for a given epitope than antibody "B," or antibody "A" may be said to bind to epitope "C" with a higher specificity than it has for related epitope "D."

By "preferentially binds," it is meant that the antibody specifically binds to an epitope more readily than it would bind to a related, similar, homologous, or analogous epitope. Thus, an antibody which "preferentially binds" to a given epitope would more likely bind to that epitope than to a related epitope, even though such an antibody may cross-react with the related epitope.

An antibody is said to "competitively inhibit" binding of a reference antibody to a given epitope if it preferentially binds to that epitope to the extent that it blocks, to some degree, binding of the reference antibody to the epitope. Competitive inhibition may be determined by any method known in the art, for example, competition ELISA assays. An antibody may be said to competitively inhibit binding of the reference antibody to a given epitope by at least 90%, at least 80%, at least 70%, at least 60%, or at least 50%.

The phrase "substantially similar," or "substantially the same", as used herein, denotes a sufficiently high degree of similarity between two numeric values (generally one associated with an antibody of the invention and the other associated with a reference/comparator antibody) such that one of skill in the art would consider the difference between the two values to be of little or no biological and/or statistical significance within the context of the biological characteristic measured by said values (e.g., Kd values). The difference between said two values can be less than about 50%, less than about 40%, less than about 30%, less than about 20%, or less than about 10% as a function of the value for the reference/comparator antibody. The difference between two "substantially similar binding affinities" is generally less than about 10% as a function of the value for the reference/comparator antibody.

"Ligand-independent binding" as used herein denotes the ability of the EGFR binding agents to bind an epitope on human EGFR in the absence of ligand interaction with EGFR.

A polypeptide, antibody, polynucleotide, vector, cell, or composition which is "isolated" is a polypeptide, antibody, polynucleotide, vector, cell, or composition which is in a form not found in nature. Isolated polypeptides, antibodies, polynucleotides, vectors, cell or compositions include those which have been purified to a degree that they are no longer in a form in which they are found in nature. In some embodiments, an antibody, polynucleotide, vector, cell, or composition which is isolated is substantially pure.

As used herein, "substantially pure" refers to material which is at least 50% pure (i.e., free from contaminants), at least 90% pure, at least 95% pure, at least 98% pure, or at least 99% pure.

The term "immunoconjugate" or "conjugate" as used herein refers to a compound or a derivative thereof that is linked to a cell binding agent (i.e., an anti-EGFR antibody or fragment thereof) and is defined by a generic formula: C-L-A, wherein C=cytotoxin, L=linker, and A=cell binding agent or anti-EGFR antibody or antibody fragment. Immunoconjugates can also be defined by the generic formula in reverse order: A-L-C.

A "linker" is any chemical moiety that is capable of linking a compound, usually a drug, such as a maytansinoid, to a cell-binding agent such as an anti-EGFR antibody or a fragment thereof in a stable, covalent manner. Linkers can be susceptible to or be substantially resistant to acid-induced cleavage, light-induced cleavage, peptidase-induced cleavage, esterase-induced cleavage, and disulfide bond cleavage, at conditions under which the compound or the antibody remains active. Suitable linkers are well known in the art and include, for example, disulfide groups, thioether groups, acid labile groups, photolabile groups, peptidase labile groups and esterase labile groups. Linkers also include charged linkers, and hydrophilic forms thereof as described herein and know in the art.

The terms "cancer" and "cancerous" refer to or describe the physiological condition in mammals in which a population of cells are characterized by unregulated cell growth. Examples of cancer include, but are not limited to, carcinoma, lymphoma, blastoma, sarcoma, and leukemia. "Tumor" and "neoplasm" refer to one or more cells that result from excessive cell growth or proliferation, either benign (noncancerous) or malignant (cancerous) including pre-cancerous lesions. Examples of "cancer" or "tumorigenic" diseases which can be treated and/or prevented include neoplasms of the abdomen, bone, breast, digestive system, liver, pancreas, peritoneum, endocrine glands (adrenal, parathyroid, pituitary, testicles, ovary, thymus, thyroid), eye, head and neck, nervous system (central and peripheral), lymphatic system, pelvic, skin, soft tissue, spleen, thoracic region, and urogenital system.

The terms "cancer cell," "tumor cell," and grammatical equivalents refer to the total population of cells derived from a tumor or a pre-cancerous lesion, including both non-tumorigenic cells, which comprise the bulk of the tumor cell population, and tumorigenic stem cells (cancer stem cells). As used herein, the term "tumor cell" will be modified by the term "non-tumorigenic" when referring solely to those tumor cells lacking the capacity to renew and differentiate to distinguish those tumor cells from cancer stem cells.

The term "subject" refers to any animal (e.g., a mammal), including, but not limited to humans, non-human primates, rodents, and the like, which is to be the recipient of a particular treatment. Typically, the terms "subject" and "patient" are used interchangeably herein in reference to a human subject.

Administration "in combination with" one or more further therapeutic agents includes simultaneous (concurrent) and consecutive administration in any order.

The term "pharmaceutical formulation" refers to a preparation which is in such form as to permit the biological activity of the active ingredient to be effective, and which contains no additional components which are unacceptably toxic to a subject to which the formulation would be administered. The formulation can be sterile.

An "effective amount" of an antibody as disclosed herein is an amount sufficient to carry out a specifically stated purpose. An "effective amount" can be determined empirically and in a routine manner, in relation to the stated purpose.

The term "therapeutically effective amount" refers to an amount of an antibody or other drug effective to "treat" a disease or disorder in a subject or mammal. In the case of cancer, the therapeutically effective amount of the drug can reduce the number of cancer cells; reduce the tumor size; inhibit (i.e., slow to some extent or stop) cancer cell infiltration into peripheral organs; inhibit (i.e., slow to some extent or stop) tumor metastasis; inhibit, to some extent, tumor growth; and/or relieve to some extent one or more of the symptoms associated with the cancer. See the definition herein of "treating". To the extent the drug can prevent growth and/or kill existing cancer cells, it can be cytostatic and/or cytotoxic. A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount.

The word "label" when used herein refers to a detectable compound or composition which is conjugated directly or indirectly to the antibody so as to generate a "labeled" antibody. The label can be detectable by itself (e.g. radioisotope labels or fluorescent labels) or, in the case of an enzymatic label, can catalyze chemical alteration of a substrate compound or composition which is detectable.

A "chemotherapeutic agent" is a chemical compound useful in the treatment of cancer, regardless of mechanism of action. Chemotherapeutic agents include, for example, antagonists of CD20 such as Rituximab and cyclophosphamide, doxorubicin, vincristine, predinisone, fludarabine, etoposide, methotrexate, lenalidomide, chlorambucil, bentamustine and/or modified versions of such chemotherapeutics.

Terms such as "treating" or "treatment" or "to treat" or "alleviating" or "to alleviate" refer to both 1) therapeutic measures that cure, slow down, lessen symptoms of, and/or halt progression of a diagnosed pathologic condition or disorder and 2) prophylactic or preventative measures that prevent and/or slow the development of a targeted pathologic condition or disorder. Thus, those in need of treatment include those already with the disorder; those prone to have the disorder; and those in whom the disorder is to be prevented. In certain embodiments, a subject is successfully "treated" for cancer according to the methods of the present invention if the patient shows one or more of the following: a reduction in the number of or complete absence of cancer cells; a reduction in the tumor size; inhibition of or an absence of cancer cell infiltration into peripheral organs including, for example, the spread of cancer into soft tissue and bone; inhibition of or an absence of tumor metastasis; inhibition or an absence of tumor growth; relief of one or more symptoms associated with the specific cancer; reduced morbidity and mortality; improvement in quality of life; reduction in tumorigenicity, tumorigenic frequency, or tumorigenic capacity, of a tumor; reduction in the number or frequency of cancer stem cells in a tumor; differentiation of tumorigenic cells to a non-tumorigenic state; or some combination of effects.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase. A polynucleotide can comprise modified nucleotides, such as methylated nucleotides and their analogs. If present, modification to the nucleotide structure can be imparted before or after assembly of the polymer. The sequence of nucleotides can be interrupted by non-nucleotide components. A polynucleotide can be further modified after polymerization, such as by conjugation with a labeling component. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, cabamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars can be replaced, for example, by phosphonate groups, phosphate groups, protected by standard protecting groups, or activated to prepare additional linkages to additional nucleotides, or can be conjugated to solid supports. The 5' and 3' terminal OH can be phosphorylated or substituted with amines or organic capping group moieties of from 1 to 20 carbon atoms. Other hydroxyls can also be derivatized to standard protecting groups. Polynucleotides can also contain analogous forms of ribose or deoxyribose sugars that are generally known in the art, including, for example, 2'—O-methyl, 2'—O-allyl, 2'-fluoro- or 2'-azido-ribose, carbocyclic sugar analogs, .alpha.-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages can be replaced by alternative linking groups. These alternative linking groups include, but are not limited to, embodiments wherein phosphate is replaced by P(O)S ("thioate"), P(S)S ("dithioate"), "(O)$NR_2$ ("amidate"), P(O)R, P(O)OR', CO or $CH_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

The term "vector" means a construct, which is capable of delivering, and optionally expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

The terms "polypeptide," "peptide," and "protein" are used interchangeably herein to refer to polymers of amino acids of any length. The polymer can be linear or branched, it can comprise modified amino acids, and it can be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that, because the polypeptides of this invention are based upon antibodies, in certain embodiments, the polypeptides can occur as single chains or associated chains.

The terms "identical" or percent "identity" in the context of two or more nucleic acids or polypeptides, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity can be measured using sequence comparison software or algorithms or by visual inspection. Various algorithms and software are known in the art that can be used to obtain alignments of amino acid or nucleotide sequences. One such non-limiting example of a sequence alignment algorithm is the algorithm described in Karlin et al, 1990, *Proc. Natl. Acad. Sci.,* 87:2264-2268, as modified in Karlin et al., 1993, *Proc. Natl. Acad. Sci.,* 90:5873-5877, and incorporated into the NBLAST and XBLAST programs (Altschul et al., 1991, *Nucleic Acids Res.,* 25:3389-3402). In certain embodiments, Gapped BLAST can be used as described in Altschul et al., 1997, *Nucleic Acids Res.* 25:3389-3402. BLAST-2, WU-BLAST-2 (Altschul et al., 1996, *Methods in Enzymology,* 266:460-480), ALIGN, ALIGN-2 (Genentech, South San Francisco, Calif.) or Megalign (DNASTAR) are additional publicly available software programs that can be used to align sequences. In certain embodiments, the percent identity between two nucleotide sequences is determined using the GAP program in GCG software (e.g., using a NWSgapdna.CMP matrix and a gap weight of 40, 50, 60, 70, or 90 and a length weight of 1, 2, 3, 4, 5, or 6). In certain alternative embodiments, the GAP program in the GCG software package, which incorporates the algorithm of Needleman and Wunsch (*J. Mol. Biol.* (48): 444-453 (1970)) can be used to determine the percent identity between two amino acid sequences (e.g., using either a Blossum 62 matrix or a PAM250 matrix, and a gap weight of 16, 14, 12, 10, 8, 6, or 4 and a length weight of 1, 2, 3, 4, 5). Alternatively, in certain embodiments, the percent identity between nucleotide or amino acid sequences is determined using the algorithm of Myers and Miller (CABIOS, 4:11-17 (1989)). For example, the percent identity can be determined using the ALIGN program (version 2.0) and using a PAM120 with residue table, a gap length penalty of 12 and a gap penalty of 4. Appropriate parameters for maximal alignment by particular alignment software can be determined by one skilled in the art. In certain embodiments, the default parameters of the alignment software are used. In certain embodiments, the percentage identity "X" of a first amino acid sequence to a second sequence amino acid is calculated as 100×(Y/Z), where Y is the number of amino acid residues scored as identical matches in the alignment of the first and second sequences (as aligned by visual inspection or a particular sequence alignment program) and Z is the total number of residues in the second sequence. If the length of a first sequence is longer than the second sequence, the percent identity of the first sequence to the second sequence will be longer than the percent identity of the second sequence to the first sequence.

As a non-limiting example, whether any particular polynucleotide has a certain percentage sequence identity (e.g., is at least 80% identical, at least 85% identical, at least 90% identical, and in some embodiments, at least 95%, 96%, 97%, 98%, or 99% identical) to a reference sequence can, in certain embodiments, be determined using the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman, *Advances in Applied Mathematics* 2: 482 489 (1981), to find the best segment of homology between two sequences. When using Bestfit or any other sequence alignment program to determine whether a particular sequence is, for instance, 95% identical to a reference sequence according to the present invention, the parameters are set such that the percentage of identity is calculated over the full length of the reference nucleotide sequence and that gaps in homology of up to 5% of the total number of nucleotides in the reference sequence are allowed.

In some embodiments, two nucleic acids or polypeptides of the invention are substantially identical, meaning they have at least 70%, at least 75%, at least 80%, at least 85%, at least 90%, and in some embodiments at least 95%, 96%, 97%, 98%, 99% nucleotide or amino acid residue identity, when compared and aligned for maximum correspondence, as measured using a sequence comparison algorithm or by visual inspection. Identity can exist over a region of the sequences that is at least about 10, about 20, about 40-60 residues in length or any integral value therebetween, and can be over a longer region than 60-80 residues, for example, at least about 90-100 residues, and in some embodiments, the sequences are substantially identical over the full length of the sequences being compared, such as the coding region of a nucleotide sequence for example.

A "conservative amino acid substitution" is one in which one amino acid residue is replaced with another amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). For example, substitution of a phenylalanine for a tyrosine is a conservative substitution. In some embodiments, conservative substitutions in the sequences of the polypeptides and antibodies of the invention do not abrogate the binding of the polypeptide or antibody containing the amino acid sequence, to the antigen(s), i.e., the EGFR to which the polypeptide or antibody binds. Methods of identifying nucleotide and amino acid conservative substitutions which do not eliminate antigen binding are well-known in the art (see, e.g., Brummell et al., *Biochem.* 32: 1180-1 187 (1993); Kobayashi et al. *Protein Eng.* 12(10):879-884 (1999); and Burks et al. *Proc. Natl. Acad. Sci. USA* 94:412-417 (1997)).

As used in the present disclosure and claims, the singular forms "a," "an," and "the" include plural forms unless the context clearly dictates otherwise.

It is understood that wherever embodiments are described herein with the language "comprising," otherwise analogous embodiments described in terms of "consisting of" and/or "consisting essentially of" are also provided.

The term "and/or" as used in a phrase such as "A and/or B" herein is intended to include both "A and B," "A or B," "A," and "B." Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

II. EGFR Binding Agents

Tumors often overexpress growth factor receptors that bind various ligands ligand and facilitate unrestricted tumor growth. One example of such growth factor receptors are the receptors of the Epidermal Growth Factor Receptor (EGFR) protein family.

Signal transduction through members of the Epidermal Growth Factor Receptor (EGFR) protein family is dependent upon the formation of homodimers or heterodimers triggered by the binding of ligand. This receptor family is comprised of four membrane-bound proteins: EGFR, HER2/neu, HER3 and HER4. Overexpression of these proteins has been correlated with a poor prognosis in a number of types of cancer, including, but not limited to, breast, colon, ovarian, endometrial, gastric, pancreatic, prostate and salivary gland cancers. While a number of groups have developed strategies to target individual members of the EGFR protein family (e.g., HER2/neu or EGFR) to inhibit tumor growth, none of the treatments has been proven to ultimately cure these forms of cancer.

In accordance with this invention novel agents (e.g. antibodies) are provided that specifically bind to human EGFR. These novel agents partially inhibit EGFR signaling and have no effect on EGFR-positive normal epithelial cells, including primary keratinocytes. However, these agents are highly cytotoxic to EGFR-overexpressing tumor cells.

Thus, present invention provides agents that specifically bind human EGFR. These agents are referred to herein as "EGFR binding agents." In certain embodiments, the EGFR binding agents are antibodies, immunoconjugates or polypeptides. In some embodiments, the EGFR binding agents are humanized antibodies.

In certain embodiments, the EGFR-binding agents have one or more of the following effects: inhibit proliferation of tumor cells, reduce the tumorigenicity of a tumor by reducing the frequency of cancer stem cells in the tumor, inhibit tumor growth, increase survival, trigger cell death of tumor cells, differentiate tumorigenic cells to a non-tumorigenic state, or prevent metastasis of tumor cells.

In some embodiments, the EGFR-binding agents are capable of reducing tumor volume. The ability of a EGFR-binding agent to reduce tumor volume can be assessed, for example, by measuring a % T/C value, which is the median tumor volume of treated subjects divided by the median tumor volume of the control subjects. In some embodiments, treatment with a EGFR-binding agent results in a % T/C value that is less than about 55%, less than about 50%, less than about 45%, less than about 40%, less than about 35%, less than about 30%, less than about 25%, less than about 20%, less than about 15%, less than about 10%, or less than about 5%.

In certain embodiments, immunoconjugates or other agents that specifically bind human EGFR trigger cell death via a cytotoxic agent. For example, in certain embodiments, an antibody to a human EGFR antibody is conjugated to a maytansinoid that is activated in tumor cells expressing the EGFR by protein internalization. In certain alternative embodiments, the agent or antibody is not conjugated.

In certain embodiments, the EGFR-binding agents are capable of inhibiting tumor growth. In certain embodiments, the EGFR-binding agents are capable of inhibiting tumor growth in vivo (e.g., in a xenograft mouse model and/or in a human having cancer).

The EGFR-binding agents include EGFR antibodies EGFR-6, EGFR-7, and EGFR-12 and fragments, variants and derivatives thereof. The EGFR-binding agents also include EGFR-binding agents that specifically bind to the same EGFR epitope as the antibodies EGFR-6, EGFR-7, and EGFR-12. The EGFR-binding agents also include EGFR-binding agents that competitively inhibit the antibodies EGFR-6, EGFR-7, and EGFR-12.

The EGFR-binding agents also include EGFR-binding agents that comprise the heavy and light chain CDR sequences of EGFR-6, EGFR-7, and EGFR-12. The CDR sequences of EGFR-7 and EGFR-12, both murine and humanized are described in Tables 1 and 2 below.

TABLE 1

| Variable heavy chain CDR amino acid sequences | | | |
|---|---|---|---|
| Antibody | VH-CDR1 | VH-CDR2 | VH-CDR3 |
| EGFR-7 | TSYWMQ (SEQ ID NO: 1) | TIYPGDGDTT (SEQ ID NO: 2) | YDAPGYAMDY (SEQ ID NO: 3) |
| EGFR-7 variant composite sequences | TSYWMQ (SEQ ID NO: 1) | $Xaa_1Xaa_2$YPGDGD$Xaa_3Xaa_4$; $Xaa_1$ = T or A $Xaa_2$ = I or L $Xaa_3$ = T or A $Xaa_4$ = T, R, or S (SEQ ID NO: 4) | YDAPGY$Xaa_1$MDY $Xaa_1$ = A or T (SEQ ID NO: 5) |
| EGFR-7 Kabat HC CDR2 | | $Xaa_1Xaa_2$YPGDGD$Xaa_3Xaa_4Xaa_5$QKF$Xaa_6$G $Xaa_1$ = T or A $Xaa_2$ = I or L $Xaa_3$ = T or A $Xaa_4$ = T, R, or S $Xaa_5$ = Y, T, or I $Xaa_6$ = Q or K (SEQ ID NO: 6) | |
| EGFR-12 | TSYWMQ (SEQ ID NO: 1) | TIYPGDGDTR (SEQ ID NO: 7) | YDAPGYAMDY (SEQ ID NO: 3) |
| Kabat HC (murine) | | TIYPGDGDTRYIQKFKG (SEQ ID NO: 8) | |
| Kabat HC (resurfaced) | | TIYPGDGDTRYIQKFQG (SEQ ID NO: 9) | |
| EGFR-6 | TSYWMQ (SEQ ID NO: 1) | ALYPGDGDAR (SEQ ID NO: 65) | YDAPGYAMDY (SEQ ID NO: 3) |
| Kabat HC (murine) | | ALYPGDGDARYTQKFKG (SEQ ID NO: 66) | |
| Kabat HC (resurfaced) | | ALYPGDGDARYTQKFQG (SEQ ID NO: 67) | |

TABLE 2

| Variable light chain CDR amino acid sequences | | | |
|---|---|---|---|
| Antibody | VL-CDR1 | VL-CDR2 | VL-CDR3 |
| EGFR-7 | KASQDINNYLA (murine and resurfaced v1.01) (SEQ ID NO: 10) | YTSTLHP (SEQ ID NO: 11) | LQYDNLLYT (SEQ ID NO: 12) |
| | RASQDINNYLA (resurfaced v1.0 and CDR grafted) (SEQ ID NO: 13) | | |
| EGFR-7 variant composite sequences | $Xaa_1$ASQDINNY$Xaa_2$A $Xaa_1$ = K or R $Xaa_2$ = L or I (SEQ ID NO: 14) | YTSTLHP (SEQ ID NO: 11) | LQYDNLLYT (SEQ ID NO: 12) |
| EGFR-12 | RASKSISKYLA (murine and resurfaced v1.01) (SEQ ID NO: 15) | | |
| | RASQSISRYLA (resurfaced v1.0) (SEQ ID NO: 16) | SGSTLQS (SEQ ID NO: 17) | QQHNEYPWT (SEQ ID NO: 18) |
| EGFR-6 (murine) | KASQDINNYIA (SEQ ID NO: 68) | YTSTLHP (SEQ ID NO: 11) | LQYDNLLYT (SEQ ID NO: 12) |
| (resurfaced) | RASQDINNYLA (SEQ ID NO: 13) | | |

The EGFR binding molecules can be antibodies or antigen binding fragments that specifically bind to EGFR that comprise the CDRs of EGFR-6, EGFR-7, and EGFR-12 with up to four (i.e. 0, 1, 2, 3, or 4) conservative amino acid substitutions per CDR.

Polypeptides can comprise one of the individual variable light chains or variable heavy chains described herein. Antibodies and polypeptides can also comprise both a variable light chain and a variable heavy chain. The variable light chain and variable heavy chain sequences of murine and humanized EGFR-7 and EGFR-12 antibodies are provided in Tables 3 and 4 below.

TABLE 3

Variable heavy chain amino acid sequences

| Antibody | VH Amino Acid Sequence |
|---|---|
| muEGFR-7 $V_H$ | QVQLQQSGAELARPGASVKLSCKASGYTFTSYWMQWVKQRPGQGLECIGTIYPG<br>DGDTTYTQKFKGKATLTADKSSSTAYMQLSSLASEDSAVYYCARYDAPGYAMD<br>YWGQGTSVTVSS<br>(SEQ ID NO: 19) |
| muEGFR-12 $V_H$ | QVQLQQSGTELARPGASVKLSCKASGYTFTSYWMQWVKQRPGQGLECIGTIYPG<br>DGDTRYIQKFKGKATLTADKSSSTAYMQLSSLASEDSAVYYCARYDAPGYAMD<br>YWGQGTSVTVSS<br>(SEQ ID NO: 20) |
| huEGFR-7 $V_H$ | QVQLVQSGAEVAKPGASVKLSCKASGYTFTSYWMQWVKQRPGQGLECIGTIYP<br>GDGDTTYTQKFQGKATLTADKSSSTAYMQLSSLRSEDSAVYYCARYDAPGYAM<br>DYWGQGTLVTVSS<br>(SEQ ID NO: 21) |
| huEGFR-7 $V_H$_CDR grafted | QVQLVQSGAEVKKPGASVKVSCKASGYTFTSYWMQWVRQAPGQGLEWMGTIY<br>PGDGDTTYTQKFKGRVTMTRDTSTSTVYMELSSLRSEDTAVYYCARYDAPGYA<br>MDYWGQGTLVTVSS<br>(SEQ ID NO: 22) |
| huEGFR-12 $V_H$ | QVQLVQSGAEVAKPGASVKLSCKASGYTFTSYWMQWVKQRPGQGLECIGTIYP<br>GDGDTRYIQKFQGKATLTADKSSSTAYMQLSSLRSEDSAVYYCARYDAPGYAM<br>DYWGQGTLVTVSS<br>(SEQ ID NO: 23) |
| muEGFR-6 $V_H$ | QVQLQQSGAELARPGASVKLSCKASGYTFTSYWMQWVKQRPGQGLECIGALYP<br>GDGDARYTQKFKGKATLTADRSSSTAYMQLSSLASEDSAVYYCARYDAPGYAM<br>DYWGQGTSVTVAS (SEQ ID NO: 69) |
| huEGFR-6 $V_H$ v1.0 | QVQLVQSGAEVAKPGASVKLSCKASGYTFTSYWMQWVKQRPGQGLECIGALYP<br>GDGDARYTQKFQGKATLTADTSSSTAYMQLSSLRSEDSAVYYCARYDAPGYAM<br>DYWGQGTLVTVSS (SEQ ID NO: 71) |
| huEGFR-6 $V_H$ v1.11 | QVQLVQSGAEVAKPGASVKLSCKASGYTFTSYWMQWVKQRPGQGLEWIGALY<br>PGDGDARYTQKFQGKATLTADTSSSTAYMQLSSLRSEDSAVYYCARYDAPGYA<br>MDYWGQGTLVTVSS (SEQ ID NO: 72) |
| huEGFR-7 $V_H$ v1.11 | QVQLVQSGAEVAKPGASVKLSCKASGYTFTSYWMQWVKQRPGQGLEWIGTIYP<br>GDGDTTYTQKFQGKATLTADKSSSTAYMQLSSLRSEDSAVYYCARYDAPGYAM<br>DYWGQGTLVTVSS (SEQ ID NO: 73) |

TABLE 4

Variable light chain amino acid sequences

| Antibody | VL Amino Acid Sequence |
|---|---|
| muEGFR-7 $V_L$ | DIQMTQSPSSLSASLGGKVTITCKASQDINNYLAWYQHKPGKGPRLLIHYTSTLHP<br>GIPSRFSGSGSGRDYSFSISNLEPEDIATYYCLQYDNLLYTFGGGTKLEIKR<br>(SEQ ID NO: 24) |
| muEGFR-12 $V_L$ | DVQITQSPSYLAASPGETITINCRASKSISKYLAWYQEKPGKTNKLLIYSGSTLQSGI<br>PSRFSGSGSGTDFTLTISSLEPEDFAMYYCQQHNEYPWTFGGGTKLEIKR<br>(SEQ ID NO: 25) |
| huEGFR-7 $V_L$ v1.0 | DIQMTQSPSSLSASVGDRVTITCRASQDINNYLAWYQHKPGKGPKLLIHYTSTLHP<br>GIPSRFSGSGSGRDYSFSISSLEPEDIATYYCLQYDNLLYTFGQGTKLEIKR<br>(SEQ. ID NO: 26) |
| huEGFR-7 $V_L$ v1.01 | DIQMTQSPSSLSASVGDRVTITCKASQDINNYLAWYQHKPGKGPKLLIHYTSTLHP<br>GIPSRFSGSGSGRDYSFSISSLEPEDIATYYCLQYDNLLYTFGQGTKLEIKR<br>(SEQ ID NO: 27) |

TABLE 4-continued

| Variable light chain amino acid sequences | |
|---|---|
| Antibody | VL Amino Acid Sequence |
| huEGFR-7 $V_L$_CDR grafted | DIQMTQSPSSLSASVGDRVTITCRASQDINNYLAWYQQKPGKAPKLLIYYTSTLHP GVPSRFSGSGSGTDFTFTISSLQPEDIATYYCLQYDNLLYTFGQGTKVEIKR (SEQ ID NO: 28) |
| huEGFR-12 $V_L$ v1.0 | DVQITQSPSSLAASVGERITINCRASQSISRYLAWYQEKPGKTNKLLIYSGSTLQSG IPSRFSGSGSGTDFTLTISSLEPEDFAMYYCQQHNEYPWTFGQGTKLEIKR (SEQ ID NO: 29) |
| huEGFR-12 $V_L$ v1.01 | DVQITQSPSSLAASVGERITINCRASKSISKYLAWYQEKPGKTNKLLIYSGSTLQSG IPSRFSGSGSGTDFTLTISSLEPEDFAMYYCQQHNEYPWTFGQGTKLEIKR (SEQ ID NO: 30) |
| muEGFR6 $V_L$ | DIQMTQSPSSLSASLGGKVTITCKASQDINNYIAWYQHKPGKGPRLLIHYTSTLHP GIPSRFSGSGSGRDYSFSISNLEPEDIATYYCLQYDNLLYTFGGGTKLEIKR (SEQ ID NO: 70) |

Also provided are polypeptides that comprise: (a) a polypeptide having at least about 90% sequence identity to SEQ ID NOs:19-23, 69, and 71-76; and/or (b) a polypeptide having at least about 90% sequence identity to SEQ ID NOs: 24-30 and 70. In certain embodiments, the polypeptide comprises a polypeptide having at least about 95%, at least about 96%, at least about 97%, at least about 98%, or at least about 99% sequence identity to SEQ ID NOs:19-30 and 69-76. Thus, in certain embodiments, the polypeptide comprises (a) a polypeptide having at least about 95% sequence identity to SEQ ID NOs: 19-23, 69, and 71-76, and/or (b) a polypeptide having at least about 95% sequence identity to SEQ ID NOs: 24-30 and 70. In certain embodiments, the polypeptide comprises (a) a polypeptide having the amino acid sequence of SEQ ID NOs: 19-23, 69, and 71-76; and/or (b) a polypeptide having the amino acid sequence of SEQ ID NOs:24-30 and 70. In certain embodiments, the polypeptide is an antibody and/or the polypeptide specifically binds EGFR. In certain embodiments, the polypeptide is a murine, chimeric, or humanized antibody that specifically binds EGFR. In certain embodiments, the polypeptide having a certain percentage of sequence identity to SEQ ID NOs: 19-30 and 69-76 differs from SEQ ID NOs: 19-30 and 69-76 by conservative amino acid substitutions only.

TABLE 5

| Full-length heavy chain and light chain amino acid sequences | |
|---|---|
| Antibody | VH Amino Acid Sequence |
| huEGFR-7 HC | QVQLVQSGAEVAKPGASVKLSCKASGYTFTSYWMQWVKQRPGQGLECIGTIYPGD GDTTYTQKFQGKATLTADKSSSTAYMQLSSLRSEDSAVYYCARYDAPGYAMDYW GQGTLVTVSSASTKGPSVFPLAPSSKSTSGGTAALGCLVKDYFPEPVTVSWNSGALT SGVHTFPAVLQSSGLYSLSSVVTVPSSSLGTQTYICNVNHKPSNTKVDKKVEPKSCD KTHTCPPCPAPELLGGPSVFLFPPKPKDTLMISRTPEVTCVVVDVSHEDPEVKFNWY VDGVEVHNAKTKPREEQYNSTYRVVSVLTVLHQDWLNGKEYKCKVSNKALPAPIE KTISKAKGQPREPQVYTLPPSRDELTKNQVSLTCLVKGFYPSDIAVEWESNGQPENN YKTTPPVLDSDGSFFLYSKLTVDKSRWQQGNVFSCSVMHEALHNHYTQKSLSLSPG (SEQ ID NO: 31) |
| huEGFR-7 HC_CDR grafted | QVQLVQSGAEVKKPGASVKVSCKASGYTFTSYWMQWVRQAPGQGLEWMGTIYPG DGDTTYTQKFKGRVTMTRDTSTSTVYMELSSLRSEDTAVYYCARYDAPGYAMDYW GQGTLVTVSSASTKGPSVFPLAPSSKSTSGGTAALGCLVKDYFPEPVTVSWNSGALT SGVHTFPAVLQSSGLYSLSSVVTVPSSSLGTQTYICNVNHKPSNTKVDKKVEPKSCDK THTCPPCPAPELLGGPSVFLFPPKPKDTLMISRTPEVTCVVVDVSHEDPEVKFNWYVD GVEVHNAKTKPREEQYNSTYRVVSVLTVLHQDWLNGKEYKCKVSNKALPAPIEKTIS KAKGQPREPQVYTLPPSRDELTKNQVSLTCLVKGFYPSDIAVEWESNGQPENNYKTT PPVLDSDGSFFLYSKLTVDKSRWQQGNVFSCSVMHEALHNHYTQKSLSLSPG (SEQ ID NO: 32) |
| huEGFR-7 LCv1.0 | DIQMTQSPSSLSASVGDRVTITCRASQDINNYLAWYQHKPGKGPKLLIHYTSTLHPGI PSRFSGSGSGRDYSFSISSLEPEDIATYYCLQYDNLLYTFGQGTKLEIKRTVAAPSVFIF PPSDEQLKSGTASVVCLLNNFYPREAKVQWKVDNALQSGNSQESVTEQDSKDSTYSL SSTLTLSKADYEKHKVYACEVTHQGLSSPVTKSFNRGEC (SEQ ID NO: 33) |
| huEGFR-7 LCv1.01 | DIQMTQSPSSLSASVGDRVTITCKASQDINNYLAWYQHKPGKGPKLLIHYTSTLHPGI PSRFSGSGSGRDYSFSISSLEPEDIATYYCLQYDNLLYTFGQGTKLEIKRTVAAPSVFIF PPSDEQLKSGTASVVCLLNNFYPREAKVQWKVDNALQSGNSQESVTEQDSKDSTYS LSSTLTLSKADYEKHKVYACEVTHQGLSSPVTKSFNRGEC (SEQ ID NO: 34) |

TABLE 5-continued

Full-length heavy chain and light chain amino acid sequences

| Antibody | VH Amino Acid Sequence |
|---|---|
| huEGFR-7<br>LC_CDR<br>grafted | DIQMTQSPSSLSASVGDRVTITCRASQDINNYLAWYQQKPGKAPKLLIYYTSTLHPG<br>VPSRFSGSGSGTDFTFTISSLQPEDIATYYCLQYDNLLYTFGQGTKVEIKRTVAAPSV<br>FIFPPSDEQLKSGTASVVCLLNNFYPREAKVQWKVDNALQSGNSQESVTEQDSKDS<br>TYSLSSTLTLSKADYEKHKVYACEVTHQGLSSPVTKSFNRGEC<br>(SEQ ID NO: 35) |
| huEGFR-12<br>HC | QVQLVQSGAEVAKPGASVKLSCKASGYTFTSYWMQWVKQRPGQGLECIGTIYPGD<br>GDTRYIQKFQGKATLTADKSSSTAYMQLSSLRSEDSAVYYCARYDAPGYAMDYW<br>GQGTLVTVSSASTKGPSVFPLAPSSKSTSGGTAALGCLVKDYFPEPVTVSWNSGAL<br>TSGVHTFPAVLQSSGLYSLSSVVTVPSSSLGTQTYICNVNHKPSNTKVDKKVEPKSC<br>DKTHTCPPCPAPELLGGPSVFLFPPKPKDTLMISRTPEVTCVVVDVSHEDPEVKFNW<br>YVDGVEVHNAKTKPREEQYNSTYRVVSVLTVLHQDWLNGKEYKCKVSNKALPAP<br>IEKTISKAKGQPREPQVYTLPPSRDELTKNQVSLTCLVKGFYPSDIAVEWESNGQPE<br>NNYKTTPPVLDSDGSFFLYSKLTVDKSRWQQGNVFSCSVMHEALHNHYTQKSLSL<br>SPG (SEQ ID NO: 36) |
| huEGFR-12<br>LCv.1.0 | DVQITQSPSSLAASVGERITINCRASQSISRYLAWYQEKPGKTNKLLIYSGSTLQSGI<br>PSRFSGSGSGTDFTLTISSLEPEDFAMYYCQQHNEYPWTFGQGTKLEIKRTVAAPSV<br>FIFPPSDEQLKSGTASVVCLLNNFYPREAKVQWKVDNALQSGNSQESVTEQDSKDS<br>TYSLSSTLTLSKADYEKHKVYACEVTHQGLSSPVTKSFNRGEC<br>(SEQ ID NO: 37) |
| huEGFR-12<br>LCv.1.01 | DVQITQSPSSLAASVGERITINCRASKSISKYLAWYQEKPGKTNKLLIYSGSTLQSGI<br>PSRFSGSGSGTDFTLTISSLEPEDFAMYYCQQHNEYPWTFGQGTKLEIKRTVAAPSV<br>FIFPPSDEQLKSGTASVVCLLNNFYPREAKVQWKVDNALQSGNSQESVTEQDSKD<br>STYSLSSTLTLSKADYEKHKVYACEVTHQGLSSPVTKSFNRGEC<br>(SEQ ID NO: 38) |
| huEGFR-6<br>HCv1.0 | QVQLVQSGAEVAKPGASVKLSCKASGYTFTSYWMQWVKQRPGQGLECIGALYPG<br>DGDARYTQKFQGKATLTADTSSSTAYMQLSSLRSEDSAVYYCARYDAPGYAMDY<br>WGQGTLVTVSSASTKGPSVFPLAPSSKSTSGGTAALGCLVKDYFPEPVTVSWNSGA<br>LTSGVHTFPAVLQSSGLYSLSSVVTVPSSSLGTQTYICNVNHKPSNTKVDKKVEPKS<br>CDKTHTCPPCPAPELLGGPSVFLFPPKPKDTLMISRTPEVTCVVVDVSHEDPEVKFN<br>WYVDGVEVHNAKTKPREEQYNSTYRVVSVLTVLHQDWLNGKEYKCKVSNKALP<br>APIEKTISKAKGQPREPQVYTLPPSRDELTKNQVSLTCLVKGFYPSDIAVEWESNGQ<br>PENNYKTTPPVLDSDGSFFLYSKLTVDKSRWQQGNVFSCSVMHEALHNHYTQKSL<br>SLSPG (SEQ ID NO: 74) |
| huEGFR-6<br>HCv1.11 | QVQLVQSGAEVAKPGASVKLSCKASGYTFTSYWMQWVKQRPGQGLEWIGALYP<br>GDGDARYTQKFQGKATLTADTSSSTAYMQLSSLRSEDSAVYYCARYDAPGYAMD<br>YWGQGTLVTVSSASTKGPSVFPLAPSSKSTSGGTAALGCLVKDYFPEPVTVSWNSG<br>ALTSGVHTFPAVLQSSGLYSLSSVVTVPSSSLGTQTYICNVNHKPSNTKVDKKVEPK<br>SCDKTHTCPPCPAPELLGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKAL<br>PAPIEKTISKAKGQPREPQVYTLPPSRDELTKNQVSLTCLVKGFYPSDIAVEWESNGQ<br>PENNYKTTPPVLDSDGSFFLYSKLTVDKSRWQQGNVFSCSVMHEALHNHYTQKSL<br>SLSPG (SEQ ID NO: 75) |
| huEGFR-7<br>HCv1.11 | QVQLVQSGAEVAKPGASVKLSCKASGYTFTSYWMQWVKQRPGQGLEWIGTIYPG<br>DGDTTYTQKFQGKATLTADKSSSTAYMQLSSLRSEDSAVYYCARYDAPGYAMDY<br>WGQGTLVTVSSASTKGPSVFPLAPSSKSTSGGTAALGCLVKDYFPEPVTVSWNSGA<br>LTSGVHTFPAVLQSSGLYSLSSVVTVPSSSLGTQTYICNVNHKPSNTKVDKKVEPKS<br>CDKTHTCPPCPAPELLGGPSVFLFPPKPKDTLMISRTPEVTCVVVDVSHEDPEVKFN<br>WYVDGVEVHNAKTKPREEQYNSTYRVVSVLTVLHQDWLNGKEYKCKVSNKALP<br>APIEKTISKAKGQPREPQVYTLPPSRDELTKNQVSLTCLVKGFYPSDIAVEWESNGQ<br>PENNYKTTPPVLDSDGSFFLYSKLTVDKSRWQQGNVFSCSVMHEALHNHYTQKSL<br>SLSPG (SEQ ID NO: 76) |

Also provided are polypeptides that comprise: (a) a polypeptide having at least about 90% sequence identity to SEQ ID NOs:31, 32, and 36; and/or (b) a polypeptide having at least about 90% sequence identity to SEQ ID NOs:33-35, 37, and 38. In certain embodiments, the polypeptide comprises a polypeptide having at least about 95%, at least about 96%, at least about 97%, at least about 98%, or at least about 99% sequence identity to SEQ ID NOs:31-38. Thus, in certain embodiments, the polypeptide comprises (a) a polypeptide having at least about 95% sequence identity to SEQ ID NOs: 31, 32, and 36, and/or (b) a polypeptide having at least about 95% sequence identity to SEQ ID NOs: 33-35, 37, and 38. In certain embodiments, the polypeptide comprises (a) a polypeptide having the amino acid sequence of SEQ ID NOs: 31, 32, and 36; and/or (b) a polypeptide having the amino acid sequence of SEQ ID NOs: 33-35, 37, and 38. In certain embodiments, the polypeptide is an antibody and/or the polypeptide specifically binds EGFR. In certain embodiments, the polypeptide is a humanized antibody that specifically binds EGFR In certain embodiments, the polypeptide having a certain percentage of sequence identity to SEQ ID NOs:31-38 differs from SEQ ID NOs:31-38 by conservative amino acid substitutions only.

In certain embodiments, the EGFR antibody is the antibody produced from a hybridoma selected from the group consisting of ATCC Deposit Designation PTA-11331 (EGFR-6), deposited with the ATCC on Oct. 6, 2010, ATCC Deposit Designation PTA-11332 (EGFR-7), deposited with the ATCC on Oct. 6, 2010, and ATCC Deposit Designation PTA-11333 (EGFR-12), deposited with the ATCC on Oct. 6, 2010. In certain embodiments, the antibody comprises the VH-CDRs and the VL-CDRS of the antibody produced from a hybridoma selected from the group consisting of PTA-11331, PTA-11332, and PTA-11333.

Monoclonal antibodies can be prepared using hybridoma methods, such as those described by Kohler and Milstein (1975) Nature 256:495. Using the hybridoma method, a mouse, hamster, or other appropriate host animal, is immunized as described above to elicit the production by lymphocytes of antibodies that will specifically bind to an immunizing antigen. Lymphocytes can also be immunized in vitro. Following immunization, the lymphocytes are isolated and fused with a suitable myeloma cell line using, for example, polyethylene glycol, to form hybridoma cells that can then be selected away from unfused lymphocytes and myeloma cells. Hybridomas that produce monoclonal antibodies directed specifically against a chosen antigen as determined by immunoprecipitation, immunoblotting, or by an in vitro binding assay (e.g. radioimmunoassay (RIA); enzyme-linked immunosorbent assay (ELISA)) can then be propagated either in vitro culture using standard methods (Goding, Monoclonal Antibodies: Principles and Practice, Academic Press, 1986) or in vivo as ascites tumors in an animal. The monoclonal antibodies can then be purified from the culture medium or ascites fluid as described for polyclonal antibodies above.

Alternatively monoclonal antibodies can also be made using recombinant DNA methods as described in U.S. Pat. No. 4,816,567. The polynucleotides encoding a monoclonal antibody are isolated from mature B-cells or hybridoma cell, such as by RT-PCR using oligonucleotide primers that specifically amplify the genes encoding the heavy and light chains of the antibody, and their sequence is determined using conventional procedures. The isolated polynucleotides encoding the heavy and light chains are then cloned into suitable expression vectors, which when transfected into host cells such as *E. coli* cells, simian COS cells, Chinese hamster ovary (CHO) cells, or myeloma cells that do not otherwise produce immunoglobulin protein, monoclonal antibodies are generated by the host cells. Also, recombinant monoclonal antibodies or fragments thereof of the desired species can be isolated from phage display libraries expressing CDRs of the desired species as described (McCafferty et al., 1990, Nature, 348:552-554; Clackson et al., 1991, Nature, 352:624-628; and Marks et al., 1991, J. Mol. Biol., 222:581-597).

The polynucleotide(s) encoding a monoclonal antibody can further be modified in a number of different manners using recombinant DNA technology to generate alternative antibodies. In some embodiments, the constant domains of the light and heavy chains of, for example, a mouse monoclonal antibody can be substituted 1) for those regions of, for example, a human antibody to generate a chimeric antibody or 2) for a non-immunoglobulin polypeptide to generate a fusion antibody. In some embodiments, the constant regions are truncated or removed to generate the desired antibody fragment of a monoclonal antibody. Site-directed or high-density mutagenesis of the variable region can be used to optimize specificity, affinity, etc. of a monoclonal antibody.

In some embodiments, the monoclonal antibody against the human EGFR is a humanized antibody. In certain embodiments, such antibodies are used therapeutically to reduce antigenicity and HAMA (human anti-mouse antibody) responses when administered to a human subject. Humanized antibodies can be produced using various techniques known in the art. In certain alternative embodiments, the antibody to EGFR is a human antibody.

Human antibodies can be directly prepared using various techniques known in the art. Immortalized human B lymphocytes immunized in vitro or isolated from an immunized individual that produce an antibody directed against a target antigen can be generated (See, e.g., Cole et al., Monoclonal Antibodies and Cancer Therapy, Alan R. Liss, p. 77 (1985); Boemer et al., 1991, J. Immunol., 147 (1):86-95; and U.S. Pat. No. 5,750,373). Also, the human antibody can be selected from a phage library, where that phage library expresses human antibodies, as described, for example, in Vaughan et al., 1996, Nat. Biotech., 14:309-314, Sheets et al., 1998, Proc. Nat'l. Acad. Sci., 95:6157-6162, Hoogenboom and Winter, 1991, J. Mol. Biol., 227:381, and Marks et al., 1991, J. Mol. Biol., 222:581). Techniques for the generation and use of antibody phage libraries are also described in U.S. Pat. Nos. 5,969,108, 6,172,197, 5,885,793, 6,521,404; 6,544,731; 6,555,313; 6,582,915; 6,593,081; 6,300,064; 6,653,068; 6,706,484; and 7,264,963; and Rothe et al., 2007, J. Mol. Bio., doi:10.1016/j.jmb.2007.12.018 (each of which is incorporated by reference in its entirety). Affinity maturation strategies and chain shuffling strategies (Marks et al., 1992, Bio/Technology 10:779-783, incorporated by reference in its entirety) are known in the art and can be employed to generate high affinity human antibodies.

Humanized antibodies can also be made in transgenic mice containing human immunoglobulin loci that are capable upon immunization of producing the full repertoire of human antibodies in the absence of endogenous immunoglobulin production. This approach is described in U.S. Pat. Nos. 5,545,807; 5,545,806; 5,569,825; 5,625,126; 5,633,425; and 5,661,016.

This invention also encompasses bispecific antibodies that specifically recognize a EGFR. Bispecific antibodies are antibodies that are capable of specifically recognizing and binding at least two different epitopes. The different epitopes can either be within the same molecule (e.g. the same EGFR) or on different molecules such that both, for example, the antibodies can specifically recognize and bind a EGFR as well as, for example, 1) an effector molecule on a leukocyte such as a T-cell receptor (e.g. CD3) or Fc receptor (e.g. CD64, CD32, or CD16) or 2) a cytotoxic agent as described in detail below.

Exemplary bispecific antibodies can bind to two different epitopes, at least one of which originates in a polypeptide of the invention. Alternatively, an anti-antigenic arm of an immunoglobulin molecule can be combined with an arm which binds to a triggering molecule on a leukocyte such as a T cell receptor molecule (e.g. CD2, CD3, CD28, or B7), or Fe receptors for IgG so as to focus cellular defense mechanisms to the cell expressing the particular antigen. Bispecific antibodies can also be used to direct cytotoxic agents to cells which express a particular antigen. These antibodies possess an antigen-binding arm and an arm which binds a cytotoxic agent or a radionuclide chelator, such as EOTUBE, DPTA, DOTA, or TETA. Techniques for making bispecific antibodies are common in the art (Millstein et al., 1983, Nature 305:537-539; Brennan et al., 1985, Science 229:81; Suresh et al, 1986, Methods in Enzymol. 121:120; Traunecker et al., 1991, EMBO J. 10:3655-3659; Shalaby et al., 1992, J. Exp. Med. 175:217-225; Kostelny et al., 1992, J. Immunol. 148:1547-1553; Gruber et al., 1994, J. Immunol. 152:5368; and U.S. Pat. No. 5,731,168). Antibodies with more than two valencies are also contemplated. For example, trispecific antibodies can be prepared (Tutt et al., J. Immunol. 147:60 (1991)). Thus, in certain embodiments the antibodies to EGFR are multispecific.

In certain embodiments are provided an antibody fragment to, for example, increase tumor penetration. Various techniques are known for the production of antibody fragments. Traditionally, these fragments are derived via proteolytic digestion of intact antibodies (for example Morimoto et al., 1993, Journal of Biochemical and Biophysical Methods 24:107-117; Brennan et al., 1985, Science, 229:81). In certain embodiments, antibody fragments are produced recombinantly. Fab, Fv, and scFv antibody fragments can all be expressed in and secreted from *E. coli* or other host cells, thus allowing the production of large amounts of these fragments. Such antibody fragments can also be isolated from the antibody phage libraries discussed above. The antibody fragment can also be linear antibodies as described in U.S. Pat. No. 5,641,870, for example, and can be monospecific or bispecific. Other techniques for the production of antibody fragments will be apparent to the skilled practitioner.

According to the present invention, techniques can be adapted for the production of single-chain antibodies specific to EGFR (see U.S. Pat. No. 4,946,778). In addition, methods can be adapted for the construction of Fab expression libraries (Huse, et al., Science 246:1275-1281 (1989)) to allow rapid and effective identification of monoclonal Fab fragments with the desired specificity for EGFR, or derivatives, fragments, analogs or homologs thereof. Antibody fragments can be produced by techniques in the art including, but not limited to: (a) a F(ab')2 fragment produced by pepsin digestion of an antibody molecule; (b) a Fab fragment generated by reducing the disulfide bridges of an F(ab')2 fragment, (c) a Fab fragment generated by the treatment of the antibody molecule with papain and a reducing agent, and (d) Fv fragments.

It can further be desirable, especially in the case of antibody fragments, to modify an antibody in order to increase its serum half-life. This can be achieved, for example, by incorporation of a salvage receptor binding epitope into the antibody fragment by mutation of the appropriate region in the antibody fragment or by incorporating the epitope into a peptide tag that is then fused to the antibody fragment at either end or in the middle (e.g., by DNA or peptide synthesis).

Heteroconjugate antibodies are also within the scope of the present invention. Heteroconjugate antibodies are composed of two covalently joined antibodies. Such antibodies have, for example, been proposed to target immune cells to unwanted cells (U.S. Pat. No. 4,676,980). It is contemplated that the antibodies can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate.

For the purposes of the present invention, it should be appreciated that modified antibodies can comprise any type of variable region that provides for the association of the antibody with the polypeptides of a human EGFR. In this regard, the variable region can comprise or be derived from any type of mammal that can be induced to mount a humoral response and generate immunoglobulins against the desired tumor associated antigen. As such, the variable region of the modified antibodies can be, for example, of human, murine, non-human primate (e.g. cynomolgus monkeys, macaques, etc.) or lupine origin. In some embodiments both the variable and constant regions of the modified immunoglobulins are human. In other embodiments the variable regions of compatible antibodies (usually derived from a non-human source) can be engineered or specifically tailored to improve the binding properties or reduce the immunogenicity of the molecule. In this respect, variable regions useful in the present invention can be humanized or otherwise altered through the inclusion of imported amino acid sequences.

In certain embodiments, the variable domains in both the heavy and light chains are altered by at least partial replacement of one or more CDRs and, if necessary, by partial framework region replacement and sequence changing. Although the CDRs can be derived from an antibody of the same class or even subclass as the antibody from which the framework regions are derived, it is envisaged that the CDRs will be derived from an antibody of different class and possibly from an antibody from a different species. It is not always necessary to replace all of the CDRs with the complete CDRs from the donor variable region to transfer the antigen binding capacity of one variable domain to another. Rather, in some cases it is only necessary to transfer those residues that are necessary to maintain the activity of the antigen binding site. Given the explanations set forth in U.S. Pat. Nos. 5,585,089, 5,693,761 and 5,693,762, it will be well within the competence of those skilled in the art, either by carrying out routine experimentation or by trial and error testing to obtain a functional antibody with reduced immunogenicity.

Alterations to the variable region notwithstanding, those skilled in the art will appreciate that the modified antibodies of this invention will comprise antibodies (e.g., full-length antibodies or immunoreactive fragments thereof) in which at least a fraction of one or more of the constant region domains has been deleted or otherwise altered so as to provide desired biochemical characteristics such as increased tumor localization or reduced serum half-life when compared with an antibody of approximately the same immunogenicity comprising a native or unaltered constant region. In some embodiments, the constant region of the modified antibodies will comprise a human constant region. Modifications to the constant region compatible with this invention comprise additions, deletions or substitutions of one or more amino acids in one or more domains. That is, the modified antibodies disclosed herein can comprise alterations or modifications to one or more of the three heavy chain constant domains (CH1, CH2 or CH3) and/or to the light chain constant domain (CL). In some embodiments, modified constant regions wherein one or more domains are partially or entirely deleted are contemplated. In some embodiments, the modified antibodies will comprise domain deleted constructs or variants wherein the entire CH2 domain has been removed (ΔCH2 constructs). In some embodiments, the omitted constant region domain will be replaced by a short amino acid spacer (e.g. 10 residues) that provides some of the molecular flexibility typically imparted by the absent constant region.

Besides their configuration, it is known in the art that the constant region mediates several effector functions. For example, binding of the C1 c omponent of complement to antibodies activates the complement system. Activation of complement is important in the opsonisation and lysis of cell pathogens. The activation of complement also stimulates the inflammatory response and can also be involved in autoimmune hypersensitivity. Further, antibodies bind to cells via the Fc region, with a Fc receptor site on the antibody Fc region binding to a Fc receptor (FcR) on a cell. There are a number of Fc receptors which are specific for different classes of antibody, including IgG (gamma receptors), IgE (eta receptors), IgA (alpha receptors) and IgM (mu receptors). Binding of antibody to Fc receptors on cell surfaces triggers a number of important and diverse biological responses including engulfment and destruction of antibody-coated particles, clearance of immune complexes, lysis of antibody-coated target cells by killer cells (called antibody-dependent cell-mediated cytotoxicity, or ADCC), release of inflammatory mediators, placental transfer and control of immunoglobulin production.

In certain embodiments, the EGFR-binding antibodies provide for altered effector functions that, in turn, affect the biological profile of the administered antibody. For example, the deletion or inactivation (through point mutations or other means) of a constant region domain can reduce Fe receptor binding of the circulating modified antibody thereby increasing tumor localization. In other cases, it can be that constant region modifications, consistent with this invention, moderate complement binding and thus reduce the serum half-life and nonspecific association of a conjugated cytotoxin. Yet other modifications of the constant region can be used to eliminate disulfide linkages or oligosaccharide moieties that allow for enhanced localization due to increased antigen specificity or antibody flexibility. Similarly, modifications to the constant region in accordance with this invention can easily be made using well known biochemical or molecular engineering techniques well within the purview of the skilled artisan.

In certain embodiments, a EGFR-binding agent that is an antibody does not have one or more effector functions. For instance, in some embodiments, the antibody has no antibody-dependent cellular cytotoxicity (ADCC) activity and/or no complement-dependent cytotoxicity (CDC) activity. In certain embodiments, the antibody does not bind to an Fc receptor and/or complement factors. In certain embodiments, the antibody has no effector function.

It will be noted that in certain embodiments, the modified antibodies can be engineered to fuse the CH3 domain directly to the hinge region of the respective modified antibodies. In other constructs it can be desirable to provide a peptide spacer between the hinge region and the modified CH2 and/or CH3 domains. For example, compatible constructs could be expressed wherein the CH2 domain has been deleted and the remaining CH3 domain (modified or unmodified) is joined to the hinge region with a 5-20 amino acid spacer. Such a spacer can be added, for instance, to ensure that the regulatory elements of the constant domain remain free and accessible or that the hinge region remains flexible. However, it should be noted that amino acid spacers can, in some cases, prove to be immunogenic and elicit an unwanted immune response against the construct. Accordingly, in certain embodiments, any spacer added to the construct will be relatively nonimmunogenic, or even omitted altogether, so as to maintain the desired biochemical qualities of the modified antibodies.

Besides the deletion of whole constant region domains, it will be appreciated that the antibodies of the present invention can be provided by the partial deletion or substitution of a few or even a single amino acid. For example, the mutation of a single amino acid in selected areas of the CH2 domain can be enough to substantially reduce Fc binding and thereby increase tumor localization. Similarly, it can be desirable to simply delete that part of one or more constant region domains that control the effector function (e.g. complement CLQ binding) to be modulated. Such partial deletions of the constant regions can improve selected characteristics of the antibody (serum half-life) while leaving other desirable functions associated with the subject constant region domain intact. Moreover, as alluded to above, the constant regions of the disclosed antibodies can be modified through the mutation or substitution of one or more amino acids that enhances the profile of the resulting construct. In this respect it can be possible to disrupt the activity provided by a conserved binding site (e.g. Fc binding) while substantially maintaining the configuration and immunogenic profile of the modified antibody. Certain embodiments can comprise the addition of one or more amino acids to the constant region to enhance desirable characteristics such as decreasing or increasing effector function or provide for more cytotoxin or carbohydrate attachment. In such embodiments it can be desirable to insert or replicate specific sequences derived from selected constant region domains.

The present invention further embraces variants and equivalents which are substantially homologous to the chimeric, humanized and human antibodies, or antibody fragments thereof, set forth herein. These can contain, for example, conservative substitution mutations, i.e. the substitution of one or more amino acids by similar amino acids. For example, conservative substitution refers to the substitution of an amino acid with another within the same general class such as, for example, one acidic amino acid with another acidic amino acid, one basic amino acid with another basic amino acid or one neutral amino acid by another neutral amino acid. What is intended by a conservative amino acid substitution is well known in the art.

The polypeptides of the present invention can be recombinant polypeptides, natural polypeptides, or synthetic polypeptides comprising an antibody, or fragment thereof, against a human EGFR. It will be recognized in the art that some amino acid sequences of the invention can be varied without significant effect of the structure or function of the protein. Thus, the invention further includes variations of the polypeptides which show substantial activity or which include regions of an antibody, or fragment thereof, against EGFR protein. Such mutants include deletions, insertions, inversions, repeats, and type substitutions.

The polypeptides and analogs can be further modified to contain additional chemical moieties not normally part of the protein. Those derivatized moieties can improve the solubility, the biological half-life or absorption of the protein. The moieties can also reduce or eliminate any desirable side effects of the proteins and the like. An overview for those moieties can be found in REMINGTON'S PHARMACEUTICAL SCIENCES, 20th ed., Mack Publishing Co., Easton, Pa. (2000).

The isolated polypeptides described herein can be produced by any suitable method known in the art. Such methods range from direct protein synthetic methods to constructing a DNA sequence encoding isolated polypeptide sequences and expressing those sequences in a suitable transformed host. In some embodiments, a DNA sequence is constructed using recombinant technology by isolating or synthesizing a DNA sequence encoding a wild-type protein of interest. Optionally, the sequence can be mutagenized by site-specific mutagenesis to provide functional analogs thereof. See, e.g. Zoeller et al., Proc. Nat'l. Acad. Sci. USA 81:5662-5066 (1984) and U.S. Pat. No. 4,588,585.

In some embodiments a DNA sequence encoding a polypeptide of interest would be constructed by chemical synthesis using an oligonucleotide synthesizer. Such oligonucleotides can be designed based on the amino acid sequence of the desired polypeptide and selecting those codons that are favored in the host cell in which the recombinant polypeptide of interest will be produced. Standard methods can be applied to synthesize an isolated polynucleotide sequence encoding an isolated polypeptide of interest. For example, a complete amino acid sequence can be used to construct a back-translated gene. Further, a DNA oligomer containing a nucleotide sequence coding for the particular isolated polypeptide can be synthesized. For example, several small oligonucleotides coding for portions of the desired polypeptide can be synthesized and then ligated. The individual oligonucleotides typically contain 5' or 3' overhangs for complementary assembly.

Once assembled (by synthesis, site-directed mutagenesis or another method), the polynucleotide sequences encoding a particular isolated polypeptide of interest will be inserted into an expression vector and operatively linked to an expression control sequence appropriate for expression of the protein in a desired host. Proper assembly can be confirmed by nucleotide sequencing, restriction mapping, and expression of a biologically active polypeptide in a suitable host. As is well known in the art, in order to obtain high expression levels of a transfected gene in a host, the gene must be operatively linked to transcriptional and translational expression control sequences that are functional in the chosen expression host.

In certain embodiments, recombinant expression vectors are used to amplify and express DNA encoding antibodies, or fragments thereof, against human EGFR. Recombinant expression vectors are replicable DNA constructs which have synthetic or cDNA-derived DNA fragments encoding a polypeptide chain of an anti-EGFR antibody, or fragment thereof, operatively linked to suitable transcriptional or translational regulatory elements derived from mammalian, microbial, viral or insect genes. A transcriptional unit generally comprises an assembly of (1) a genetic element or elements having a regulatory role in gene expression, for example, transcriptional promoters or enhancers, (2) a structural or coding sequence which is transcribed into mRNA and translated into protein, and (3) appropriate transcription and translation initiation and termination sequences, as described in detail below. Such regulatory elements can include an operator sequence to control transcription. The ability to replicate in a host, usually conferred by an origin of replication, and a selection gene to facilitate recognition of transformants can additionally be incorporated. DNA regions are operatively linked when they are functionally related to each other. For example, DNA for a signal peptide (secretory leader) is operatively linked to DNA for a polypeptide if it is expressed as a precursor which participates in the secretion of the polypeptide; a promoter is operatively linked to a coding sequence if it controls the transcription of the sequence; or a ribosome binding site is operatively linked to a coding sequence if it is positioned so as to permit translation. Structural elements intended for use in yeast expression systems include a leader sequence enabling extracellular secretion of translated protein by a host cell. Alternatively, where recombinant protein is expressed without a leader or transport sequence, it can include an N-terminal methionine residue. This residue can optionally be subsequently cleaved from the expressed recombinant protein to provide a final product.

The choice of expression control sequence and expression vector will depend upon the choice of host. A wide variety of expression host/vector combinations can be employed. Useful expression vectors for eukaryotic hosts, include, for example, vectors comprising expression control sequences from SV40, bovine papilloma virus, adenovirus and cytomegalovirus. Useful expression vectors for bacterial hosts include known bacterial plasmids, such as plasmids from *Escherichia coli*, including pCR 1, pBR322, pMB9 and their derivatives, wider host range plasmids, such as M13 and filamentous single-stranded DNA phages.

Suitable host cells for expression of a EGFR-binding polypeptide or antibody (or a EGFR protein to use as an antigen) include prokaryotes, yeast, insect or higher eukaryotic cells under the control of appropriate promoters. Prokaryotes include gram negative or gram positive organisms, for example *E. coli* or bacilli. Higher eukaryotic cells include established cell lines of mammalian origin as described below. Cell-free translation systems could also be employed. Appropriate cloning and expression vectors for use with bacterial, fungal, yeast, and mammalian cellular hosts are described by Pouwels et al. (Cloning Vectors: A Laboratory Manual, Elsevier, N.Y., 1985), the relevant disclosure of which is hereby incorporated by reference. Additional information regarding methods of protein production, including antibody production, can be found, e.g., in U.S. Patent Publication No. 2008/0187954, U.S. Pat. Nos. 6,413,746 and 6,660,501, and International Patent Publication No. WO 04009823, each of which is hereby incorporated by reference herein in its entirety.

Various mammalian or insect cell culture systems are also advantageously employed to express recombinant protein. Expression of recombinant proteins in mammalian cells can be performed because such proteins are generally correctly folded, appropriately modified and completely functional. Examples of suitable mammalian host cell lines include the COS-7 lines of monkey kidney cells, described by Gluzman (Cell 23:175, 1981), and other cell lines capable of expressing an appropriate vector including, for example, L cells, C127, 3T3, Chinese hamster ovary (CHO), HeLa and BHK cell lines. Mammalian expression vectors can comprise nontranscribed elements such as an origin of replication, a suitable promoter and enhancer linked to the gene to be expressed, and other 5' or 3' flanking nontranscribed sequences, and 5' or 3' nontranslated sequences, such as necessary ribosome binding sites, a polyadenylation site, splice donor and acceptor sites, and transcriptional termination sequences. Baculovirus systems for production of heterologous proteins in insect cells are reviewed by Luckow and Summers, Bio/Technology 6:47 (1988).

The proteins produced by a transformed host can be purified according to any suitable method. Such standard methods include chromatography (e.g., ion exchange, affinity and sizing column chromatography), centrifugation, differential solubility, or by any other standard technique for protein purification. Affinity tags such as hexahistidine, maltose binding domain, influenza coat sequence and glutathione-S-transferase can be attached to the protein to allow easy purification by passage over an appropriate affinity column. Isolated proteins can also be physically characterized using such techniques as proteolysis, nuclear magnetic resonance and x-ray crystallography.

For example, supernatants from systems which secrete recombinant protein into culture media can be first concentrated using a commercially available protein concentration filter, for example, an Amicon or Millipore Pellicon ultrafiltration unit. Following the concentration step, the concentrate can be applied to a suitable purification matrix. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Finally, one or more reversed-phase high performance liquid chromatography (RP-HPLC) steps employing hydrophobic RP-HPLC media, e.g., silica gel having pendant methyl or other aliphatic groups, can be employed to further purify a EGFR-binding agent. Some or all of the foregoing purification steps, in various combinations, can also be employed to provide a homogeneous recombinant protein.

Recombinant protein produced in bacterial culture can be isolated, for example, by initial extraction from cell pellets, followed by one or more concentration, salting-out, aqueous ion exchange or size exclusion chromatography steps. High performance liquid chromatography (HPLC) can be employed for final purification steps. Microbial cells employed in expression of a recombinant protein can be disrupted by any convenient method, including freeze-thaw cycling, sonication, mechanical disruption, or use of cell lysing agents.

Methods known in the art for purifying antibodies and other proteins also include, for example, those described in U.S. Patent Publication No. 2008/0312425, 2008/0177048, and 2009/0187005, each of which is hereby incorporated by reference herein in its entirety.

In certain embodiments, the EGFR-binding agent is a polypeptide that is not an antibody. A variety of methods for identifying and producing non-antibody polypeptides that bind with high affinity to a protein target are known in the art. See, e.g., Skerra, Curr. Opin. Biotechnol., 18:295-304 (2007), Hosse et al., Protein Science, 15:14-27 (2006), Gill et al., Curr. Opin. Biotechnol., 17:653-658 (2006), Nygren, FEBS J., 275:2668-76 (2008), and Skerra, FEBS J., 275:2677-83 (2008), each of which is incorporated by reference herein in its entirety. In certain embodiments, phage display technology has been used to identify/produce the EGFR-binding polypeptide. In certain embodiments, the polypeptide comprises a protein scaffold of a type selected from the group consisting of protein A, a lipocalin, a fibronectin domain, an ankyrin consensus repeat domain, and thioredoxin.

In some embodiments, the agent is a non-protein molecule. In certain embodiments, the agent is a small molecule. Combinatorial chemistry libraries and techniques useful in the identification of non-protein EGFR-binding agents are known to those skilled in the art. See, e.g., Kennedy et al., J. Comb. Chem, 10:345-354 (2008), Dolle et al, J. Comb. Chem., 9:855-902 (2007), and Bhattacharyya, Curr. Med. Chem., 8:1383-404 (2001), each of which is incorporated by reference herein in its entirety. In certain further embodiments, the agent is a carbohydrate, a glycosaminoglycan, a glycoprotein, or a proteoglycan.

In certain embodiments, the agent is a nucleic acid aptamer. Aptamers are polynucleotide molecules that have been selected (e.g., from random or mutagenized pools) on the basis of their ability to bind to another molecule. In some embodiments, the aptamer comprises a DNA polynucleotide. In certain alternative embodiments, the aptamer comprises an RNA polynucleotide. In certain embodiments, the aptamer comprises one or more modified nucleic acid residues. Methods of generating and screening nucleic acid aptamers for binding to proteins are well known in the art. See, e.g., U.S. Pat. Nos. 5,270,163, 5,683,867, 5,763,595, 6,344,321, 7,368,236, 5,582,981, 5,756,291, 5,840,867, 7,312,325, and 7,329,742, International Patent Publication No. WO 02/077262, International Patent Publication No. WO 03/070984, U.S. Patent Application Publication No. 2005/0239134, U.S. Patent Application Publication No. 2005/0124565, and U.S. Patent Application Publication No. 2008/0227735, each of which is incorporated by reference herein in its entirety.

III. Immunoconjugates

The present invention is also directed to conjugates (also referred to herein as immunoconjugates), comprising the anti-EGFR antibodies, antibody fragments, and their functional equivalents as disclosed herein, linked or conjugated to a drug or prodrug. Suitable drugs or prodrugs are known in the art. The drugs or prodrugs can be cytotoxic agents. The cytotoxic agent used in the cytotoxic conjugate of the present invention can be any compound that results in the death of a cell, or induces cell death, or in some manner decreases cell viability, and includes, for example, maytansinoids and maytansinoid analogs. Other suitable cytotoxic agents are for example benzodiazepines, taxoids, CC-1065 and CC-1065 analogs, duocarmycins and duocarmycin analogs, enediynes, such as calicheamicins, dolastatin and dolastatin analogs including auristatins, tomaymycin derivatives, leptomycin derivaties, methotrexate, cisplatin, carboplatin, daunorubicin, doxorubicin, vincristine, vinblastine, melphalan, mitomycin C, chlorambucil and morpholino doxorubicin.

Such conjugates can be prepared by using a linking group in order to link a drug or prodrug to the antibody or functional equivalent. Suitable linking groups are well known in the art and include, for example, disulfide groups, thioether groups, acid labile groups, photolabile groups, peptidase labile groups and esterase labile groups.

The drug or prodrug can, for example, be linked to the anti-EGFR antibody or fragment thereof through a disulfide bond. The linker molecule or crosslinking agent comprises a reactive chemical group that can react with the anti-EGFR antibody or fragment thereof. The reactive chemical groups for reaction with the cell-binding agent can be N-succinimidyl esters and N-sulfosuccinimidyl esters. Additionally the linker molecule comprises a reactive chemical group, which can be a dithiopyridyl group that can react with the drug to form a disulfide bond. Linker molecules include, for example, N-succinimidyl 3-(2-pyridyldithio) propionate (SPDP) (see, e.g., Carlsson et al., *Biochem. J.,* 173: 723-737 (1978)), N-succinimidyl 4-(2-pyridyldithio)butanoate (SPDB) (see, e.g., U.S. Pat. No. 4,563,304), N-succinimidyl 4-(2-pyridyldithio)2-sulfobutanoate (sulfo-SPDB) (see US Publication No. 20090274713), N-succinimidyl 4-(2-pyridyldithio) pentanoate (SPP) (see, e.g., CAS Registry number 341498-08-6), 2-iminothiolane, or acetylsuccinic anhydride. For example, the antibody or cell binding agent can be modified with crosslinking reagents and the antibody or cell binding agent containing free or protected thiol groups thus derived is then reacted with a disulfide- or thiol-containing maytansinoid to produce conjugates. The conjugates can be purified by chromatography, including but not limited to HPLC, size-exclusion, adsorption, ion exchange and affinity capture, dialysis or tangential flow filtration.

In another aspect of the present invention, the anti-EGFR antibody is linked to cytotoxic drugs via disulfide bonds and a polyethylene glycol spacer in enhancing the potency, solubility or the efficacy of the immunoconjugate. Such cleavable hydrophilic linkers are described in WO2009/0134976. The additional benefit of this linker design is the desired high monomer ratio and the minimal aggregation of the antibody-drug conjugate. Specifically contemplated in this aspect are conjugates of cell-binding agents and drugs linked via disulfide group (—S—S—) bearing polyethylene glycol spacers ($(CH_2CH_2O)_{n=1-14}$) with a narrow range of drug load of 2-8 are described that show relatively high potent biological activity toward cancer cells and have the desired biochemical properties of high conjugation yield and high monomer ratio with minimal protein aggregation.

Specifically contemplated in this aspect is an anti-EGFR antibody drug conjugate of formula (I) or a conjugate of formula (I'):

$$CB—[X_1—(—CH_2—CH_2O—)_n—Y\text{-}D]_m \quad (I)$$

$$[D\text{-}Y—(—CH_2—CH_2O—)_n—X_1]_m—CB \quad (I')$$

wherein:

CB represents an anti-EGFR antibody or fragment;

D represents a drug;

X represents an aliphatic, an aromatic or a heterocyclic unit attached to the cell-binding agent via a thioether bond, an amide bond, a carbamate bond, or an ether bond;

Y represents an aliphatic, an aromatic or a heterocyclic unit attached to the drug via a disulfide bond;

l is 0 or 1;

m is an integer from 2 to 8; and n is an integer from 1 to 24.

In some embodiments, m is an integer from 2 to 6.

In some embodiments, m is an integer from 3 to 5.

In some embodiments, n is an integer form 2 to 8. Alternatively, as disclosed in, for example, U.S. Pat. Nos. 6,441,163 and 7,368,565, the drug can be first modified to introduce a reactive ester suitable to react with a cell-binding agent. Reaction of these drugs containing an activated linker moiety with a cell-binding agent provides another method of producing a cell-binding agent drug conjugate. Maytansinoids can also be linked to anti-EGFR antibody or fragment using PEG linking groups, as set forth for example in U.S. Pat. No. 6,716,821. These PEG non-cleavable linking groups are soluble both in water and in non-aqueous solvents, and can be used to join one or more cytotoxic agents to a cell binding agent. Exemplary PEG linking groups include heterobifunctional PEG linkers that react with cytotoxic agents and cell binding agents at opposite ends of the linkers through a functional sulfhydryl or disulfide group at one end, and an active ester at the other end. As a general example of the synthesis of a cytotoxic conjugate using a PEG linking group, reference is again made to U.S. Pat. No. 6,716,821 which is incorporated entirely by reference herein. Synthesis begins with the reaction of one or more cytotoxic agents bearing a reactive PEG moiety with a cell-binding agent, resulting in displacement of the terminal active ester of each reactive PEG moiety by an amino acid residue of the cell binding agent, to yield a cytotoxic conjugate comprising one or more cytotoxic agents covalently bonded to a cell binding agent through a PEG linking group. Alternatively, the cell binding can be modified with the bifunctional PEG crosslinker to introduce a reactive disulfide moiety (such as a pyridyldisulfide), which can then be treated with a thiol-containing maytansinoid to provide a conjugate. In another method, the cell binding can be modified with the bifunctional PEG crosslinker to introduce a thiol moiety which can then can be treated with a reactive disulfide-containing maytansinoid (such as a pyridyldisulfide), to provide a conjugate.

Antibody-maytansinoid conjugates with non-cleavable links can also be prepared. Such crosslinkers are described in the art (see US Publication No. 20050169933) and include but are not limited to, N-succinimidyl 4-(maleimidomethyl) cyclohexanecarboxylate (SMCC). In some embodiments, the antibody is modified with crosslinking reagents such as succinimidyl 4-(N-maleimidomethyl)-cyclohexane-1-carboxylate (SMCC), sulfo-SMCC, maleimidobenzoyl-N-hydroxysuccinimide ester (MBS), sulfo-MBS or succinimidyl-iodoacetate, as described in the literature, to introduce 1-10 reactive groups (Yoshitake et al, Eur. J. Biochem., 101:395-399 (1979); Hashida et al, J. Applied Biochem., 56-63 (1984); and Liu et al, Biochem., 18:690-697 (1979)). The modified antibody is then reacted with the thiol-containing maytansinoid derivative to produce a conjugate. The conjugate can be purified by gel filtration through a Sephadex G25 column or by dialysis or tangential flow filtration. The modified antibodies are treated with the thiol-containing maytansinoid (1 to 2 molar equivalent/maleimido group) and antibody-maytansinoid conjugates are purified by gel filtration through a Sephadex G-25 column, chromatography on a ceramic hydroxyapatite column, dialysis or tangential flow filtration or a combination of methods thereof. Typically, an average of 1-10 maytansinoids per antibody are linked. One method is to modify antibodies with succinimidyl 4-(N-maleimidomethyl)-cyclohexane-1-carboxylate (SMCC) to introduce maleimido groups followed by reaction of the modified antibody with a thiol-containing maytansinoid to give a thioether-linked conjugate. Again conjugates with 1 to 10 drug molecules per antibody molecule result. Maytansinoid conjugates of antibodies, antibody fragments, and other proteins are made in the same way.

In another aspect of the invention, the EGFR antibody is linked to the drug via a non-cleavable bond through the intermediacy of a PEG spacer. Suitable crosslinking reagents comprising hydrophilic PEG chains that form linkers between a drug and the anti-EGFR antibody or fragment are also well known in the art, or are commercially available (for example from Quanta Biodesign, Powell, Ohio). Suitable PEG-containing crosslinkers can also be synthesized from commercially available PEGs themselves using standard synthetic chemistry techniques known to one skilled in the art. The drugs can be reacted with bifunctional PEG-containing cross linkers to give compounds of the following formula, $Z—X_1—(—CH_2—CH_2—O—)_n—Y_p\text{-}D$, by methods described in detail in US Patent Publication 20090274713 and in WO2009/0134976, which can then react with the cell binding agent to provide a conjugate. Alternatively, the cell binding can be modified with the bifunctional PEG crosslinker to introduce a thiol-reactive group (such as a maleimide or haloacetamide) which can then be treated with a thiol-containing maytansinoid to provide a conjugate. In another method, the cell binding can be modified with the bifunctional PEG crosslinker to introduce a thiol moiety which can then be treated with a thiol-reactive maytansinoid (such as a maytansinoid bearing a maleimide or haloacetamide), to provide a conjugate.

Accordingly, another aspect of the present invention is an anti-EGFR antibody drug conjugate of formula (II) or of formula (IP):

$$CB—[X_1—(—CH_2—CH_2—O—)_n—Y_p\text{-}D]_m \quad \text{(II)}$$

$$[D\text{-}Y_p—(—CH_2—CH_2—O—)_n—X_1]_m—CB \quad \text{(II')}$$

wherein, CB represents an anti-EGFR antibody or fragment;

D represents a drug;

X represents an aliphatic, an aromatic or a heterocyclic unit bonded to the cell-binding agent via a thioether bond, an amide bond, a carbamate bond, or an ether bond;

Y represents an aliphatic, an aromatic, or a heterocyclic unit bonded to the drug via a covalent bond selected from the group consisting of a thioether bond, an amide bond, a carbamate bond, an ether bond, an amine bond, a carbon-carbon bond and a hydrazone bond;

l is 0 or 1;

p is 0 or 1;

m is an integer from 2 to 15; and n is an integer from 1 to 2000.

In some embodiments, m is an integer from 2 to 8; and

In some embodiments, n is an integer from 1 to 24.

In some embodiments, m is an integer from 2 to 6.

In some embodiments, m is an integer from 3 to 5.

In some embodiments, n is an integer from 2 to 8. Examples of suitable PEG-containing linkers include linkers having an N-succinimidyl ester or N-sulfosuccinimidyl ester moiety for reaction with the anti-EGFR antibody or fragment thereof, as well as a maleimido- or haloacetyl-based moiety for reaction with the compound. A PEG spacer can be incorporated into any crosslinker known in the art by the methods described herein.

Many of the linkers disclosed herein are described in detail in U.S. Patent Publication Nos. 20050169933 and 20090274713, and in WO2009/0134976; the contents of which are entirely incorporated herein by reference.

The present invention includes aspects wherein about 2 to about 8 drug molecules ("drug load"), for example, maytansinoid, are linked to an anti-EGFR antibody or fragment thereof, the anti-tumor effect of the conjugate is much more efficacious as compared to a drug load of a lesser or higher number of drugs linked to the same cell binding agent. "Drug load", as used herein, refers to the number of drug molecules (e.g., a maytansinoid) that can be attached to a cell binding agent (e.g., an anti-EGFR antibody or fragment thereof). In one aspect the number of drug molecules that can be attached to a cell binding agent can average from about 2 to about 8 (e.g., 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1). $N^{2'}$-deacetyl-$N^{2'}$-(3-mercapto-1-oxopropyl)-maytansine (DM1) and $N^{2'}$-deacetyl-$N^{2'}$-(4-mercapto-4-methyl-1-oxopentyl) maytansine (DM4) can be used.

The anti-EGFR antibody or fragment thereof can be modified by reacting a bifunctional crosslinking reagent with the anti-EGFR antibody or fragment thereof, thereby resulting in the covalent attachment of a linker molecule to the anti-EGFR antibody or fragment thereof. As used herein, a "bifunctional crosslinking reagent" is any chemical moiety that covalently links a cell-binding agent to a drug, such as the drugs described herein. In another method, a portion of the linking moiety is provided by the drug. In this respect, the drug comprises a linking moiety that is part of a larger linker molecule that is used to join the cell-binding agent to the drug. For example, to form the maytansinoid DM1, the side chain at the C-3 hydroxyl group of maytansine is modified to have a free sulfhydryl group (SH). This thiolated form of maytansine can react with a modified cell-binding agent to form a conjugate. Therefore, the final linker is assembled from two components, one of which is provided by the crosslinking reagent, while the other is provided by the side chain from DM1.

The drug molecules can also be linked to the antibody molecules through an intermediary carrier molecule such as serum albumin.

As used herein, the expression "linked to a cell-binding agent" or "linked to an anti-EGFR antibody or fragment" refers to the conjugate molecule comprising at least one drug derivative bound to a cell-binding agent anti-EGFR antibody or fragment via a suitable linking group, or a precursor thereof. One linking group is SMCC.

In certain embodiments, cytotoxic agents useful in the present invention are maytansinoids and maytansinoid analogs. Examples of suitable maytansinoids include esters of maytansinol and maytansinol analogs. Included are any drugs that inhibit microtubule formation and that are highly toxic to mammalian cells, as are maytansinol and maytansinol analogs.

Examples of suitable maytansinol esters include those having a modified aromatic ring and those having modifications at other positions. Such suitable maytansinoids are disclosed in U.S. Pat. Nos. 4,424,219; 4,256,746; 4,294,757; 4,307,016; 4,313,946; 4,315,929; 4,331,598; 4,361,650; 4,362,663; 4,364,866; 4,450,254; 4,322,348; 4,371,533; 5,208,020; 5,416,064; 5,475,092; 5,585,499; 5,846,545; 6,333,410; 7,276,497 and 7,473,796.

In a certain embodiment, the immunoconjugates of the invention utilize the thiol-containing maytansinoid (DM1), formally termed $N^{2'}$-deacetyl-$N^{2'}$-(3-mercapto-1-oxopropyl)-maytansine, as the cytotoxic agent. DM1 is represented by the following structural formula (III):

(III)

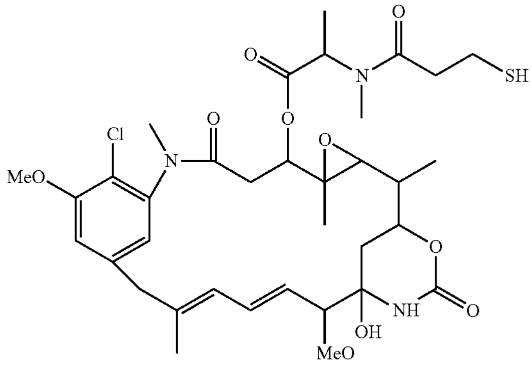

In another embodiment, the conjugates of the present invention utilize the thiol-containing maytansinoid $N^{2'}$-deacetyl-$N^{2'}$(4-methyl-4-mercapto-1-oxopentyl)-maytansine (e.g., DM4) as the cytotoxic agent. DM4 is represented by the following structural formula (IV):

(IV)

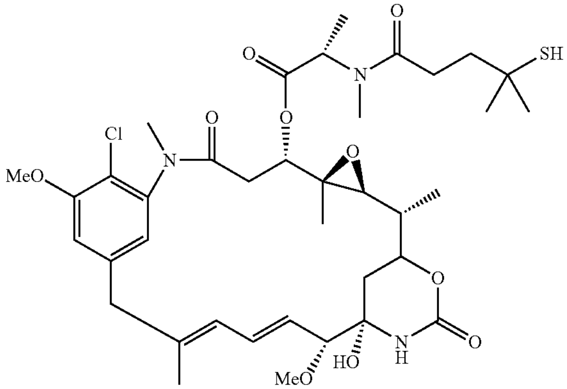

Another maytansinoid comprising a side chain that contains a sterically hindered thiol bond is $N^{2'}$-deacetyl-N-$^{2'}$(4-mercapto-1-oxopentyl)-maytansine (termed DM3), represented by the following structural formula (V):

(V)

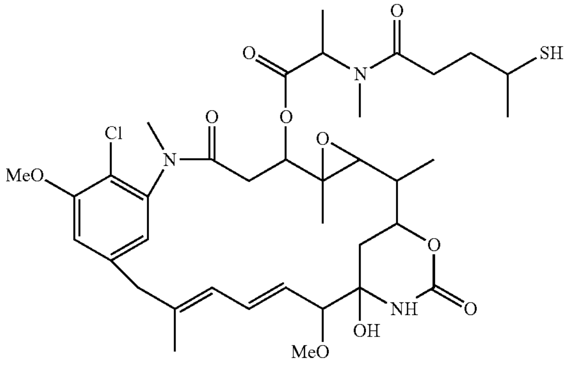

Each of the maytansinoids taught in U.S. Pat. Nos. 5,208,020 and 7,276,497, can also be used in the conjugate of the present invention. In this regard, the entire disclosure of U.S. Pat. No. 5,208,020 and U.S. Pat. No. 7,276,697 is incorporated herein by reference.

Many positions on maytansinoids can serve as the position to chemically link the linking moiety. For example, the C-3 position having a hydroxyl group, the C-14 position modified with hydroxymethyl, the C-15 position modified with hydroxy and the C-20 position having a hydroxy group are all expected to be useful. In some embodiments, the C-3 position serves as the position to chemically link the linking moiety, and in some particular embodiments, the C-3 position of maytansinol serves as the position to chemically link the linking moiety.

Structural representations of some conjugates are shown below:

(VI)

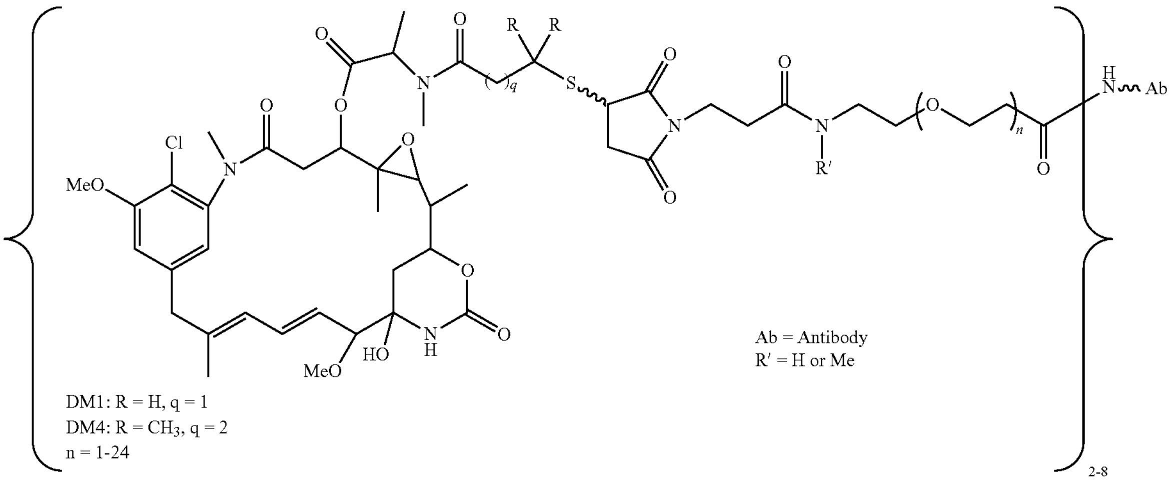

Ab-PEG-Mal-DM1/DM4

(VII)

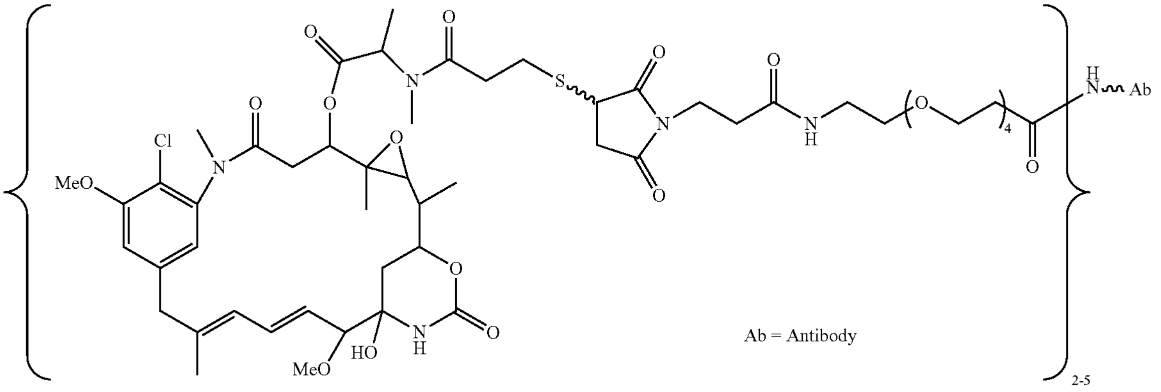

Ab-PEG4-Mal-DM1

(VIII)

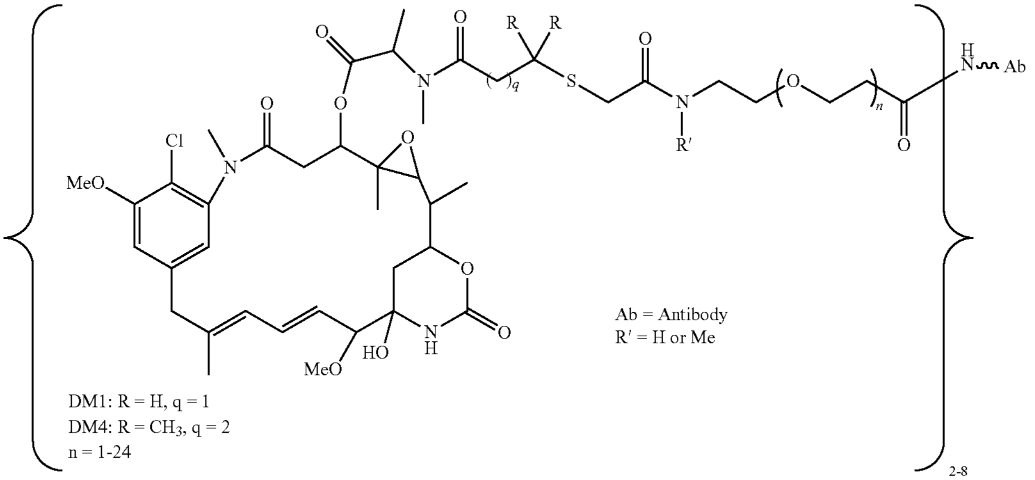

Ab-PEG-SIA-DM1/DM4

-continued
(IX)
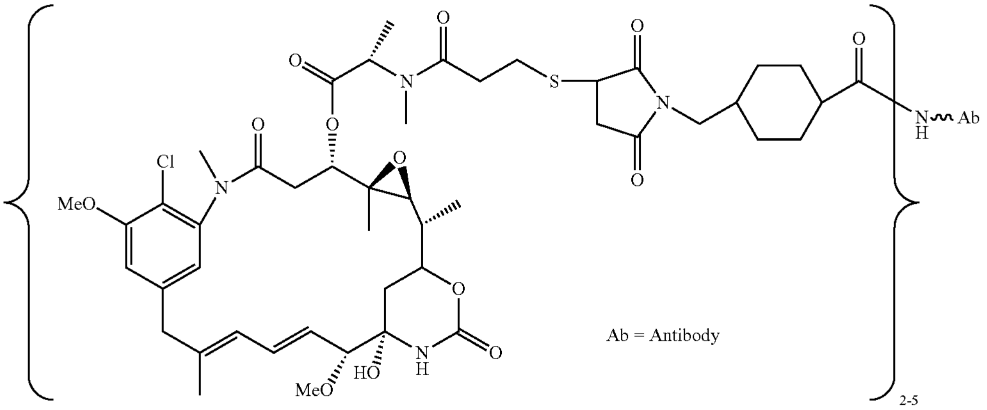
Ab-SMCC-DM1
(X)
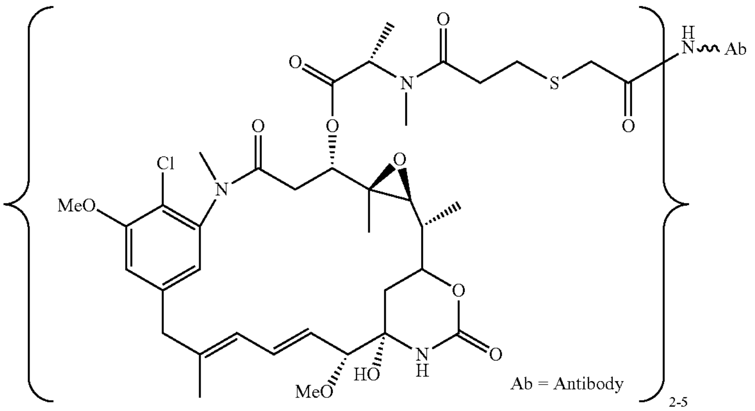
Ab-SIA-DM1
(XI)
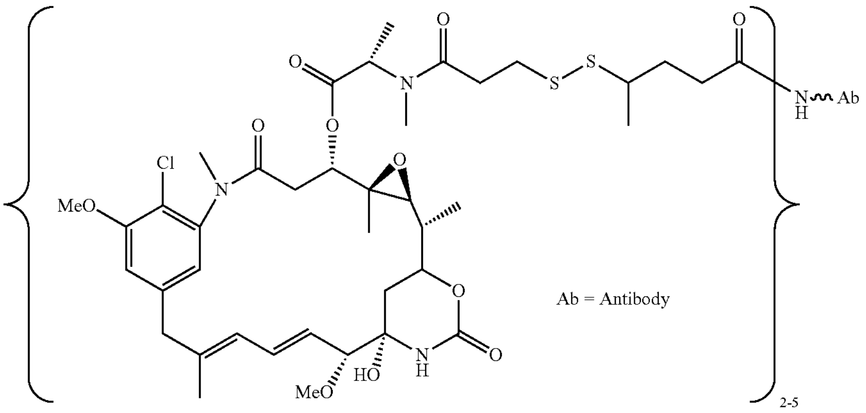
Ab-SPP-DM1

-continued (XII)

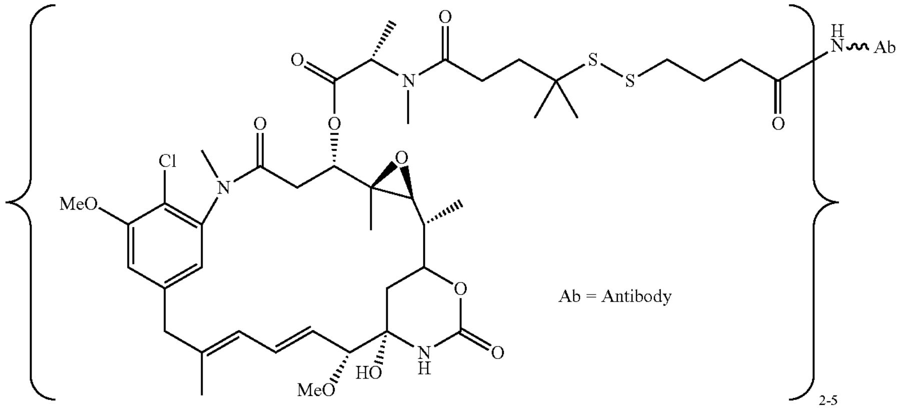

Ab-SPDB-DM4

(XIII)

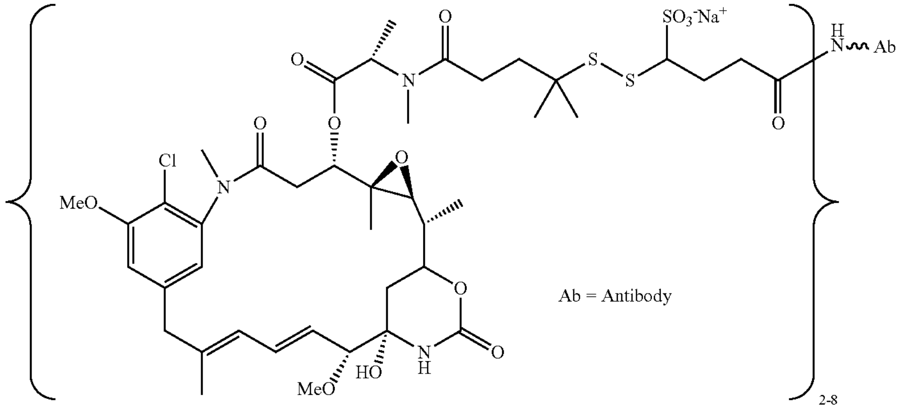

Ab-sulfo-SPDB-DM4

Several descriptions for producing such antibody-maytansinoid conjugates are provided in U.S. Pat. Nos. 6,333,410, 6,441,163, 6,716,821, and 7,368,565, each of which is incorporated herein in its entirety.

In general, a solution of an antibody in aqueous buffer can be incubated with a molar excess of maytansinoids having a disulfide moiety that bears a reactive group. The reaction mixture can be quenched by addition of excess amine (such as ethanolamine, taurine, etc.). The maytansinoid-antibody conjugate can then be purified by gel filtration.

The number of maytansinoid molecules bound per antibody molecule can be determined by measuring spectrophotometrically the ratio of the absorbance at 252 nm and 280 nm. The average number of maytansinoid molecules/antibody can be, for example, 1-10 or 2-5.

Anthracycline compounds, as well as derivatives, intermediates and modified versions thereof, can also be used to prepare anti-EGFR immunoconjugates. For example, doxorubicin, doxorubicin derivatives, doxorubicin intermediates, and modified doxorubicins can be used in anti-EGFR conjugates. Exemplary compounds are described in WO 2010/009124, which is herein incorporated by reference in its entirety. Such compounds include, for example, compounds of the following formula:

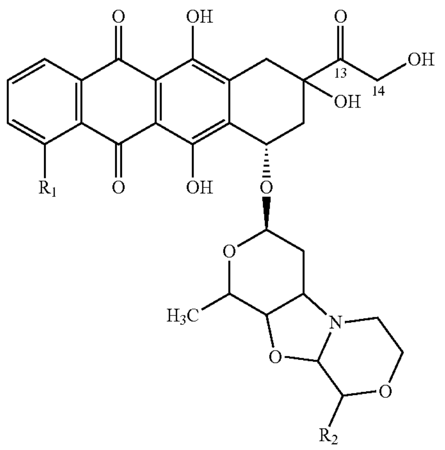

wherein $R_1$ is a hydrogen atom, hydroxy or methoxy group and $R_2$ is a $C_1$-$C_5$ alkoxy group, or a pharmaceutically acceptable salt thereof.

Conjugates of antibodies with maytansinoid or other drugs can be evaluated for their ability to suppress proliferation of various unwanted cell lines in vitro. For example, cell lines such NCI-H226, NCI-H292, and NCI-H322M, can easily be used for the assessment of cytotoxicity of these compounds. Cells to be evaluated can be exposed to the compounds for 4 to 5 days and the surviving fractions of cells measured in direct assays by known methods. $IC_5O$ values can then be calculated from the results of the assays.

The immunoconjugates can, according to some embodiments described herein, be internalized into cells. The immunoconjugate, therefore, can exert a therapeutic effect when it is taken up by, or internalized, by a EGFR-expressing cell. In some particular embodiments, the immunoconjugate comprises an antibody, antibody fragment, or polypeptide, linked to a cytotoxic agent by a cleavable linker, and the cytotoxic agent is cleaved from the antibody, antibody fragment, or polypeptide, wherein it is internalized by a EGFR-expressing cell.

In some embodiments, the immunoconjugates are capable of reducing tumor volume. For example, in some embodiments, treatment with an immunoconjugate results in a % T/C value that is less than about 50%, less than about 45%, less than about 40%, less than about 35%, less than about 30%, less than about 25%, less than about 20%, less than about 15%, less than about 10%, or less than about 5%.

In another aspect of the invention siRNA molecules can be linked to the antibodies of the present invention instead of a drug. siRNAs can be linked to the antibodies of the present invention by methods commonly used for the modification of oligonucleotides (see, for example, US Patent Publications 20050107325 and 20070213292). Thus the siRNA in its 3' or 5'-phosphoromidite form can be reacted with one end of the crosslinker bearing a hydroxyl functionality to give an ester bond between the siRNA and the crosslinker. Similarly reaction of the siRNA phosphoramidite with a crosslinker bearing a terminal amino group results in linkage of the crosslinker to the siRNA through an amine. Alternatively, the siRNA can be derivatized by standard chemical methods to introduce a thiol group. This thiol-containing siRNA can be reacted with an antibody that has been modified to introduce an active disulfide or maleimide moiety, to produce a cleavable or non-cleavable conjugate. Between 1-20 siRNA molecules can be linked to an antibody by this method.

III. Polynucleotides

In certain embodiments, the invention encompasses polynucleotides comprising polynucleotides that encode a polypeptide that specifically binds EGFR or a fragment of such a polypeptide. For example, the invention provides a polynucleotide comprising a nucleic acid sequence that encodes an antibody to a human EGFR or encodes a fragment of such an antibody. The polynucleotides of the invention can be in the form of RNA or in the form of DNA. DNA includes cDNA, genomic DNA, and synthetic DNA; and can be double-stranded or single-stranded, and if single stranded can be the coding strand or non-coding (anti-sense) strand.

In certain embodiments, the polynucleotides are isolated. In certain embodiments, the polynucleotides are substantially pure.

The invention provides a polynucleotide comprising a polynucleotide encoding a polypeptide comprising a sequence selected from the group consisting of SEQ ID NOs: 1-38 and 69-76.

The invention further provides a polynucleotide comprising a sequence selected from those shown in Tables 7-9 below.

TABLE 7

Variable heavy chain polynucleotide sequences

| Antibody | VH Polynucleotide Sequence |
|---|---|
| muEGFR-7 $V_H$ | caggttcagctccagcagtctggggctgagctggcaagacctggggcttcagtgaagttgtcctgcaagg cttctggctacacctttactagctactggatgcagtgggtaaaacagaggcctggacagggtctggaatg tattgggactatttatcctggagatggtgatactacgtacactcagaagttcaagggcaaggccacattg actgcagataaatcctccagcacagcctacatgcaactcagcagcttggcatctgaggactctgcggtct attactgtgcaagatatgatgcccccggctatgctatggactactggggtcaaggaacctcagtcaccgt ctcctca (SEQ ID NO: 39) |
| muEGFR-12 $V_H$ | caggttcagctccagcagtctgggactgagctggcaagacctggggcttcagtgaagttgtcctgcaagg cttctggctacacctttactagctactggatgcagtgggtaaaacagaggcctggacagggtctggaatg tattgggactatctatcctggagatggtgatactaggtacattcagaagttcaagggcaaggccacattg actgcagataaatcctccagcacagcctacatgcaactcagcagcttggcatctgaggactctgcggtct attactgtgcaagatatgatgcccccggctatgctatggactactggggtcaaggaacctcagtcaccgt ctcctca (SEQ ID NO: 40) |
| huEGFR-7 $V_H$ | aagcttgccaccatgggctggtcatgtatcattctgttcctggtggccaccgcaaccggtgtccattccca ggtgcagctcgtgcagagcggggctgaagtggccaagccaggtgcttctgtcaaattgtcttgtaaggcc agtgggtacaccttcacaagctactggatgcagtgggttaagcaacgcccaggccagggactggagtgc atcggcaccatttatccaggggatggagataccacttatacacaaaagtttcaaggcaaagccaccctgac cgccgacaaatccagcagcacagcatacatgcagctttctagcctcaggtctgaagactccgccgtgtact attgtgcccgctacgacgcccccggctatgcaatggattactggggccagggtactctggtcacagtgtcct ccgcctctacaaagggccc (SEQ ID NO: 41) |
| huEGFR-7 $V_H$_CDR grafted | aagcttgccaccatggggtggtcctgtataatactgtttctggtggccactgccacaggagtccacagccaag tgcagctggtgcagagtggcgctgaggtcaagaagcctggggcatccgtcaaggtttcttgtaaggcatctgg atataccttcacttcctattggatgcagtgggtgagacaggcaccaggacagggactggagtggatgggcact atttatccaggtgacggtgacactacttatactcagaaattcaaggggcgagtgaccatgactcgtgatactagc actagtaccgtgtatatggagcttagttctctccggtccgaggacacagcagtctactactgtgctagatatgacg cacccggatatgccatggactattgggggcagggcaccctggtcaccgtgagttccgccagcactaagggccc (SEQ ID NO: 42) |

TABLE 7-continued

Variable heavy chain polynucleotide sequences

| Antibody | VH Polynucleotide Sequence |
|---|---|
| huEGFR-12 $V_H$ | aagcttgccaccatgggctggtcctgtattatcctctttttggtggccactgctaccggcgtacacagtcaggtgc agctggtgcagtccggggctgaagtggcaaagcccggggcctccgtaaagctctcttgcaaggcatccggct acacttttacttcctactggatgcagtgggtcaaacagcgcccaggacaggggttggaatgtataggtacaatct atcccggcgatggtgacacacgatatatccagaagttccagggcaaggctaccctgactgccgacaaatcttcta gcaccgcttatatgcagctgtcatctcttcgaagtgaagactctgcagtgtattactgcgcccgatatgacgcaccc ggttacgccatggattactggggtcaggggaccttggtaaccgtatcaagcgccagtaccaagggccc (SEQ ID NO: 43) |
| muEGFR-6 $V_H$ | caggttcagctccagcagtctggggctgagctggcaagacctggggcttcagtgaag ttgtcctgcaaggcttctggctacacctttactagctactggatgcagtgggtaaaacagaggcctggac agggtctggaatgtattggggctctttatcctggagatggtgatgctaggtacactcagaaattcaaggg caaggccacattgactgcagatagatcctccagcacagcctacatgcaactcagcagcttggcatctgag gactctgcggtctattactgtgcaagatatgatgcccccggctatgctatggactactggggtcaaggaa cctcagtcaccgtcgcctca (SEQ ID NO: 77) |
| huEGFR-$V_H$ v1.0 | aagcttgccaccatggggtggagttgtatcatcctcttccttgtcgctaccgccactggagtgcattcccaggtg cagttggtgcaatctggcgccgaggtggccaagcccggtgcctccgtaaaattgagttgtaaagcctctggcta tacatttacatcttattggatgcagtgggtcaagcagcgccctggtcaaggcctggagtgcatcggagctctgta tcctggcgacggggacgcccgttacactcagaaatttcagggcaaagctaccctcaccgcagatacatccagc agcactgcttatatgcaacttagtagcctccgcagcgaggatagtgccgtgtactactgtgccagatatgacgccc caggttatgctatggactactggggtcaaggaaccctggtgacagtgtcaagcgctagcacaaagggccc (SEQ ID NO: 78) |
| huEGFR-6 $V_H$ v1.11 | aagcttgccaccatggggtggagttgtatcatcctcttccttgtcgctaccgccactggagtgcattcccaggtgca gttggtgcaatctggcgccgaggtggccaagcccggtgcctccgtaaaattgagttgtaaagcctctggctataca tttacatcttattggatgcagtgggtcaagcagcgccctggtcaaggcctggagtggatcggagctctgtatcctgg cgacggggacgcccgttacactcagaaatttcagggcaaagctaccctcaccgcagatacatccagcagcactg cttatatgcaacttagtagcctccgcagcgaggatagtgccgtgtactactgtgccagatatgacgccccaggttat gctatggactactggggtcaaggaaccctggtgacagtgtcaagcgctagcacaaagggccc (SEQ ID NO: 79) |
| huEGFR-7 $V_H$ v1.11 | aagcttgccaccatgggctggtcatgtatcattctgttcctggtggccaccgcaaccggtgtccattcccaggtgcag ctcgtgcagagcggggctgaagtggccaagccaggtgcttctgtcaaattgtcttgtaaggccagtgggtacacctt cacaagctactggatgcagtgggttaagcaacgcccaggccagggactggagtggatcggcaccatttatccagg ggatggagataccacttatacacaaaagtttcaaggcaaagccaccctgaccgccgacaaatccagcagcacagc atacatgcatgctttctagcctcaggtctgaagactccgccgtgtactattgtgcccgctacgacgcccccggctatgc aatggattactggggccagggtactctggtcacagtgtcctccgcctctacaaagggccc (SEQ ID NO: 80) |

TABLE 8

Variable light chain polynucleotide sequences

| Antibody | VL Polynucleotide Sequence |
|---|---|
| muEGFR-7 $V_L$ | gacatccagatgacacagtctccatcctcactgtctgcatctctgggaggcaaagtcaccatcacttgca aggcaagccaagacattaacaactatttggcttggtaccaacacaagcctggaaaaggtcctaggctgct catacattacacatctacattacatccaggcatcccatcaaggttcagtggaagtgggtctgggagagat tattccttcagcatcagcaacctggagcctgaagatattgcaacttattattgtctacagtatgataatc ttctgtacacgttcggaggggggaccaagctggaaataaaacgg (SEQ ID NO: 44) |
| muEGFR-12 $V_L$ | gatgtccagataacccagtctccatcttatcttgctgcatctcctggagaaaccattactattaattgca gggcaagtaagagcattagcaaatatttagcctggtatcaagagaaacctgggaaaactaataagcttct tatctactctggatccactttgcaatctggaattccatcaaggttcagtggcagtggatctggtacagat ttcactctcaccatcagtagcctggagcctgaagattttgcaatgtattactgtcaacagcataatgaat acccgtggacgttcggtggaggcaccaagctggaaatcaaacgg (SEQ ID NO: 45) |
| huEGFR-7 $V_L$ v1.0 | gaattcgccaccatgggctggagctgcatcatcttgttcttggtcgccactgccacaggagtgcatagcgata ttcagatgacccagtctcccagctctctgagcgctagcgtgggcgatcgggtgactattacttgccgtgcatc ccaggatatcaacaactacttggcctggtaccagcacaagcccggcaaaggcccaaagctgctgatccact ataccagtacactgcaccctggtatcccttctagattcagcggctccggtagtggtcgggattactcattctcta tctcttccctggagcccgaggatatagctacatattattgtctccagtacgataatctcttgtacacatttggacag gggacaaagctggagatcaagcgtacg (SEQ ID NO: 46) |
| huEGFR-7 $V_L$ v1.01 | gaattcgccaccatgggatggtcctgcattatcctttttcctggtcgccaccgccacaggcgtccactctgacata caaatgacccagtccccttcttcactgagcgcctccgttggggatagagttacaatcacttgtaaagctagccag gacatcaacaactatctggcttggtatcagcataaacctgggaagggacccaagctcttgattcattacacctcta ccttgcacccaggcataccaagccgctttagcggtagtggcagtggccgcgattactcattctccatcagttcctt ggaaccagaagatatagccacctattattgtctccagtatgataatttgctctacacttttggccagggcaccaaac ttgagatcaagcgtacg (SEQ ID NO: 47) |

TABLE 8-continued

| Variable light chain polynucleotide sequences | |
|---|---|
| Antibody | VL Polynucleotide Sequence |
| huEGFR-7 $V_L$ CDR grafted | gaattcgccaccatgggatggagttgcattattttgtttctggtagctaccgctacaggcgttcatagcgacattca gatgacacagagcccctcctctttgtccgcctccgtgggcgatagagtcacaatcacctgccgcgcaagccag gatatcaacaactaccttgcatggtaccagcagaagcaggaaaagccccaaagctgctcatatactacacctc cacccttcacccaggagttccatccaggttctctgggtctggaagtggaacagattttaccttcacaatcagctcat tgcaacccgaggacatagctacatattactgcctgcagtatgacaatctgctgtacacatttggacagggaacca aagttgaaatcaagcgtacg (SEQ ID NO: 48) |
| huEGFR-12 $V_L$ v1.0 | gaattcgccaccatgggctggagttgcatcatcctgttcttggttgctaccgcaaccggagtacactccgacgt gcagatcacccaatctccatcatccctcgccgccagtgtgggagaacgaattactatcaactgccgagcaagc cagagtatcagccgttatctggcatggtaccaggagaaacccggtaagactaacaaactgttgatttactcagg cagtacactgcaatctggtatccctagccgctttagcggctccggcagtggcaccgatttcaccctgacaatttc ctccctggagccagaggatttcgcaatgtattattgtcagcaacacaacgagtacccatggacatttggccagg gcacaaagctggagattaagcgtacg (SEQ ID NO: 49) |
| huEGFR-12 $V_L$ v1.01 | gaattcgccaccatgggatggtcctgcattatcctgttcctcgtggcaacagctacaggggtgcatagcgatgtg cagatcacccagtccccaagctcccttgcagcttccgttggtgagcgcattaccatcaactgtcgagctagtaag tctatttccaagtacctggcttggtatcaagagaagccaggaaagacaaacaagctgctcatttacagtggctcta cccttcagtccggtattccctctagatttagtggcagtggtagtggaaccgattttacccttacaattagctctctgg aaccagaagacttcgcaatgtactactgccagcaacacaatgagtacccatggacttttggccagggaacaaag ctggaaattaaacgtacg (SEQ ID NO: 50) |
| muEGFR-6 $V_L$ | gacatccagatgacacagtctccatcctcactgtctgcatctctgggaggcaaagtcaccatc acttgcaaggcaagccaagacattaacaactatatagcttggtaccaacacaagcctggaaaaggtccta ggctgctcattcattacacatctacattacatccaggcatcccatcaaggttcagtggaagtgggtctgg gagagattattccttcagcatcagcaacctggagcctgaagatattgcaacttattattgtctacagtat gataatcttctgtacacgttcggaggggggaccaagctggaaataaaacgg (SEQ ID NO: 81) |

TABLE 9

| Full-length heavy and light chain polynucleotide sequences | |
|---|---|
| Antibody | Polynucleotide Sequence |
| huEGFR-7 HC | aagcttgccaccatgggctggtcatgtatcattctgttcctggtggccaccgcaaccggtgtccattcccaggtg cagctcgtgcagagcggggctgaagtggccaagccaggtgcttctgtcaaattgtcttgtaaggccagtgggt acaccttcacaagctactggatgcagtgggttaagcaacgcccaggccagggactggagtgcatcggcacca tttatccaggggatggagataccacttatacacaaaagtttcaaggcaaagccaccctgaccgccgacaaatcc agcagcacagcatacatgcagctttctagcctcaggtctgaagactccgccgtgtactattgtgcccgctacga cgcccccggctatgcaatggattactggggccagggtactctggtcacagtgtcctccgcctctacaaagggc ccatcagttttccccttggctccaagttctaaatccacaagcggtggaacagctgcactgggatgcctcgttaaa gattatttccctgagcctgtgacagtgagctggaatagcggagcattgacttcaggtgtgcacacttttcccgctg tgttgcagtcctccggtctgtactcactgtccagtgtcgtaaccgtcccttctagcagcttgggaacccagaccta catctgtaacgtcaaccataaaccatccaacacaaaggtggataagaaggttgaaccaaagagctgtgataag acacatacatgccctccttgtcctgcaccagagctcctcggaggtccatctgtgttcctgtttcccccaaaccca aggacactcttatgatctctcgtaactccagaggtcacctgtgttgttgtcgacgtgagccatgaagatcccgagg ttaaattcaactggtacgtggatggagtcgaggttcacaatgccaagaccaagcccagggaggagcaatataa ttctacatatcgggtagtgagcgttctgaccgtgctccaccaagattggctcaatggaaaagagtacaagtgcaa ggtgtccaacaaggctcttcccgctcccattgagaaaactatctccaaagccaagggcagccacgggaaccc caggtgtatacattgcccccatctagagacgagctgaccaagaaccaggtgagtctcacttgtctggtcaaggg gttttacccttctgacattgctgtagagtgggagtctaacggacagccagaaaacaactacaagacaactcccc cagtgctggacagcgacgggagcttcttcctctactccaagttgactgtagacaagtctagatggcagcaaggaa acgttttctcctgctcagtaatgcatgaggctctgcacaatcactatacccagaaatcactgtcccttagcccaggg tgactcgag (SEQ ID NO: 51) |
| huEGFR-7 LC v1.0 | gaattcgccaccatgggctggagctgcatcatcttgttcttggtcgccactgccacaggagtgcatagcgatattc agatgacccagtctcccagctctctgagcgctagcgtgggcgatcgggtgactattacttgccgtgcatcccag gatatcaacaactacttggcctggtaccagcacaagcccggcaaaggcccaaagctgctgatccactataccag tacactgcaccctggtatcccttctagattcagcggctccggtagtggtcgggattactcattctctatctcttcccttg gagcccgaggatatagctacatattattgtctccagtacgataatctcttgtacacatttggacaggggacaaagc tggagatcaagcgtacggtggctgcaccatctgtcttcatcttcccgccatctgatgagcagttgaaatctggaac tgcctctgttgtgtgcctgctgaataacttctatcccagagaggccaaagtacagtggaaggtggataacgccctc caatcgggtaactcccaggagagtgtcacagagcaggacagcaaggacagcacctacagcctcagcagcacc ctgacgctgagcaaagcagactacgagaaacacaaagtctacgcctgcgaagtcacccatcagggcctgagct cgcccgtcacaaagagcttcaacaggggagagtgttag (SEQ ID NO: 52) |

TABLE 9-continued

Full-length heavy and light chain polynucleotide sequences

| Antibody | Polynucleotide Sequence |
|---|---|
| huEGFR-7 LC v1.01 | gaattcgccaccatgggatggtcctgcattatccttttcctggtcgccaccgccacaggcgtccactctgacatac aaatgacccagtccccttcttcactgagcgcctccgttggggatagagttacaatcacttgtaaagctagccagga catcaacaactatctggcttggtatcagcataaacctgggaagggacccaagctcttgattcattacacctctacct tgcacccaggcataccaagccgctttagcggtagtggcagtggccgcgattactcattctccatcagttccttgg aaccagaagatatagccacctattattgtctccagtatgataatttgctctacacttttggccagggcaccaaacttg agatcaagcgtacggtggctgcaccatctgtcttcatcttcccgccatctgatgagcagttgaaatctggaactgc ctctgttgtgtgcctgctgaataacttctatcccagagaggccaaagtacagtggaaggtggataacgccctcca atcgggtaactcccaggagagtgtcacagagcaggacagcaaggacagcacctacagcctcagcagcacc ctgacgctgagcaaagcagactacgagaaacacaaagtctacgcctgcgaagtcacccatcagggcctgagct cgcccgtcacaaagagcttcaacaggggagagtgttag (SEQ ID NO: 53) |
| huEGFR-7 HC_CDR grafted | aagcttgccaccatggggtggtcctgtataatactgtttctggtggccactgccacaggagtccacagccaag tgcagctggtgcagagtggcgctgaggtcaagaagcctggggcatccgtcaaggtttcttgtaaggcatctg gatataccttcacttcctattggatgcagtgggtgagacaggcaccaggacagggactggagtggatgggc actatttatcccaggtgacggtgacactacttatactcagaaattcaagggcgagtgaccatgactcgtgatac tagcactagtaccgtgtatatggagcttagttctctccggtccgaggacacagcagtctactactgtgctagata tgacgcacccggatatgccatggactattgggggcagggcaccctggtcaccgtgagttccgccagcactaa gggcccatcagttttccccttggctccaagttctaaatccacaagcggtggaacagctgcactgggatgcctcg ttaaagattatttccctgagcctgtgacagtgagctggaatagcggagcattgacttcaggtgtgcacacttttcc cgctgtgttgcagtcctccggtctgtactcactgtccagtgtcgtaaccgtcccttctagcagcttgggaaccca gacctacatctgtaacgtcaaccataaaccatccaacacaaaggtggataagaaggttgaaccaaagagctg tgataagacacatacatgccctccttgtcctgcaccagagctcctcggaggtccatctgtgttcctgtttcccccc aaacccaaggacactcttatgatctctcgtactccagaggtcacctgtgttgttgtcgacgtgagccatgaagat cccgaggttaaattcaactggtacgtggatggagtcgaggttcacaatgccaagaccaagcccagggagga gcaatataattctacatatcgggtagtgagcgttctgaccgtgctccaccaagattggctcaatggaaaagag tacaagtgcaaggtgtccaacaaggctcttcccgctcccattgagaaaactatctccaaagccaaggggca gccacgggaaccccaggtgtatacattgcccccatctagagacgagctgaccaagaaccaggtgagtctc acttgtctggtcaaggggttttacccttctgacattgctgtagagtgggagtctaacggacagccagaaaac aactacaagacaactcccccagtgctggacagcgacgggagcttcttcctctactccaagttgactgtaga caagtctagatggcagcaaggaaacgttttctcctgctcagtaatgcatgaggctctgcacaatcactatacc cagaaatcactgtcccttagcccagggtgactcgag (SEQ ID NO: 54) |
| huEGFR-7 LC_CDR grafted | gaattcgccaccatgggatggagttgcattatttgtttctggtagctaccgctacaggcgttcatagcgacatt cagatgacacagagcccctcctctttgtccgcctccgtgggcgatagagtcacaatcacctgccgcgcaag ccaggatatcaacaactaccttgcatggtaccagcagaagcctggaaaagccccaaagctgctcatatact acacctccacccttcacccaggagttccatccaggttctctgggtctggaagtggaacagattttaccttcac aatcagctcattgcaacccgaggacatagctacatattactgcctgcagtatgacaatctgctgtacacatttg gacagggaaccaaagttgaaatcaagcgtacggtggctgcaccatctgtcttcatcttcccgccatctgatga gcagttgaaatctggaactgcctctgttgtgtgcctgctgaataacttctatcccagagaggccaaagtacag tggaaggtggataacgccctccaatcgggtaactcccaggagagtgtcacagagcaggacagcaaggac agcacctacagcctcagcagcaccctgacgctgagcaaagcagactacgagaaacacaaagtctacgcct gcgaagtcacccatcagggcctgagctcgcccgtcacaaagagcttcaacaggggagagtgttag (SEQ ID NO: 55) |
| huEGFR-12 HC | aagcttgccaccatgggctggtcctgtattatcctctttttggtggccactgctaccggcgtacacagtcagg tgcagctggtgcagtccggggctgaagtggcaaagcccggggcctccgtaaagctctcttgcaaggcat ccggctacacttttacttcctactggatgcagtgggtcaaacagcgcccaggacaggggttggaatgtata ggtacaatctatcccggcgatggtgacacacgatatatccagaagttccagggcaaggctaccctgactg ccgacaaatcttctagcaccgcttatatgcagctgtcatctcttcgaagtgaagactctgcagtgtattactg cgcccgatatgacgcacccggttacgccatggattactggggtcaggggaccttggtaaccgtatcaagc gccagtaccaagggcccatcagttttccccttggctccaagttctaaatccacaagcggtggaacagctgca ctgggatgcctcgttaaagattatttccctgagcctgtgacagtgagctggaatagcggagcattgacttcag gtgtgcacacttttcccgctgtgttgcagtcctccggtctgtactcactgtccagtgtcgtaaccgtcccttcta gcagcttgggaacccagacctacatctgtaacgtcaaccataaaccatccaacacaaaggtggataagaa ggttgaaccaaagagctgtgataagacacatacatgccctccttgtcctgcaccagagctcctcggaggtcc atctgtgttcctgtttccccccaaacccaaggacactcttatgatctctcgtactccagaggtcacctgtgttgtt gtcgacgtgagccatgaagatcccgaggttaaattcaactggtacgtggatggagtcgaggttcacaatgcc aagaccaagcccagggaggagcaatataattctacatatcgggtagtgagcgttctgaccgtgctccacca agattggctcaatggaaaagagtacaagtgcaaggtgtccaacaaggctcttcccgctcccattgagaaaa ctatctccaaagccaaggggcagccacgggaaccccaggtgtatacattgcccccatctagagacgagc tgaccaagaaccaggtgagtctcacttgtctggtcaaggggttttacccttctgacattgctgtagagtggg agtctaacggacagccagaaaacaactacaagacaactcccccagtgctggacagcgacgggagcttct tcctctactccaagttgactgtagacaagtctagatggcagcaaggaaacgttttctcctgctcagtaatgcat gaggctctgcacaatcactatacccagaaatcactgtcccttagcccagggtgactcgag (SEQ ID NO: 56) |

TABLE 9-continued

Full-length heavy and light chain polynucleotide sequences

| Antibody | Polynucleotide Sequence |
|---|---|
| huEGFR-<br>12 LC<br>v1.0 | gaattcgccaccatgggctggagttgcatcatcctgttcttggttgctaccgcaaccggagtacactccgacg<br>tgcagatcacccaatctccatcatccctcgccgccagtgtgggagaacgaattactatcaactgccgagcaa<br>gccagagtatcagccgttatctggcatggtaccaggagaaacccggtaagactaacaaactgttgatttactc<br>aggcagtacactgcaatctggtatccctagccgctttagcggctccggcagtggcaccgatttcaccctgac<br>aatttcctccctggagccagaggatttcgcaatgtattattgtcagcaacacaacgagtacccatggacatttgg<br>ccagggcacaaagctggagattaagcgtacggtggctgcaccatctgtcttcatcttcccgccatctgatgag<br>cagttgaaatctggaactgcctctgttgtgtgcctgctgaataacttctatcccagagaggccaaagtacagtgg<br>aaggtggataacgccctccaatcgggtaactcccaggagagtgtcacagagcaggacagcaaggacagcac<br>ctacagcctcagcagcaccctgacgctgagcaaagcagactacgagaaacacaaagtctacgcctgcgaag<br>tcacccatcagggcctgagctcgcccgtcacaaagagcttcaacaggggagagtgttag<br>(SEQ ID NO: 57) |
| huEGFR-<br>12 LC<br>v1.01 | gaattcgccaccatgggatggtcctgcattatcctgttcctcgtggcaacagctacaggggtgcatagcgatgt<br>gcagatcacccagtccccaagctcccttgcagcttccgttggtgagcgcattaccatcaactgtcgagctagta<br>agtctatttccaagtacctggcttggtatcaagagaagccaggaaagacaaacaagctgctcatttacagtggc<br>tctacccttcagtccggtattccctctagatttagtggcagtggtagtggaaccgattttacccttacaattagctct<br>ctggaaccagaagacttcgcaatgtactactgccagcaacacaatgagtacccatggacttttggccagggaa<br>caaagctggaaattaaacgtacggtggctgcaccatctgtcttcatcttcccgccatctgatgagcagttgaaat<br>ctggaactgcctctgttgtgtgcctgctgaataacttctatcccagagaggccaaagtacagtggaaggtggata<br>acgccctccaatcgggtaactcccaggagagtgtcacagagcaggacagcaaggacagcacctacagcctc<br>agcagcaccctgacgctgagcaaagcagactacgagaaacacaaagtctacgcctgcgaagtcacccatca<br>gggcctgagctcgcccgtcacaaagagcttcaacaggggagagtgttag<br>(SEQ ID NO: 58) |
| huEGFR-<br>6 HC v1.0 | aagcttgccaccatggggtggagttgtatcatcctcttccttgtcgctaccgccactggagtgcattcccaggtg<br>cagttggtgcaatctggcgccgaggtggccaagcccggtgcctccgtaaaattgagttgtaaagcctctggcta<br>tacatttacatcttattggatgcagtgggtcaagcagcgccctggtcaaggcctggagtgcatcggagctctgta<br>tcctggcgacgggacgcccgttacactcagaaatttcagggcaaagctaccctcaccgcagatacatccagc<br>agcactgcttatatgcaacttagtagcctccgcagcgaggatagtgccgtgtactactgtgccagatatgacgcc<br>ccaggttatgctatggactactggggtcaaggaaccctggtgacagtgtcaagcgctagcacaaagggcccatc<br>agtttttccccttggctccaagttctaaatccacaagcggtggaacagctgcactgggatgcctcgttaaagattatt<br>tccctgagcctgtgacagtgagctggaatagcggagcattgacttcaggtgtgcacacttttcccgctgtgttgca<br>gtcctccggtctgtactcactgtccagtgtcgtaaccgtcccttctagcagcttgggaacccagacctacatctgta<br>acgtcaaccataaaccatccaacacaaaggtggataagaaggttgaaccaaagagctgtgataagacacatac<br>atgccctccttgtcctgcaccagagctcctcggaggtccatctgtgttcctgtttcccccaaacccaaggacact<br>cttatgatctctcgtactccagaggtcacctgtgttgttgtcgacgtgagccatgaagatcccgaggttaaattcaa<br>ctggtacgtggatggagtcgaggttcacaatgccaagaccaagcccagggaggagcaatataattctacatatc<br>gggtagtgagcgttctgaccgtgctccaccaagattggctcaatggaaaagagtacaagtgcaaggtgtccaac<br>aaggctcttcccgctcccattgagaaaactatctccaaaagccaaggggcagccacgggaaccccaggtgtatac<br>attgcccccatctagagacgagctgaccaagaaccaggtgagtctcacttgtctggtcaaggggttttacccttctg<br>acattgctgtagagtgggagtctaacggacagccagaaaacaactacaagacaactcccccagtgctggacag<br>cgacgggagcttcttcctctactccaagttgactgtagacaagtctagatggcagcaaggaaacgttttctcctgctc<br>agtaatgcatgaggctctgcacaatcactatacccagaaatcactgtcccttagcccagggtgactcgag<br>(SEQ ID NO: 82) |
| huEGFR-<br>6 HC<br>v1.11 | aagcttgccaccatggggtggagttgtatcatcctcttccttgtcgctaccgccactggagtgcattcccaggtgca<br>gttggtgcaatctggcgccgaggtggccaagcccggtgcctccgtaaaattgagttgtaaagcctctggctatacat<br>ttacatcttattggatgcagtgggtcaagcagcgccctggtcaaggcctggagtggatcggagctctgtatcctggc<br>gacggggacgcccgttacactcagaaatttcagggcaaagctaccctcaccgcagatacatccagcagcactgct<br>tatatgcaacttagtagcctccgcagcgaggatagtgccgtgtactactgtgccagatatgacgccccaggttatgc<br>tatggactactggggtcaaggaaccctggtgacagtgtcaagcgctagcacaaagggcccatcagtttttccccttg<br>gctccaagttctaaatccacaagcggtggaacagctgcactgggatgcctcgttaaagattatttccctgagcctgtg<br>acagtgagctggaatagcggagcattgacttcaggtgtgcacacttttcccgctgtgttgcagtcctccggtctgtac<br>tcactgtccagtgtcgtaaccgtcccttctagcagcttgggaacccagacctacatctgtaacgtcaaccataaacca<br>tccaacacaaaggtggataagaaggttgaaccaaagagctgtgataagacacatacatgccctccttgtcctgcacc<br>agagctcctcggaggtccatctgtgttcctgtttcccccaaacccaaggacactcttatgatctctcgtactccagagg<br>tcacctgtgttgttgtcgacgtgagccatgaagatcccgaggttaaattcaactggtacgtggatggagtcgaggttca<br>caatgccaagaccaagcccagggaggagcaatataattctacatatcgggtagtgagcgttctgaccgtgctccacca<br>agattggctcaatggaaaagagtacaagtgcaaggtgtccaacaaggctcttcccgctcccattgagaaaactatctc<br>caaagccaaggggcagccacgggaaccccaggtgtatacattgcccccatctagagacgagctgaccaagaacc<br>aggtgagtctcacttgtctggtcaaggggttttacccttctgacattgctgtagagtgggagtctaacggacagccaga<br>aaacaactacaagacaactcccccagtgctggacagcgacgggagcttcttcctctactccaagttgactgtagacaa<br>gtctagatggcagcaaggaaacgttttctcctgctcagtaatgcatgaggctctgcacaatcactatacccagaaatca<br>ctgtcccttagcccagggtgactcgag (SEQ ID NO: 83) |
| huEGFR-<br>7 HC<br>v1.11 | aagcttgccaccatgggctggtcatgtatcattctgttcctggtggccaccgcaaccggtgtccattcccaggtgcagct<br>cgtgcagagcggggctgaagtggccaagccaggtgcttctgtcaaattgtcttgtaaggccagtgggtacaccttcaca<br>agctactggatgcagtgggttaagcaacgcccaggccagggactggagtggatcggcaccatttatccaggggatgg<br>agataccacttatacacaaaagtttcaaggcaaagccaccctgaccgccgacaaatccagcagcacagcatacatgcag<br>ctttctagcctcaggtctgaagactccgccgtgtactattgtgcccgctacgacgcccccggctatgcaatggattactggg<br>gccagggtactctggtcacagtgtcctccgcctctacaaagggcccatcagtttttccccttggctccaagttctaaatccaca<br>agcggtggaacagctgcactgggatgcctcgttaaagattatttccctgagcctgtgacagtgagctggaatagcggagca<br>ttgacttcaggtgtgcacacttttcccgctgtgttgcagtcctccggtctgtactcactgtccagtgtcgtaaccgtcccttctag<br>cagcttgggaacccagacctacatctgtaacgtcaaccataaaccatccaacacaaaggtggataagaaggttgaaccaa<br>agagctgtgataagacacatacatgccctccttgtcctgcaccagagctcctcggaggtccatctgtgttcctgtttccccc<br>caaacccaaggacactcttatgatctctcgtactccagaggtcacctgtgttgttgtcgacgtgagccatgaagatcccga |

TABLE 9-continued

Full-length heavy and light chain polynucleotide sequences

| Antibody | Polynucleotide Sequence |
| --- | --- |
| | ggttaaattcaactggtacgtggatggagtcgaggttcacaatgccaagaccaagcccagggaggagcaatataattcta catatcgggtagtgagcgttctgaccgtgctccaccaagattggctcaatggaaaagagtacaagtgcaaggtgtccaac aaggctcttcccgctcccattgagaaaactatctccaaagccaaggggcagccacgggaaccccaggtgtatacattgcc cccatctagagacgagctgaccaagaaccaggtgagtctcacttgtctggtcaaggggttttacccttctgacattgctgta gagtgggagtctaacggacagccagaaaacaactacaagacaactcccccagtgctggacagcgacgggagcttcttc ctctactccaagttgactgtagacaagtctagatggcagcaaggaaacgttttctcctgctcagtaatgcatgaggctctgc acaatcactatacccagaaatcactgtcccttagcccagggtgactcgag (SEQ ID NO: 84) |

Also provided is a polynucleotide having at least about 95%, at least about 96%, at least about 97%, at least about 98%, or at least about 99% sequence identity to SEQ ID NOs:39-58, 77-84. Thus, in certain embodiments, the polypeptide comprises (a) a polypeptide having at least about 95% sequence identity to SEQ ID NOs:39-43, 51, 54, 56, 77-80 or 82-84 and/or (b) a polypeptide having at least about 95% sequence identity to SEQ ID NOs:44-50, 52, 53, 55, 57, 58, 81. In certain embodiments, the polypeptide comprises (a) a polypeptide having the amino acid sequence of SEQ ID NOs: 39-43, 51, 54, 56, 77-80 or 82-84; and/or (b) a polypeptide having the amino acid sequence of SEQ ID NOs: 44-50, 52, 53, 55, 57, 58, 81.

In certain embodiments the polynucleotides comprise the coding sequence for the mature polypeptide fused in the same reading frame to a polynucleotide which aids, for example, in expression and secretion of a polypeptide from a host cell (e.g. a leader sequence which functions as a secretory sequence for controlling transport of a polypeptide from the cell). The polypeptide having a leader sequence is a preprotein and can have the leader sequence cleaved by the host cell to form the mature form of the polypeptide. The polynucleotides can also encode for a proprotein which is the mature protein plus additional 5' amino acid residues. A mature protein having a prosequence is a proprotein and is an inactive form of the protein. Once the prosequence is cleaved an active mature protein remains.

In certain embodiments the polynucleotides comprise the coding sequence for the mature polypeptide fused in the same reading frame to a marker sequence that allows, for example, for purification of the encoded polypeptide. For example, the marker sequence can be a hexa-histidine tag supplied by a pQE-9 vector to provide for purification of the mature polypeptide fused to the marker in the case of a bacterial host, or the marker sequence can be a hemagglutinin (HA) tag derived from the influenza hemagglutinin protein when a mammalian host (e.g. COS-7 cells) is used.

The present invention further relates to variants of the hereinabove described polynucleotides encoding, for example, fragments, analogs, and derivatives.

The polynucleotide variants can contain alterations in the coding regions, non-coding regions, or both. In some embodiments the polynucleotide variants contain alterations which produce silent substitutions, additions, or deletions, but do not alter the properties or activities of the encoded polypeptide. In some embodiments, nucleotide variants are produced by silent substitutions due to the degeneracy of the genetic code. Polynucleotide variants can be produced for a variety of reasons, e.g., to optimize codon expression for a particular host (change codons in the human mRNA to those preferred by a bacterial host such as *E. coli*).

Vectors and cells comprising the polynucleotides described herein are also provided.

IV. Methods of Use and Pharmaceutical Compositions

The EGFR-binding agents (including antibodies, immunoconjugates, and polypeptides) of the invention are useful in a variety of applications including, but not limited to, therapeutic treatment methods, such as the treatment of cancer. In certain embodiments, the agents are useful for inhibiting tumor growth, inducing differentiation, reducing tumor volume, and/or reducing the tumorigenicity of a tumor. The methods of use can be in vitro, ex vivo, or in vivo methods. In certain embodiments, the EGFR-binding agent or antibody or immunoconjugate, or polypeptide is not antagonistic of the human EGFR to which it binds.

In one aspect, anti-EGFR antibodies and immunoconjugates of the invention are useful for detecting the presence of EGFR in a biological sample. The term “detecting” as used herein encompasses quantitative or qualitative detection. In certain embodiments, a biological sample comprises a cell or tissue.

In one aspect, the invention provides a method of detecting the presence of EGFR in a biological sample. In certain embodiments, the method comprises contacting the biological sample with an anti-EGFR antibody under conditions permissive for binding of the anti-EGFR antibody to EGFR, and detecting whether a complex is formed between the anti-EGFR antibody and EGFR.

In one aspect, the invention provides a method of diagnosing a disorder associated with increased expression of EGFR. In certain embodiments, the method comprises contacting a test cell with an anti-EGFR antibody; determining the level of expression (either quantitatively or qualitatively) of EGFR by the test cell by detecting binding of the anti-EGFR antibody to EGFR; and comparing the level of expression of EGFR by the test cell with the level of expression of EGFR by a control cell (e.g., a normal cell of the same tissue origin as the test cell or a cell that expresses EGFR at levels comparable to such a normal cell), wherein a higher level of expression of EGFR by the test cell as compared to the control cell indicates the presence of a disorder associated with increased expression of EGFR. In certain embodiments, the test cell is obtained from an individual suspected of having a disorder associated with increased expression of EGFR. In certain embodiments, the disorder is a cell proliferative disorder, such as a cancer or a tumor.

In certain embodiments, a method of diagnosis or detection, such as those described above, comprises detecting binding of an anti-EGFR antibody to EGFR expressed on the surface of a cell or in a membrane preparation obtained from a cell expressing EGFR on its surface. In certain embodiments, the method comprises contacting a cell with an anti-EGFR antibody under conditions permissive for binding of the anti-EGFR antibody to EGFR, and detecting whether a complex is formed between the anti-EGFR antibody and EGFR on the cell surface. An exemplary assay for detecting binding of an anti-EGFR antibody to EGFR expressed on the surface of a cell is a "FACS" assay.

Certain other methods can be used to detect binding of anti-EGFR antibodies to EGFR. Such methods include, but are not limited to, antigen-binding assays that are well known in the art, such as western blots, radioimmunoassays, ELISA (enzyme linked immunosorbent assay), "sandwich" immunoassays, immunoprecipitation assays, fluorescent immunoassays, protein A immunoassays, and immunohistochemistry (IHC).

In certain embodiments, anti-EGFR antibodies are labeled. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction.

In certain embodiments, anti-EGFR antibodies are immobilized on an insoluble matrix. Immobilization entails separating the anti-EGFR antibody from any EGFR that remains free in solution. This conventionally is accomplished by either insolubilizing the anti-EGFR antibody before the assay procedure, as by adsorption to a water-insoluble matrix or surface (Bennich et al., U.S. Pat. No. 3,720,760), or by covalent coupling (for example, using glutaraldehyde cross-linking), or by insolubilizing the anti-EGFR antibody after formation of a complex between the anti-EGFR antibody and EGFR, e.g., by immunoprecipitation.

Any of the above embodiments of diagnosis or detection can be carried out using an immunoconjugate of the invention in place of or in addition to an anti-EGFR antibody.

In certain embodiments, the disease treated with the EGFR-binding agent or antagonist (e.g., an anti-EGFR antibody) is a cancer. In certain embodiments, the cancer is characterized by EGFR expressing cells to which the EGFR-binding agent (e.g., antibody) binds.

In a further aspect, the invention is directed to an improved method for treating cell proliferation disorders wherein EGFR is expressed, particularly wherein EGFR is abnormally expressed (e.g. overexpressed), including cancers of the bladder, brain, head and neck, pancreas, lung, breast, ovary, colon, prostate, skin, and kidney, comprising administering a therapeutically effective amount of an anti-EGFR binding agent of the present invention to a human subject in need thereof. In another embodiment the antibody is humanized. Examples of cell proliferation disorders that can be treated by an anti-EGFR binding agent of the present invention include, but are not limited to neoplasms located in the: abdomen, bone, breast, digestive system, liver, pancreas, peritoneum, endocrine glands (adrenal, parathyroid, pituitary, testicles, ovary, thymus, thyroid), eye, head and neck, nervous system (central and peripheral), lymphatic system, pelvic, skin, soft tissue, spleen, thoracic region, and urogenital system.

Similarly, other cell proliferation disorders can also be treated by the anti-EGFR binding agents of the present invention. Examples of such cell proliferation disorders include, but are not limited to: adrenal cortex hyperplasia (Cushing's disease), congenital adrenal hyperplasia, endometrial hyperplasia, benign prostatic hyperplasia, breast hyperplasia, intimal hyperplasia, focal epithelial hyperplasia (Heck's disease), sebaceous hyperplasia, compensatory liver hyperplasia, and any other cell proliferation disease, besides neoplasia, located in an organ system listed above.

The present invention further provides methods for inhibiting tumor growth using the antibodies or other agents described herein. In certain embodiments, the method of inhibiting the tumor growth comprises contacting the cell with an EGFR-binding agent (e.g., antibody) in vitro. For example, an immortalized cell line or a cancer cell line that expresses EGFR is cultured in medium to which is added the antibody or other agent to inhibit tumor growth. In some embodiments, tumor cells are isolated from a patient sample such as, for example, a tissue biopsy, pleural effusion, or blood sample and cultured in medium to which is added an EGFR-binding agent to inhibit tumor growth.

In some embodiments, the method of inhibiting tumor growth comprises contacting the tumor or tumor cells with the EGFR-binding agent (e.g., antibody) in vivo. In certain embodiments, contacting a tumor or tumor cell with a EGFR-binding agent is undertaken in an animal model. For example, EGFR-binding agents can be administered to xenografts expressing one or more EGFRs that have been grown in immunocompromised mice (e.g. NOD/SCID mice) to inhibit tumor growth. In some embodiments, cancer stem cells are isolated from a patient sample such as, for example, a tissue biopsy, pleural effusion, or blood sample and injected into immunocompromised mice that are then administered a EGFR-binding agent to inhibit tumor cell growth. In some embodiments, the EGFR-binding agent is administered at the same time or shortly after introduction of tumorigenic cells into the animal to prevent tumor growth. In some embodiments, the EGFR-binding agent is administered as a therapeutic after the tumorigenic cells have grown to a specified size.

In certain embodiments, the method of inhibiting tumor growth comprises administering to a subject a therapeutically effective amount of a EGFR-binding agent. In certain embodiments, the subject is a human. In certain embodiments, the subject has a tumor or has had a tumor removed.

In certain embodiments, the tumor expresses the EGFR to which the EGFR-binding agent or antibody binds.

In addition, the invention provides a method of reducing the tumorigenicity of a tumor in a subject, comprising administering a therapeutically effective amount of a EGFR-binding agent to the subject. In certain embodiments, the tumor comprises cancer stem cells. In certain embodiments, the frequency of cancer stem cells in the tumor is reduced by administration of the agent.

The invention further provides methods of differentiating tumorigenic cells into non-tumorigenic cells comprising contacting the tumorigenic cells with a EGFR-binding agent (for example, by administering the EGFR-binding agent to a subject that has a tumor comprising the tumorigenic cells or that has had such a tumor removed.

The use of the EGFR-binding agents, polypeptides, or antibodies described herein to induce the differentiation of cells, including, but not limited to tumor cells, is also provided. For example, methods of inducing cells to differentiate comprising contacting the cells with an effective amount of a EGFR-binding agent (e.g., an anti-EGFR antibody) described herein are envisioned. Methods of inducing cells in a tumor in a subject to differentiate comprising administering a therapeutically effective amount of a EGFR-binding agent, polypeptide, or antibody to the subject are also provided. In certain embodiments, the tumor is a pancreatic tumor. In certain other embodiments, the tumor is a colon tumor. In some embodiments, the treatment methods comprise administering a therapeutically effective amount of the EGFR-binding agent, polypeptide, or antibody to the subject.

The present invention further provides pharmaceutical compositions comprising one or more of the EGFR-binding agents described herein. In certain embodiments, the pharmaceutical compositions further comprise a pharmaceutically acceptable vehicle. These pharmaceutical compositions find use in inhibiting tumor growth and treating cancer in human patients.

In certain embodiments, formulations are prepared for storage and use by combining a purified antibody or agent of the present invention with a pharmaceutically acceptable vehicle (e.g. carrier, excipient) (Remington, The Science and Practice of Pharmacy 20th Edition Mack Publishing, 2000). Suitable pharmaceutically acceptable vehicles include, but are not limited to, nontoxic buffers such as phosphate, citrate, and other organic acids; salts such as sodium chloride; antioxidants including ascorbic acid and methionine; preservatives (e.g. octadecyldimethylbenzyl ammonium chloride; hexamethonium chloride; benzalkonium chloride; benzethonium chloride; phenol, butyl or benzyl alcohol; alkyl parabens, such as methyl or propyl paraben; catechol; resorcinol; cyclohexanol; 3-pentanol; and m-cresol); low molecular weight polypeptides (e.g. less than about 10 amino acid residues); proteins such as serum albumin, gelatin, or immunoglobulins; hydrophilic polymers such as polyvinylpyrrolidone; amino acids such as glycine, glutamine, asparagine, histidine, arginine, or lysine; carbohydrates such as monosaccharides, disaccharides, glucose, mannose, or dextrins; chelating agents such as EDTA; sugars such as sucrose, mannitol, trehalose or sorbitol; salt-forming counter-ions such as sodium; metal complexes (e.g. Zn-protein complexes); and non-ionic surfactants such as TWEEN or polyethylene glycol (PEG).

The pharmaceutical compositions of the present invention can be administered in any number of ways for either local or systemic treatment Administration can be topical (such as to mucous membranes including vaginal and rectal delivery) such as transdermal patches, ointments, lotions, creams, gels, drops, suppositories, sprays, liquids and powders; pulmonary (e.g., by inhalation or insufflation of powders or aerosols, including by nebulizer; intratracheal, intranasal, epidermal and transdermal); oral; or parenteral including intravenous, intraarterial, subcutaneous, intraperitoneal or intramuscular injection or infusion; or intracranial (e.g., intrathecal or intraventricular) administration.

An antibody or immunoconjugate of the invention can be combined in a pharmaceutical combination formulation, or dosing regimen as combination therapy, with a second compound having anti-cancer properties. The second compound of the pharmaceutical combination formulation or dosing regimen can have complementary activities to the ADC of the combination such that they do not adversely affect each other. Pharmaceutical compositions comprising the EGFR-binding agent and the second anti-cancer agent are also provided.

For the treatment of the disease, the appropriate dosage of an antibody or agent of the present invention depends on the type of disease to be treated, the severity and course of the disease, the responsiveness of the disease, whether the antibody or agent is administered for therapeutic or preventative purposes, previous therapy, patient's clinical history, and so on all at the discretion of the treating physician. The antibody or agent can be administered one time or over a series of treatments lasting from several days to several months, or until a cure is effected or a diminution of the disease state is achieved (e.g. reduction in tumor size). Optimal dosing schedules can be calculated from measurements of drug accumulation in the body of the patient and will vary depending on the relative potency of an individual antibody or agent. The administering physician can easily determine optimum dosages, dosing methodologies and repetition rates. In certain embodiments, dosage is from 0.01 μg to 100 mg per kg of body weight, and can be given once or more daily, weekly, monthly or yearly. In certain embodiments, the antibody or other EGFR-binding agent is given once every two weeks or once every three weeks. In certain embodiments, the dosage of the antibody or other EGFR-binding agent is from about 0.1 mg to about 20 mg per kg of body weight. The treating physician can estimate repetition rates for dosing based on measured residence times and concentrations of the drug in bodily fluids or tissues.

The combination therapy can provide "synergy" and prove "synergistic", i.e. the effect achieved when the active ingredients used together is greater than the sum of the effects that results from using the compounds separately. A synergistic effect can be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect can be attained when the compounds are administered or delivered sequentially, e.g. by different injections in separate syringes. In general, during alternation therapy, an effective dosage of each active ingredient is administered sequentially, i.e. serially, whereas in combination therapy, effective dosages of two or more active ingredients are administered together.

VI. Kits Comprising EGFR Binding Agents

The present invention provides kits that comprise the antibodies, immunoconjugates or other agents described herein and that can be used to perform the methods described herein. In certain embodiments, a kit comprises at least one purified antibody against EGFR in one or more containers. In some embodiments, the kits contain all of the components necessary and/or sufficient to perform a detection assay, including all controls, directions for performing assays, and any necessary software for analysis and presentation of results. One skilled in the art will readily recognize that the disclosed antibodies, immunoconjugates or other agents of the present invention can be readily incorporated into one of the established kit formats which are well known in the art.

Further provided are kits comprising a EGFR-binding agent (e.g., a EGFR-binding antibody), as well as a second anti-cancer agent. In certain embodiments, the second anti-cancer agent is a chemotherapeutic agent (e.g., rituximab).

EXAMPLES

It is understood that the examples and embodiments described herein are for illustrative purposes only and that various modifications or changes in light thereof will be suggested to persons skilled in the art and are to be included within the spirit and purview of this application.

Example 1

Production of Murine EGFR Antibodies

To produce murine anti-EGFR antibodies, head and neck squamous carcinoma cell lines such as CA922 (Japanese Collection of Research Bioresources (JCRB), Shinjuku, Japan) and HSC4 (JCRB, Shinjuku, Japan) were injected subcutaneously into Balb/c female mice (Charles River Laboratory, Wilmington, Mass.) at the dose of $5\times10^6$ cells per mouse every 2 weeks for 5 times. Three days before being sacrificed for hybridoma generation, the immunized mice received intraperitoneal injection of another dose of antigen. The spleen from the mouse was collected according to standard animal protocols and was ground between two sterile, frosted microscopic slides to obtain a single cell suspension in RPMI-1640 medium. After the red blood cells were lysed with ACK lysing buffer, the spleen cells were then mixed with murine myeloma P3X63Ag8.653 cells (P3 cells) (J. F. Kearney et al. 1979, *J Immunol,* 123: 1548-1550) at ratio of 1 P3 cells:3 spleen cells. The mixture of spleen cells and P3 cells was washed and treated with pronase in fusion media (0.3M mannitol/D-sorbitol, 0.1 mM CaCl2, 0.5 mM MgCl2 and 1 mg/ml BSA) at room temperature for 3 min. The reaction was stopped by addition of FBS (Fetal Bovine Serum, Invitrogen); cells were then washed, resuspended in 2 ml cold fusion media and fused with BTX ECM 2001 electrofusion machine (Harvard Apparatus). The fused cells were added gently to RPMI-1640 selection medium containing hypoxanthine-aminopterin-thymidine (HAT) (Sigma Aldrich), incubated for 20 min at 37° C., and then seeded into flat bottom 96-well plates at 200 μl/well. The plates were then incubated in 5% $CO_2$ incubator at 37° C. until hybridoma clones were ready for antibody screening. Other techniques of immunization and hybridoma production can also be used, including those described in J. Langone and H. Vunakis (Eds., Methods in Enzymology, Vol. 121, "Immunochemical Techniques, Part I"; Academic Press, Florida) and E. Harlow and D. Lane ("Antibodies: A Laboratory Manual"; 1988; Cold Spring Harbor Laboratory Press, New York, N.Y.).

Murine Hybridoma Screening and Selection

Hybridoma screening was done using flow cytometric binding assay with immunizing cells that are either untreated or treated with EGF (R&D Systems). Because incubation with EGF downregulates EGFR level on the cell surface, EGFR specific hybridoma supernatant would only react to the untreated cells and not to the EGF-treated cells. Cells for screening were first cultured in serum free media for overnight and separated into two parts. One part of the cells was left untreated and the other part was treated with EGF for 3 hours at 37° C. The EGF treated cells were labeled with CellTrace™ far red DDAO-SE (Invitrogen), mixed with untreated cells at 1:1 ratio and incubated with the hybridoma supernatant for 2 hours on ice. Cells were then washed, incubated with FITC-labeled anti-mouse IgG (Jackson Immunoresearch), washed, fixed with formalin and analyzed using FACScalibur (BD Bioscience). The EGFR specific hybridomas were expanded and the supernatants were rescreened by ELISA using soluble recombinant human EGFR extracellular domain (RELIATech) as antigen. The positive hybridomas were rescreened using flow cytometric binding assay with human EGFR-expressing A431 epidermal carcinoma cell line (ATCC) and monkey EGFR-expressing Vero cell line (an African green monkey kidney epithelial cell line) (ATCC). In brief, the hybridoma supernatant was incubated with A431 cells and DDAO-labeled Vero cells on ice for 1 hour. The cells were washed twice and incubated with PE-conjugated goat anti-mouse IgG antibody (Jackson Immunoresearch) for 1 hour on ice. The cells were then washed with FACS buffer, fixed in formalin and analyzed using a FACSCalibur flow cytometer (BD Biosciences).

The positive hybridoma clones that reacted to both human and monkey antigens were tested for the capacity to inhibit basal proliferation of EGFR-overexpressing HCC827 cells (ATCC). In brief, exponentially growing HCC827 cells were plated at 2000 cells/well in 96 well plates in 100 μl complete media containing 10% FBS. 100 μl of hybridoma supernatant was added to the cells and the mixture was incubated at 37° C. in a humidified 5% $CO_2$ incubator for 5 days. Level of cell proliferation was determined using colorimetric WST-8 assay (Dojindo Molecular Technologies, Rockville, Md.). WST-8 is reduced by dehydrogenases in the living cells to an orange formazan product that is soluble in tissue culture medium, and the amount of formazan produced is directly proportional to the number of living cells. 10% of the final volume of WST-8 was added to each well and plates were incubated at 37° C. for an additional 2-4 h. Plates were then analyzed by measuring the absorbance at 450 nm (A450) in the Spectra Max M2 plate reader (Molecular Devices, Sunnyvale, Calif.). Background A450 absorbance of wells with media and WST-8 only was subtracted from all values. The surviving fraction was calculated by dividing each treated sample value by the average value of wells with untreated cell (surviving fraction=(A450 treated sample−A450 background)/(A450 untreated sample−A450 background)). The results were normalized so that surviving fraction 0 indicated the value of wells without cells and 1 indicated the level of cell proliferation in the serum containing media without any EGFR antibody. Hybridoma clones that inhibited at least 50% HCC827 cell growth were subcloned by limiting dilution. One subclone from each hybridoma, which showed the same reactivity against EGFR as the parental cells by flow cytometry, was chosen for subsequent analysis. Stable subclones were cultured and the antibody was isotyped using commercial isotyping reagents (Roche).

Antibody Purification

Antibodies were purified from hybridoma subclone supernatants using standard methods, such as, for example Protein A or G chromatography (HiTrap Protein A or G HP, 1 mL, Amersham Biosciences). Briefly, supernatant was prepared for chromatography by the addition of 1/10 volume of 1M Tris/HCl buffer, pH 8.0. The pH-adjusted supernatant was filtered through a 0.22 μm filter membrane and loaded onto column equilibrated with binding buffer (PBS, pH 7.3). The column was washed with binding buffer until a stable baseline was obtained with no absorbance at 280 nm. Antibody was eluted with 0.1M acetic acid buffer containing 0.15M NaCl, pH 2.8, using a flow rate of 0.5 mL/min. Fractions of approximately 0.25 mL were collected and neutralized by the addition of 1/10 volume of 1M Tris/HCl, pH 8.0. The peak fraction(s) was dialyzed overnight twice against 1×PBS and sterilized by filtering through a 0.2 μm filter membrane. Purified antibody was quantified by absorbance at A280.

Protein A purified fractions were further polished using ion exchange chromatography (IEX) with quaternary ammonium (Q) chromatography for murine antibodies. Briefly, samples from protein A purification were buffer exchanged into binding buffer (10 mM Tris, 10 mM sodium chloride, pH 8.0) and filtered through 0.22 μm filer. The prepared sample was then loaded onto a Q fast flow resin (GE Lifesciences) that was equilibrated with binding buffer at a flow rate of 120 cm/hr. Column size was chosen to have sufficient capacity to bind all the MAb in the sample. The column was then washed with binding buffer until a stable baseline was obtained with no absorbance at 280 nm. Antibody was eluted by initiating a gradient from 10 mM to 500 mM sodium chloride in 20 column volume (CV). Peak fractions were collected based on absorbance measurement at 280 nm (A280). The percentage of monomer was assessed with size exclusion chromatography (SEC) on a TSK gel G3000SWXL, 7.8×300 mm with a SWXL guard column, 6.0×40 mm (Tosoh Bioscience, Montgomeryville, Pa.) using an Agilent HPLC 1100 system (Agilent, Santa Clara, Calif.). Fractions with monomer content above 95% were pooled, buffer exchanged to PBS (pH 7.4) using a TFF system, and sterilized by filtering through a 0.2 μm filter membrane. The IgG concentration of purified antibody was determined by A280 using an extinction coefficient of 1.47. Alternative methods such as ceramic hydroxyapatite (CHT) were also used to polish antibodies with good selectivity. Type II CHT resin with 40 μm particle size (Bio-Rad Laboratories) were used with a similar protocol as described for IEX chromatography. The binding buffer for CHT corresponds to 20 mM sodium phosphate, pH 7.0 and antibody was eluted with a gradient of 20-160 mM sodium phosphate over 20 CV.

Example 2

Binding Affinity to Human and Monkey EGFR Antigen

To determine the binding affinity of the EGFR antibodies to the human and monkey antigens, EGFR expressing human tumor cell lines such as MDA-MB468 (ATCC) and A431 (ATCC), and Vero monkey kidney cell line (ATCC) were used in a flow cytometric binding assay. In brief, the cells were incubated with various concentration of EGFR antibody for 1h at 4° C. The cells were washed and incubated with PE-conjugated secondary antibody (Jackson Immunoresearch) for 1h at 4° C. The cells were then washed, fixed in formalin and analyzed in FACSarray (BD Bioscience). To determine the binding affinity of these antibodies, geometric mean fluorescence intensity was plotted against the antibody concentration in a semi-log plot. A dose-response curve was generated by non-linear regression and the EC50 value of the curve, which corresponds to the apparent dissociation constant (Kd) of each antibody, was calculated using GraphPad Prism v4 (GraphPad software). The EGFR antibodies of the invention as well as positive control antibodies, cetuximab and panitumumab, showed strong specific binding to both human tumor cells and monkey Vero cells. A table shown in FIG. 1 lists the Kd of each antibody to the human and monkey EGFR. The EGFR antibodies of the invention exhibited similarly strong binding affinity to both human and monkey antigens.

Example 3

Inhibition of Ligand-Induced EGFR Activation

EGFR ligand binding induces EGFR phosphorylation followed by activation of downstream signaling pathways. To investigate the effect of anti-EGFR antibodies in ligand-induced EGFR activation, Western blot analysis was performed using MDA-MB468 tumor cell line and human primary adult keratinocytes. In brief, cells were seeded at 1e6 cells/well in a 6 well plate and cultured in normal media for overnight. Cells were washed and starved in serum free media containing 0.1% BSA for 2 hours at 37° C. 10 μg/ml antibody was added to the cells and the mixture was incubated for 3 hours at 37° C. 50 ng/ml EGF (R&D Systems) was added to the mixture and incubated for 15 minutes at 37° C. Cells were then washed with ice-cold PBS and lysed in RIPA buffer containing protease and phosphatase inhibitors. The protein lysates were separated in SDS-PAGE and transferred to a nitrocellulose membrane. The membrane was blocked with 5% BSA and incubated with anti-phosphotyrosine antibody (clone 4G10, Millipore) for overnight at 4° C. The membrane was washed, incubated with HRP conjugated anti-mouse antibody (Jackson Immunoresearch) for 1 hour at room temperature, and washed again. The signal was detected using an ECL (enhanced chemiluminescene) system (GE Healthcare). To ensure equal amount of proteins loaded into each lane, the membrane was stripped and reprobed with anti-β-tubulin antibody (Sigma Aldrich).

As shown in FIG. 2, EGF stimulation led to strong EGFR phosphorylation in both MDA-MB468 cells and human primary keratinocytes. Treatment of cells with cetuximab and panitumumab strongly inhibited the EGF-induced EGFR phosphorylation while the EGFR antibodies of the invention did not completely inhibit EGFR activation. Anti-KTI (Kunitz Trypsin inhibitor) antibody (produced from hybridoma obtained from ATCC) was used as negative control.

Example 4

Agonistic Activity of EGFR Antibodies

Figure 3:
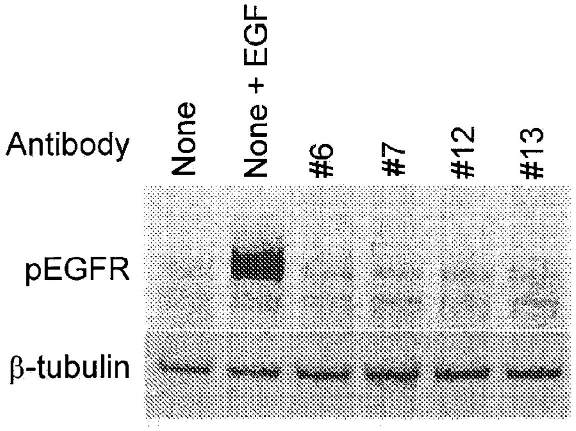
FIG. 3 is a Western blot data depicting the effect of the indicated anti-EGFR antibodies on EGFR phosphorylation in MDA-MB468 cells in absence of exogenous EGFR ligand.

To investigate the effect of the EGFR antibodies of the invention on EGFR signaling in absence of EGFR ligands, MDA-MB468 tumor cells were starved in serum free media as described in Example 5. The cells were then incubated with 10 μg/ml EGFR antibodies for 3 hours at 37° C. As positive control, untreated cells were incubated with 50 ng/ml EGF for 15 minutes at 37° C. The protein lysates were prepared and analyzed using Western blot as described in Example 5. The representative result is shown in FIG. 3. EGF treatment clearly induced a strong EGFR phosphorylation in MDA-MB468 cells while the EGFR antibodies of the invention did not affect EGFR signaling in absence of the ligand.

Example 5

Ligand Binding Competition

Figure 4:
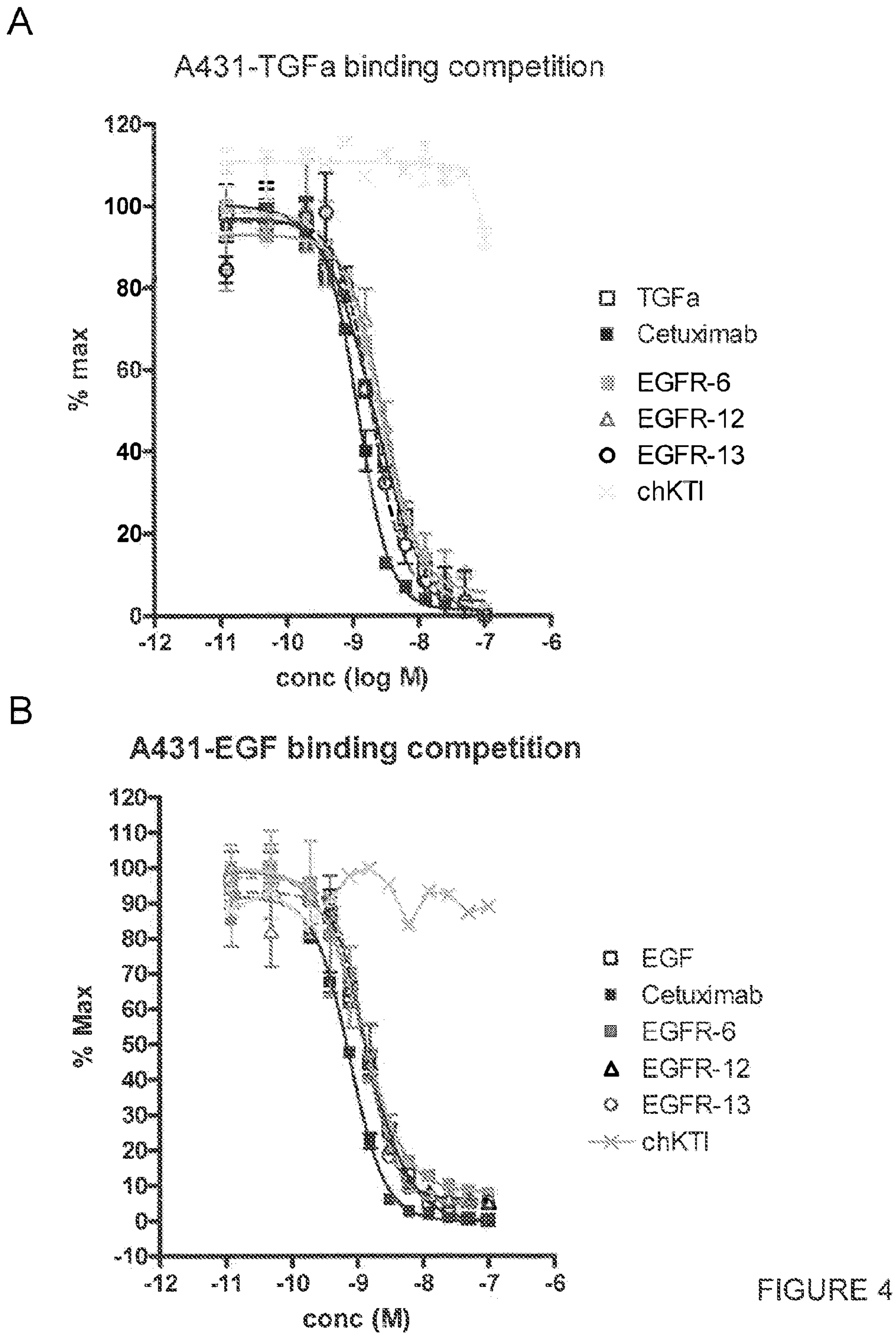
FIG. 4 is a line graph depicting the binding of biotinylated TGFα (A) and EGF (B) to the A431 cells in presence of the indicated antibodies.

One mechanism of EGFR signaling inhibition is blockade of ligand binding. To examine if the EGFR antibodies inhibit the ligand binding to the EGFR, the binding of biotinylated EGFR ligand to the A431 cells was measured by flow cytometry in the presence of anti-EGFR antibodies. Biotinylation of TGFα was done using EZ-link Micro Sulfo-NHS-LC-biotinylation kit (Pierce, Rockland, Ill.) according to the manufacturer's instruction. Biotinylated EGF was obtained from Invitrogen. Prior to competition assay, the binding curve of the biotinylated ligands was established. Varying concentrations of anti-EGFR antibodies were pre-mixed with biotinylated ligands at EC50 concentration (1.8 nM and 10 nM for EGF and TGFα, respectively), and the mixture was incubated with the cells for 30 min on ice. Cells were then washed twice with FACS buffer and incubated with streptavidin-APC conjugate (Jackson Immunoresearch) for 15 min on ice. Cells were washed twice with FACS buffer and analyzed in FACS Calibur (BD Bioscience) using FlowJo program (Tree Star). The geometric mean fluorescence intensities were plotted against the antibody concentration in a semi-log plot. As shown in FIG. 4, the negative control antibody, anti-KTI antibody does not affect the ligand binding while all anti-EGFR antibodies compete the ligand binding with the following EC50 (Table 10).

TABLE 10

| | EC50 of TGFa binding competition (nM) | EC50 of EGF binding competition (nM) |
|---|---|---|
| Ligand | 1.336 | 2.097 |
| Cetuximab | 0.769 | 1.226 |
| EGFR-6 | 1.181 | 2.552 |
| EGFR-12 | 1.341 | 2.927 |
| EGFR13 | 1.321 | 1.957 |

The EGFR antibodies of the invention completely blocked the TGFα and EGF binding with similar EC50 as cetuximab (FIG. 4 and Table 10). This result cannot explain the differential effect of cetuximab and the EGFR antibodies of the invention on ligand induced EGFR signaling (Example 3) and growth of normal epithelial cell lines including human primary keratinocytes (Example 6).

Example 6

Growth Inhibition Assay of Human Primary Keratinocytes and Normal Epithelial Cell Line Human normal basal epithelial cells in skin, gastrointestinal tract and other organs physiologically express EGFR. The EGFR signaling in these tissues is critical for the epithelial cell growth. Disruption of EGFR signaling pathway by cetuximab and panitumumab as well as small tyrosine kinase inhibitors such as erlotinib and gefitinib causes significant skin toxicity. To mimic the potential toxicity in skin and other epithelial cells, proliferation assays using human primary keratinocytes (Invitrogen) and a non-tumorigenic breast epithelial cell line, MCF10A (ATCC), were established. In this assay, cells were plated at 1,500-2,000 cells per well in EGFR ligand-containing media suggested by the manufacturers and incubated with anti-EGFR antibodies at 37° C. for 5 days. In the keratinocytes assay (FIG. 5), cells were grown in presence of 1 nM EGF with varying concentration of antibodies. While in MCF10A cell assay (FIG. 6), cells were grown in presence of 10 nM EGF with a fixed concentration (10 μg/ml) of antibodies. Level of cell proliferation was determined using colorimetric WST-8 assay (Dojindo Molecular Technologies, Rockville, Md.) as described in example 1. The surviving fraction was calculated by dividing each treated sample value by the average value of wells with untreated cell (surviving fraction=(A450 treated sample−A450 background)/(A450 untreated sample−A450 background)). The results were normalized so that 0 indicated the level of cell proliferation in absence of EGF and 1 indicated the level of cell proliferation in presence of EGF without any anti-EGFR antibody treatment.

Figure 5:
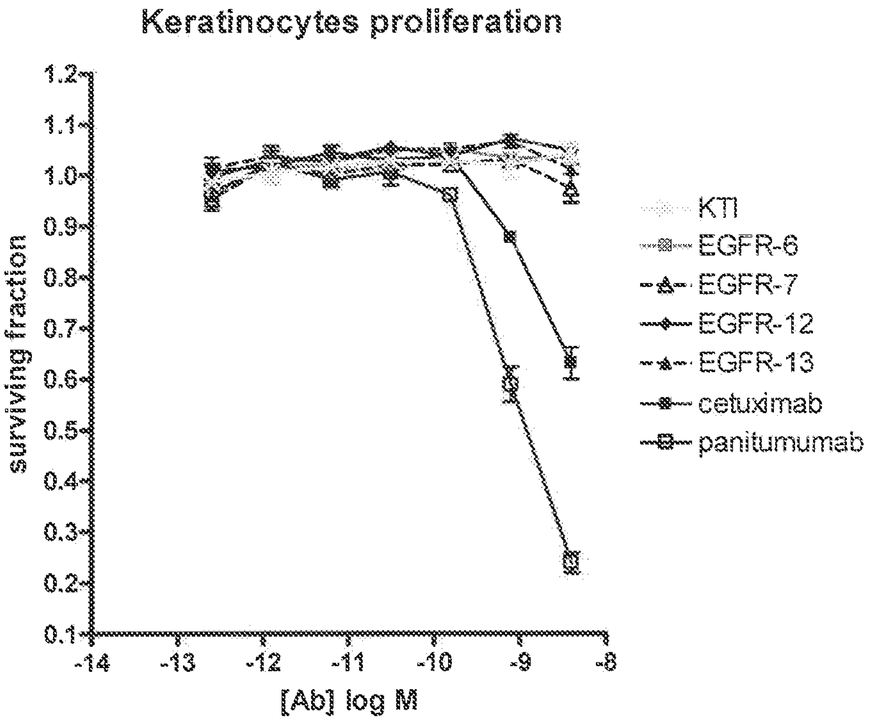
FIG. 5 is a line graph depicting the growth of human primary keratinocytes in presence of the indicated antibodies at various concentrations.
Figure 6:
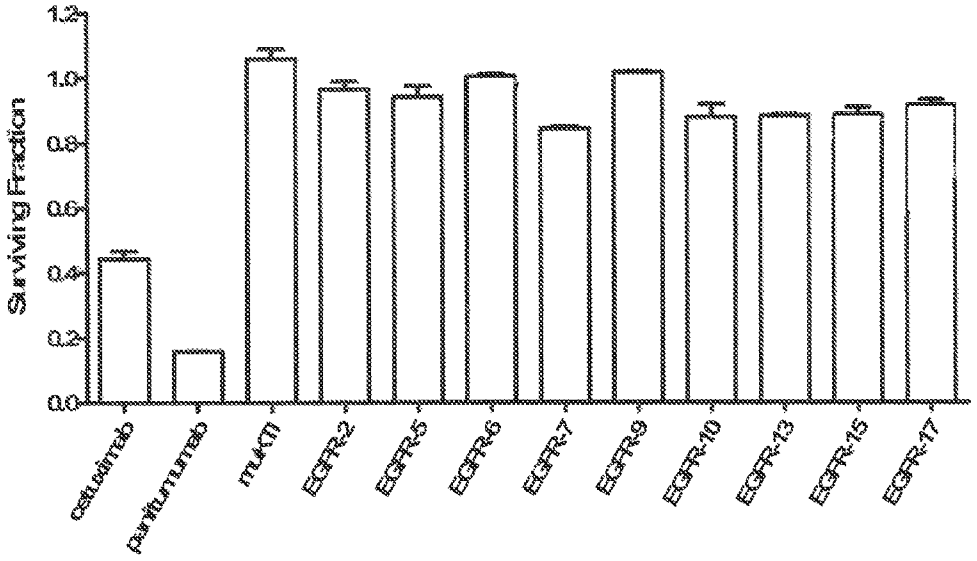
FIG. 6 is a bar graph depicting the growth of MCF 10A cells in the presence of 10 μg/ml of the indicated antibodies.

The binding of the anti-EGFR antibodies to human primary keratinocytes as well as MCF10A cells was confirmed before the proliferation assays were performed. A representative result of the keratinocytes proliferation assay is shown in FIG. 5. As expected from the toxicity profile, cetuximab and panitumumab strongly inhibited the keratinocytes proliferation in dose dependent manner with the maximal inhibition of 40% for cetuximab and 78% for panitumumab. Surprisingly, the EGFR antibody of the invention, similar as the negative control chimeric KTI antibody, had little or no effect on the keratinocytes. This result was confirmed in the MCF10A proliferation assay (FIG. 6). The cetuximab and panitumumab strongly inhibited MCF10A cell proliferation while the EGFR antibodies of the invention had little or no effect on MCF10A cell growth. These data suggest that the EGFR antibodies of the invention are less toxic than cetuximab and panitumumab on normal epithelial cells that express EGFR.

Example 7

Inhibition of Basal Proliferation of HCC827 and NCI-H292 Cell Lines

To determine the capacity of anti-EGFR antibodies in inhibiting the basal proliferation of tumor cells, proliferation assays with EGFR-expressing HCC827 (ATCC) and NCI-H292 (ATCC) lung tumor cell lines were established. Cells were plated at 2,000 cells per well in normal growth media containing 10% FBS and grown at 37° C. for 5 days in presence of varying concentration of anti-EGFR antibodies. Level of cell proliferation was determined using colorimetric WST-8 assay. The OD results were normalized so that surviving fraction 1 represents cells grown in normal growth media without anti-EGFR antibodies, and 0 represents the value of wells without cells.

Figure 7:
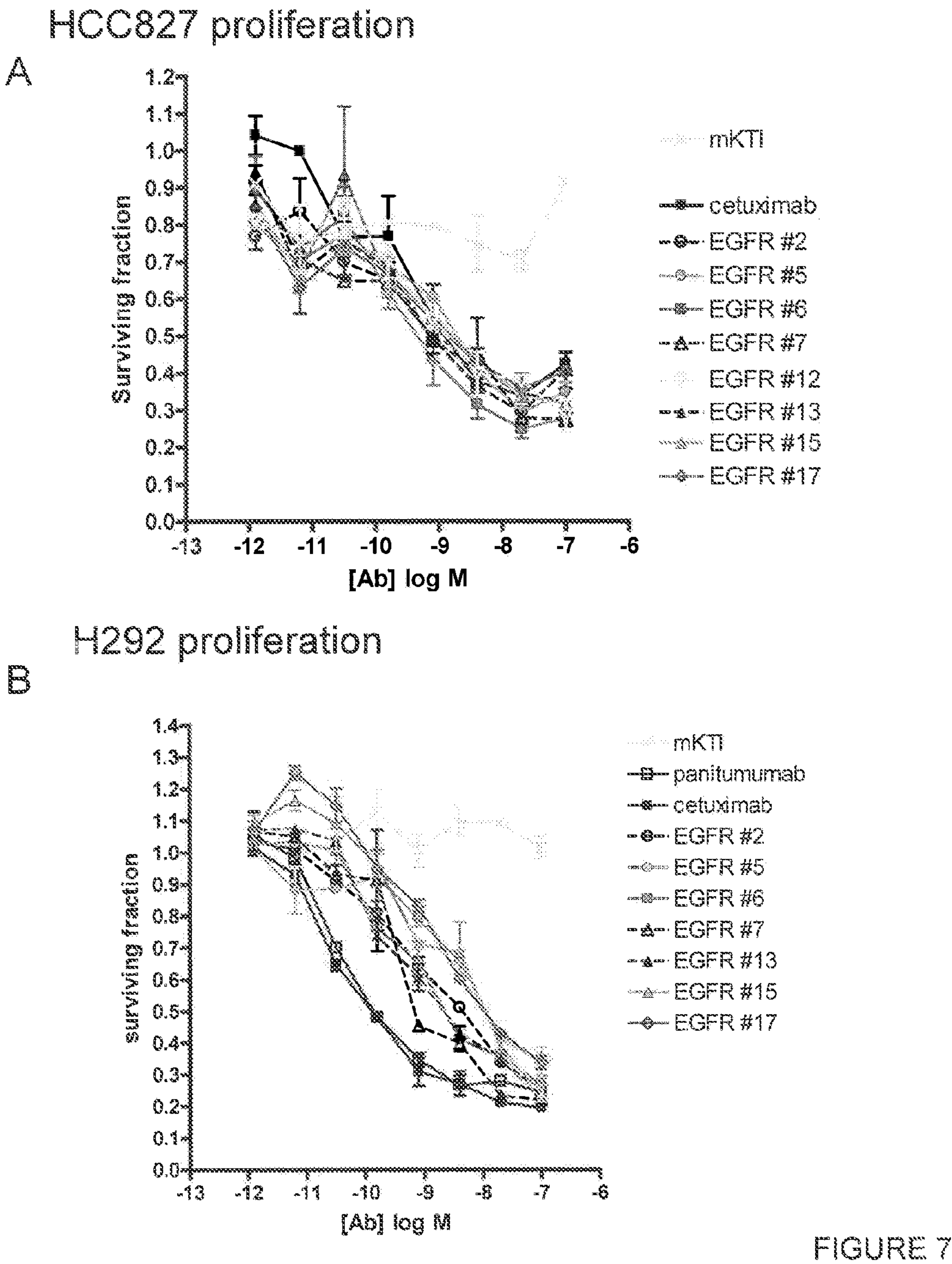
FIG. 7 is a line graph depicting the growth of HCC827 cells (A) and NCI-H292 cells (B) in the presence of the indicated antibodies.

FIGS. 7A and 7B show the representative proliferation assay results with HCC827 and NCI-H292 cells, respectively. In HCC827 cell line (FIG. 7A), cetuximab strongly inhibited the tumor cell growth in dose dependent manner. Despite being harmless to EGFR expressing normal epithelial cells, anti-EGFR antibodies of the invention showed similar or better inhibitory activity than cetuximab. Table 11 describes the EC50 and % maximal inhibition of each antibody.

TABLE 11

Anti-proliferative activity of anti-EGFR antibodies in HCC827 cells

| Antibody | EC50 (nM) | Maximal inhibition (%) |
|---|---|---|
| Cetuximab | 0.13 | 65 |
| 2 | 0.32 | 70 |
| 5 | 1.3 | 72 |
| 6 | 0.3 | 72 |
| 7 | 0.03 | 72 |
| 12 | 0.7 | 63 |
| 13 | 0.03 | 69 |
| 15 | 0.7 | 67 |
| 17 | 0.06 | 64 |

In NCI-H292 cell line (FIG. 7B), cetuximab and panitumumab strongly inhibited the basal cell proliferation in dose dependent manner. The EGFR antibodies of the invention were also significantly active in this cell line with the maximal proliferation inhibition was similar to cetuximab and panitumumab. Table 12 describes the EC50 and % maximal inhibition of each antibody.

TABLE 12

Anti-proliferative activity of anti-EGFR antibodies in NCI-H292 cells

| Antibody | EC50 (nM) | Maximal inhibition (%) |
|---|---|---|
| Panitumumab | 0.039 | 76 |
| Cetuximab | 0.035 | 74 |
| 2 | 1.3 | 75 |
| 5 | 4.7 | 60 |
| 6 | 5.6 | 65 |
| 7 | 0.4 | 77 |
| 13 | 0.4 | 78 |
| 15 | 4.7 | 75 |
| 17 | 1.5 | 67 |

These data strongly argue that the EGFR antibodies of the invention are as active as cetuximab and panitumumab in EGFR overexpressing cells while they do not affect the normal epithelial cell growth.

Example 8

Anti-EGFR Antibody Binding Competition

Figure 8:
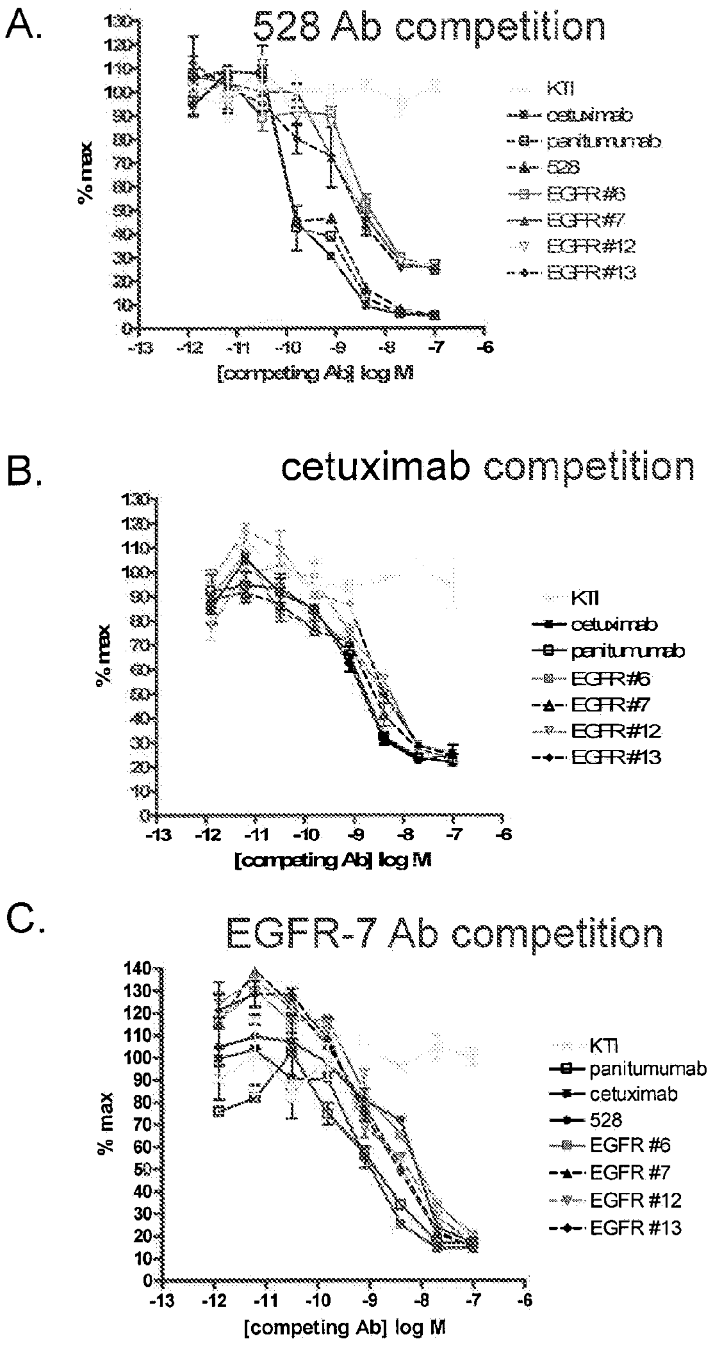
FIG. 8 is a line graph depicting the binding of biotinylated 528 antibody (A), biotinylated cetuximab (B), and biotinylated EGFR-7 antibody (C) to the MDA-MB468 cells in presence of the indicated competing antibodies at the indicated concentration.

To distinguish binding epitopes of anti-EGFR antibodies, antibody binding competition assays were done using flow cytometry. In this experiment, binding of 0.3 nM biotinylated 528 (FIG. 8A), 0.2 nM biotinylated cetuximab (FIG. 8B) and 0.2 nM biotinylated EGFR-7 antibody (FIG. 8C) to the MDA-MB468 cells was measured in presence of varying concentration of 'competing' antibodies. In brief, the biotinylated antibody was pre-mixed with varying concentration of 'competing' antibodies. The antibody mixture was then incubated with cells on ice for 2h. The cells were washed and incubated with streptavidin-alexa 488 conjugate on ice for 1h. After washing, the cells were fixed and analyzed in FACScalibur. The geometric mean fluorescence intensity was plotted against antibody concentration in semi-log plot and normalized so that 100% represents the maximal binding of the biotinylated antibody in absence of other antibody and 0% represents the background staining in absence of the biotinylated antibody. As shown in FIG. 8, all the EGFR antibodies compete with each other. Cetuximab and panitumumab competed the 528 antibody binding as strong as the naked 528 antibody while the EGFR antibodies of the invention had slightly less capacity to compete with 528 antibody (FIG. 8A). All EGFR antibodies competed the binding of cetuximab and EGFR-7 biotinylated antibodies in similar manner (FIGS. 8B and 8C).

Example 9

Cloning and Sequencing of the VL and VH Regions of the EGFR Antibodies

Total cellular RNA was prepared from $5\times10^6$ cells of the EGFR hybridomas using an RNeasy kit (QIAgen) according to the manufacturer's protocol. cDNA was subsequently synthesized from total RNA using the SuperScript II cDNA synthesis kit (Invitrogen).

The procedure for the first round degenerate PCR reaction on the cDNA derived from hybridoma cells was based on methods described in Wang et al. ((2000) *J Immunol Methods.* 233:167-77) and Co et al. ((1992) *J Immunol.* 148:1149-54). VH sequences were amplified by PCR using the following degenerate primers: EcoMH1 CTTCCGGAATTCSARGTNMAGCTGSAGSAGTC (SEQ ID NO:59), EcoMH2 CTTCCGGAATTCSARGTNMAGCTGSAGSAGTCWGG (SEQ ID NO:60) and BamIgG1 GGAGGATCCATAGACAGATGGGGGTGTCGTTTTGGC (SEQ ID NO:61). VL sequences were amplified by PCR using the following degenerate primers: SacIMK GGAGCTCGAYATTGTGMTSACMCARWCTMCA (SEQ ID NO:62) and HindKL TATAGAGCTCAAGCTTGGATGGTGGGAAGATGGATACAGTTGGTGC (SEQ ID NO:85). (Mixed bases are defined as follows: N=G+A+T+C, S=G+C, Y=C+T, M=A+C, R=A+G, W=A+T). The PCR reaction mixtures were then run on a 1% low melt agarose gel, the 300 to 400 bp bands were excised, purified using Zymo DNA mini columns, and sent to Agencourt Biosciences for sequencing. The respective 5' and 3' PCR primers were used as sequencing primers to generate the variable region cDNAs from both directions. The amino acid sequences of VH and VL regions were predicted from the DNA sequencing results.

Since the degenerate primers used to clone the VL and VH cDNA sequences alters the 5' end sequences, additional sequencing efforts were needed to verify the complete sequences. The preliminary cDNA sequences were used to search the NCBI IgBlast site for the murine germline sequences from which the antibody sequences are derived. PCR primers were then designed to anneal to the germline linked leader sequence of the murine antibody so that this new PCR reaction would yield a complete variable region cDNA sequence, unaltered by the PCR primers. The PCR reactions, band purifications, and sequencing were performed as described above.

Mass Determination for Sequence Confirmation

The cDNA sequence information for the variable region was combined with the germline constant region sequence to obtain full length antibody cDNA sequences. The molecular weights of the heavy chain and light chain were then calculated and compared with the molecular weights obtained by LC/MS analyses of the murine EGFR antibodies. The molecular weight measurements are consistent with the cDNA sequences for both the EGFR-7 and EGFR-12 light and heavy chains.

Composite CDR Sequences for the EGFR-7 Variants

A number of murine anti-EGFR hybridomas were sequenced and found to express antibodies with light and heavy chain variable region sequences nearly identical to EGFR-7, but with some CDR amino acid substitutions, particularly in heavy chain CDR2 (FIG. 9). Since these CDR variants of murine EGFR-7 were found to be functionally identical, they provide some structural insight into the sequence flexibility of the EGFR-7 CDR's. Light chain CDR's 2 and 3 as well as heavy chain CDR 1 were identical in each of the variants while a single residue substitution was found at a low frequency in light chain CDR1 and heavy chain CDR3. As opposed to the CDR's with an apparently tight sequence conservation, the variants of EGFR-7 frequently contained as many as 4 amino acid substitutions in heavy chain CDR2. These sequence variants of EGFR-7 suggest that the 5 tightly conserved CDR's may provide the structural basis for EGFR binding, while heavy chain CDR2 has some sequence flexibility resulting in a somatic mutation hotspot during affinity maturation. Table 4 provides a composite CDR sequence listing based on EGFR-7 variants together with the CDR variants described above for humanization. Humanized antibodies derived from these composite CDR's would be expected to preserve the functional attributes of EGFR-7.

TABLE 13

| EGFR-7 variant composite CDR's | |
|---|---|
| **Light Chain** | |
| CDR1: [KorR]ASQDINNY[L or I]A | (SEQ ID NO: 14) |
| CDR2: YTSTLHP | (SEQ ID NO: 11) |
| CDR3: LQYDNLLYT | (SEQ ID NO: 12) |
| **Heavy Chain** | |
| CDR1: TSYWMQ | (SEQ ID NO: 1) |
| CDR2: [T or A][I or L]YPGDGD[T or A] [T, R, or S] | (SEQ ID NO: 4) |
| Kabat CDR2: [T or A][I or L]YPGDGD [T or A][T, R, or S][YT or I]QKF [Q or K]G | (SEQ ID NO: 6) |
| CDR3: YDAPGY[A or T]MDY | (SEQ ID NO: 5) |

Example 10

Antibody Humanization

The EGFR-7 and EGFR-12 antibodies were humanized following resurfacing methods previously described, such as, for example in Roguska et al., Proc. Natl. Acad. Sci., USA, 91(3):969-973 (1994) and Roguska et al., Protein Eng. 9(10): 895-904 (1996), which are incorporated in their entirety herein by reference. Resurfacing generally involves identification of the variable region framework surface residues in both the light and heavy chains and replacing them with human equivalents. The murine CDR's are preserved in the resurfaced antibody. Exemplary CDRs of EGFR-7 and EGFR-12 antibodies are defined as indicated in Table 13. To minimize concerns about the impact of conjugating lysines that fall in CDR's, lysine 24 in murine EGFR-7 antibody light chain CDR1 was replaced with arginine for humanized version 1.0 (shown in italic), so both versions of the LC CDR1 are given. Similarly, lysine 27 and lysine 31 in murine EGFR-12 antibody light chain CDR1 were replaced with glutamine and arginine, respectively, for humanized version 1.0 (shown in italic). The replacement of lysine 27 with glutamine instead of arginine was because glutamine is reserved in human germline sequences at this position. In addition to the AbM heavy chain CDR2 definition employed for resurfacing, the table provides exemplary Kabat defined heavy chain CDR2's for both the murine and human versions of EGFR-7 and EGFR-12 antibodies. The underlined sequence marks the portion of the Kabat heavy chain CDR2 that was not considered a CDR for resurfacing.

Surface residue positions were defined as any position with a relative accessibility of 30% or greater (Pedersen J. T. et. Al, J. Mol. Biol. 1994; 235: 959-973). The calculated surface residues were then aligned with human germline surface sequences to identify the most homologous human surface sequence. The human germline sequence used as the replacement surface for the light chain variable domains of EGFR-7 antibody was IGKV1-12*01 while IGKV1-16*01 was used as the replacement surface for EGFR-12 antibody VL. The human germline sequences used as the replacement surfaces for the heavy chain variable domains of EGFR-7 and EGFR-12 antibodies were IGHV1-69*02 and IGHV1-69*08, respectively. The specific framework surface residue changes for EGFR-7 and EGFR-12 antibodies are given in FIGS. 10 and 11, respectively. Since the resurfaced light chain of both antibodies included the CDR1 lysine substitution(s) for preferred version, a resurfaced version (v1.01) was also generated with murine lysine(s) retained in CDR-L1. Finally, heavy chain framework 2 for murine EGFR-7 and its variants, contained a somatic W47C mutation resulting in an unpaired cysteine residue. For this reason, EGFR-7 heavy chain W47 germline revertant versions (v1.11) were also tested. FIG. 12 shows the alignment of the resurfaced sequences for EGFR-7 and EGFR-12 antibodies variable domain of both light and heavy chain with their murine counterparts.

TABLE 14

| EGFR-7 CDR's (Resurfacing) | EGFR-12 CDR's |
|---|---|
| **Light Chain** | **Light Chain** |
| Murine and resurfaced v1.01 CDR1: KASQDINNYLA (SEQ ID NO: 10) | Murine and resurfaced v1.01 CDR1: RASKSISKYLA (SEQ ID NO: 15) |
| Resurfaced v1.0 CDR1: RASQDINNYLA (SEQ ID NO: 13) | Resurfaced v1.0 CDR1: RASQSISRYLA (SEQ ID NO: 16) |
| CDR2: YTSTLHP (SEQ ID NO: 11) | CDR2: SGSTLQS (SEQ ID NO: 17) |
| CDR3: LQYDNLLYT (SEQ ID NO: 12) | CDR3: QQHNEYPWT (SEQ ID NO: 18) |

TABLE 14-continued

| EGFR-7 CDR's (Resurfacing) | EGFR-12 CDR's |
|---|---|
| **Heavy Chain** | **Heavy Chain** |
| CDR1: TSYWMQ (SEQ ID NO: 1) | CDR1: TSYWMQ (SEQ ID NO: 1) |
| CDR2: TIYPGDGDTT (SEQ ID NO: 2) | CDR2: TIYPGDGDTR (SEQ ID NO: 7) |
| CDR3: YDAPGYAMDY (SEQ ID NO: 3) | CDR3: YDAPGYAMDY (SEQ ID NO: 3) |
| **Kabat EGFR-7 HC CDR2** | **Kabat EGFR-12 HC CDR2** |
| Murine HC CDR2: TIYPGDGDTTYTQKFKG (SEQ ID NO: 63) | Murine HC CDR2: TIYPGDGDTRYIQKFKG (SEQ ID NO: 8) |
| Humanized HC CDR2: TIYPGDGDTTYTQKFQG (SEQ ID NO: 64) | Humanized HC CDR2: TIYPGDGDTRYIQKFQG (SEQ ID NO: 9) |

In addition to humanization by variable domain resurfacing, EGFR-7 antibody was also humanized following complementary determining region (CDR) grafting technology described, such as for example in Jones et al., Nature 321: 604-608 (1986) and Verhoeyen et al., Science 239: 1534-1536 (1988). CDR grafting method consists of grafting the CDRs from a naturally evolved murine antibody onto the Fv framework regions (FRs) of a human antibody. The main step of the process was to choose the appropriate human acceptor frameworks. Kabat numbering scheme and Kabat CDR definition were used for CDR grafting of EGFR-7 antibody. Exemplary CDRs of EGFR-7 antibody for CDR grafting are defined as indicated in Table 15. Human immunoglobulin germline sequence with the highest homology with the murine EGFR-7 antibody was identified through the interactive tool, V-QUEST, of the International ImMunoGeneTics information System® (IMGT (http://imgt.cines.fr/) as described in Lefranc, Nucleic Acids Res. 29: 207-209 (2001). The human germline sequences used as the acceptor frameworks for the VL and VH domains of EGFR-7 antibody were IGKV1-33*01 and IGHV1-46*03, respectively. To minimize concerns about the impact of conjugating lysines that fall in CDR's, lysine 24 in murine EGFR-7 antibody light chain CDR1 was replaced with arginine in CDR grafting (Table 6). The specific framework residue changes as well as the substitution in CDR-L1 in CDR-grafting of EGFR-7 antibody are given in FIG. 13, and the alignments of the CDR-grafted sequences for EGFR-7 antibody variable domains with its murine counterparts is illustrated in FIG. 14.

TABLE 15

| EGFR-7 CDR's (CDR grafting) | |
|---|---|
| **Light Chain** | |
| Murine CDR1: KASQDINNYLA | (SEQ ID NO: 10) |
| CDR grafted CDR1: RASQDINNYLA | (SEQ ID NO: 13) |
| CDR2: YTSTLHP | (SEQ ID NO: 11) |
| CDR3: LQYDNLLYT | (SEQ ID NO: 12) |
| **Heavy Chain** | |
| CDR1: TSYWMQ | (SEQ ID NO: 1) |

TABLE 15-continued

| EGFR-7 CDR's (CDR grafting) | |
|---|---|
| CDR2: TIYPGDGDTTYTQKFKG | (SEQ ID NO: 63) |
| CDR3: YDAPGYAMDY | (SEQ ID NO: 3) |

Recombinant Expression of the Humanized EGFR Antibodies

The variable region sequences for huEGFR-7 and huEGFR-12 were codon-optimized and synthesized by Blue Heron Biotechnology. The sequences were flanked by restriction enzyme sites for cloning in-frame with the respective constant sequences in single chain mammalian expression plasmids. The light chain variable region was cloned into EcoRI and BsiWI sites in the pAbKZeo plasmid. The heavy chain variable region was cloned into the HindIII and Apa1 sites in the pAbG1Neo plasmid. These plasmids were used to express the recombinant antibodies in either transient or stable mammalian cell transfections. Transient transfections to express recombinant antibodies in HEK 293T cells were performed using a modified PEI procedure (Durocher, Y. et al., *Nucleic Acids Res.* 30:E9 (2002)). Supernatant was purified by Protein A and polishing chromatography steps using standard procedures as described above for murine antibodies.

Example 11

Binding Competition Between Murine and Humanized Anti-EGFR Antibodies

To examine the binding of humanized anti-EGFR antibodies, antibody competition assays were performed as described in Example 8. Because muEGFR-6 and muEGFR-7 antibodies cross-compete with one another (FIG. 8C), this experiment examines the ability of murine or humanized antibodies of EGFR-6 (FIG. 15A) or EGFR-7 (FIG. 15B) to compete with the binding of biotinylated muEGFR-7 antibody to the MDA-MB468 cells. In brief, 1 nM of biotinylated muEGFR-7 antibody was pre-mixed with various concentration of 'competing' antibody. The antibody mixture was then incubated with target cells on ice for 1 hour, washed, incubated with streptavidin-APC conjugate on ice for another hour, washed, fixed and analyzed using flow cytometer. The geometric mean fluorescence intensity was plotted against antibody concentration in semi-log plot and normalized so that 100% represents the maximal binding of the biotinylated antibody in absence of other antibody and 0% represents the background staining in absence of the biotinylated antibody. As shown in FIG. 15A, both muEGFR-6 and huEGFR-6 antibodies compete the binding of muEGFR7 at similar EC50 (8.13 nM for muEGFR-6 and 11.09 nM for huEGFR-6). FIG. 15B shows that muEGFR-7, hu-EGFR-7 and huEGFR-7R antibodies also compete the muEGFR-7 antibody binding at similar EC50 (3.54 nM for muEGFR7, 3.35 nM for huEGFR-7R and 4.12 nM for huEGFR-7). These results indicate that humanization does not affect the binding of antibodies of the invention.

Anti-Tumor Activity of Humanized Anti-EGFR Antibodies

Figure 16:
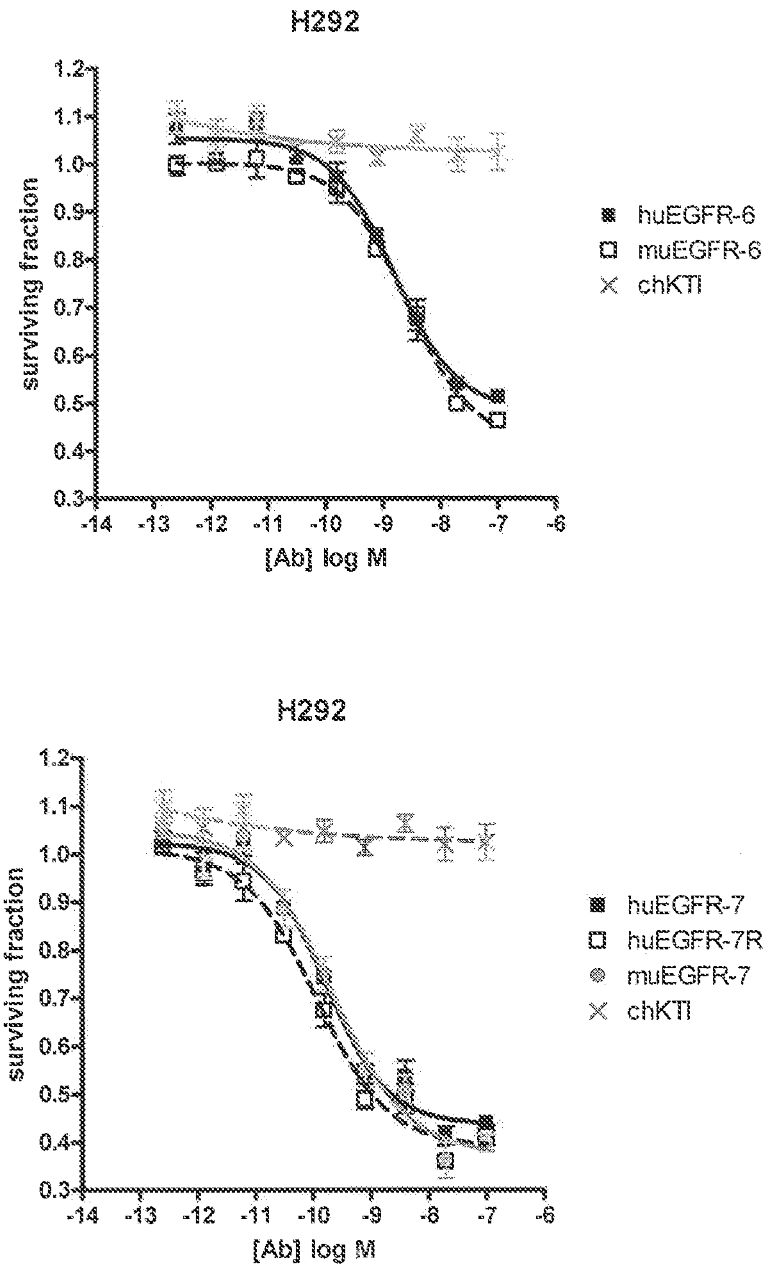
FIG. 16 shows line graphs depicting the ability of the murine antibody and its corresponding humanized antibody in inhibiting tumor cell growth.

To examine the anti-tumor activity of the humanized antibodies of the invention, H292 tumor cell growth inhibition assays were performed as described in Example 7. As shown in FIG. 16, murine and humanized antibodies of EGFR-6 and EGFR-7 were potent in inhibiting H292 tumor cell growth with EC50 included in Table 16. It is apparent that all humanized antibodies maintain the anti-tumor activity of the murine counterparts and humanization does not affect the biological activity of these antibodies.

TABLE 16

Anti-proliferative activity of anti-EGFR antibodies in NCI-H292 cells

| Antibody | EC50 (nM) |
|---|---|
| muEGFR-6 | 2.59 |
| huEGFR-6 | 1.61 |
| muEGFR-7 | 0.21 |
| huEGFR-7 | 0.17 |
| huEGFR-7R | 0.11 |

Example 12

Antibody-Dependent-Cellular-Cytotoxicity (ADCC) Activity of huEGFR Antibodies

A lactate dehydrogenase (LDH) release assay was used to measure antibody-dependent cell mediated cytotoxicity (ADCC) of tumor cells lines using freshly isolated human natural killer (NK) cells as effector cells (Shields R L, *J Biol Chem.* 2001 276(9):6591-604). The NK cells were first isolated from human peripheral blood from a normal donor (Research Blood Components, Inc., Brighton, Mass.) using a modified protocol for the NK cell Isolation Kit II (#130-091-152; Miltenyi Biotec, Auburn, Calif.). Peripheral blood was diluted 2-fold with 1×PBS. 25 mL of diluted blood was carefully layered over 25 mL of Ficoll Paque in a 50 mL conical tube and centrifuged at 400 g for 45 min at RT. The peripheral blood mononuclear cells (PBMC) were collected from the interface, transferred into a new conical 50 mL tube, and washed once with 1× PBS. The PBMC were counted and resuspended at concentration of $2.5\times10^7$ cells/100 μl with MACS buffer (1×PBS, 0.5% BSA, 2 mM EDTA), and then ¼× volume of NK cell Biotin-Antibody Cocktail were added to the cell suspension. The NK cell Biotin-Antibody Cocktail contains biotinylated antibodies that bind to the lymphocytes, except for NK cells, resulting in a negative selection of NK cells. The mixture was incubated at 4° C. for 10 min, and then ⅗× volume of MACS buffer and ⅖× volume of NK cell MicroBead cocktail that would bind to the biotinylated antibodies were added. The cell-antibody mixture was incubated for another 15 min at 4° C. Next, cells were washed once with 50 mL of MACS buffer and resuspended in 3 mL of MACS buffer. NK cells were separated as negative fraction using autoMACS separator (Miltenyi Biotec). The resulting NK cells were plated into 30 mL of complete RPMI media (RPMI-1640 supplemented with 5% fetal bovine serum, 1% penicillin-streptomycin, 1 mM HEPES, 1 mM Sodium Pyruvate, 1% 100×MEM non-essential Amino Acid Solution) overnight. The subsequent assay and all dilutions were carried out in RHBP medium (RPMI-1640 medium supplemented with 20 mM HEPES, pH 7.4, 0.1% BSA and 1% penicillin-streptomycin).

Various concentrations of antibodies in RHBP medium were aliquoted in duplicate at 50 μL/well into a round bottom 96-well plate. The target cells (in this experiment A431 cell line) were resuspended at $10^6$ cells/mL in RHBP medium and added at 100 μL/well to each well containing antibody dilutions. The plate containing target cells and antibody dilutions was incubated for 30 min at RT. NK cells were then added to the wells containing the target cells at 50 μL/well. The typical ratio was 1 target cell to 3-4 NK cells. The following controls were set up for each experiment: NK cells alone, target cells alone (spontaneous LDH release), target cells with NK cells (antibody independent LDH release), target cells with 10% Triton X-100 (maximum LDH release). The mixtures were incubated at 37° C. for 4 h to allow for cell lysis. Plates were centrifuged for 10 min at 1200 rpm, and 100 μL of the supernatant was carefully transferred to a new flat-bottom 96-well plate. LDH reaction mixture (100 μL/well) from the Cytotoxicity Detection Kit (Roche 1 644 793) was added to each well and incubated at room temperature for 5 to 30 min. The optical density (OD) of samples was measured at 490 nm (OD490). The percent specific lysis of each sample was determined using the following formula: percent specific lysis=(sample value−spontaneous release)/(maximum release−spontaneous release)*100.

Figure 17:
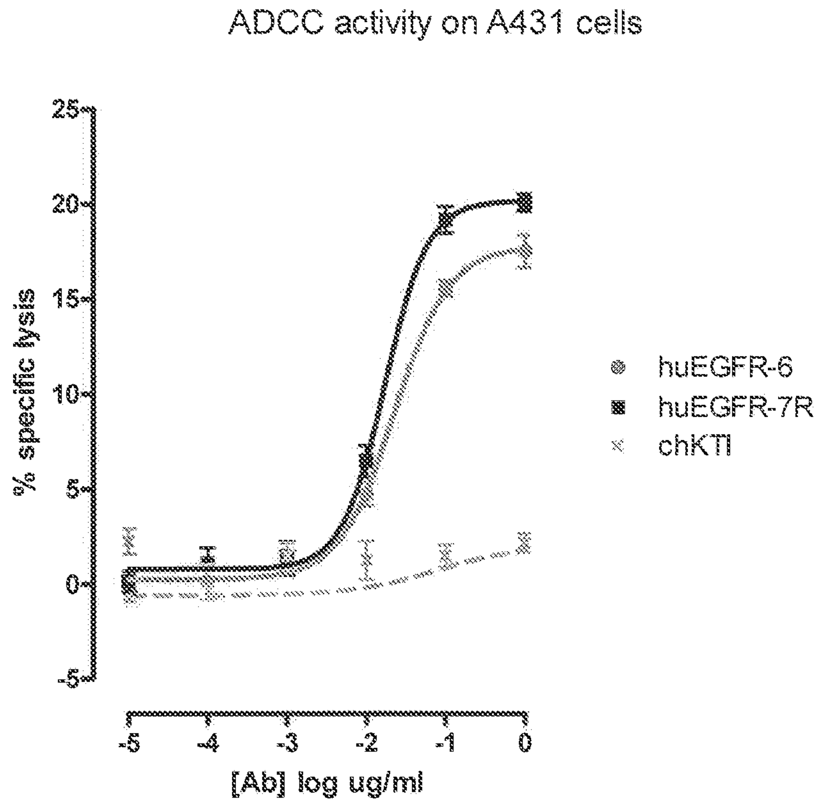
FIG. 17 shows a line graph depicting NK cell mediated ADCC activity of humanized EGFR-6 and EGFR-7R on A431 cells.

FIG. 17 shows a representative ADCC activity of huEGFR-6 and huEGFR-7R antibodies in comparison to that of chKTI antibody. The huEGFR-6 and huEGFR-7R antibodies induced NK cell mediated killing of target cells in dose dependent manner with maximal specific killing reached around 20% and EC50 of 22 ng/ml and 17 ng/ml for huEGFR6 and huEGFR-7R, respectively. In contrast, chKTI antibody that did not bind to target cells failed to mediate ADCC.

Example 13

Preparation of huEGFR-7R-SMCC-DM1

The (Succinimidyl 4-(N-maleimidomethyl)cyclohexane-1-carboxylate (SMCC, Pierce Biotechnology, Inc) linker was dissolved in dimethylacetamide (DMA). The huEGFR antibody was modified with SMCC to introduce maleimides into the antibody by incubating the antibody at 5 mg/mL in 50 mM potassium phosphate, 50 mM NaCl, 2 mM EDTA, pH 6.5 with a 10 molar excess of SMCC. After approximately 100 minutes at ambient temperature, the reaction mixture was purified using a SEPHADEX™ G25 column equilibrated with the same potassium phosphate buffer. Antibody containing fractions were pooled and used for subsequent steps.

The SMCC-modified antibody was reacted with a 10 mM solution of DM1 at a 1.7 molar excess relative to the maleimide linker. The reaction was stirred at ambient temperature under for approximately 18 hours. The conjugation reaction mixture was filtered through a SEPHADEX™ G25 gel filtration column equilibrated with 1×PBS at pH 6.5. The huEGFR antibody-SMCC-DM1 conjugate was then dialyzed into buffer containing 10 mM histidine, 250 mM glycine, 1% sucrose pH 5.5. The number of DM1 molecules linked per antibody molecule was determined using the previously reported extinction coefficients for antibody and DM1 (Liu et al., *Proc. Natl. Acad. Sci. USA,* 93, 8618-8623 (1996)). The percentage of free maytansinoid present after the conjugation reaction was determined by injecting 20-50 μg conjugate onto a HiSep column equilibrated in 25% acetonitrile in 100 mM ammonium acetate buffer, pH 7.0, and eluting in acetonitrile. The peak area of total free maytansinoid species (eluted in the gradient and identified by comparison of elution time with known standards) was measured using an absorbance detector set to a wavelength of 252 nm and compared with the peak area related to bound maytansinoid (eluted in the conjugate peak in the column flow-through fractions) to calculate the percentage of total free maytansinoid species. Conjugates with 3.5-4 DM1 molecules per huEGFR antibody were obtained with <1% present as unconjugated maytansinoid.

Preparation of huEGFR-7R-SPDB-DM4

The exemplary N-succinimidyl 4-(2-pyridyldithio) butanoate (SPDB) linker was dissolved in ethanol. The huEGFR antibody was incubated at 8 mg/mL with a 5.5-5 fold molar excess of SPDB linker for approximately 2 hours at room temperature in 50 mM potassium phosphate buffer (pH 6.5) containing 50 mM NaCl, 2 mM EDTA, and 3% ethanol. The SPDB modified antibody was diluted 2-fold in PBS, pH 6.5 and modified with a 1.5 fold molar excess of the maytansinoid DM4 by the addition of a concentrated solution (15-30 mM) of DM4 in dimethylacetamide (DMA). After overnight incubation at room temperature, the conjugated antibody was purified by chromatography on SEPHADEX™ G25F equilibrated with 10 mM histidine, 250 mM glycine, 1% sucrose pH 5.5. The number of DM4 molecules linked per antibody molecule was determined using the previously reported extinction coefficients for antibody and maytansinoid (Widdison W C et al. J Med Chem, 49:4392-4408 (2006)). The percentage of total free maytansinoid species were determined as described above. Conjugates with 3.5-4 DM4 molecules per huEGFR antibody were obtained with <1% present as unconjugated maytansinoid.

Example 14

Binding Affinity of Maytansinoid Conjugates

Figure 18:
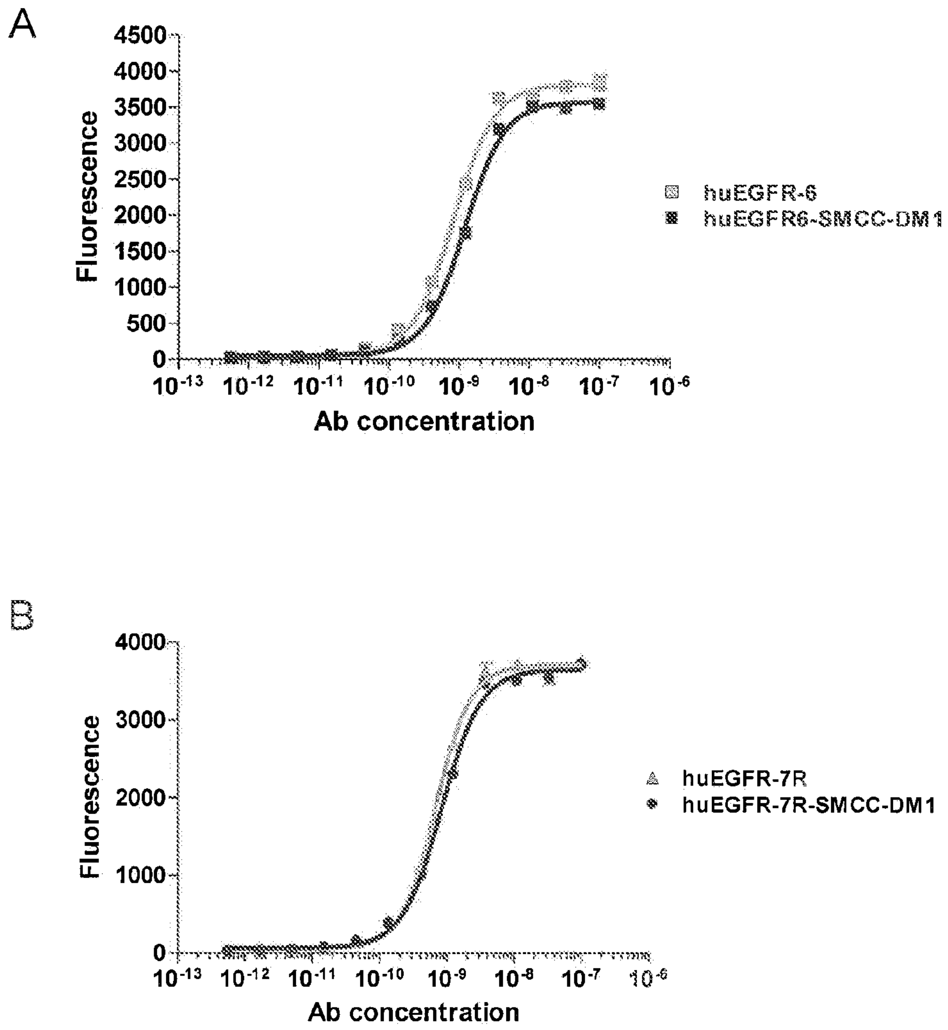
FIG. 18 depicts the binding curves of the indicated antibody and the corresponding antibody-maytansinoid conjugate.

Binding affinity of the huEGFR-6 and huEGFR-7R antibody maytansinoid conjugates was compared with that of the naked antibodies using MDA-MB468 cells as described in the Example 2. The Kds calculated from binding curves of the huEGFR-6 antibody and conjugates (FIG. 18 A) were 0.81 nM for naked huEGFR-6 antibody and 1.18 nM for huEGFR-6-SMCC-DM1 conjugate. The Kds calculated from binding curves of the huEGFR-7R antibody and conjugates (FIG. 18 B) were 0.67 nM for naked huEGFR-7R antibody and 0.83 nM for huEGFR-7R-SMCC-DM1 conjugate. This data demonstrates that DM conjugation does not notably alter the binding affinity of the huEGFR-6 and huEGFR-7R antibody to the huEGFR antigen.

Example 15

In Vitro Cytotoxic Assay on Tumor Cells

The ability of EGFR antibody maytansinoid conjugates to inhibit the tumor cell growth was measured using in vitro cytotoxicity assays. Briefly, target cells were plated at 1,500 to 3,000 cells per well in 100 μL, complete RPMI media containing 10% FBS. Conjugates were diluted into complete RPMI media using 5-fold dilution series and 100 μL were added per well. The final concentration typically ranged from $3\times10^{-8}$ M to $8\times10^{-14}$ M. Cells were incubated at 37° C. in a humidified 5% CO2 incubator for 5 days. Viability of the remaining cells was determined by colorimetric WST-8 assay and the absorbance at 450 nm (A450) was measured in a multiwell plate reader. The surviving fraction was calculated by dividing each treated sample value by the average value of untreated controls. The surviving fraction value was plotted against the antibody-conjugate concentration in a semi-log plot for each treatment.

The in vitro cytotoxicity of naked antibodies and antibody-maytansinoid conjugates of the invention was compared to the activity of a non-specific antibody and its corresponding maytansinoid conjugate such as chKTI and chKTI-SMCC-DM1. The results from a typical cytotoxicity assay are shown in FIGS. 19 and 20.

In FIG. 19A, the activity of naked antibodies and maytansinoid conjugates of the invention was tested in FaDu cell line. The huEGFR-6 and huEGFR-7R naked antibodies inhibited 40% and 55% H292 cell growth, respectively while the chKTI antibody had no activity. Maytansinoid conjugation further enhances the activity of the EGFR antibody of the invention. Both huEGFR-6 and huEGFR-7R-SMCC-DM1 conjugates completely abolished the target cells with EC50 of 0.22 nM and 0.06 nM, respectively. The control chKTI-SMCC-DM1 conjugate also killed the target cells but with much lower EC50 (0.59 μM).

In FIG. 19B, the activity of naked antibodies and maytansinoid conjugates of the invention was tested in H292 cell line. The huEGFR-6 and huEGFR-7R naked antibodies inhibited 60-70% H292 cell growth while the chKTI antibody had no activity. Maytansinoid conjugation further enhances the activity of the EGFR antibody of the invention. Both huEGFR-6 and huEGFR-7R-SMCC-DM1 conjugates completely abolished the target cells with EC50 of 0.16 nM and 0.03 nM, respectively. The control chKTI-SMCC-DM1 conjugate also killed the target cells but with much lower EC50 (38.51 nM).

In FIG. 20A, the activity of naked antibodies and maytansinoid conjugates of the invention was compared with cetuximab in H226 cell line. The cetuximab, huEGFR-6, huEGFR-7R naked antibodies as well as the chKTI control antibody had no anti-proliferative activity. Maytansinoid conjugates of both huEGFR-6 and huEGFR-7R antibodies completely eliminated the target cells with EC50 of 0.68 nM and 0.14 nM, respectively while the control chKTI-SMCC-DM1 conjugate failed to kill the target cells.

In FIG. 20B, the activity of naked antibodies and maytansinoid conjugates of the invention was compared with cetuximab in the SCC-4 cell line. The cetuximab, huEGFR-6 and huEGFR-7R naked antibodies showed a dose dependent growth inhibition with maximal inhibition of around 30%, while the chKTI antibody had no activity. Maytansinoid conjugation further potentiates the activity of the EGFR antibody of the invention. Both huEGFR-6 and huEGFR-7R-SMCC-DM1 conjugates completely eliminated the target cells with EC50 of 0.07 nM and 0.03 nM, respectively. The control chKTI-SMCC-DM1 conjugate also killed the target cells but with a much lower EC50 (17.62 nM). Altogether, these results show that the maytansinoid conjugation dramatically enhances the anti-tumor activity of the EGFR antibodies of the invention.

Example 16

Figure 21:
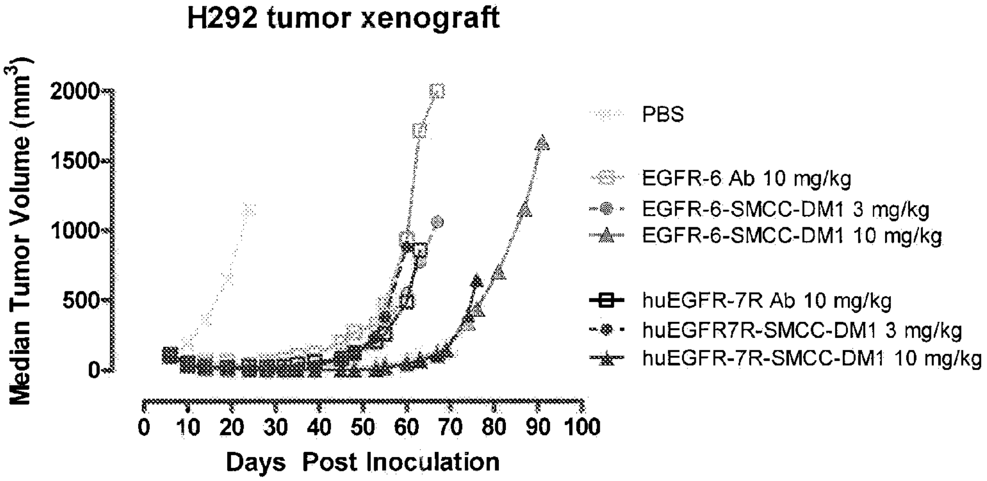
FIG. 21 shows a line graph depicting the growth of H292 tumor xenograft in mice treated with a single dose of the indicated antibodies and antibody-maytansinoid conjugates.
Figure 22:
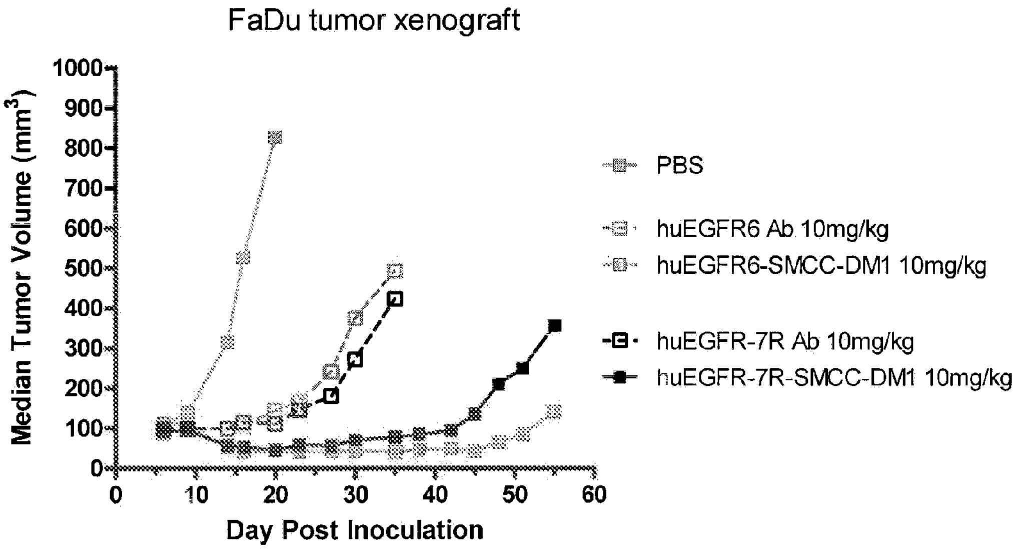
FIG. 22 shows a line graph depicting the growth of FaDu tumor xenograft in mice treated with a single dose of the indicated antibodies and antibody-maytansinoid conjugates.

In Vivo Efficacy Study Comparing huEGFR-6 and huEGFR-7R Antibodies and Maytansinoid Conjugates The activity of naked antibody and antibody-maytansinoid conjugates of the huEGFR-6 and huEGFR-7R antibodies was tested in EGFR expressing 11292 NSCLC (non-small cell lung cancer) (FIG. 21) and FaDu SCCHN (squamous cell carcinoma of head and neck) (FIG. 22) tumor xenograft models. $1\times10^7$ tumor cells were injected subcutaneously into SCID mice. Animals were randomized by tumor volume into treatment groups when tumors reached a mean tumor volume of approximately 100 $mm^3$ and injected once with the indicated dosage of naked antibodies or antibody-maytansinoid conjugates. Median tumor volume of each treatment groups is plotted against time post tumor cell inoculation (FIGS. 21 and 22). Tables 17 and 18 show the number of mice with complete response (CR) (no palpable tumor) and percent of tumor growth inhibition (% T/C) which corresponds to the median of tumor volume of each treated group divided by the median tumor volume of control group when the tumor volume of the control group reaches a predetermined size. A treatment with a % T/C value of below 42% is considered active, while a treatment with a % T/C value of below 12% is considered highly active.

Both the naked antibodies and antibody maytansinoid conjugates of the invention were very active and they significantly delayed the growth of both H292 and FaDu tumor xenografts (FIGS. 21 and 22). In H292 tumor xenograft study (FIG. 21 and Table 17), all mice treated with the huEGFR-6-SMCC-DM1 and huEGFR-7R-SMCC-DM1 conjugates as low as 3 mg/kg exhibited a complete response. Even the huEGFR-6 and huEGFR-7R antibodies at 10 mg/kg were highly active. In FaDu tumor xenograft study (FIG. 22 and Table 18), the huEGFR-6 and the huEGFR-7R antibodies at 10 mg/kg were active and the antibody-maytansinoid conjugates were even more active with complete response in some mice.

TABLE 17

Activity of EGFR Ab and maytansinoid conjugates in H292 tumor xenograft

| Ab and conjugate | % T/C | CR |
|---|---|---|
| huEGFR-6 Ab 10 mg/kg | 3.1 | 1/6 |
| huEGFR-6-SMCC-DM1 3 mg/kg | 0.0 | 6/6 |
| huEGFR-6-SMCC-DM1 10 mg/kg | 0.0 | 6/6 |
| huEGFR-7R Ab 10 mg/kg | 2.2 | 4/6 |
| huEGFR-7R-SMCC-DM1 3 mg/kg | 1.2 | 6/6 |
| huEGFR-7R-SMCC-DM1 10 mg/kg | 0.6 | 6/6 |

TABLE 18

Activity of EGFR Ab and maytansinoid conjugates in FaDu tumor xenograft

| Ab and conjugate | % T/C | CR |
|---|---|---|
| huEGFR-6 Ab 10 mg/kg | 17.5 | 0/6 |
| huEGFR-6-SMCC-DM1 10 mg/kg | 5.8 | 2/6 |
| huEGFR-7R Ab 10 mg/kg | 13.4 | 0/6 |
| huEGFR-7R-SMCC-DM1 10 mg/kg | 5.5 | 1/6 |

In Vivo Efficacy Study Comparing huEGFR-7R-SMCC-DM1 and huEGFR-7R-PEG-MAL-DM1

Figure 25:
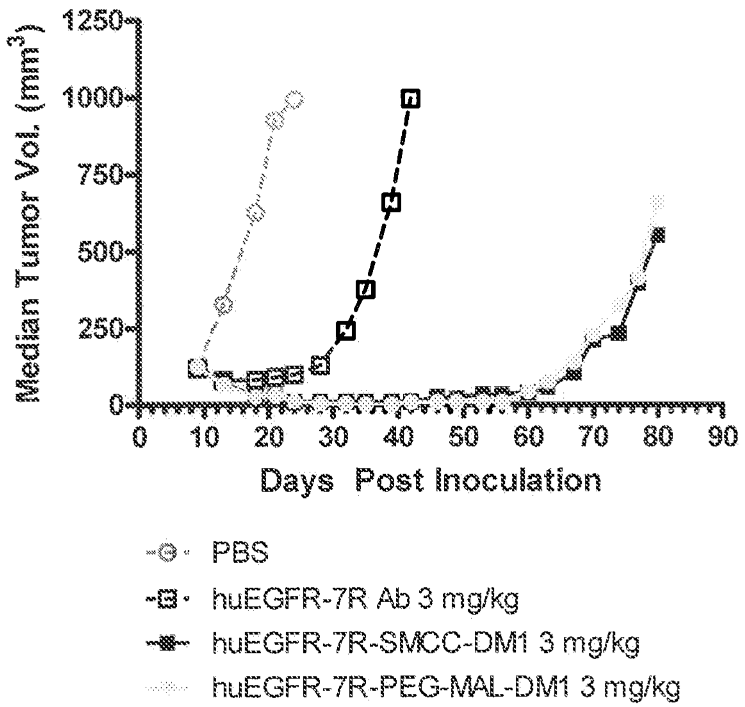
FIG. 25 shows a line graph depicting the growth of H292 tumor xenograft in mice treated with a single 3 mg/kg dose of either the huEGFR-7R antibody or the huEGFR-7R-SMCC-DM1, or huEGFR-7R-PEG-MAL-DM1 antibody-maytansinoid conjugates.
Figure 26:
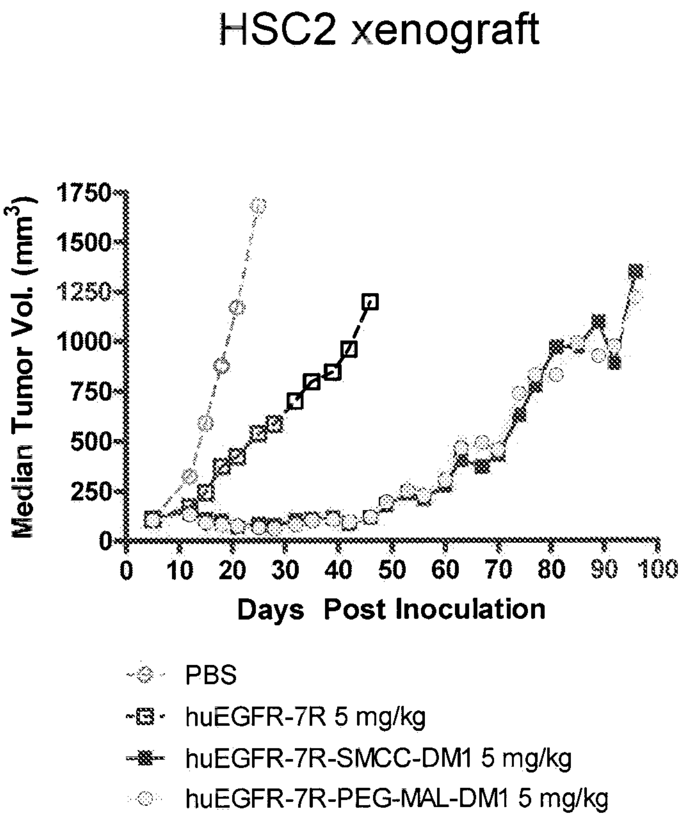
FIG. 26 shows a line graph depicting the growth of HSC2 tumor xenograft in mice treated with a single 5 mg/kg dose of either the huEGFR-7R antibody or the huEGFR-7R-SMCC-DM1, or huEGFR-7R-PEG-MAL-DM1 antibody-maytansinoid conjugates.
Figure 27:
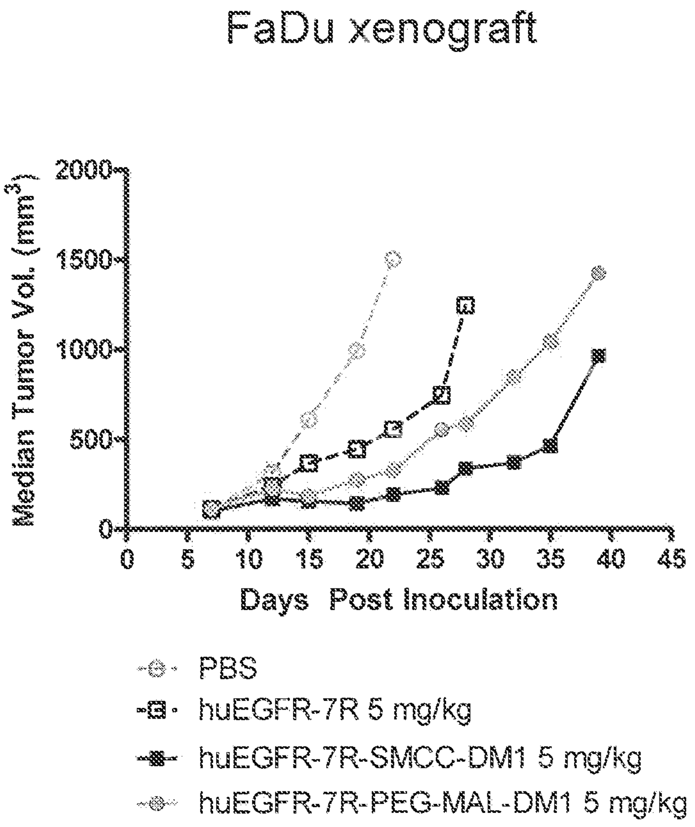
FIG. 27 shows a line graph depicting the growth of FaDu tumor xenograft in mice treated with a single 5 mg/kg dose of either the huEGFR-7R antibody or the huEGFR-7R-SMCC-DM1, or huEGFR-7R-PEG-MAL-DM1 antibody-maytansinoid conjugates.

The activity of naked antibody, the huEGFR-7R-SMCC-DM1 and the huEGFR-7R-PEG-MAL-DM1 conjugates was compared in EGFR expressing H292 NSCLC (non-small cell lung cancer) (FIG. 25), HSC2 SCCHN (squamous cell carcinoma of head and neck) (FIG. 26) and FaDu SCCHN (FIG. 27) tumor xenograft models. The experiment and data analysis were done as described above.

In H292 NSCLC tumor xenograft study (FIG. 25 and Table 19), all of the test articles were highly active at 3 mg/kg single dose. All mice treated with both the huEGFR-7R-SMCC-DM1 and the huEGFR-7R-PEG-MAL-DM1 conjugates showed a complete response, while none of the mice treated with the huEGFR-7R antibody had a complete response. In HSC2 SCCHN tumor xenograft study (FIG. 26 and Table 20), both the huEGFR-7R-SMCC-DM1 and the huEGFR-7R-PEG-MAL-DM1 conjugates were highly active with T/C of 8%, while the huEGFR-7R antibody was barely active at 5 mg/kg single dose. In FaDu SCCHN tumor xenograft study (FIG. 27 and Table 21), both the huEGFR-7R-SMCC-DM1 and the huEGFR-7R-PEG-MAL-DM1 conjugates were active with T/C of 15% and 28%, respectively. The huEGFR-7R antibody treatment showed some tumor growth inhibition but it was not significantly active. In conclusion, these results show that the naked antibodies of the invention are potent in inhibiting the growth of NSCLC and SCCHN tumors, and the conjugation with maytansinoid further enhances the anti-tumor activity.

TABLE 19

| Activity of huEGFR-7R Ab and maytansinoid conjugates in H292 tumor xenograft | | |
|---|---|---|
| Ab and conjugate | % T/C | CR |
| huEGFR-7R Ab 3 mg/kg | 10 | 0/6 |
| huEGFR-7R-SMCC-DM1 3 mg/kg | <1 | 6/6 |
| huEGFR-7R-PEG-MAL-DM1 3 mg/kg | <1 | 6/6 |

TABLE 20

| Activity of huEGFR-7R Ab and maytansinoid conjugates in HSC2 tumor xenograft | | |
|---|---|---|
| Ab and conjugate | % T/C | CR |
| huEGFR-7R Ab 5 mg/kg | 41 | 0/6 |
| huEGFR-7R-SMCC-DM1 5 mg/kg | 8 | 0/6 |
| huEGFR-7R-PEG-MAL-DM1 5 mg/kg | 8 | 0/6 |

TABLE 21

| Activity of huEGFR-7R Ab and maytansinoid conjugates in FaDu tumor xenograft | | |
|---|---|---|
| Ab and conjugate | % T/C | CR |
| huEGFR-7R Ab 5 mg/kg | 45 | 0/6 |
| huEGFR-7R-SMCC-DM1 5 mg/kg | 15 | 0/6 |
| huEGFR-7R-PEG-MAL-DM1 5 mg/kg | 28 | 0/6 |

Example 17

In Vitro Cytotoxicity Assay on Human Primary Keratinocytes

EGFR signaling plays a key role in human primary keratinocyte proliferation. Inhibition of EGFR signaling by small molecule tyrosine kinase inhibitors or antagonistic anti-EGFR antibodies such as cetuximab leads to growth arrest and apoptosis in keratinocyte culture (Stoll et al., Oncogene 16, 1493-1499 (1998)). Keratinocyte apoptosis is thought to be one of the mechanism underlying dermatologic toxicities caused by the anti-EGFR therapies in the clinic. To examine the potential of skin toxicity, the EGFR antibodies and antibody-maytansinoid conjugates of the invention was tested in an in vitro cytotoxicity assay using human primary keratinocytes. Briefly, human primary keratinocytes (Invitrogen) were plated at 1,500 to 3,000 cells per well in 100 μL EGF containing media suggested by the manufacturer. Test articles were diluted in EGF containing media using 5-fold dilution series and 100 μL were added per well. The final concentration typically ranged from $3\times10^{-8}$ M to $8\times10^{-14}$ M. Cells were incubated at 37° C. in a humidified 5% CO2 incubator for 5 days. Viability of the remaining cells was determined by colorimetric WST-8 assay and the absorbance at 450 nm (A450) was measured in a multiwell plate reader. The surviving fraction was calculated by dividing each treated sample value by the average value of untreated controls. The surviving fraction value was plotted against the antibody-conjugate concentration in a semi-log plot for each treatment.

The in vitro cytotoxicity of huEGFR-7R naked antibodies and huEGFR-7R-SMCC-DM1 conjugate was compared to the activity of a non-specific antibody (chKTI), chKTI-SMCC-DM1 conjugate, a non antagonistic antibody (huML66) and its corresponding maytansinoid conjugate on the human primary keratinocytes (FIG. 23A) as well as H292 tumor cells (FIG. 23B) in the same experiment. In H292 cell line (FIG. 23B), huML66 antibody had no activity, while the huEGFR-7R antibody inhibited cell growth up to 55%. The maytansinoid conjugates of huML66 and huEGFR-7R had the best activity; they were able to completely inhibit tumor cell growth with EC50 between 0.05 and 0.07 nM. In human primary keratinocytes (FIG. 23A), chKTI and huML66 antibodies had no effect on keratinocyte proliferation. However, the huML66-SMCC-DM1 was very potent in killing the keratinocytes with 0.55 nM EC50. The huEGFR-7R naked antibody had very little effect on keratinocytes. Surprisingly, the huEGFR-7R-SMCC-DM1 conjugate was much less toxic to the keratinocytes as compared to the huML66-SMCC-DM1 conjugate. At the concentration of 3.3 nM, the huEGFR-7R naked antibody and its corresponding conjugate only inhibited less than 40% of the keratinocyte growth. In summary, antibody and antibody-maytansinoid conjugate of the invention has little effect on the human primary keratinocyte cell growth while they are very potent in eliminating tumor cells.

Example 18

Chemokine/Cytokine Production by Human Primary Keratinocytes

The skin epithelium, which is composed mainly of keratinocytes interspersed with dendritic cells, melanocytes, and rare T lymphocytes and monocytes, is highly committed to host defense. Physical, chemical, or immune-specific insults rapidly evoke an epidermal response characterized by the increase expression of chemokine and cytokines, which attract and activate distinct leukocyte subpopulations to induce inflammatory response. TNFα induces human keratinocytes to express numerous chemokines and cytokines including CCL5/RANTES, CXCL10/IFNγ-inducible-protein 10 and CXCL8/IL-8. CCL5 attracts T cells, monocytes as well as neturophils. CXCL10 induces migration of type 1 T cells. CXCL8 is a chemoattractants active in neutrophil recruitment as well as in epithelial and endothelial cell proliferation.

EGFR signaling governs the homeostatic maintenance and repair of epithelial tissue. EGFR activation leads to keratinocyte proliferation, migration and controlled differentiation. In response to TNFα, keratinocytes produce EGFR ligands which activate EGFR signaling. The enhanced EGFR activation in keratinocytes increases CXCL8 expression and reduces CCL5 and CXCL10 expression. In contrast, impairment of EGFR signaling led to an opposite pattern. Skin application of a selective EGFR tyrosine kinase inhibitor led to more severe contact hypersensitivity responses, with increased epidermal levels of CCL5 and CXCL10, and a higher number of monocytes/macrophages and T cells in the skin. These findings suggested that EGFR signaling modulates skin inflammation by affecting chemokine expression in keratinocytes (Pastore, *J. Immunol.,* 174: 5047-5056 (2005)). It is now believed that skin toxicity manifested in the clinic upon EGFR therapies are caused by apoptosis and sustained inflammation in the skin.

Figure 24:
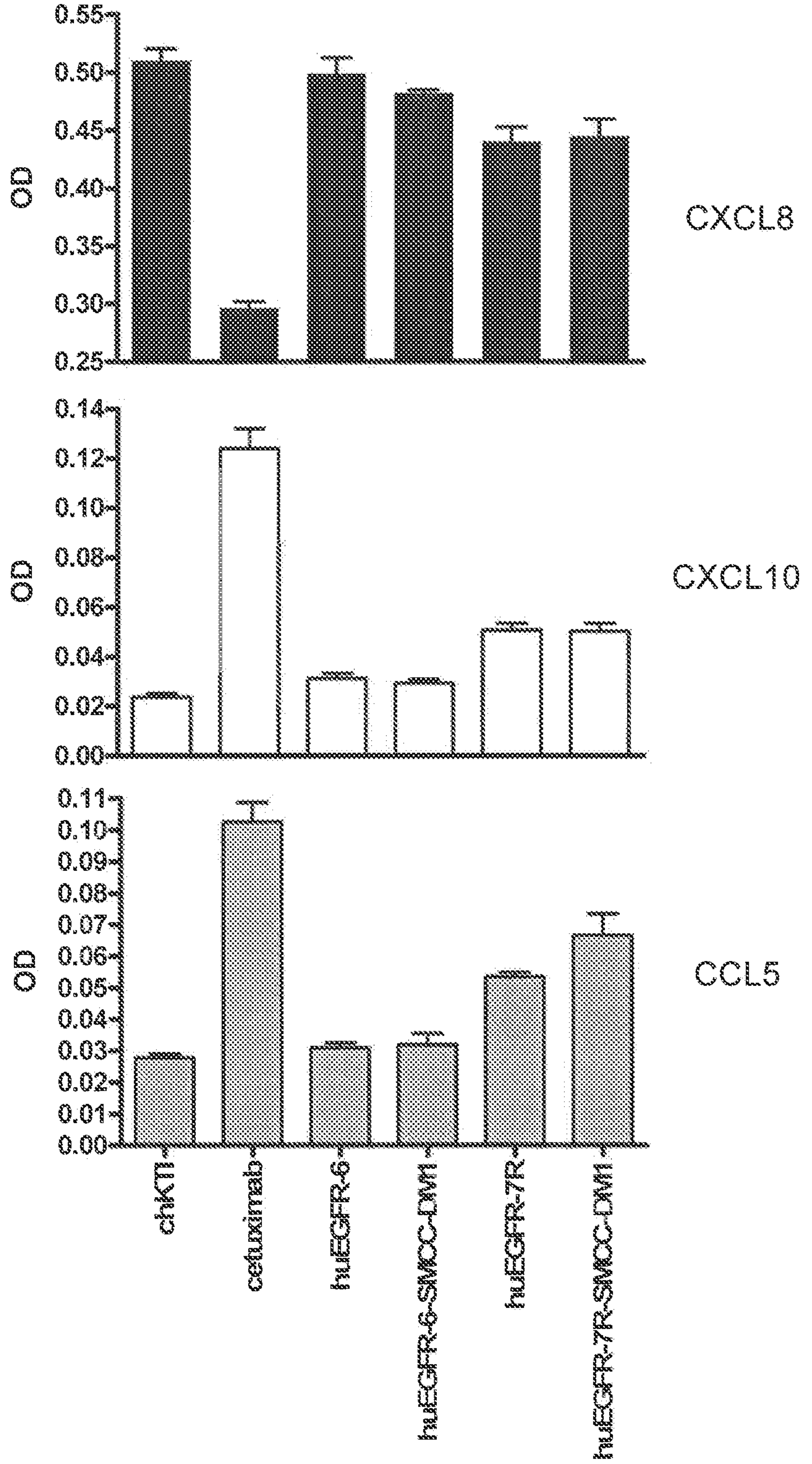
FIG. 24 shows bar graphs depicting the amount of CXCL8, CXCL10, CCL5 produced by the human primary keratinocytes in presence of the indicated antibodies and antibody -maytansinoid-conjugates.

The effect of antibodies and antibody-maytansinoid conjugates of the invention in modulating chemokine/cytokine production by human primary keratinocytes was tested in the following in vitro assay. $1\times10^5$ human primary keratinocytes/well (Invitrogen) were first seeded in 6 well plate. The cells were starved overnight and then cultured with 100 ng/ml TNFα and 10 μg/ml test antibodies in the EGF containing media for 14 hours. The amount of CCL5, CXCL10 and CXCL8 in the culture supernatant was measured using ELISA kits from R&D systems according to the manufacturer's protocol. As shown in FIG. 24, cetuximab reduced the expression of CXCL8 and increased the production of CXCL10 and CCL5. In contrast, the naked antibodies of the invention had no or little effect on the expression of these chemokines/cytokines when compared to the chKTI control. Surprisingly, the maytansinoid conjugates of the EGFR antibodies of the invention also had no or little effect on the keratinocytes. Altogether, the results shown in Examples 17 and 18 strongly suggest that both the antibodies and antibody maytansinoid conjugates of the invention had minimal effect on the human primary keratinocytes in vitro, therefore are likely to be less toxic to the skin in humans. In contrast to the effect on keratinocytes, the antibodies and antibody maytansinoid conjugates of the invention are very potent in killing the EGFR positive tumor cells in vitro and in vivo as shown in Examples 7, 12, 15 and 16. In summary, the antibodies and antibody cytotoxic agent conjugates of the invention are unique class of anti-EGFR molecules that have distinct effect on normal vs. tumor cells.

Example 19

Epitope Mapping

The human EGFR is a large (1186 residues), monomeric glycoprotein with an extracellular ligand binding region, a single transmembrane region and a cytoplasmic tyrosine kinase domain flanked by noncatalytic regulatory regions. The extracellular domain (ECD) of human EGFR (residues 1-618) contains four subdomains (FIG. 28), here termed domain I (amino acids 1-165), domain II (amino acids 166-309), domain III (amino acids 310-481), and domain IV (amino acids 482-618). These domains are also referred to as L1, CR1, L2, and CR2, where L and CR are acronyms for large and Cys-rich, respectively. The epitope of the huEGFR-7R of the invention were mapped mainly to the defined region containing amino acids 460-480 in the human EGFR ECD domain III by engineering truncated and chimeric human/murine EGFR molecules.

EGFR Variants Cloning and Expression

The entire human EGFR ECD (amino acids 1-618) was expressed as an Fc fusion protein (huEGFR-Fc). The protein sequence was codon optimized, synthesized, and cloned in frame with a murine IgG2A hinge, CH2, and CH3 region in the pmuFc2ANL mammalian expression vector by Blue Heron Biotechnologies. As antibodies of the invention compete with cetuximab binding to EGFR (FIG. 8B), and cetuximab binds exclusively to domain III, the epitope of the antibodies of the invention may also be located in domain III and might overlap with that of cetuximab. To further identify the epitope, an Fc fusion of the truncated human EGFR (huEGFRdIII-Fc), containing entire domain III (amino acids 310-481) plus 20 extra residues from domain IV (amino acids 482-501), which was suggested to be required for binding of cetuximab, was similarly constructed as huEGFR-Fc. Further, a truncated murine EGFR containing amino acids 310-501 (muEGFRdIII-Fc), and chEGFRdIII-Fc, a chimeric version containing murine EGFR amino acids 310-501 with nucleotide sequence coding for amino acids 460-481 being replaced by the corresponding sequence from human EGFR, were also similarly constructed to be expressed as Fc fusion proteins (FIG. 29). The chEGFRdIII-Fc constructs consists of 10 amino acids mutations to their human counterparts, including residues 460, 461, 467, 468, 471, 473, 474, and 478-480. All forms of EGFR ECD Fc tagged proteins were expressed via transient transfection of HEK 293T cells and purified from the supernatant of the transfected cells using protein A affinity chromatography.

Antibody Binding to Various EGFR ECD-Fc Constructs

The huEGFR-7R was tested in ELISA format for binding to the various EGFR-Fc constructs described above. As shown in FIG. 30, huEGFR-7R antibody binds to both human EGFR (huEGFR-Fc) and human EGFR domain III (huEGFRdIII-Fc) with similar affinity. FIG. 30 also demonstrates that huEGFR-7R antibody practically does not recognize the murine EGFR domain III (muEGFRdIII-Fc), despite the high sequence homology with the human receptor (88% sequence identity in domain III). Additionally, the huEGFR-7R antibody binds to the human/murine EGFR chimera (chEGFRdIII-Fc), containing mainly murine EGFR domain III sequence with ten amino acids at positions 460, 461, 467, 468, 471, 473, 474, and 478-480 mutated to their human counterparts (FIG. 30). These data indicate that huEGFR-7R antibody binds exclusively to the domain III of human EGFR and the binding epitope is largely confined within amino acid positions 460-480. When the binding affinities to different truncated formats of huEGFR are compared, it is apparent that there was an approximately two fold decrease in the binding affinity of the huEGFR-7R antibody to chEGFRdIII-Fc as compared to huEGFR and huEGFRdIII, suggesting that the epitope of huEGFR-7R antibody consists of additional amino acid residues besides those in the positions 460-480. This data was confirmed with the muEGFR-7 antibody binding results (FIG. 32).

In parallel, other anti-EGFR antibodies of the invention, such as huEGFR-6 (FIG. 31), muEGFR-6 (FIG. 33), muEGFR-12 (FIG. 34) and muEGFR-13 (FIG. 35) antibodies that share unique biological activities with the EGFR-7 antibody, exhibit similar binding properties as the EGFR-7 antibody. They bind to human EGFR domain III (huEGFRdIII-Fc) but not murine EGFR domain III (muEGFRdIII-Fc), and importantly, they all bind to the chEGFRdIII-Fc at a lower affinity than to the huEGFRdIII-Fc. These data suggest that the epitope recognized by the antibodies of the invention constitutes other residues in domain III in addition to the amino acid residues in positions 460-480. In contrast, cetuximab binds to chEGFRdIII as well as wild type human EGFR and huEGFRdIII at similar affinity (FIG. 36), suggesting that the cetuximab binding epitope is confined to amino acid residues in positions 460-480. In summary, the huEGFR-7R antibody along with other anti-EGFR antibodies of the invention binds exclusively to domain III of the huEGFR extracellular domain. Moreover, through constructing chimeric EGFR, it has been confirmed that the epitope recognized by the antibodies of the invention is displaced toward the C-terminus of huEGFR domain III and largely overlaps with, but is not identical, to the cetuximab binding site and very likely consists of additional critical amino acids The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. A method for treating cancer in a patient comprising administering to the patient a therapeutically effective amount of an antibody or antigen binding fragment thereof that specifically binds to human EGFR, wherein the antibody or antigen binding fragment thereof comprises:

a) an immunoglobulin heavy chain variable region (VH) comprising a CDR1sequence of SEQ ID NO:1, a CDR2 sequence of SEQ ID NO: 2 or 4, and a CDR3sequence of SEQ ID NO: 3 or 5; and b) an immunoglobulin light chain variable region (VL) comprising a CDR1sequence of SEQ ID NO: 13 or 14, a CDR2 sequence of SEQ ID NO:11, and a CDR3 sequence of SEQ ID NO:12.

2. The method of claim 1, wherein the antibody or antigen binding fragment thereof is murine, non-human, humanized, chimeric, resurfaced, or human.

3. The method of claim 1, wherein the antibody or antigen binding fragment thereof is a full length antibody.

4. The method of claim 1, wherein the antibody or antigen binding fragment thereof is an antigen binding fragment.

5. The method of claim 1, wherein the antibody or antigen binding fragment thereof is a Fab, Fab', F(ab')2,single chain Fv or scFv, disulfide linked Fv, intrabody, IgGACH2,minibody, F(ab')3, tetrabody, triabody, diabody, DVD-Ig, mAb2, (scFv)2or scFv-Fc.

6. The method of claim 1, wherein the antibody or antigen binding fragment thereof comprises (a) a VH sequence at least 90% identical to the reference VH sequence of SEQ ID NO: 21; and (b) a VL sequence at least 90% identical to the reference VL sequence of SEQ ID NO: 26.

7. The method of claim 6, wherein the antibody or antigen binding fragment thereof comprises (a) the VH sequence of SEQ ID NO: 21; and (b) the VL sequence of SEQ ID NO: 26.

8. The method of claim 1, wherein the antibody or antigen binding fragment thereof has at least one characteristic selected from the group consisting of: (a) inhibits at least 80% of epidermal growth factor (EGF) and transforming growth factor alpha (TGFα) binding to A431 cells at a concentration of 10 nM or higher, (b) causes at least 50% inhibition of H292 and HCC827 tumor cell proliferation at 30 nM or higher, and (c) does not inhibit more than 20% proliferation of keratinocytes or MCF-10A epithelial cells at 60 nM or lower.

9. The method of claim 8, wherein the antibody or antigen binding fragment thereof has at least two characteristics selected from the group consisting of:

(a) inhibits at least 80% of epidermal growth factor (EGF) and transforming growth factor alpha (TGFα) binding to A431 cells at a concentration of 10 nM or higher, (b) causes at least 50% inhibition of H292 and HCC827 tumor cell proliferation at 30 nM or higher, and (c) does not inhibit more than 20% proliferation of keratinocytes or MCF-10A epithelial cells at 60nM or lower.

10. The method of claim 9, wherein the antibody or antigen binding fragment thereof: (a) inhibits at least 80% of epidermal growth factor (EGF) and transforming growth factor alpha (TGFα) binding to A431 cells at a concentration of 10 nM or higher, (b) causes at least 50% inhibition of H292 and HCC827 tumor cell proliferation at 30 nM or higher, and (c) does not inhibit more than 20% proliferation of keratinocytes or MCF-10A epithelial cells at 60 nM or lower.

11. The method of claim 1, wherein the antibody or antigen binding fragment thereof is produced by the hybridoma having American Type Culture Collection (ATCC) Deposit Designation PTA-11332, deposited with the ATCC on Oct. 6, 2010.

12. The method of claim 1, further comprising administering a second anti-cancer agent to the subject.

13. The method of claim 12, wherein the second anti-cancer agent is a chemotherapeutic agent.

14. The method of claim 1, wherein the cancer is selected from the group consisting of: non-small cell lung cancer, breast cancer, colorectal cancer, head and neck cancers, and prostate cancer.

15. The method of claim 14, wherein the cancer is non-small cell lung cancer or head and neck cancer.

16. A method for treating cancer in a patient comprising administering to the patient a therapeutically effective amount of an immunoconjugate having the formula (A)-(L)-(C), wherein:

(A) is an antibody or antigen binding fragment thereof comprising a VH CDR1 sequence of SEQ ID NO:1, a VH CDR2 sequence of SEQ ID NO: 2 or 4, a VH CDR3 sequence of SEQ ID NO: 3 or 5; a VL CDR1 sequence of SEQ ID NO: 13or 14, a VL CDR2 sequence of SEQ ID NO:11, and a VL CDR3 sequence of SEQ ID NO:12;

(L) is a linker; and (C) is a cytotoxic agent; and wherein the linker (L) links (A) to (C).

17. The method of claim 16, wherein the antibody or antigen binding fragment thereof comprises the heavy chain variable region of SEQ ID NO:21 and the light chain variable region of SEQ ID NO:26.

18. The method of claim 16, wherein the linker is selected from the group consisting of a cleavable linker, a non-cleavable linker, a hydrophilic linker, and a dicarboxylic acid based linker.

19. The method of claim 18, wherein the linker is selected from the group consisting of: N-succinimidyl 4-(2-pyridyldithio)pentanoate (SPP); N -succinimidyl 4-(2-pyridyldithio)butanoate (SPDB); and N-succinimidyl 4-(2-pyridyldithio)-2-sulfobutanoate (sulfo-SPDB).

20. The method of claim 18, wherein the linker is a non-cleavable linker.

21. The method of claim 20, wherein the linker is selected from the group consisting of: N-succinimidyl 4-(maleimidomethyl) cyclohexanecarboxylate (SMCC); N-sulfosuccinimidyl 4-(maleimidomethyl) cyclohexanecarboxylate (sulfoSMCC); N-succinimidyl -4-(iodoacetyl)-aminobenzoate (SiAB); and N-succinimidyl-[(N-maleimidopropionamido) -tetraethyleneglycol] ester (NHS-PEG4-maleimide).

22. The method of claim 21, wherein the linker is N-succinimidyl 4-(maleimidomethyl) cyclohexanecarboxylate (SMCC).

23. The method of claim 16, wherein the cytotoxic agent is selected from the group consisting of: a maytansinoid, maytansinoid analog, doxorubicin, a modified doxorubicin, benzodiazepine, taxoid, CC-1065, CC-1065 analog, duocarmycin, duocarmycin analog, calicheamicin, dolastatin, dolastatin analog, auristatin, tomaymycin derivative, and leptomycin derivative or a prodrug of the agent.

24. The method of claim 23, wherein the cytotoxic agent is a maytansinoid.

25. The method of claim 24, wherein the cytotoxic agent is N(2')-deacetyl-N(2')-(3-mercapto-l-oxopropyl)-maytansine (DM1) or N(2')-deacetyl-N(2')-(4-mercapto -4-methyl-1-oxopentyl)-maytansine (DM4).

26. The method of claim 24, wherein the cytotoxic agent is N(2')-deacetyl-N(2')-(3-mercapto-1-oxopropyl)-maytansine (DM1).

27. The method of claim 26, wherein the antibody or antigen binding fragment thereof comprises the heavy chain variable region of SEQ ID NO:21 and the light chain variable region of SEQ ID NO:26.

28. The method of claim 26, wherein the linker is N-succinimidyl 4-(maleimidomethyl) cyclohexanecarboxylate (SMCC).

29. The method of claim 28, wherein the antibody or antigen binding fragment thereof comprises the heavy chain variable region of SEQ ID NO:21 and the light chain variable region of SEQ ID NO:26.

30. The method of claim 24, wherein the antibody or antigen binding fragment thereof comprises the heavy chain variable region of SEQ ID NO:21 and the light chain variable region of SEQ ID NO:26.

31. The method of claim 16, further comprising administering a second anti-cancer agent to the subject.

32. The method of claim 31, wherein the second anti-cancer agent is a chemotherapeutic agent.

33. The method of claim 16, wherein the cancer is selected from the group consisting of: non-small cell lung cancer, breast cancer, colorectal cancer, head and neck cancers, and prostate cancer.

34. The method of claim 33, wherein the cancer is non-small cell lung cancer or head and neck cancer.

35. A method for treating cancer in a patient comprising administering to the patient a therapeutically effective amount of an immunoconjugate having the formula (A)-(L)-(C), wherein:

(A) is an antibody or antigen binding fragment thereof comprising the heavy chain variable region of SEQ ID NO:21 and the light chain variable region of SEQ ID NO:26;

(L) is a N-succinimidyl 4-(maleimidomethyl) cyclohexanecarboxylate (SMCC) linker; and (C) is the cytotoxic agent N(2')-deacetyl-N(2')-(3-mercapto- 1-oxopropyl) -maytansine (DM1); and wherein the linker (L) links (A) to (C).

36. The method of claim 35, further comprising administering a second anti-cancer agent to the subject.

37. The method of claim 36, wherein the second anti-cancer agent is a chemotherapeutic agent.

38. The method of claim 35, wherein the cancer is selected from the group consisting of non-small cell lung cancer, breast cancer, colorectal cancer, head and neck cancers, and prostate cancer.

39. The method of claim 38, wherein the cancer is non-small cell lung cancer or head and neck cancer.

* * * * *

UNITED STATES PATENT AND TRADEMARK OFFICE

CERTIFICATE OF CORRECTION

PATENT NO. : 9,125,896 B2
APPLICATION NO. : 13/800624
DATED : September 8, 2015
INVENTOR(S) : Julianto Setiady et al.

It is certified that error appears in the above-identified patent and that said Letters Patent is hereby corrected as shown below:

IN THE CLAIMS

At column 175, line 21, please replace “CDR1sequence” with --CDR1 sequence--.

At column 175, line 22, please replace “CDR3sequence” with --CDR3 sequence--.

At column 175, line 25, please replace “CDR1sequence” with --CDR1 sequence--.

At column 175, line 36, please replace “F(ab')2,single” with --F(ab')2, single--.

At column 175, line 37, please replace “IgGACH2,minibody” with --IgGΔCH2, minibody--.

At column 175, line 39, please replace “(scFv)2or scFv-Fc” with --(scFv)2 or scFv-Fc--.

At column 176, line 42, please replace “CDR1sequence” with --CDR1 sequence--.

At column 176, line 45, please replace “SEQ ID NO: 13or 14” with --SEQ ID NO: 13 or 14--.

At column 176, line 60, please replace “N -succinimidyl” with --N-succinimidyl--.

At column 177, line 2, please replace “N-succinimidyl -4” with --N-succinimidyl-4--.

At column 177, line 3, please replace “(SiAB)” with --(SIAB)--.

At column 177, line 18, please replace “4-mercapto -4-methyl” with --4-mercapto-4-methyl--.

Signed and Sealed this
Twenty-second Day of March, 2016

Michelle K. Lee

Michelle K. Lee
*Director of the United States Patent and Trademark Office*

At column 178, line 23, please replace “capto- 1-oxopropyl) -maytansine” with --capto-1-oxopropyl)-maytansine--.

At column 178, line 31, please insert a --:-- after “of”.